United States Patent
Himmelsbach et al.

(10) Patent No.: US 6,972,288 B1
(45) Date of Patent: Dec. 6, 2005

(54) 4-AMINO-QUINAZOLINE AND QUINOLINE DERIVATIVES HAVING AN INHIBITORY EFFECT ON SIGNAL TRANSDUCTION MEDIATED BY TYROSINE KINASES

(75) Inventors: Frank Himmelsbach, Mittelbiberach (DE); Elke Langkopf, Warthausen (DE); Birgit Jung, Schwabenheim (DE); Thomas Metz, Vienna (AT); Flavio Solca, Vienna (AT); Stefan Blech, Warthausen (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/914,323

(22) PCT Filed: Feb. 24, 2000

(86) PCT No.: PCT/EP00/01496

§ 371 (c)(1),
(2), (4) Date: Feb. 6, 2002

(87) PCT Pub. No.: WO00/51991

PCT Pub. Date: Sep. 8, 2000

Related U.S. Application Data

(60) Provisional application No. 60/149,329, filed on Aug. 17, 1999.

(30) Foreign Application Priority Data

| Feb. 27, 1999 | (DE) | 199 08 567 |
| Mar. 15, 1999 | (DE) | 199 11 366 |
| Jun. 21, 1999 | (DE) | 199 28 306 |
| Nov. 13, 1999 | (DE) | 199 54 816 |

(51) Int. Cl.$^7$ .............. A61K 31/517; C07D 239/94
(52) U.S. Cl. ............. 514/234.8; 514/235.2; 514/266.4; 514/313; 544/119; 544/128; 544/293; 546/159; 546/160
(58) Field of Search .............. 514/230.8, 234.5, 514/256.2, 311, 313, 234.8, 266.4; 544/119, 293; 546/153, 156, 157, 159, 160, 161

(56) References Cited

U.S. PATENT DOCUMENTS

| 6,002,008 A | * 12/1999 | Wissner et al. ............. 546/160 |
| 6,384,051 B1 | * 5/2002 | Frost et al. ................. 514/313 |
| 6,403,580 B1 | * 6/2002 | Himmelsbach et al. ... 514/230.8 |
| 6,653,305 B2 | * 11/2003 | Himmelsbach et al. ... 514/233.5 |
| 6,740,651 B2 | * 5/2004 | Himmelsbach et al. ... 514/228.8 |

FOREIGN PATENT DOCUMENTS

| EP | 0 787 722 A | 8/1997 |
| WO | WO96 33980 A1 | 10/1996 |
| WO | WO97 30035 A1 | 8/1997 |
| WO | WO97 32856 A1 | 9/1997 |
| WO | WO98 13354 A1 | 4/1998 |
| WO | WO 98-43960 | * 10/1998 |
| WO | WO99 09016 A | 2/1999 |
| WO | WO00 18740 A | 4/2000 |
| WO | WO00 55141 A1 | 9/2000 |

OTHER PUBLICATIONS

Boschelli; "Small molecule inhibitors of receptor tyrosine kinases"; Review Article—Chemical Sciences, Drugs of the Future, vol. 24, No. 5, 1999, pp. 515–537.

* cited by examiner

Primary Examiner—Richard L. Raymond
(74) Attorney, Agent, or Firm—Michael P. Morris; Mary-Ellen M. Devlin; Alan R. Stempel

(57) ABSTRACT

The present invention relates to bicyclic heterocycles of general formula

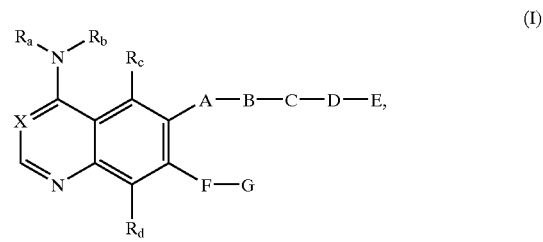

wherein $R_a$ to $R_d$, A to G and X are defined as in claim 1, the tautomers, the steroisomers and the salts thereof, particularly the physiologically acceptable salts thereof with inorganic or organic acids or bases which have valuable pharmacological properties, particularly an inhibiting effect on signal transduction mediated by tyrosine kinases, their use for treating diseases, particularly tumoral diseases, diseases of the lungs and respiratory tract, and the preparation thereof.

15 Claims, No Drawings

4-AMINO-QUINAZOLINE AND QUINOLINE DERIVATIVES HAVING AN INHIBITORY EFFECT ON SIGNAL TRANSDUCTION MEDIATED BY TYROSINE KINASES

RELATED APPLICATIONS

This application is derived from International Application No. PCT/EP00/01496, filed Feb. 24, 2000, pursuant to 35 USC §371. Benefit of provisional application 60/149,329, filed Aug. 17, 1999 is claimed.

DESCRIPTION OF THE INVENTION

The present invention relates to bicyclic heterocycles of general formula

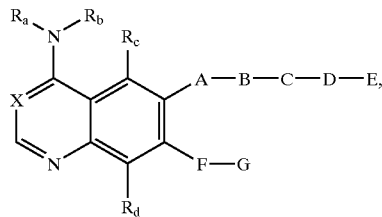

the tautomers, the stereoisomers and the salts thereof, particularly the physiologically acceptable salts thereof with inorganic or organic acids or bases which have valuable pharmacological properties, particularly an inhibitory effect on signal transduction mediated by tyrosine kinases, their use for treating diseases, particularly tumoral diseases, diseases of the lungs and respiratory tract and the preparation thereof.

In the above general formula I $R_b$ denotes a phenyl, benzyl or 1-phenylethyl group wherein the phenyl nucleus is substituted in each case by the groups $R_1$ to $R_2$ whilst $R_1$ and $R_2$, which may be identical or different, in each case denote a hydrogen, fluorine, chlorine, bromine or iodine atom, A $C_{1-4}$-alkyl, hydroxy, $C_{1-4}$-alkoxy, $C_{3-6}$-cycloalkyl, $C_{4-6}$-cycloalkoxy, $C_{2-5}$-alkenyl or $C_{2-5}$-alkynyl group, an aryl, aryloxy, arylmethyl or arylmethoxy group, a $C_{2-5}$-alkenyloxy or $C_{2-5}$-alkynyloxy group, wherein the unsaturated part may not be linked to the oxygen atom, a $C_{1-4}$-alkylsulphenyl, $C_{1-4}$-alkylsulphinyl, $C_{1-4}$-alkylsulfphonyl, $C_{1-4}$-alkylsulphonyloxy, trifluoromethylsulphenyl, trifluoromethylsulphinyl or trifluoromethylsulphonyl group, a methyl or methoxy group substituted by 1 to 3 fluorine atoms, an ethyl or ethoxy group substituted by 1 to 5 fluorine atoms, a cyano or nitro group or an amino group optionally substituted by one or two $C_{1-4}$-alkyl groups, while the substituents may be identical or different, or $R_1$ together with $R_2$, if they are bound to adjacent carbon atoms, denote a —CH=CH—CH=CH, —CH=CH—NH or —CH=N—NH group and $R_1$ denotes a hydrogen, fluorine, chlorine or bromine atom, a $C_{1-4}$-alkyl, trifluoromethyl or $C_{1-4}$-alkoxy group, $R_c$ and $R_d$, which may be identical or different, in each case denote a hydrogen, fluorine or chlorine atom, a methoxy group or a methyl group optionally substituted by a methoxy, dimethylamino, diethylamino, pyrrolidino, piperidino or morpholino group, X denotes a methine group substituted by a cyano group or a nitrogen atom, A denotes an oxygen atom or an —NH— group optionally substituted by a $C_{1-4}$-alkyl group, B denotes a carbonyl or sulphonyl group, C denotes a 1,3-allenylene, 1,1- or 1,2-vinylene group which may be substituted in each case by one or two methyl groups or by a trifluoromethyl group, an ethynylene group or a 1,3-butadien-1,4-ylene group optionally substituted by 1 to 4 methyl groups or by a trifluoromethyl group, D denotes an alkylene, —CO-alkylene or —$SO_2$-alkylene group wherein the alkylene moiety in each case contains 1 to 8 carbon atoms and additionally 1 to 4 hydrogen atoms in the alkylene moiety may be replaced by fluorine atoms, whilst the linking of the —CO-alkylene and —$SO_2$-alkylene group to the adjacent group C in each case must take place via the carbonyl or sulphonyl group, a —CO—O-alkylene, —CO—$NR_4$-alkylene or —$SO_2$—$NR_4$-alkylene group wherein the alkylene moiety in each case contains 1 to 8 carbon atoms, whilst the linking to the adjacent group C in each case must take place via the carbonyl or sulphonyl group wherein $R_4$ denotes a hydrogen atom or a $C_{1-4}$-alkyl group, or, if D is bound to a carbon atom of the group E, it may also denote a bond or, if D is bound to a nitrogen atom of the group E, it may also denote a carbonyl or sulphonyl group, E denotes an $R_4O$—CO-alkylene-$NR_5$, ($R_2O$—PO—$OR_8$)-alkylene-$NR_5$ or ($R_7O$—PO—$R_9$)-alkylene-$NR_6$-group wherein in each case the alkylene moiety, which is straight-chained and contains 1 to 6 carbon atoms, may additionally be substituted by one or two $C_{1-2}$-alkyl groups or by an $R_6O$—CO or $R_6O$—CO—$C_{1-2}$-alkyl group, wherein $R_5$ denotes a hydrogen atom, a $C_{1-4}$-alkyl group, which may be substituted by an $R_6O$—CO, ($R_7O$—PO—$OR_8$) or ($R_7O$—PO—$R_9$) group, an ethyl or propyl group optionally substituted by one or two methyl or ethyl groups, which may be terminally substituted in each case by a $C_{1-6}$-alkylcarbonylsulphenyl, $C_{3-7}$-cycloalkylcarbonylsulphenyl, $C_{3-7}$-cycloalkyl-$C_{2-3}$-alkyl-carbonylsulphenyl, arylcarbonylsulphenyl or aryl-$C_{1-3}$-alkylcarbonylsulphenyl group, an ethyl or propyl group optionally substituted by one or two methyl or ethyl groups which may be terminally substituted in each case by a $C_{1-6}$-alkylcarbonyloxy, $C_{1-7}$-cycloalkylcarbonyloxy, $C_{3-7}$-cycloalkyl-$C_{2-3}$-alkylcarbonyloxy, alkylcarbonyloxy or aryl-$C_{1-7}$-alkylcarbonyloxy group, an ethyl or propyl group optionally substituted by one or two methyl or ethyl groups, each of which may be terminally substituted by a hydroxy, $C_{1-4}$-alkoxy, amino, $C_{1-4}$-alkylamino or di-($C_{1-4}$-alkyl)-amino group or by a 4- to 7-membered alkyleneimino group, whilst in the abovementioned 6- to 7-membered alkyleneimino groups a methylene group in the 4 position may be replaced by an oxygen or sulphur atom, by a sulphinyl, sulphonyl, imino or N-($C_{1-4}$-alkyl)-imino group, a $C_{3-7}$-cycloalkyl or $C_{3-7}$-cycloalkyl-$C_{1-3}$-alkyl group, $R_6$, $R_7$ and $R_8$, which may be identical or different, in each case denote a hydrogen atom, a $C_{1-8}$-alkyl group, which may be substituted by a hydroxy, $C_{1-4}$-alkoxy, amino, $C_{1-4}$-alkylamino or di-($C_{1-4}$-alkyl)-amino group or by a 4- to 7-membered alkyleneimino group, whilst in the abovementioned 6- to 7-membered alkyleneimino groups in each case a methylene group in the 4 position may be replaced by an oxygen or sulphur atom or by a sulphinyl, sulphonyl, imino or N-($C_{1-4}$-alkyl)-imino group, a $C_{4-7}$-cycloalkyl group optionally substituted by 1 or 2 methyl groups, a $C_{3-5}$-alkenyl or $C_{3-5}$-alkynyl group, wherein the unsaturated part may not be linked to the oxygen atom, a $C_{3-7}$-cycloalkyl-$C_{1-4}$-alkyl, aryl, aryl-$C_{1-4}$-alkyl or $R_g$CO—O—($R_eCR_f$)-group, whilst $R_e$ and $R_f$, which may be identical or different, in each case denote a hydrogen atom or a $C_{1-4}$-alkyl group and $R_g$ denotes a $C_{1-4}$-alkyl, $C_{3-7}$-cycloalkyl, $C_{3-4}$-alkoxy or $C_{5-7}$-cycloalkoxy group, and $R_9$ denotes a $C_{1-4}$-alkyl, aryl or aryl-$C_{1-4}$-alkyl group, a 4- to 7-membered alkyleneimino group which may be substituted by an $R_6O$—CO, ($R_7O$—PO—$OR_8$), ($R_7O$—PO—$R_9$), $R_6O$—CO—$C_{1-4}$-alkyl, bis-($R_6O$—CO)—$C_{2-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_9$ are as hereinbefore defined, a 4- to 7-membered alkyleneimino group which may be substituted by two $R_6$OCO or $R_6$OCO—$C_{1-4}$-alkyl groups or by an $R_6$OCO-group and an $R_6$OCO—$C_{1-4}$-alkyl group wherein $R_6$ is as hereinbefore defined, a piperazino or homopiperazino group which is substituted in the 4 position by the group $R_{10}$ and is additionally substituted at a cyclic carbon atom by an $R_6O$—CO, ($R_7O$—PO—$OR_8$), ($R_7O$—PO—$R_9$), $R_6O$—CO—$C_{1-4}$-alkyl, bis-($R_6O$—CO)—$C_{1-8}$-alkyl, ($R_7O$—PO—$OR_8$)—$C_{1-4}$-alkyl or ($R_7O$—PO—$R_9$)—$C_{1-4}$-alkyl group wherein $R_6$ to $R_9$ are as hereinbefore defined and $R_{10}$ denotes a hydrogen atom, a $C_{1-4}$-alkyl, formyl, $C_{1-4}$-alkylcarbonyl or $C_{1-4}$-alkylsulphonyl group, a piperazino or homopiperazino group which is substituted in the 4 position by the group $R_{10}$ and additionally at cyclic carbon atoms by two $R_6O$—CO or $R_6O$—CO—$C_{1-4}$-alkyl groups or by an $R_6O$—CO-group and an $R_6O$—CO—$C_{1-4}$-alkyl group wherein $R_6$ and $R_{10}$ are as hereinbefore defined.

a piperazino or homopiperazino group which is substituted in each case in the 4 position by an $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_9$ are as hereinbefore defined, a piperazino or homopiperazino group which is substituted in the 4 position by an $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group and is additionally substituted at cyclic carbon atoms by one or two $R_6O$—CO or $R_6O$—CO—$C_{1-4}$-alkyl groups or by an $R_6O$—CO-group and an $R_6O$—CO—$C_{1-4}$-alkyl group wherein $R_6$ to $R_9$ are as hereinbefore defined, a morpholino or homomorpholino group which is substituted in each case by an $R_6O$—CO, ($R_7O$—PO—$OR_8$), ($R_7O$—PO—$R_9$), $R_6O$—CO—$C_{1-4}$-alkyl, bis-($R_4O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_7$ are as hereinbefore defined, a morpholino or homomorpholino group which is substituted by two $R_6O$—CO or $R_6O$—CO—$C_{1-4}$-alkyl groups or by an $R_6O$—CO-group and an $R_6O$—CO—$C_{1-4}$-alkyl group wherein $R_4$ is as hereinbefore defined, a pyrrolidinyl, piperidinyl or hexahydroazepinyl group substituted in the 1 position by the group $R_{10}$, whilst the above-mentioned 5- to 7-membered rings are additionally substituted in each case at a carbon atom by an $R_6O$—CO, ($R_7O$—PO—$OR_8$), ($R_7O$—PO—$R_9$), $R_6O$—CO—$C_{1-4}$-alkyl, bis-($R_7O$—PO—$R_9$)—$C_{1-4}$-alkyl ($R_7O$—PO—$OR_8$)—$C_{1-4}$-alkyl or ($R_7O$—PO—$R_9$)—$C_{1-4}$-alkyl group wherein $R_6$ to $R_{10}$ are as hereinbefore defined, a pyrrolidinyl, piperidinyl or hexahydroazepinyl group substituted in the 1 positioned by the group $R_{10}$, while the abovementioned 5- to 7-membered rings are in each case additionally substituted at carbon atoms by two $R_6O$—CO or $R_6O$—CO—$C_{1-4}$-alkyl groups or by an $R_6O$—CO-group and an $R_6O$—CO—$C_{1-4}$-alkyl group wherein $R_6$ and $R_{10}$ are as hereinbefore defined, a pyrrolidinyl, piperidinyl or hexahydroazepinyl group substituted in the 1 position by an $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_9$ are as hereinbefore defined, a pyrrolidinyl, piperidinyl or hexahydroazepinyl group substituted in the 1 position by an $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group, while the abovementioned 5- to 7-membered rings are in each case additionally substituted at carbon atoms by one or two $R_6O$—CO or $R_6O$—CO—$C_{1-4}$-alkyl groups or by an $R_6O$—CO-group and an $R_6O$—CO—$C_{1-4}$-alkyl group wherein $R_6$ to $R_9$ are as hereinbefore defined, a 2-oxo-morpholino group which may be substituted by 1 to 4 $C_{1-2}$-alkyl groups, a 2-oxo-thiomorpholino group which may be substituted by 1 to 4 $C_{1-2}$-alkyl groups, a morpholino or thiomorpholino group which is substituted in the 2 position by a $C_{1-4}$-alkoxy group, a morpholino or thiomorpholino group which is substituted in the 2 and 6 position by a $C_{1-6}$-alkoxy group, a $C_{1-4}$-alkyl-$NR_5$-group wherein the $C_{1-4}$-alkyl moiety, which is straight-chained and may additionally be substituted by one or two methyl groups, is in each case terminally substituted by a di-($C_{1-4}$-alkoxy)-methyl or tri-($C_{1-4}$-alkoxy)-methyl group, whilst $R_5$ is as hereinbefore defined, a $C_{1-4}$-alkyl-$NR_5$-group wherein the $C_{1-4}$-alkyl moiety, which is straight-chained and may additionally be substituted by one or two methyl groups, is in each case terminally substituted by a 1,3-dioxolan-2-yl or 1,3-dioxan-2-yl group optionally substituted by one or two methyl groups, while $R_3$ is as hereinbefore defined, an $R_{13}NR_5$-group wherein $R_5$ is as hereinbefore defined and $R_{11}$ denotes a 2-oxo-tertrahydrofuran-3-yl, 2-oxo-tertrahydrofuran-4-yl, 2-oxo-tetrahydropyran-3-yl, 2-oxo-tetrahydropyran-4-yl, 2-oxo-tetrahydropyran-5-yl, 2-oxo-tetrahydrothiophen-3-yl, 2-oxo-tetrahydrothiophen-4-yl, 2-oxo-tetrahydrothiopyran-3-yl, 2-oxo-tetrahydrothiopyran-4-yl or 2-oxo-tetrahydrothiopyran-5-yl group optionally substituted by one or two methyl groups, an amino group or an amino group optionally substituted by 1 or 2 $C_{1-4}$-alkyl groups wherein the alkyl groups may be identical or different and each alkyl moiety may be substituted from position 2 by a hydroxy, $C_{1-4}$-alkoxy, amino, $C_{1-4}$-alkylamino or di-($C_{1-4}$-alkyl)-amino group or by a 4- to 7-membered alkyleneimino group, whilst in the abovementioned 6- to 7-membered alkyleneimino groups in each case a methylene group in the 4 position may be replaced by an oxygen or sulphur atom, or by a sulphinyl, sulphonyl, imino or N-($C_{1-4}$-alkyl)-imino group, a 4- to 7-membered alkyleneimino group optionally substituted by 1 to 4 methyl groups, a 6- to 7-membered alkyleneimino group optionally substituted by 1 or 2 methyl groups wherein in each case a methylene group in the 4 position is replaced by an oxygen or sulphur atom, by an imino group substituted by the group $R_{10}$, by a sulphinyl or sulphonyl group, whilst $R_{10}$ is as hereinbefore defined, an imidazolyl group optionally substituted by 1 to 3 methyl groups, a $C_{5-7}$-cycloalkyl group wherein a methylene group is replaced by an oxygen or sulphur atom, by an imino group substituted by the group $R_{16}$, by a sulphinyl or sulphonyl group, wherein $R_{10}$ is as hereinbefore defined, or D together with E denotes a hydrogen, fluorine or chlorine atom, a $C_{1-4}$-alkyl group optionally substituted by 1 to 5 fluorine atoms, a $C_{3-6}$-cycloalkyl group, an aryl, heteroaryl, $C_{1-4}$-alkylcarbonyl, arylcarbonyl, carboxy, $C_{1-4}$-alkoxycarbonyl, $R_g$CO—O—($R_eCR_f$)—O—CO, ($R_7$O—PO—$OR_8$) or ($R_7$O—PO—$R_9$)-group wherein $R_e$ to $R_g$ and $R_7$ to $R_9$ are as hereinbefore defined, an aminocarbonyl, $C_{1-4}$-alkylaminocarbonyl or di-($C_{1-4}$-alkyl)-aminocarbonyl group or a carbonyl group, which is substituted by a 4- to 7-membered alkyleneimino group, whilst in the abovementioned 6- to 7-membered alkyleneimino groups, a methylene group in the 4 position may be replaced by an oxygen or sulphur atom, by an imino group substituted by the group $R_{16}$, by a sulphinyl or sulphonyl group, wherein $R_{10}$ is as hereinafter defined, F denotes a $C_{1-6}$-alkylene group, a —O—$C_{1-6}$-alkylene group, whilst the alkylene moiety is linked to the group G, or an oxygen atom, whilst the latter may not be linked to a nitrogen atom of the group G, and G denotes an $R_6$O—CO-alkylene-$NR_5$, ($R_7$O—PO—$OR_8$)-alkylene-$NR_5$ or ($R_7$O—PO—$R_9$)-alkylene-$NR_5$-group wherein in each case the alkylene moiety, which is straight-chained and contains 1 to 6 carbon atoms, may additionally be substituted by one or two $C_{1-2}$-alkyl groups or by an $R_6$O—CO or $R_6$O—CO—$C_{1-2}$-alkyl group, wherein $R_5$ to $R_9$ are as hereinbefore defined, a 4- to 7-membered alkyleneimino group which is substituted by an $R_6$O—CO, ($R_7$O—PO—$OR_8$), ($R_7$O—PO—$R_9$), $R_6$O—CO—$C_{1-4}$-alkyl, bis-($R_6$O—CO)-$C_{1-4}$-alkyl, ($R_7$O—PO—$OR_8$)—$C_{1-4}$-alkyl or ($R_7$O—PO—$R_9$)—$C_{1-4}$-alkyl group wherein $R_6$ to $R_9$ are as hereinbefore defined.

a 4- to 7-membered alkyleneimino group which is substituted by two $R_6$O—CO or $R_6$O—CO—$C_{1-4}$-alkyl groups or by an $R_6$O—CO-group and an $R_6$O—CO—$C_{1-4}$-alkyl group wherein $R_6$ is as hereinbefore defined, a piperazino or homopiperazino group which is substituted in the 4 position by the group $R_{10}$ and is additionally substituted at a cyclic carbon atom by an $R_6$O—CO, ($R_7$O—PO—$OR_8$), ($R_7$O—PO—$R_9$), $R_6$O—CO—$C_{1-4}$-alkyl, bis-$R_6$O—CO)-$C_{1-4}$-alkyl, ($R_7$O—PO—$OR_8$)—$C_{1-4}$-alkyl or ($R_7$O—PO—$R_9$)—$C_{1-4}$-alkyl group wherein $R_6$ to $R_{10}$ are as hereinbefore defined, a piperazino or homopiperazino group which is substituted in the 4 position by the group $R_{10}$ and is additionally substituted at cyclic carbon atoms by two $R_6$O—CO or $R_6$O—CO—$C_{1-4}$-alkyl groups or by an $R_6$O—CO-group and an $R_6$O—CO—$C_{1-4}$-alkyl group wherein $R_6$ and $R_{10}$ are as hereinbefore defined, a piperazino or homopiperazino group which is substituted in each case in the 4 position by an $R_6$O—CO—$C_{1-4}$-alkyl, bis-($R_6$O—CO)-$C_{1-4}$-alkyl, ($R_7$O—PO—$OR_8$)—$C_{1-4}$-alkyl or ($R_7$O—PO—$R_9$)—$C_{1-4}$-alkyl group wherein $R_6$ to $R_9$ are as hereinbefore defined, a piperazino or homopiperazino group which is substituted in the 4 position by an $R_6$O—CO—$C_{1-4}$-alkyl, bis-($R_6$O—CO)—$C_{1-4}$-alkyl, ($R_7$O—PO—$OR_8$)—$C_{1-4}$-alkyl or ($R_7$O—PO—$R_9$)—$C_{1-4}$-alkyl group and is additionally substituted at cyclic carbon atoms by one or two $R_6$O—CO or $R_6$O—CO—$C_{1-4}$-alkyl groups or by an $R_6$O—CO-groups and an $R_6$O—CO—$C_{1-4}$-alkyl group wherein $R_6$ to $R_7$ are as hereinbefore defined, a morpholino or homomorpholino group which is substituted in each case by an $R_6$O—CO, ($R_7$O—PO—$OR_8$), ($R_7$O—PO—$R_9$), $R_6$O—CO—$C_{1-4}$-alkyl, bis-($R_4$O—CO)—$C_{1-4}$-alkyl, ($R_7$O—PO—$OR_8$)—$C_{1-4}$-alkyl or ($R_7$O—PO—$R_9$)—$C_{1-4}$-alkyl group wherein $R_6$ to $R_9$ are as hereinbefore defined, a morpholino or homomorpholino group which is substituted by two $R_6$O—CO or $R_6$O—CO—$C_{1-4}$-alkyl groups or by an $R_6$O—CO-group and an $R_6$O—CO—$C_{1-4}$-alkyl group wherein $R_4$ is as hereinbefore defined, a pyrrolidinyl, piperidinyl or hexahydroazepinyl group substituted in the 1 position by the group $R_{10}$, whilst the abovementioned 5- to 7-membered rings are in each case additionally substituted at a carbon atom by an $R_6$O—CO, ($R_7$O—PO—$OR_8$), ($R_7$O—PO—$R_9$), $R_6$O—CO—$C_{1-4}$-alkyl, bis-($R_6$O—CO)—$C_{1-4}$-alkyl, ($R_7$O—PO—$OR_8$)—$C_{1-4}$-alkyl or ($R_7$O—PO—$R_9$)—$C_{1-4}$-alkyl group wherein $R_6$ to $R_{10}$ are as hereinbefore defined, a pyrrolidinyl, piperidinyl or hexahydroazepinyl group substituted in the 1 position by the group $R_{10}$, while the abovementioned 5- to 7-membered rings are in each case additionally substituted at carbon atoms by two $R_4$O—CO or $R_6$O—CO—$C_{1-4}$-alkyl groups or by an $R_6$O—CO-group and an $R_6$O—CO—$C_{1-4}$-alkyl group wherein $R_6$ and $R_{10}$ are as hereinbefore defined.

a pyrrolidinyl, piperidinyl or hexahydroazepinyl group substituted in the 1 position by an $R_6$O—CO—$C_{1-4}$-alkyl, bis-($R_6$O—CO)—$C_{1-4}$-alkyl, ($R_7$O—PO—$OR_8$)—$C_{1-4}$-alkyl or ($R_7$O—PO—$R_9$)—$C_{1-4}$-alkyl group wherein $R_6$ to $R_9$ are as hereinbefore defined, a pyrrolidinyl, piperidinyl or hexahydroazepinyl group substituted in the 1 position by an $R_6$O—CO—$C_{1-4}$-alkyl, bis-($R_6$O—CO)—$C_{1-4}$-alkyl, ($R_7$O—PO—$OR_8$)—$C_{1-4}$-alkyl or ($R_7$O—PO—$R_7$)—$C_{1-4}$-alkyl group, while the abovementioned 5- to 7- membered rings are in each case additionally substituted at carbon atoms by one or two $R_6$O—CO or $R_6$O—CO—$C_{1-4}$-alkyl groups or by an $R_6$O—CO-group and an $R_6$O—CO—$C_{1-4}$-alkyl group wherein $R_6$ to $R_9$ are as hereinbefore defined, a 2-oxo-morpholino group which may be substituted by 1 or 2 methyl groups, a 2-oxo-morpholinyl group which is substituted in the 4 position by a hydrogen atom, by a $C_{1-4}$-alkyl, $R_4$O—CO—$C_{1-4}$-alkyl, ($R_7$O—PO—$OR_8$)—$C_{1-4}$-alkyl or ($R_7$O—PO—$R_9$)-$C_{1-4}$-alkyl group, while $R_6$ to $R_9$ are as hereinbefore defined and the abovementioned 2-oxo-morpholinyl morpholinyl groups are in each case linked to a carbon atom of the group F, a morpholino or thiomorpholino group which is substituted in the 2 position by a $C_{1-4}$-alkoxy group, a morpholino or thiomorpholino group which is substituted in the 2 and 6 position by a $C_{1-4}$-alkoxy group, a $C_{1-4}$-alkyl-$NR_5$-group wherein the $C_{1-4}$-alkyl moiety, which is straight-chained and may additionally be substituted by one or two methyl groups, is in each case terminally substituted by a di-($C_{1-4}$-alkoxy)-methyl or tri-($C_{1-4}$-alkoxy)-methyl group, whilst $R_9$ is as hereinbefore defined, a $C_{1-4}$-alkyl-$NR_5$-group wherein the $C_{1-4}$-alkyl moiety, which is straight-chained and may additionally be substituted by one or two methyl groups, is terminally substituted in each case by a 1,3-dioxolan-2-yl or 1,3-dioxan-2-yl-group optionally substituted by one or two methyl groups, while $R_9$ is as hereinbefore defined, an $R_hNR_5$-group wherein $R_5$ is as hereinbefore defined and $R_h$ denotes a 2-oxo-tetrahydrofuran-3-yl, 2-oxo-tetrahydrofuran-4-yl, 2-oxo-tetrahydropyran-3-yl, 2-oxo-tetrahydropyran-4-yl or 2-oxo-tetrahydropyran-5-yl group optionally substituted by one or two methyl groups, an amino group or an amino group optionally substituted by 1 or 2 $C_{1-4}$-alkyl groups wherein the alkyl groups may be identical or different and each alkyl moiety ay be substituted from position 2 by a hydroxy, $C_{1-4}$-alkoxy, amino, $C_{1-4}$-alkoxy, amino, $C_{1-6}$-alkylamino or di-($C_{1-4}$-alkyl)-amino group or by a 4- to 7-membered alkyleneimino groups a methylene group a methylene group in the 4 position may be replaced in each case by an oxygen or sulphur atom, by a sulphinyl, sulphonyl, imino or N-($C_{1-4}$-alkyl)-imino group, a 4- to 7-membered alkyleneimino group optionally substituted by 1 to 4 methyl groups, a 6- to 7-membered alkyleneimino group optionally substituted by 1 or 2 methyl groups wherein in each case a methylene group in the 4 position is replaced by an oxygen or sulphur atom, by an imino group substituted by the group $R_{10}$, a by a sulphinyl or sulphonyl group, wherein $R_{10}$ is as hereinbefore defined.

an imidazolyl group optionally substituted by 1 to 3 methyl groups, a $C_{5-7}$-cycloalkyl group wherein a methylene group is replaced by an oxygen or sulphur atom, by an imino group substituted by the group $R_{10}$, by a sulphinyl or sulphonyl group, while $R_{10}$ is as hereinbefore defined, or F and G together denote a hydrogen, fluorine or chlorine atom;

a $C_{1-4}$-alkoxy group optionally substituted from position 2 by a hydroxy or $C_{1-4}$-alkoxy group, a $C_{1-6}$-alkoxy group which is substituted by an $R_6O$—CO, ($R_7O$—PO—$OR_8$) or ($R_7O$—PO—$R_9$)-group, while $R_6$ to $R_9$ are as hereinbefore defined, a $C_{3-7}$-cycloalkoxy or $C_{3-7}$-cycloalkyl-$C_{1-4}$-alkoxy group, an amino group optionally substituted by 1 or 2 $C_{1-4}$-alkyl groups, a 5- to 7-membered alkyleneimino group, wherein in the above-mentioned 6- to 7-membered alkyleneimino groups a methylene group in the 4 position may be replaced in each case by an oxygen or sulphur atom, by an imino group substituted by the group $R_{10}$, or by a sulphinyl or sulphonyl group, wherein $R_{10}$ is as hereinbefore defined, with the proviso that at least one of the groups E, G or F together with G contains an $R_6O$—CO, ($R_7O$—PO—$OR_8$) or ($R_7O$—PO—$R_9$)-group or D together with E contains an $R_gCO$—O—($R_eCR_f$)—O—CO, ($R_7O$—PO—$OR_8$) or ($R_7O$—PO—$R_9$)-group or E or G contains an optionally substituted 2-oxo-morpholinyl group, a morpholino or thiomorpholino group substituted in the 2 position or in the 2 and 6 positions by a $C_{1-4}$-alkoxy group, a di-($C_{1-4}$-alkoxy)-methyl or tri-($C_{1-4}$-alkoxy)-methyl group or an optionally substituted 1,3-dioxolan-2-yl, 1,3-dioxan-2-yl, 2-oxo-tetrahydrofuran-3-yl, 2-oxo-tetrahydrofuran-4-yl, 2-oxo-tetrahydropyran-3-yl, 2-oxo-tetrahydropyran-4-yl or 2-oxo-tetrahydropyran-5-yl group or E contains an optionally substituted 2-oxo-thiomorpholino group or an optionally substituted 2-oxo-tetrahydrothiophen-3-yl, 2-oxo-tetrahydrothiophen-4-yl or 2-oxo-tetrahydrothiopyran-5-yl group.

By the aryl moieties mentioned in the definitions of the abovementioned groups is meant a phenyl group which in each case may be monosubstituted by $R_{12}$, mono-, di- or trisubstituted by $R_{13}$ or monosubstituted by $R_{12}$ and additionally mono- or disubstituted by $R_{12}$, whilst the substituents may be identical or different and $R_{12}$ denotes a cyano, carboxy, $C_{1-4}$-alkoxycarbonyl, aminocarbonyl, $C_{1-4}$-alkylaminocarbonyl, di-($C_{1-4}$-alkyl)-aminocarbonyl, $C_{1-4}$-alkylsulphenyl, $C_{1-4}$-alkylsulphinyl, $C_{1-4}$-alkylsulphonyl, hydroxy, $C_{1-4}$-alkylsulphonyloxy, trifluoromethyloxy, nitro, amino, $C_{1-4}$-alkylamino, di-($C_{1-4}$-alkyl)-amino, $C_{3-4}$-alkylcarbonylamino, N-($C_{1-4}$-alkyl)-$C_{1-4}$-alkylcarbonylamino, $C_{1-4}$-alkylsulphonylamino, N-($C_{1-4}$-alkyl)-$C_{3-4}$-alkylsulphonylamino, aminosulphonyl, $C_{1-4}$-alkylaminosulphonyl or di-($C_{1-4}$-alkyl)-aminosulphonyl group or a carbonyl group, which is substituted by a 5- to 7-membered alkyleneimino group, wherein in the above-mentioned 6- to 7-membered alkyleneimino groups in each case a methylene group in the 4 position may be replaced by an oxygen or sulphur atom, by a sulphinyl, sulphonyl, imino or N-($C_{1-4}$-alkyl)-imino-group, and $R_{22}$ denotes a fluorine, chlorine, bromine or iodine atom, a $C_{1-4}$-alkyl, trifluoromethyl or $C_{1-4}$-alkoxy group or two groups $R_{13}$, if they are bound to adjacent carbon atoms, together denote a $C_{3-5}$-alkylene, methylenedioxy or 1,3-butadien-1,4-ylene group.

Moreover, the heteroaryl groups mentioned in the definitions of the abovementioned groups also include a 5-membered heteroaromatic group which contains an imino group, an oxygen sulphur atom or an imino group, an oxygen or or sulphur atom and one or two nitrogen atoms, or a 6-membered heteroaromatic group, which contains one, two or three nitrogen atoms, whilst the abovementioned 5-membered heteroaromatic groups may be substituted in each case by 1 or 2 methyl or ethyl groups and the abovementioned 6-membered heteroaromatic groups may be substituted in each case by 1 or 2 methyl or ethyl groups or by a fluorine, chlorine, bromine or iodine atom, or by a trifluoromethyl, hydroxy, methoxy or ethoxy group.

Preferred compounds of the above general formula I are those wherein $R_a$ denotes a hydrogen atom or a $C_{1-6}$-alkyl group, $R_b$ denotes a phenyl, benzyl or 1-phenylethyl group wherein the phenyl nucleus is substituted in each case by the groups $R_1$ to $R_2$, wherein $R_3$ and $R_2$, which may be identical or different, each denote a hydrogen, fluorine, chlorine, bromine or iodine atom, a $C_{1-4}$-alkyl, hydroxy, $C_{1-4}$-alkoxy, $C_{1-4}$-cycloalkyl, $C_{4-6}$-cycloalkoxy, $C_{3-5}$-alkenyl or $C_{2-5}$-alkynyl group, a $C_{3-5}$-alkenyloxy or $C_{2-5}$-alkynyloxy group, while the unsaturated moiety may not be linked to the oxygen atom, a $C_{1-4}$-alkylsulphenyl, $C_{3-4}$-alkylsulphinyl, $C_{1-4}$-alkylsulphonyl, $C_{1-4}$-alkylsulphonyloxy, trifluoromethylsulphenyl, trifluoromethylsulphinyl or trifluoromethylsulphonyl group, a methyl or methoxy group substituted by 1 to 3 fluorine atoms, an ethyl or ethoxy group substituted by 1 to 5 fluorine atoms, a cyano or nitro group or an amino group optionally substituted by one or two $C_{3-4}$-alkyl groups, wherein the substituents may be identical or different, and $R_3$ denotes a hydrogen, fluorine, chlorine or bromine atom, a $R_{1-4}$-alkyl, trifluoromethyl- or $C_{1-4}$-alkoxy group, $R_c$ and $R_d$, which may be identical or different, each denote a hydrogen, fluorine or chlorine atom, a methoxy group or a methyl group optionally substituted by a methoxy, dimethylamino, diethylamino, pyrrolidino, piperidino or morpholino group, X denotes a methine group substituted by a cyano group or a nitrogen atom, A denotes an oxygen atom or an —NH—group optionally substituted by a $C_{1-4}$-alkyl group, B denotes a carbonyl or sulphonyl group, C denotes a 1,3-allenylene, 1,1- or 1,2-vinylene group, which may be substituted in each case by one or two methyl groups or by a trifluoromethyl group, an ethynylene group or a 1,3-butadien-1,4-ylene group optionally substituted by 1 to 4 methyl groups or by a trifluoromethyl group, D denotes an alkylene, —CO-alkylene or —SO$_3$-alkylene group wherein the alkylene moiety contains 1 to 8 carbon atoms in each case and additionally 1 to 4 hydrogen atoms in the alkylene moiety may be replaced by fluorine atoms, while the linking of the —CO-alkylene or —SO$_2$-alkylene group to the adjacent group C must take place via the carbonyl or sulphonyl group, a —CO—O-alkylene, —CO—NR$_4$-alkylene or —SO$_2$—NR$_6$-alkylene group wherein the alkylene moiety contains 1 to 8 carbon atoms in each case, while the linking to the adjacent group C must take place via the carbonyl or sulphonyl group wherein $R_4$ denotes a hydrogen atom or a $C_{1-4}$-alkyl group, or, if D is bound to a carbon atom of the group E, it may also denote a bond or, if D is bound to a nitrogen atom of the group E, it may also denote a carbonyl or sulphonyl group, E denotes an $R_6O$—CO-alkylene-NR$_5$, $(R_7O$—PO—OR$_8)$-alkylene-NR$_5$ or $(R_7O$—PO—R$_9)$-alkylene-NR$_5$ group wherein in each case the alkylene moiety, which is straight-chained and contains 1 to 6 carbon atoms, may additionally be substituted by one or two $C_{1-2}$-alkyl groups or by an $R_6O$—CO or $R_6O$—CO—$C_{1-2}$-alkyl group, while $R_5$ denotes a hydrogen atom, a $C_{1-4}$-alkyl group which may be substituted by a hydroxy, $C_{1-4}$-alkoxy, carboxy, $R_6O$—CO, $(R_7O$—PO—OR$_8)$, $(R_7O$—PO—R$_9)$, amino $C_{1-4}$-alkylamino or di-$(C_{1-4}$-alkyl)-amino group or by a 4- to 7-membered alkyleneimino group, while in the abovementioned 6- to 7-membered alkyleneimino groups in each case a methylene group may be replaced in the 4 position by an oxygen or sulphur atom, by a sulphinyl, sulphonyl, imino or N-$(C_{1-4}$-alkyl)-imino group, a $C_{3-7}$-cycloalkyl or $C_{3-7}$-cycloalkyl-$C_{1-3}$-alkyl group, $R_6$, $R_7$ and $R_8$, which may be identical or different, in each case denote a hydrogen atom, a $C_{3-8}$-alkyl group which may be substituted by a hydroxy, $C_{1-4}$-alkoxy, amino, $C_{1-4}$-alkylamino or di-$(C_{1-4}$-alkyl)-amino group or by a 4- to 7-membered alkyleneimino group, while in the abovementioned 6- to 7-membered alkyleneimino groups in each case a methylene group in the 4 position may be replaced by an oxygen or sulphur atom, by a sulphinyl, sulphonyl, imino or N-$(C_{1-4}$-alkyl)-imino group, a $C_{6-7}$-cycloalkyl group optionally substituted by 1 or 2 methyl groups, a $C_{3-5}$-alkenyl or $C_{3-5}$-alkynyl group, while the unsaturated moiety may not be linked to the oxygen atom, a $C_{3-7}$-cycloalkyl-$C_{1-4}$alkyl, aryl, aryl-$C_{1-4}$-alkyl or $R_gCO$—O—$(R_eCR_f)$ group, wherein $R_e$ and $R_f$, which may be identical or different, in each case denote a hydrogen atom or a $C_{1-4}$-alkyl group and $R_g$ denotes a $C_{1-4}$-alkyl, $C_{3-7}$-cycloalkyl, $C_{1-4}$-alkoxy or $C_{5-7}$-cycloalkoxy group, and $R_g$ denotes a $C_{1-4}$-alkyl, aryl or aryl-$C_{1-4}$-alkyl group, a 4- to 7-membered alkyleneimino group, which is substituted by an $R_6O$—CO, $(R_7O$—PO—OR$_8)$, $(R_7O$—PO—R$_9)$, $R_6O$—CO—$C_{1-4}$-alkyl, $(R_7O$—PO—OR$_8)$—$C_{1-4}$-alkyl or $(R_7O$—PO—R$_9)$—$C_{1-4}$-alkyl group wherein $R_6$ to $R_9$ are as hereinbefore defined, a piperazino or homopiperazino group which is substituted in the 4 position by the group $R_{10}$ and additionally at a cyclic carbon atom by an $R_6O$—CO, $(R_7O$—PO—OR$_8)$, $(R_7O$—PO—R$_9)$, $R_6O$—CO—$C_{1-4}$-alkyl, $(R_7O$—PO—OR$_8)$—$C_{1-4}$-alkyl or $(R_7O$—PO—R$_9)$—$C_{1-4}$-alkyl group wherein $R_6$ to $R_9$ are as hereinbefore defined and $R_{10}$ denotes a hydrogen atom, a $C_{1-4}$-alkyl, formyl, $C_{1-4}$-alkylcarbonyl or $C_{1-4}$-alkylsulphonyl group, a piperazino or homopiperazino group which is substituted in each case in the 4 position by an $R_6O$—CO—$C_{1-4}$-alkyl, $(R_7O$—PO—OR$_8)$—$C_{1-4}$-alkyl or $(R_7O$—PO—R$_9)$—$C_{1-4}$-alkyl group wherein $R_6$ to $R_9$ are as hereinbefore defined, a pyrrolidinyl, piperidinyl or hexahydroazepinyl group substituted in the 1 position by the group $R_{10}$, while the abovementioned 5- to 7-membered rings in each case are additionally substituted at a carbon atom by an $R_6O$—CO, $(R_7O$—PO—OR$_8)$, $(R_7O$—PO—R$_9)$, $R_6O$—CO—$C_{1-4}$-alkyl, $(R_7O$—PO—OR$_8)$—$C_{1-4}$alkyl or $(R_7O$—PO—R$_9)$—$C_{1-4}$-alkyl group wherein $R_6$ to $R_{10}$ are as hereinbefore defined, a pyrrolidinyl, piperidinyl or hexahydroazepinyl group substituted in the 1 position by an $R_6O$—CO—$C_{1-4}$alkyl, $(R_7O$—PO—OR$_8)$—$C_{1-4}$-alkyl or $(R_7O$—PO—R$_9)$—$C_{1-4}$alkyl group wherein $R_6$ to $R_9$ are as hereinbefore defined, an amino group or an amino group optionally substituted by 1 or 2 $C_{1-4}$-alkyl groups, wherein the alkyl groups may be identical or different and each alkyl moiety may be substituted from position 2 onwards by a hydroxy, $C_{1-4}$-alkoxy, amino, $C_{1-4}$-alkylamino or di-$(C_{1-4}$-alkyl)-amino group or by a 4- to 7-membered alkyleneimino group, while in the abovementioned 6- to 7-membered alkyleneimino groups, in each case a methylene group may be replaced in the 4 position by an oxygen or sulphur atom, by a sulphinyl, sulphonyl, imino or N-$(C_{1-4}$-alkyl)-imino group, a 4- to 7-membered alkyleneimino group optionally substituted by 1 to 4 methyl groups, a 6- to 7-membered alkyleneimino group optionally substituted by 1 or 2 methyl groups, wherein each case a methylene group in the 4 position is replaced by an oxygen or sulphur atom, by an imino group substituted by the group $R_{10}$, by a sulphinyl or sulphonyl group, while $R_{10}$ is as hereinbefore defined, an imidazolyl group optionally substituted by 1 to 3 methyl groups, a $C_{5-7}$-cycloalkyl group, wherein a methylene group is replaced by an oxygen or sulphur atom, by an imino group substituted by the group $R_{10}$, or by a sulphinyl or sulphonyl group, while $R_{10}$ is as hereinbefore defined, or D together with E denotes a hydrogen, fluorine or chlorine atom, a $C_{1-4}$-alkyl group optionally substituted by 1 to 5 fluorine atoms, a $C_{3-6}$-cycloalkyl group, an aryl, heteroaryl, $C_{1-4}$-alkylcarbonyl, arylcarbonyl, carboxy, $C_{1-4}$-alkoxycarbonyl, $R_gCO$—O—$(R_eCR_f)$—O—CO, $(R_7O$—PO—OR$_8)$ or $(R_7O$—PO—R$_9)$ group wherein $R_e$ to $R_g$ and $R_7$ to $R_9$ are as hereinbefore defined, an aminocarbonyl, $C_{1-4}$-alkylaminocarbonyl or di-$(C_{1-4}$-alkyl)-aminocarbonyl group or a carbonyl group which is substituted by a 4- to 7-membered alkyleneimino group, while in the abovementioned 6- to 7-membered alkyleneimino groups in each case a methylene group in the 4 position may be replaced by an oxygen or sulphur atom, by an imino group substituted by the group $R_{10}$ or by a sulphinyl or sulphonyl group, while $R_{10}$ is as hereinbefore defined, F denotes a $C_{1-6}$-alkylene group, an —O—$C_{1-6}$-alkylene group, wherein the alkylene moiety is linked to the group G, or an oxygen atom, which may not be linked to a nitrogen atom of the group G, and G denotes an $R_6O$—CO-alkylene-$NR_5$, ($R_7O$—PO—$OR_8$)-alkylene-$NR_5$ or ($R_7O$—PO—$R_9$)-alkylene-$NR_5$ group wherein in each case the alkylene moiety, which is straight-chained and contains 1 to 6 carbon atoms, may additionally be substituted by one or two $C_{1-2}$-alkyl groups or by $R_6O$—CO or $R_6O$—CO—$C_{1-2}$-alkyl group, wherein $R_5$ to $R_9$ are as hereinbefore defined, a 4- to 7-membered alkyleneimino group, which is substituted by an $R_6O$—CO, ($R_7O$—PO—$OR_8$), ($R_7O$—PO—$R_9$), $R_6O$—CO—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_9$ are as hereinbefore defined, a piperazino or homopiperazino group which is substituted in the 4 position by the group $R_{10}$ and additionally at a cyclic carbon atom by an $R_6O$—CO, ($R_7O$—PO—$OR_8$), ($R_7O$—PO—$R_9$), $R_6O$—CO—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_{10}$ are as hereinbefore defined, a piperazino or homopiperazino group, which is substituted in each case in the 4 position by an $R_6O$—CO—$C_{1-4}$-alkyl, $R_7O$—PO—$OR_8$)—$C_{1-4}$-alkyl or ($R_7O$—PO—$R_9$)—$C_{1-4}$-alkyl group wherein $R_6$ to $R_9$ are as hereinbefore defined, a pyrrolidinyl, piperidinyl or hexahydroazepinyl group substituted in the 1 position by the group $R_{10}$, while the abovementioned 5- to 7-membered rings in each case are additionally substituted at a carbon atom by an $R_6$-O—CO, ($R_7O$—PO—$OR_8$), ($R_7O$—PO—$R_9$), $R_6O$—CO—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_{10}$ are as hereinbefore defined, a pyrrolidinyl, piperidinyl or hexahydroazepinyl group substituted in the 1 position by an $R_6O$—CO—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_9$ are as hereinbefore defined, an amino group or an amino group optionally substituted by 1 or 2 $C_{1-4}$-alkyl groups wherein the alkyl groups may be identical or different and each alkyl moiety may be substituted from position 2 by a hydroxy, $C_{1-4}$-alkoxy, amino, $C_{1-4}$-alkylamino or di-($C_{1-4}$-alkyl)-amino group or by a 4- to 7-membered alkyleneimino group, while in the abovementioned 6- to 7-membered alkyleneimino groups in each case a methylene group in the 4 position may be replaced by an oxygen or sulphur atom, by a sulphinyl, sulphonyl, imino or N-($C_{1-4}$-alkyl)-amino group, a 4- to 7-membered alkyleneimino group optionally substituted by 1 to 4 methyl groups, a 6- to 7-membered alkyleneimino group optionally substituted by 1 or 2 methyl groups wherein in each case a methylene group in the 4 position is replaced by an oxygen or sulphur atom, by an imino group substituted by the group $R_{10}$, by a sulphinyl or sulphonyl group, while $R_{10}$ is as hereinbefore defined, an imidazolyl group optionally substituted by 1 to 3 methyl groups, a $C_{5-7}$-cycloalkyl group wherein a methylene group is replaced by an oxygen or sulphur atom, by an imino group substituted by the group $R_{10}$, by a sulphinyl or sulphonyl group, while $R_{10}$ is as hereinbefore defined, or F and G together denote a hydrogen, fluorine or chlorine atom, a $C_{1-6}$-alkoxy group optionally substituted from position 2 onwards by a hydroxy or $C_{1-4}$-alkoxy group, a $C_{1-6}$-alkoxy group which is substituted by an $R_6O$—CO, ($R_7O$—PO—$OR_8$) or ($R_7O$—PO—$R_9$) group, while $R_6$ to $R_9$ are as hereinbefore defined, a $C_{4-7}$-cycloalkoxy or $C_{3-7}$-cycloalkoxy-$C_{1-4}$-alkoxy group, an amino group optionally substituted by 1 or 2 $C_{1-4}$-alkyl groups, a 5- to 7-membered alkyleneimino group, while in the abovementioned 6- to 7-membered alkyleneimino groups in each case a methylene group in the 4 position may be replaced by an oxygen or sulphur atom, by an imino group substituted by the group $R_{10}$, or by a sulphinyl or sulphonyl group, while $R_{10}$ is as hereinbefore defined, with the proviso that at least one of the groups E, G or F together with G contains an $R_6O$—CO, ($R_7O$—PO—$OR_8$) or ($R_7O$—PO—$R_9$) group or D together with E contains an $R_gCO$—O—($R_eCR_f$)—O—CO, ($R_7O$—PO—$OR_8$) or ($R_7O$—PO—$R_9$) group, and also the compounds of the abovementioned general formula I wherein $R_a$ to $R_d$, A to G and X are as hereinbefore defined, but additionally the 4- to 7-membered alkyleneimino groups mentioned above in the definition of groups E and G, the piperazino and homopiperazino groups substituted by $R_{10}$ are each additionally substituted at a cyclic carbon atom by a bis-($R_6O$—CO)—$C_{1-4}$-alkyl group and the piperazino, homopiperazino, pyrrolidinyl, piperidinyl and hexahydroazepinyl group mentioned above in the definition of the groups E and G are each substituted at the nitrogen atom by a bis-($R_6O$—CO)—$C_{1-4}$-alkyl group, $R_1$ and $R_2$, which may be identical or different, denote aryl, aryloxy, arylmethyl or arylmethoxy groups or $R_1$ together with $R_2$, if they are bound to adjacent carbon atoms, denote an —CH=CH—CH=CH, —CH=CH—NH or —CH=N—NH group, E denotes a 2-oxo-morpholino group which may be substituted by 1 or 2 methyl groups, G denotes a 2-oxo-morpholino group which may be substituted by 1 or 2 methyl groups, or a 2-oxo-morpholinyl group which is substituted in the 4 position by a hydrogen atom, by a $C_{1-4}$-alkyl, $R_6O$—CO—$C_{1-4}$-alkyl, ($R_7O$—PO—$OR_8$)—$C_{1-4}$-alkyl or ($R_7O$—PO—$R_9$)—$C_{1-4}$-alkyl group, while $R_6$ to $R_9$ are as hereinbefore defined and the abovementioned 2-oxo-morpholinyl groups in each case are linked to a carbon atom of the group F, and/or F and G together may denote a $C_{3-7}$-cycloalkyl-$C_{1-4}$-alkoxy group, with the proviso that at least one of the groups E, G or F together with G contains an $R_6O$—CO, ($R_7O$—PO—$OR_8$) or ($R_7O$—PO—$R_9$) group or D together with E contains an $R_gCO$—O—($R_eCR_f$)—O—CO, ($R_7O$—PO—$OR_8$) or ($R_7O$—PO—$R_9$) group or E or G contains an optionally substituted 2-oxo-morpholinyl group, the compounds of the abovementioned general formula I wherein $R_a$ to $R_d$, A to G and X are as hereinbefore defined, but additionally $R_5$ denotes an ethyl or propyl group optionally substituted by one or two methyl groups, which is terminally substituted in each case by a $C_{1-6}$-alkylcarbonylsulphenyl, $C_{3-7}$-cycloalkylcarbonylsulphenyl, $C_{3-7}$-cycloalkyl-$C_{1-3}$-alkylcarbonylsulphenyl, arylcarbonylsulphenyl or aryl-$C_{1-3}$-alkylcarbonylsulphenyl group, E denotes a morpholino or homomorpholino group, which is substituted in each case by an $R_6O$—CO, ($R_7O$—PO—$OR_8$), ($R_7O$—PO—$R_9$), $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_7$ are as hereinbefore defined, a 2-oxo-morpholino group substituted by 1 to 4 $C_{1-2}$-alkyl groups with the proviso that a 2-oxo-morpholine group substituted by 1 or 2 methyl groups is excluded, a 2-oxo-thiomorpholine group which may be substituted by 1 to 4 $C_{1-2}$-alkyl groups, a morpholine group which is substituted in the 2 position by a $C_{1-4}$-alkoxy group, a morpholino group which is substituted in the 2- and 6-positions in each case by a $C_{1-4}$-alkoxy group, a $C_{1-4}$-alkyl-$NR_5$ group wherein the $C_{1-4}$-alkyl moiety, which is straight-chained and may additionally be substituted by one or two methyl groups, is terminally substituted in each case by a di-($C_{1-4}$-alkoxy)-methyl or tri-($C_{1-4}$-alkoxy)-methyl group, while $R_5$ is as hereinbefore defined, a $C_{1-4}$-alkyl-$NR_5$ group wherein the $C_{1-4}$-alkyl moiety, which is straight-chained and may additionally be substituted by one or two methyl groups, is terminally substituted in each case by a 1,3-dioxolan-2-yl or 1,3-dioxan-2-yl group optionally substituted by one or two methyl groups, while $R_5$ is as hereinbefore defined, or an $R_{11}NR_5$ group wherein $R_5$ is as hereinbefore defined and $R_{11}$ denotes a 2-oxo-tetrahydrofuran-3-yl, 2-oxo-tetrahydrofuran-4-yl, 2-oxo-tetrahydropyran-3-yl, 2-oxo-tetrahydropyran-4-yl, 2-oxo-tetrahydropyran-5-yl, 2-oxo-tetrahydrothiophen-3-yl, 2-oxo-tetrahydrothiophen-4-yl, 2-oxo-tetrahydrothiopyran-3-yl, 2-oxo-tetrahydrothiopyran-4-yl or 2-oxo-tetrahydrothiopyran-5-yl group optionally substituted by one or two methyl groups, and/or G denotes a morpholino or homomorpholino group which is substituted in each case by an $R_6O$—CO, ($R_7O$—PO—$OR_8$), ($R_7O$—PO—$R_9$), $R_6O$—CO—$C_{1-4}$-alkyl, bis-($R_6O$—CO)-$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_7$ are as hereinbefore defined, a morpholino group which is substituted in the 2 position by a $C_{1-4}$-alkoxy group, a morpholino group which is substituted in the 2 and 6 positions in each case by a $C_{1-4}$-alkoxy group, a $C_{1-4}$-alkyl-$NR_5$ group wherein the $C_{1-4}$-alkyl moiety, which is straight-chained and may additionally be substituted by one or two methyl groups, is terminally substituted in each case by a di-($C_{1-4}$-alkoxy)-methyl or tri-($C_{1-4}$-alkoxy)-methyl group, while $R_5$ is as hereinbefore defined, a $C_{1-4}$-alkyl-$NR_5$ group wherein the $C_{1-4}$-alkyl moiety, which is straight-chained and may additionally be substituted by one or two methyl groups, is terminally substituted in each case by a 1,3-dioxolan-2-yl or 1,3-dioxan-2-yl group optionally substituted by one or two methyl groups, while $R_5$ is as hereinbefore defined, or a $R_hNR_5$ group wherein $R_5$ is as hereinbefore defined and $R_h$ denotes a 2-oxo-tetrahydrofuran-3-yl, 2-oxo-tetrahydrofuran-4-yl, 2-oxo-tetrahydropyran-3-yl, 2-oxo-tetrahydropyran-4-yl or 2-oxo-tetrahydropyran-5-yl group optionally substituted by one or two methyl groups, with the proviso that at least one of the groups E, G or F together with G contains an $R_6O$—CO, ($R_7O$—PO—$OR_8$) or ($R_7O$—PO—$R_9$) group or D together with E contains an $R_gCO$—O—($R_eCR_f$)—O—CO, ($R_7O$—PO—$OR_8$) or ($R_7O$—PO—$R_9$) group or E or G contains an optionally substituted 2-oxo-morpholinyl group, a morpholino group in each case substituted in the 2 position or in the 2 and 6 positions by a $C_{1-4}$-alkoxy group, a di($C_{1-4}$-alkoxy)-methyl or tri-($C_{1-4}$-alkoxy)-methyl group or an optionally substituted 1,3-dioxolan-2-yl, 1,3-dioxan-2-yl, 2-oxo-tetrahydrofuran-3-yl, 2-oxo-tetrahydrofuran-4-yl, 2-oxo-tetrahydropyran-3-yl, 2-oxo-tetrahydropyran-4-yl or 2-oxo-tetrahydropyran-5-yl group or E contains an optionally substituted 2-oxo-thiomorpholino group or an optionally substituted 2-oxo-tetrahydrothiophen-3-yl, 2-oxo-tetrahydrothiophen-4-yl, 2-oxo-tetrahydrothiopyran-3-yl, 2-oxo-tetrahydrothiopyran-4-yl or 2-oxo-tetrahydrothiopyran-5-yl group, and the compounds of the abovementioned general formula I wherein $R_a$ to $R_d$, A to G and X are as hereinbefore defined, but additionally $R_5$ denotes an ethyl or propyl group substituted by a methyl group and a ethyl group or by two ethyl groups, which is terminally substituted in each case by a $C_{1-6}$-alkylcarbonylsulphenyl, $C_{3-7}$-cycloalkylcarbonylsulphenyl, $C_{3-7}$-cycloalkyl-$C_{1-3}$-alkylcarbonylsulphenyl, arylcarbonylsulphenyl or aryl-$C_{1-3}$-alkylcarbonylsulphenyl group, an ethyl or propyl group optionally substituted by one or two methyl or ethyl groups, which is terminally substituted in each case by a $C_{1-6}$-alkylcarbonyloxy, $C_{3-7}$-cycloalkylcarbonyloxy, $C_{3-7}$-cycloalkyl-$C_{1-3}$-alkylcarbonyloxy, arylcarbonyloxy or aryl-$C_{1-3}$-alkylcarbonyloxy group, E denotes a 4- to 7-membered alkyleneimino group which is substituted by two $R_6OCO$ or $R_6OCO$—$C_{1-4}$-alkyl groups or by an $R_6OCO$ group and an $R_6OCO$—$C_{1-4}$-alkyl group wherein $R_6$ is as hereinbefore defined, a piperazino or homopiperazino group which is substituted in the 4 position by the group $R_{10}$ and is additionally substituted at cyclic carbon atoms by two $R_6O$—CO or $R_6O$—CO—$C_{1-4}$-alkyl groups or by an $R_6O$—CO group and an $R_6O$—CO—$C_{1-4}$-alkyl group wherein $R_6$ and $R_{10}$ are as hereinbefore defined, a piperazino or homopiperazino group which is substituted in the 4 position by an $R_6O$—CO—$C_{1-4}$-alkyl, Bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group and is additionally substituted at cyclic carbon atoms by one or two $R_6O$—CO or $R_6O$—CO—$C_{1-4}$-alkyl groups or by an $R_6O$—CO group and an $R_6O$—CO—$C_{1-4}$-alkyl group wherein $R_6$ to $R_9$ are as hereinbefore defined, a morpholino or homomorpholino group which is substituted by two $R_6O$—CO or $R_6O$—CO—$C_{1-4}$-alkyl groups or by an $R_6O$—CO group and an $R_6O$—CO—$C_{1-4}$-alkyl group wherein $R_6$ is as hereinbefore defined, a pyrrolidinyl, piperidinyl or hexahydroazepinyl group substituted in the 1 position by the group $R_{10}$, while the abovementioned 5- to 7-membered rings are additionally substituted in each case at carbon atoms by two $R_6O$—CO or $R_6O$—CO—$C_{1-4}$-alkyl groups or by an $R_6O$—CO group and an $R_6O$—CO—$C_{1-4}$-alkyl group wherein $R_6$ and $R_{10}$ are as hereinbefore defined, a pyrrolidinyl, piperidinyl or hexahydroazepinyl group substituted in the 1 position by an $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group, while the abovementioned 5- to 7-membered rings in each case are additionally substituted at carbon atoms by one or two $R_6O$—CO or $R_6O$—CO—$C_{1-4}$alkyl groups or by an $R_6O$—CO group and an $R_6O$—CO—$C_{1-4}$-alkyl group wherein $R_6$ to $R_9$ are as hereinbefore defined, a thiomorpholino group which is substituted in the 2 position by a $C_{1-4}$-alkoxy group, or a thiomorpholino group which is substituted in the 2 and 6 positions in each case by a $C_{1-4}$-alkoxy group, and/or G denotes a 4- to 7-membered alkyleneimino group which is substituted by two $R_6O$—CO or $R_6O$—CO—$C_{1-4}$-alkyl groups or by an $R_6O$—CO group and an $R_6O$—CO—$C_{1-4}$-alkyl group wherein $R_6$ is as hereinbefore defined, a piperazino or homopiperazino group which is substituted in the 4 position by the group $R_{10}$ and is additionally substituted at cyclic carbon atoms by two $R_6O$—CO or $R_6O$—CO—$C_{1-4}$-alkyl groups or by an $R_6O$—CO group and an $R_6O$—CO—$C_{1-4}$-alkyl group wherein $R_6$ and $R_{10}$ are as hereinbefore defined, a piperazino or homopiperazino group which is substituted in the 4 position by an $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group and additionally at cyclic carbon atoms by one or two $R_6O$—CO or $R_6O$—CO—$C_{1-4}$-alkyl groups or by an $R_6O$—CO group and an $R_6O$—CO—$C_{1-4}$-alkyl group wherein $R_6$ to $R_9$ are as hereinbefore defined, a morpholino or homomorpholino group which is substituted by two $R_6O$—CO or $R_6O$—CO—$C_{1-4}$-alkyl groups or by an $R_6O$—CO group and an $R_6O$—CO—$C_{1-4}$-alkyl group wherein $R_6$ is as hereinbefore defined, a pyrrolidinyl, piperidinyl or hexahydroazepinyl group substituted in the 1 position by the group $R_{10}$, while the abovementioned 5- to 7-membered rings in each case are additionally substituted at carbon atoms by two $R_6O$—CO or $R_6O$—CO—$C_{1-4}$-alkyl groups or by an $R_6O$—CO group and an $R_6O$—CO—$C_{1-4}$-alkyl group wherein $R_6$ and $R_{10}$ are as hereinbefore defined, a pyrrolidinyl, piperidinyl or hexahydroazepinyl group substituted in the 1 position by an $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group, while the abovementioned 5- to 7-membered rings in each case are additionally substituted at carbon atoms by one or two $R_6O$—CO or $R_6O$—CO—$C_{1-4}$-alkyl groups or by an $R_6O$—CO group and an $R_6O$—CO—$C_{1-4}$-alkyl group wherein $R_6$ to $R_9$ are as hereinbefore defined, a thiomorpholino group which is substituted in the 2 position by a $C_{1-4}$-alkoxy group, or a thiomorpholino group which is substituted in the 2 and 6 positions in each case by a $C_{1-4}$-alkoxy group, with the proviso that at least one of the groups E, G or F together with G contains an $R_6O$—CO, ($R_7O$—PO—$OR_8$) or ($R_7O$—PO—$R_9$) group or D together with E contains an $R_gCO$—O—($R_eCR_f$)—O—CO, ($R_7O$—PO—$OR_8$) or ($R_7O$—PO—$R_9$) group or E or G contains an optionally substituted 2-oxo-morpholinyl group, a morpholino or thiomorpholino group substituted in the 2 position or in the 2 and 6 positions in each case by a $C_{1-4}$-alkoxy group, a di($C_{1-4}$-alkoxy)-methyl or tri-($C_{1-4}$-alkoxy)-methyl group or an optionally substituted 1,3-dioxolan-2-yl, 1,3-dioxan-2-yl, 2-oxo-tetrahydrofuran-3-yl, 2-oxo-tetrahydrofuran-4-yl, 2-oxo-tetrahydropyran-3-yl, 2-oxo-tetrahydropyran-4-yl or 2-oxo-tetrahydropyran-5-yl group or E contains an optionally substituted 2-oxo-thiomorpholino group or an optionally substituted 2-oxo-tetrahydrothiophen-3-yl, 2-oxo-tetrahydrothiophen-4-yl, 2-oxo-tetrahydrothiopyran-3-yl, 2-oxo-tetrahydrothiopyran-4-yl or 2-oxo-tetrahydrothiopyran-5-yl group, while the abovementioned aryl and heteroaryl moieties are as hereinbefore defined, the tautomers, the stereoisomers and the salts thereof.

Particularly preferred compounds of the above general formula I are those wherein $R_a$ denotes a hydrogen atom, $R_b$ denotes a phenyl, benzyl or 1-phenylethyl group wherein the phenyl nucleus is substituted in each case by the groups $R_1$ to $R_3$, wherein $R_1$ and $R_2$, which may be identical or different, each denote a hydrogen, fluorine, chlorine, bromine or iodine atom, a methyl, ethyl, hydroxy, methoxy, ethoxy, amino, cyano, vinyl or ethynyl group, an aryl, aryloxy, arylmethyl or arylmethoxy group, a methyl or methoxy group substituted by 1 to 3 fluorine atoms or $R_1$ together with $R_2$, if they are bound to adjacent carbon atoms, denote a —CH=CH—CH=CH, —CH=CH—NH or —CH=N—NH group and $R_3$ denotes a hydrogen, fluorine, chlorine or bromine atom, $R_c$ and $R_d$ in each case denote a hydrogen atom, X denotes a methine group substituted by a cyano group or a nitrogen atom, A denotes an —NH— group optionally substituted by a methyl or ethyl group, B denotes a carbonyl group, C denotes a 1,1- or 1,2-vinylene group which is substituted in each case by one or two methyl groups or may be substituted by a trifluoromethyl group, an ethynylene group or a 1,3-butadien-1,4-ylene group optionally substituted by a methyl or trifluoromethyl group, D denotes an alkylene or —CO-alkylene group wherein the alkylene moiety in each case contains 1 to 4 carbon atoms, while the linking of the —CO-alkylene group to the adjacent group C in each case must take place via the carbonyl group, a —CO—O-alkylene or —CO—NR$_5$-alkylene-group wherein the alkylene moiety in each case contains 1 to 4 carbon atoms, while the linking to the adjacent group C in each case must take place via the carbonyl group wherein $R_4$ denotes a hydrogen atom or a methyl or ethyl group, or, if D is bound to a carbon atom of the group E, it may also denote a bond or, if D is bound to a nitrogen atom of the group E, it may also denote a carbonyl or sulphonyl group, E denotes an $R_6O$—CO-alkylene-NR$_5$, ($R_7O$—PO—$OR_8$)-alkylene-NR$_5$ or ($R_7O$—PO—$R_9$)-alkylene-NR$_5$ group wherein in each case the alkylene moiety, which is straight-chained and contains 1 to 4 carbon atoms, may additionally be substituted by one or two $C_{1-2}$-alkyl groups or by an $R_6O$—CO or $R_6O$—CO—$C_{1-2}$-alkyl group, wherein $R_5$ denotes a hydrogen atom, a $C_{1-4}$-alkyl group which may be substituted by an $R_6O$—CO group, an ethyl or propyl group optionally substituted by one or two methyl or ethyl groups which is terminally substituted in each case by a hydroxy, $C_{1-6}$-alkoxy, di-($C_{1-4}$-alkyl)amino, $C_{2-6}$-alkylcarbonylsulphenyl, $C_{3-6}$-cycloalkylcarbonylsulphenyl, $C_{3-6}$-cycloalkyl-$C_{1-3}$-alkylcarbonylsulphenyl, arylcarbonylsulphenyl or aryl-$C_{1-3}$-alkylcarbonylsulphenyl group, an ethyl or propyl group optionally substituted by one or two methyl or ethyl groups which is terminally substituted in each case by a $C_{1-6}$-alkylcarbonyloxy, $C_{3-6}$-cycloalkylcarbonyloxy, $C_{3-6}$-cycloalkyl-$C_{1-3}$-alkylcarbonyloxy, arylcarbonyloxy or aryl-$C_{1-3}$-alkylcarbonyloxy group, a $C_{3-6}$-cycloalkyl or $C_{3-6}$-cycloalkyl-$C_{1-2}$-alkyl group, $R_6$, $R_7$ and $R_8$, which may be identical or different, in each case denote a hydrogen atom, a $C_{1-2}$-alkyl group which may be substituted by a hydroxy, $C_{1-4}$-alkoxy, or di-($C_{1-4}$-alkyl)-amino group or by a 4- to 7-membered alkyleneimino group, while in the abovementioned 6- to 7-membered alkyleneimino groups in each case a methylene group in the 4 position may be replaced by an oxygen atom or by an N—($C_{1-2}$-alkyl)-imino group, a $C_{4-6}$-cycloalkyl group, a $C_{3-5}$-alkenyl or $C_{3-5}$-alkynyl group, while the unsaturated moiety may not be linked to the oxygen atom, a $C_{3-6}$-cycloalkyl-$C_{1-4}$-alkyl, aryl, aryl-$C_{1-4}$-alkyl or $R_gCO$—)—($R_eCR_f$) group, while $R_e$ and $R_f$, which may be identical or different, in each case denote a hydrogen atom or a $C_{1-4}$-alkyl group and $R_g$ denotes a $C_{1-4}$-alkyl, $C_{3-6}$-cycloalkyl, $C_{1-4}$-alkoxy or $C_{5-6}$-cycloalkoxy group, and $R_g$ denotes a $C_{1-4}$-alkyl group, a 4- to 7-membered alkyleneimino group which is substituted by an $R_6O$—CO, $R_6O$—CO—$C_{1-4}$-alkyl or bis-($R_6O$—CO)—$C_{1-4}$-alkyl group wherein $R_6$ is as hereinbefore defined, a 4- to 7-membered alkyleneimino group which is substituted by two $R_6O$—CO or $R_6O$—CO—$C_{1-4}$-alkyl groups wherein $R_6$ is as hereinbefore defined, a piperizino or homopiperazino group which is substituted in the 4 position by the group $R_{10}$ and additionally at a cyclic carbon atom by an $R_6O$—CO, $R_6O$—CO—$C_{1-4}$-alkyl or bis-($R_6O$—CO)—$C_{1-4}$-alkyl group wherein $R_6$ is as hereinbefore defined and $R_{10}$ denotes a hydrogen atom, a methyl, ethyl, acetyl or methylsulfonyl group, a piperazino or homopiperazino group which is substituted in the 4 position by the group $R_{10}$ and is additionally substituted at cyclic carbon atoms by two $R_6O$—CO or $R_6O$—CO—$C_{1-4}$-alkyl groups wherein $R_6$ and $R_{10}$ are as hereinbefore defined, a piperazino or homopiperazino group which is substituted in each case in the 4 position by an $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_9$ are as hereinbefore defined, a piperazino or homopiperazino group which is substituted in the 4 position by an $R_6O$—CO—$C_{1-4}$-alkyl or bis-($R_6O$—CO)—$C_{1-4}$-alkyl group and is additionally substituted at cyclic carbon atoms by one or two $R_6O$—CO or $R_6O$—CO—$C_{1-4}$-alkyl groups wherein $R_6$ is as hereinbefore defined, a morpholino or homomorpholino group which is substituted in each case by an $R_6O$—CO, $R_6O$—CO—$C_{1-4}$-alkyl or bis-($R_6O$—CO)—$C_{1-4}$-alkyl group wherein $R_6$ is as hereinbefore defined, a morpholino or homomorpholino group which is substituted by two $R_6O$—CO or $R_6O$—CO—$C_{1-4}$-alkyl groups wherein $R_6$ is as hereinbefore defined, a pyrrolidinyl, piperidinyl or hexahydroazepinyl group substituted in the 1 position by the group $R_{10}$, while the abovementioned 5- to 7-membered rings in each case are additionally substituted at a carbon atom by an $R_6O$—CO, $R_6O$—CO—$C_{1-4}$-alkyl or bis-($R_6O$—CO)—$C_{1-4}$-alkyl group wherein $R_6$ and $R_{10}$ are as hereinbefore defined, a pyrrolidinyl, piperidinyl or hexahydroazepinyl group substituted in the 1 position by the group $R_{10}$, while the abovementioned 5- to 7-membered rings in each case are additionally substituted at carbon atoms by two $R_6O$—CO or $R_6O$—CO—$C_{1-4}$-alkyl groups wherein $R_6$ and $R_{10}$ are as hereinbefore defined, a pyrrolidinyl, piperidinyl or hexahydroazepinyl group substituted in the 1 position by an $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_9$ are as hereinbefore defined, a pyrrolidinyl, piperidinyl or hexahydroazepinyl group substituted in the 1 position by an $R_6O$—CO—$C_{1-4}$-alkyl or bis-($R_6O$—CO)—$C_{1-4}$-alkyl group, while the abovementioned 5- to 7-membered rings in each case are additionally substituted at carbon atoms by one or two $R_6O$—CO or $R_6O$—CO—$C_{1-4}$-alkyl groups wherein $R_6$ is as hereinbefore defined, a 2-oxo-morpholino group which may be substituted by 1 to 4 $C_{1-2}$-alkyl groups, a 2-oxo-thiomorpholino group which may be substituted by 1 to 4 $C_{1-2}$-alkyl groups, a morpholino group which is substituted in the 2 position by a $C_{1-4}$-alkoxy group, a morpholino group which is substituted in the 2 and 6 positions in each case by a $C_{1-4}$-alkoxy group, a $C_{1-4}$-alkyl-$NR_5$ group wherein the $C_{1-4}$-alkyl moiety, which is straight-chained, is terminally substituted by a di-($C_{1-4}$-alkoxy)-methyl group, while $R_5$ is as hereinbefore defined, a $C_{1-4}$-alkyl-$NR_5$ group wherein the $C_{1-4}$-alkyl moiety, which is straight-chained, is terminally substituted by a 1,3-dioxolan-2-yl or 1,3-dioxan-2-yl group, while $R_b$ is as hereinbefore defined, a $R_{11}NR_5$ group wherein $R_5$ is as hereinbefore defined and $R_{11}$ denotes a 2-oxo-tetrahydrofuran-3-yl, 2-oxo-tetrahydrofuran-4-yl, 2-oxo-tetrahydropyran-3-yl, 2-oxo-tetrahydropyran-4-yl, 2-oxo-tetrahydropyran-5-yl, 2-oxo-tetrahydrothiophehn-3-yl, 2-oxo-tetrahydrothiophen-4-yl, 2-oxo-tetrahydrothiopyran-3-yl, 2-oxo-tetrahydrothiopyran-4-yl or 2-oxo-tetrahydrothiopyran-5-yl group optionally substituted by one or two methyl groups, or D together with E denotes a hydrogen atom, a methyl, trifluoromethyl, aryl, $R_gCO$—O—($R_eCR_f$)—O—CO or ($R_7O$—PO—$OR_8$) group wherein $R_e$ to $R_g$ and $R_7$ and $R_8$ are as hereinbefore defined, F denotes an —O—$C_{1-4}$-alkylene group, while the alkylene moiety is linked to the group G, or an oxygen atom, while this may not be linked to a nitrogen atom of the group G, and G denotes an $R_6O$—CO-alkylene-$NR_5$, ($R_7O$—PO—$OR_8$)-alkylene-$NR_5$ or ($R_7O$—PO—$R_9$)-alkylene-$NR_5$ group wherein in each case the alkylene moiety, which is straight-chained and contains 1 to 4 carbon atoms, may additionally be substituted by one or two $C_{1-2}$-alkyl groups or by an $R_6O$—CO or $R_6O$—CO—$C_{1-2}$-alkyl group, while $R_5$ to $R_9$ are as hereinbefore defined, a 4- to 7-membered alkyleneimino group which is substituted by an $R_6O$—CO, $R_6O$—CO—$C_{1-4}$-alkyl or bis-($R_6O$—CO)—$C_{1-4}$-alkyl group wherein $R_6$ is as hereinbefore defined, a 4- to 7-membered alkyleneimino group which is substituted by two $R_6O$—CO or $R_6O$—CO—$C_{1-4}$-alkyl groups wherein $R_6$ is as hereinbefore defined, a piperazino or homopiperazino group which is substituted in the 4 position by the group $R_{10}$ and is additionally substituted at a cyclic carbon atom by an $R_6O$—CO, $R_6O$—CO—$C_{1-4}$-alkyl or bis-$(R_6O$—CO)—$C_{1-4}$-alkyl group wherein $R_6$ and $R_{10}$ are as hereinbefore defined, a piperazino or homopiperazino group which is substituted in the 4 position by the group $R_{10}$ and is additionally substituted at cyclic carbon atoms by two $R_6O$—CO or $R_6O$—CO—$C_{1-4}$-alkyl groups wherein $R_6$ and $R_{10}$ are as hereinbefore defined, a piperazino or homopiperazino group which is substituted in each case in the 4 position by an $R_6O$—CO—$C_{1-4}$-alkyl, bis-$(R_6O$—CO)—$C_{1-4}$-alkyl, $(R_7O$—PO—$OR_8)$—$C_{1-4}$-alkyl or $(R_7O$—PO—$R_9)$—$C_{1-4}$-alkyl group wherein $R_6$ to $R_9$ are as hereinbefore defined.

a piperazino or homopiperazino group which is substituted in the 4 position by an $R_6O$—CO—$C_{1-4}$-alkyl or bis-$(R_6O$—CO)—$C_{1-4}$-alkyl group and additionally at cyclic carbon atoms by one or two $R_6O$—CO or $R_6O$—CO—$C_{1-4}$-alkyl groups wherein $R_6$ is as hereinbefore defined, a morpholino or homomorpholino group which is substituted in each case by an $R_6O$—CO, $R_6O$—CO—$C_{1-4}$-alkyl or bis-$(R_6O$—CO)—$C_{1-4}$-alkyl group wherein $R_6$ is as hereinbefore defined, a morpholino or homomorpholino group which is substituted by two $R_6O$—CO or $R_6O$—CO—$C_{1-4}$—alkyl groups wherein $R_6$ is as hereinbefore defined, a pyrrolidinyl, piperidinyl or hexahydroazepinyl group substituted in the 1 position by the group $R_{10}$, while the above-mentioned 5- to 7-membered rings in each case are additionally substituted at a carbon atom by an $R_6O$—CO, $R_6O$—CO—$C_{1-4}$-alkyl or bis-$(R_6O$—CO)—$C_{1-4}$-alkyl group wherein $R_6$ and $R_{10}$ are as hereinbefore defined, a pyrrolidinyl, piperidinyl or hexahydroazepinyl group substituted on the 1 position by the group $R_{10}$, while the above-mentioned 5- to 7-membered rings in each case are additionally substituted at carbon atoms by two $R_6O$—CO or $R_6O$—CO—$C_{1-4}$-alkyl groups wherein $R_6$ and $R_{10}$ are as hereinbefore defined, a pyrrolidinyl, piperidinyl or hexahydroazepinyl group substituted in the 1 position by an $R_6O$—CO—$C_{1-4}$-alkyl, bis-$(R_6O$—CO)—$C_{1-4}$-alkyl, $(R_7O$—PO—$OR_8)$—$C_{1-4}$-alkyl or $(R_7O$—PO—$R_9)$—$C_{1-4}$-alkyl group wherein $R_6$ to $R_9$ are as hereinbefore defined, a pyrrolidinyl, piperidinyl or hexahydroazepinyl group substituted in the 1 position by an $R_6O$—CO—$C_{1-4}$-alkyl or bis-$(R_6O$—CO)—$C_{1-4}$-alkyl group, while the abovementioned 5- to 7-membered rings in each case are additionally substituted at carbon atoms by one or two $R_6O$—CO or $R_6O$—CO—$C_{1-4}$-alkyl groups wherein $R_6$ is as hereinbefore defined.

a 2-oxo-morpholino group which may be substituted by 1 or 2 methyl groups, a 2-oxo-morpholinyl group which is substituted in the 4 position by a $C_{1-4}$-alkyl or $R_6O$—CO—$C_{1-4}$alkyl group, while $R_6$ is as hereinbefore defined and the abovementioned 2-oxo-morpholinyl groups in each case are linked to a carbon atom of the group F, a morpholino group which is substituted in the 2 position by a $C_{1-4}$-alkoxy group, a morpholino group which is substituted in the 2 and 6 positions in each case by a $C_{1-4}$-alkoxy group, a $C_{1-4}$-alkyl-$NR_5$ group wherein the $C_{1-4}$-alkyl moiety, which is straight-chained, is terminally substituted by a di-$(C_{1-4}$-alkoxy)-methyl group, while $R_5$ is as hereinbefore defined, a $C_{1-4}$-alkyl-$NR_5$ group wherein the $C_{1-4}$-alkyl moiety, which is straight-chained, is terminally substituted by a 1,3-dioxolan-2-yl or 1,3-dioxan-2-yl group, while $R_5$ is as hereinbefore defined, an $R_nNR_5$ group where $R_5$ is as hereinbefore defined $R_n$ denotes a substituted 2-oxo-tetrahydrofuran-3-yl, 2-oxo-tetrahydrofuran-4-yl, 2-oxo-tetrahydropyran-3-yl, 2-oxo-tetrahydropyran-4-yl or 2-oxo-tetrahydropyran-5-yl group optionally by one or two methyl groups, or F and G together denote a hydrogen atom, a $C_{1-4}$-alkoxy group optionally substituted from position 2 onwards by a hydroxy or $C_{1-4}$-alkoxy group, a $C_{1-4}$-alkoxy group which is substituted by an $R_6O$—CO group, where $R_6$ is as hereinbefore defined, or a $C_{4-7}$-cycloalkoxy or $C_{3-7}$-cycloalkyl-$C_{1-4}$-alkoxy group with the proviso that at least one of the groups E, G or F together with G contains an $R_6O$—CO, $(R_7O$—PO—$OR_8)$ or $(R_7O$—PO—$R_9)$ group or D together with E contains an $R_gCO$—O—$(R_eCR_f)$—O—CO or $(R_7O$—PO—$OR_8)$ group or E or G contains an optionally substituted 2-oxo-morpholinyl group, a morpholino group substituted in the 2 position or in the 2 and 6 positions in each case by a $C_{1-4}$-alkoxy group, a di-$(C_{1-4}$-alkoxy)-methyl group or an optionally substituted 1,3-dioxolan-2-yl, 1,3-dioxan-2-yl, 2-oxo-tetrahydrofuran-3-yl, 2-oxo-tetrahydrofuran-4-yl, 2-oxo-tetrahydropyran-3-yl, 2-oxo-tetrahydropyran-4-yl or 2-oxo-tetrahydropyran-5-yl group or E contains an optionally substituted 2-oxo-thiomorpholino group or an optionally substituted 2-oxo-tetrahydrothiophen-3-yl, 2-oxo-tetrahydrothiophen-4-yl, 2-oxo-tetrahydrothiopyran-3-yl, 2-oxo-tetrahydrothiopyran-4-yl or 2-oxo-tetrahydrothiopyran-5-yl group, while the aryl moieties mentioned in the definition of the abovementioned groups denote a phenyl group which may in each case be monosubstituted by $R_{12}$, mono- or disubstituted by $R_{13}$ or monosubstituted by $R_{12}$ and additionally mono or disubstituted by $R_{13}$, while the substituents may be identical or different and $R_{12}$ denotes a cyano, $C_{1-2}$-alkoxycarbonyl, aminocarbonyl, $C_{1-2}$-alkylaminocarbonyl, di-$(C_{1-2}$-alkyl)-aminocarbonyl, $C_{1-2}$-alkylsulphenyl, $C_{1-2}$-alkylsulphinyl, $C_{1-2}$-alkylsulphonyl, hydroxy, nitro amino, $C_{1-2}$-alkylamino or di-$(C_{1-2}$-alkyl)-amino group and $R_{13}$ a fluorine, chlorine, bromine or iodine atom, a $C_{1-2}$-alkyl, trifluoromethyl or $C_{1-2}$-alkoxy group or two groups $R_{13}$, if they are bound to adjacent carbon atoms, together denote a $C_{3-5}$-alkylene, methylenedioxy or 1,3-butadien-1,4-ylene group, the tautomers, the stereoisomers and the salts thereof.

Most particularly preferred compounds of the above general formula I are those wherein $R_a$ denotes a hydrogen atom, $R_b$ denotes a phenyl, benzyl or 1-phenylethyl group wherein the phenyl nucleus is substituted in each case by the groups $R_1$ to $R_3$, wherein $R_1$ and $R_2$, which may be identical or different, each denote a hydrogen, fluorine, chlorine or bromine atom, or a methyl, trifluoromethyl, methoxy, ethynyl or cyano group, $R_3$ denotes a hydrogen atom, $R_c$ and $R_d$ in each case denote a hydrogen atom, X denotes a methine group substituted by a cyano group, or a nitrogen atom, A denotes an NH- group, B denotes a carbonyl group, C denotes a 1,2- or 1,2-vinylene group, a ethynylene group or a 1,3-butadien-1,4-ylene group, D denotes a $C_{1-4}$-alkylene group, a —CO—NR$_4$-alkylene group wherein the alkylene moiety contains 2 to 4 carbon atoms, while the linking to the adjacent group C in each case must take place via the carbonyl group and wherein R$_4$ denotes a hydrogen atom, or, if D is bound to a carbon atom of the group E, it may also denote a bond or, if D is bound to a nitrogen atom of the group E, it may also denote a carbonyl group, E denotes an R$_6$O—CO—alkylene—NR$_3$, (R$_7$O—PO—OR$_8$)-alkylene-NR$_5$ or (R$_7$O—PO—R$_9$)-alkylene-NR$_5$ group wherein in each case the alkylene moiety, which is straight-chained and contains 1 to 4 carbon atoms, may additionally be substituted by one or two $C_{1-2}$-alkyl groups or by an R$_6$O—CO or R$_6$O—CO—$C_{1-2}$-alkyl group, while R$_5$ denotes a hydrogen atom, a $C_{1-4}$-alkyl group which may be substituted by an R$_6$O—CO group, an ethyl group optionally substituted by one or two methyl or ethyl groups which is terminally substituted by a $C_{1-4}$-alkylcarbonylsulphenyl, arylcarbonylsulphenyl or arylmethylcarbonylsulphenyl group, an ethyl group optionally substituted by one or two methyl or ethyl groups which is terminally substituted by a hydroxy, $C_{1-4}$-alkylcarbonyloxy, arylcarbonyloxy or arylmethylcarbonyloxy group, a 2,2-dimethoxyethyl or 2,2-diethoxyethyl group, a $C_{1-6}$-cycloalkyl or $C_{3-6}$-cycloalkyl-methyl group, R$_6$, R$_7$ and R$_8$, which may be identical or different, in each case denote a hydrogen atom, a $C_{1-8}$-alkyl group, a cyclopentyl, cyclopentylmethyl, cyclohexyl or cyclohexylmethyl group, an aryl, arylmethyl or R$_g$CO—O—(R$_e$CR$_f$) group, while R$_e$ denotes a hydrogen atom or a $C_{1-4}$-alkyl group, R$_f$ denotes a hydrogen atom and R$_g$ denotes a $C_{1-4}$-alkyl, cyclopentyl, cyclohexyl, $C_{1-4}$-alkoxy, cyclopentyloxy or cyclohexyloxy group, and R$_9$ denotes a methyl or ethyl group, a pyrrolidino or piperidino group which is substituted by an R$_6$O—CO or R$_6$O—CO—$C_{1-2}$-alkyl group wherein R$_6$ is as hereinbefore defined, a pyrrolidino or piperidino group which is substituted by two R$_6$O—CO or R$_6$O—CO—$C_{1-2}$-alkyl groups wherein R$_6$ is as hereinbefore defined, a piperazino group which is substituted in the 4 position by the group R$_{10}$ and is additionally substituted at a cyclic carbon atom by an R$_6$O—CO or R$_6$O—CO—$C_{1-2}$-alkyl group, while R$_6$ is as hereinbefore defined and R$_{10}$ denotes a hydrogen atom, a methyl, ethyl, acetyl or methylsulfonyl group, a piperazino or homopiperazino group which is substituted in the 4 position by an R$_6$O—CO—$C_{1-4}$-alkyl, bis-(R$_6$O—CO)—$C_{1-4}$-alkyl or (R$_7$O—PO—OR$_8$)—$C_{1-2}$-alkyl group wherein R$_6$ to R$_8$ are as hereinbefore defined, a piperazino group which is substituted in the 4 position by an R$_6$O—CO—$C_{1-2}$-alkyl group and is additionally substituted at a cyclic carbon atom by an R$_6$O—CO or R$_6$O—CO—$C_{1-2}$-alkyl group wherein R$_6$ is as hereinbefore defined, a morpholino group which is substituted by an R$_6$O—CO or R$_6$O—CO—$C_{1-2}$-alkyl group, while R$_6$ is as hereinbefore defined, a piperidinyl group substituted in the 1 position by an R$_6$O—CO—$C_{1-4}$alkyl, bis-(R$_6$O—CO)—$C_{1-4}$-alkyl or (R$_7$O—PO—OR$_8$)—$C_{1-2}$-alkyl group wherein R$_6$ to R$_8$ are as hereinbefore defined, a 2-oxo-morpholino group which may be substituted by 1 to 2 $C_{1-2}$alkyl groups, a 2-oxo-thiomorpholino group which may be substituted by 1 to 2 $C_{1-2}$-alkyl groups, a morpholino group which is substituted in the 2 position by a methoxy or ethoxy group, a morpholino group which is substituted in the 2 and 6 positions in each case by a methoxy or ethoxy group, a 2,2-dimethoxyethyl-NR$_5$, 2,2-diethoxyethyl-NR$_5$, 1,3-dioxolan-2-yl-methyl-NR$_5$ or 1,3-dioxan-2-yl-methyl-NR$_5$ group wherein R$_5$ is as hereinbefore defined, a N-methyl-R$_{11}$N or N-ethyl-R$_{11}$N group wherein R$_{11}$ denotes a 2-oxo-tetrahydrofuran-3-yl, 2-oxo-tetrahydrofuran-4-yl, 2-oxo-tetrahydropyran-3-yl, 2-oxo-tetrahydropyran-4-yl, 2-oxo-tetrahydropyran-5-yl, 2-oxo-tetrahydrothiophen-3-yl, 2-oxo-tetrahydrothiophen-4-yl, 2-oxo-tetrahydrothiopyran-3-yl, 2-oxo-tetrahydrothiopyran-4-yl or 2-oxo-tetrahydrothiopyran-5-yl group optionally substituted by one or two methyl groups, or D together with E denotes a hydrogen atom, a methyl, trifluoromethyl, aryl, R$_g$CO—O—(R$_e$CR$_f$)—O—CO or (R$_7$O—PO—OR$_8$) group wherein R$_e$ to R$_g$ and R$_7$ and R$_8$ are as hereinbefore defined, F denotes an —O—$C_{1-4}$-alkylene group, while the alkylene moiety is linked to the group G, or an oxygen atom, which may not be linked to a nitrogen atom of the group G, and G denotes an R$_6$O—CO-alkylene-NR$_5$ group wherein the alkylene moiety, which is straight-chained and contains 1 to 4 carbon atoms, may additionally be substituted by one or two $C_{1-2}$-alkyl groups or by an R$_6$O—CO or R$_6$O—CO—$C_{1-2}$-alkyl group, while R$_5$ and R$_6$ are as hereinbefore defined, a pyrrolidino or piperidino group which is substituted by an R$_6$O—CO or R$_6$O—CO—$C_{1-2}$-alkyl group wherein R$_6$ is as hereinbefore defined, a pyrrolidino or piperidino group which is substituted by two R$_6$O—CO or R$_6$O—CO—$C_{1-2}$-alkyl groups wherein R$_6$ is as hereinbefore defined, a piperazino group which is substituted in the 4 position by the group R$_{10}$ and additionally at a cyclic carbon atom by an R$_6$O—CO or R$_6$O—CO—$C_{1-2}$-alkyl group, while R$_6$ and R$_{10}$ are as hereinbefore defined, a piperazino group which is substituted in the 4 position by an R$_6$O—CO—$C_{1-4}$-alkyl, bis-(R$_6$O—CO)—$C_{1-4}$alkyl or (R$_7$O—PO—OR$_8$)—$C_{1-2}$-alkyl group wherein R$_6$ to R$_8$ are as hereinbefore defined, a piperazino group which is substituted in the 4 position by an R$_6$O—CO—$C_{1-2}$-alkyl group and additionally at a cyclic carbon atom by an R$_6$O—CO or R$_6$O—CO—$C_{1-2}$-alkyl group wherein R$_6$ is as hereinbefore defined, a morpholino group which is substituted by an R$_6$O—CO or R$_6$O—CO—$C_{1-2}$-alkyl group, while R$_6$ is as hereinbefore defined, a piperidinyl group substituted in the 1 position by an R$_6$O—CO—$C_{1-4}$-alkyl, bis-(R$_6$O—CO)—$C_{1-4}$-alkyl or (R$_7$O—PO—OR$_8$)—$C_{1-2}$-alkyl group wherein R$_6$ to R$_8$ are as hereinbefore defined, a 2-oxo-morpholino group which may be substituted by 1 or 2 methyl groups, a 2-oxo-morpholinyl group which is substituted in the 4-position by a methyl, ethyl or R$_6$O—CO—$C_{1-2}$-alkyl group, while R$_6$ is as hereinbefore defined and the abovementioned 2-oxo-morpholinyl groups in are each case linked to a carbon atom of the group F, a morpholino group which is substituted in the 2 position by a methoxy or ethoxy group, a morpholino group which is substituted in the 2 and 6 positions in each case by a methoxy or ethoxy group, a 2,2-dimethoxyethyl-NR$_5$, 2,2-diethoxyethyl-NR$_5$, 1,3-dioxolan-2-yl-methyl-NR$_5$ or 1,3-dioxan-2-yl-methyl-NR$_5$- group or F and G together denote a hydrogen atom, a methoxy or ethoxy group, a C$_{1-3}$-alkoxy group which is substituted by an R$_5$O—CO group, while R$_6$ is as hereinbefore defined, a C$_{4-6}$-cycloalkoxy or C$_{3-6}$-cycloalkyl-C$_{1-3}$-alkoxy group with the proviso that at least one of the groups E, G or F together with G contains an R$_6$O—CO, (R$_7$O—PO—OR$_8$) or (R$_7$O—PO—R$_9$)

D together with E contains an R$_g$CO—O—(R$_e$CR$_f$)—O—CO or (R$_7$O—PO—OR$_8$) group or E or G contains an optionally substituted 2-oxo-morpholinyl group, morpholino group substituted in the 2 position or in the 2 and 6 positions in each by a methoxy or ethoxy group, a dimethoxymethyl or diethoxymethyl group or an optionally substituted 1,3-dioxolan-2-yl or 1,3-dioxan-2-yl- group or E contains an optionally substituted 2-oxo-tetrahydrofuran-3-yl, 2-oxo-tetrahydrofuran-4-yl, 2-oxo-tetrahydrofuran-3-yl, 2-oxo-tetrahydropyran-4-yl, 2-oxo-tetrahydropyran-5-yl, 2-oxo-thiomorpholino, 2-oxo-tetrahydrothiophen-3-yl, 2-oxo-tetrahydrothiophen-4-yl, 2-oxo-tetrahydrothiopyran-3-yl, 2-oxo-tetrahydrothiopyran-4-yl or 2-oxo-tetrahydrothiopyran-5-yl group, while the aryl moieties mentioned in the definition of the abovementioned groups denote a phenyl group which may be mono- or disubstituted by R$_{13}$, wherein the substituents may be identical or different and R$_{13}$ denotes a fluorine, chlorine, bromine or iodine atom, a C$_{1-2}$-alkyl, trifluoromethyl or C$_{1-2}$-alkoxy group or two groups R$_{13}$, if they are bound to adjacent carbon atoms, together denote a C$_{3-4}$-alkylene, methylenedioxy or 1,3-butadien-1,4-ylene group, the tautomers, the stereoisomers and the salts thereof.

However, the most preferred compounds of the above general formula I are those wherein R$_a$ denotes a hydrogen atom, R$_b$ denotes a phenyl, benzyl or 1-phenylethyl group wherein the phenyl nucleus is substituted in each case by the groups R$_1$ to R$_3$, while R$_1$ and R$_2$, which may be identical or different, each denote a hydrogen, fluorine, chlorine or bromine atom or a methyl group and R$_3$ denotes a hydrogen atom, R$_c$ and R$_d$ in each case denote a hydrogen atom, X denotes a methine group substituted by a cyano group, or a nitrogen atom, A denotes an NH- group, B denotes a carbonyl group, C denotes a 1,2-vinylene or an ethynylene group, D denotes a C$_{1-4}$-alkylene group, a —CO—NR$_4$-alkylene group wherein the alkylene moiety contains 2 or 3 carbon atoms, while the linking to the adjacent group C must take place via the carbonyl group, wherein R$_6$ denotes a hydrogen atom, or, if D is bound to a nitrogen atom of the group E, it may also denote a carbonyl group, E denotes an R$_6$O—CO-alkylene-NR$_5$ or (R$_7$O—PO—OR$_8$)-alkylene-NR$_5$ group wherein in each case the alkylene moiety, which is straight-chained and contains 1 to 2 carbon atoms, may additionally be substituted by a methyl group or by an R$_6$O—CO or R$_6$O—CO-methyl group, while R$_5$ denotes a hydrogen atom, a C$_{1-2}$-alkyl group which may be substituted by an R$_4$O—CO group, an ethyl group optionally substituted by one or two methyl groups, which is terminally substituted by a hydroxy C$_{1-2}$-alkylcarbonylsulphenyl or C$_{1-2}$-alkylcarbonyloxy group, a 2,2-dimethoxyethyl or 2,2-diethoxyethyl group, R$_6$ denotes a hydrogen atom, a C$_{1-8}$-alkyl group, a cyclopentyl, cyclopentylmethyl, cyclohexyl or cyclohexylmethyl group, a phenyl group optionally substituted by one or two methyl groups, a phenylmethyl group which may be substituted in the phenyl moiety by one or two methyl groups, a 5-indanyl group or an R$_6$CO—O—(R$_e$CR$_f$) group, while R$_e$ denotes a hydrogen atom or a methyl group, R$_f$ denotes a hydrogen atom and R$_g$ denotes a C$_{1-4}$-alkyl or C$_{1-2}$alkoxy group, R$_7$ and R$_8$, which may be identical or different, in each case denote a hydrogen atom, a methyl, ethyl or phenyl group, a pyrrolidino or piperidino group which is substituted by an R$_4$O—CO or R$_6$O—CO-methyl group, wherein R$_6$ is as hereinbefore defined, a pyrrolidino or piperidino group which is substituted by two R$_6$O—CO or R$_6$O—CO-methyl groups wherein R$_6$ is as hereinbefore defined, a piperazino group which is substituted in the 4 position by the group R$_{10}$ and additionally at a cyclic carbon atom by an R$_6$O—CO group, wherein R$_6$ is as hereinbefore defined and R$_{10}$ denotes a hydrogen atom, a methyl, ethyl, acetyl or methylsulfonyl group, a piperazino or homopiperazino group which is substituted in the 4 position by an R$_6$O—CO—C$_{1-4}$-alkyl, bis-(R$_6$O—CO)—C$_{1-6}$-alkyl or (R$_7$O—PO—OR$_8$)—C$_{1-2}$-alkyl group wherein R$_6$ to R$_8$ are as hereinbefore defined, a piperazino group which is substituted in the 4 position by an R$_6$O—CO—methyl group and additionally at a cyclic carbon atom by an R$_6$O—CO group wherein R$_6$ is as hereinbefore defined, a morpholino group which is substituted by an R$_6$O—CO— group, while R$_6$ is as hereinbefore defined, a 2-oxo-morpholino group which may be substituted by 1 or 2 C$_{1-2}$-alkyl groups, a 2-oxo-thiomorpholino group which may be substituted by 1 or 2 C$_{1-2}$-alkyl groups, a morpholino group which is substituted in the 2 position by a methoxy or ethoxy group, a morpholino group which is substituted in the 2 and 6 positions in each case by a methoxy or ethoxy group, a 2,2-dimethoxyethyl-NR$_5$, 2,2-diethoxyethyl-NR$_5$ or 1,3-dioxolan-2-yl-methyl-NR$_5$- group wherein R$_5$ is as hereinbefore defined, an N-methyl-R$_{11}$N or N-ethyl-R$_{11}$N group wherein R$_{11}$ denotes a 2-oxo-tetrahydrofuran-3-yl or 2-oxo-tetrahydrofuran-4-yl group, or D together with E denotes a hydrogen atom, a methyl group or an R$_g$CO—O—(R$_e$CR$_f$)—O—CO group wherein R$_e$ to R$_g$ are as hereinbefore defined, F denotes an —O—C$_{1-4}$-alkylene group, while the alkylene moiety is linked to the group G, or an oxygen atom, which may not be linked to a nitrogen atom of the group G, and G denotes an $R_6O\!-\!CO$-alkylene-$NR_5$ group wherein the alkylene moiety, which is straight-chained and contains 1 or 2 carbon atoms, may additionally be substituted by a methyl group or by an $R_6O\!-\!CO$ or $R_6O\!-\!CO$-methyl group, while $R_5$ and $R_6$ are as hereinbefore defined, a pyrrolidino or piperidino group which is substituted by an $R_6O\!-\!CO$ or $R_6O\!-\!CO$-methyl group wherein $R_6$ is as hereinbefore defined, a pyrrolidino or piperidino group which is substituted by two $R_6O\!-\!CO$ or $R_6O\!-\!CO$-methyl groups wherein $R_6$ is as hereinbefore defined, a piperazino group which is substituted in the 4 position by an $R_6O\!-\!CO\!-\!C_{1-4}$-alkyl, bis-$(R_6O\!-\!CO)\!-\!C_{1-4}$-alkyl or $(R_7O\!-\!PO\!-\!OR_8)\!-\!C_{1-2}$-alkyl group wherein $R_4$ to 8 are as hereinbefore defined, a piperidinyl group substituted in the 1 position by an $R_6O\!-\!CO\!-\!C_{1-2}$-alkyl group wherein $R_6$ is as hereinbefore defined, or F and G together denote a hydrogen atom, a methoxy or ethoxy group, a $C_{4-6}$-cycloalkoxy or $C_{1-6}$-cycloalkyl-1-3-alkoxy group, with the proviso that at least one of the groups E or G contains an $R_6O\!-\!CO$ or $(R_7O\!-\!PO\!-\!OR_8)$ group or D together with E contains an $R_gCO\!-\!O\!-\!(R_eCR_f)\!-\!O\!-\!CO$ group or E contains an optionally substituted 2-oxo-morpholinyl group, a morpholino group substituted in the 2 position or in the 2 and 6 positions in each case by a methoxy or ethoxy group, a dimethoxymethyl or diethoxymethyl group or a 1,3-dioxolan-2-yl, 2-oxo-tetrahydrofuran-3-yl or 2-oxo-tetrahydrofuran-4-yl group or an optionally substituted 2-oxo-thiomorpholino group, the tautomers, the stereoisomers and the salts thereof.

|Subgeneric aspect (5)| of the invention is bicyclic heterocycles of general formula

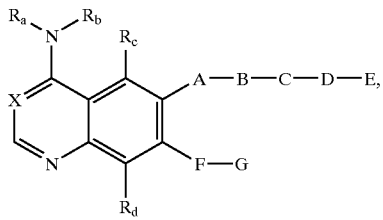

(I)

wherein $R_a$ denotes a hydrogen atom or a $C_{1-4}$-alkyl group, $R_b$ denotes a phenyl, benzyl or 1-phenylethyl group wherein the phenyl nucleus is substituted in each case by the groups $R_1$ to $R_1$, whilst $R_1$ and $R_2$, which may be identical or different, in each case denote a hydrogen, fluorine, chlorine, bromine or iodine atom, a $C_{1-4}$-alkyl, hydroxy, $C_{1-4}$-alkoxy, $C_{3-6}$-cycloalkyl, $C_{4-6}$-cyloalkoxy, $C_{2-5}$-alkenyl or $C_{2-5}$-alkynyl group, an aryl, aryloxy, arylmethyl or arylmethoxy group, a $C_{1-5}$-alkenyloxy or $C_{2-5}$-alkynyloxy group, wherein the unsaturated moiety may not be linked to the oxygen atom, a $C_{1-4}$-alkylsulphenyl, $C_{1-4}$-alkylsulphinyl, $C_{1-4}$-alkylsulphonyl, $C_{1-4}$-alkylsulphonyloxy, trifluoromethylsulphenyl, trifluoromethylsulphinyl or trifluoromethylsulphonyl group, a methyl or methoxy group substituted by 1 to 3 fluorine atoms, an ethyl or ethoxy group substituted by 1 to 5 fluorine atoms, a cyano or nitro group or an amino group optionally substituted by one or two $C_{1-4}$-alkyl groups, wherein the substituents may be identical or different, or $R_1$ with $R_3$, if they are bound to adjacent carbon atoms, denote a $-CH\!=\!CH\!-\!CH\!=\!CH$, $-CH\!=\!Ch\!-\!NH$ or $-CH\!=\!N\!-\!NH$ group and $R_3$ denotes a hydrogen, fluorine, chlorine or bromine atom, a $C_{1-4}$-alkyl, trifluoromethyl or $C_{1-4}$-alkoxy group, $R_c$ $R_d$, which may be identical or different, in each case denote a hydrogen, fluorine or chlorine atom, a methoxy group, or a methyl group optionally substituted by a methoxy, dimethylamino, diethylamino, pyrrolidino, piperidino or morpholino group, X denotes a methine group substituted by a cyano group or a nitrogen atom, A denotes an oxygen atom or an NH- group optionally substituted by a $C_{1-4}$-alkyl group, B denotes a carbonyl or sulphonyl group, C denotes a 1,3-allenylene, 1,1 or 1,2-vinylene group which may be substituted in each case by one or two methyl groups or by a trifluoromethyl group, an ethynylene group or a 1,3-butadien-1,4-ylene group optionally substituted by 1 to 4 methyl groups or by a trifluoromethyl |group|, D denotes an alkylene, $-CO$-alkylene or $-SO_2$-alkylene group wherein the alkylene moiety in each case contains 1 to 8 carbon atoms and additionally 1 to 4 hydrogen atoms in the alkylene moiety may be replaced by fluorine atoms, whilst the linking of the $-CO$-alkylene and $-SO_2$-alkylene group to the adjacent group C in each case must take place via the carbonyl or sulphonyl group, a $-CO\!-\!O$-alkylene, $-CO\!-\!NR_4$-alkylene or $-SO_2NR_4$-alkylene group wherein the alkylene moiety in each case contains 1 to 8 carbon atoms, whilst the linking to the adjacent group C in each case must take place via the carbonyl or sulphonyl group wherein $R_4$ denotes a hydrogen atom or a $C_{1-4}$-alkyl group, or, if D is bound to a carbon atom of the group E, it may also denote a bond or, if D is bound to a nitrogen atom of the group E, it may also denote a carbonyl or sulphonyl group, E denotes an $R_6O\!-\!CO$-alkylene-$NR_5$, $(R_7O\!-\!PO\!-\!OR_8)$-alkylene-$NR_5$ or $(R_7O\!-\!PO\!-\!R_9)$-alkylene-$NR_5$-group wherein in each case the alkylene moiety, which is straight-chained and contains 1 to 6 carbon atoms, may additionally be substituted by one or two $C_{1-2}$-alkyl groups or by an $R_6O\!-\!CO$ or $R_6O\!-\!CO\!-\!C_{1-2}$-alkyl group, wherein $R_5$ denotes a hydrogen atom, a $C_{1-4}$-alkyl group, which may be substituted by an $R_6O\!-\!CO$, $(R_7O\!-\!PO\!-\!OR_8)$ or $(R_7O\!-\!PO\!-\!P_9)$ group, an ethyl or propyl group optionally substituted by one or two methyl or ethyl groups, which may be terminally substituted in each case by a $C_{1-6}$-alkylcarbonylsulphenyl, $C_{1-7}$-cycloalkylcarbonylsulphenyl, $C_{3-7}$-cycloalkyl-$C_{1-3}$-alkylcarbonylsulphenyl, arylcarbonylsulphenyl or aryl-$C_{1-3}$-alkylcarbonylsulphenyl group, an ethyl or propyl group optionally substituted by one or two methyl or ethyl groups which may be terminally substituted in each case by a $C_{1-6}$-alkylcarbonyloxy, $C_{1-7}$-cycloalkylcarbonyloxy, $C_{3-7}$-cycloalkyl-$C_{1-3}$-alkylcarbonyloxy, arylcarbonyloxy or aryl-$C_{1-2}$-alkylcarbonyloxy group, an ethyl or propyl group optionally substituted by one or two methyl or ethyl groups, each of which may be terminally substituted by a hydroxy, $C_{1-4}$-alkoxy, amino, $C_{1-4}$-alkylamino or di-$(C_{1-4}$-alkyl)-amino group or by a 4- to 7-membered alkyleneimino group, whilst in the abovementioned 6- to 7-membered alkyleneimino groups a methylene group in the 4 position may be replaced by an oxygen or sulphur atom, by a sulphinyl, sulphonyl, imino or N—($C_{1-4}$-alkyl)-imino group, a $C_{3-7}$-cycloalkyl or $C_{3-7}$-cycloalkyl-$C_{1-3}$-alkyl group, $R_6$, $R_7$ and $R_8$, which may be identical or different, in each case denote a hydrogen atom, a $C_{1-8}$-alkyl group, which may be substituted by a hydroxy, $C_{1-4}$-alkoxy, amino, $C_{1-4}$-alkylamino or di-($C_{1-4}$-alkyl)-amino group or by a 4- to 7-membered alkyleneimino group, whilst in the abovementioned 6- to 7-membered alkyleneimino groups in each case a methylene group in the 4 position may be replaced by an oxygen or sulphur atom or by a sulphinyl, sulphony, imino or N—($C_{1-4}$-alkyl)-imino group, a $C_{4-7}$-cycloalkyl group optionally substituted by 1 or 2 methyl groups, a $C_{3-5}$-alkenyl or $C_{3-5}$-alkynyl group, wherein the unsaturated part may not be linked to the oxygen atom, a $C_{3-7}$-cycloalkyl-$C_{1-4}$-alkyl, aryl, aryl-$C_{3-4}$-alkyl or $R_gCO$—O—($R_eCR_f$)-group, whilst $R_g$ and $R_f$, which may be identical or different, in each case denote a hydrogen atom or a $C_{1-4}$alkyl group and $R_g$ denotes a $C_{1-4}$-alkyl, $C_{3-7}$-cycloalkyl, $C_{1-4}$alkoxy or $C_{5-7}$-cycloalkoxy group, and $R_4$ denotes a $C_{1-4}$-alkyl, aryl or aryl-$C_{1-4}$-alkyl group, a 4- to 7-membered alkyleneimino group which may be substituted by an $R_6O$—CO, ($R_7O$—PO—$OR_8$), ($R_7O$—PO—$R_9$), $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_9$ are as hereinbefore defined, a 4- to 7-membered alkyleneimino group which is substituted by two $R_6OCO$ or $R_6OCO$—$C_{1-4}$-alkyl groups or by an $R_6OCO$-group and an $R_6OCO$—$C_{1-4}$-alkyl group wherein $R_6$ is as hereinbefore defined, a piperazino or homopiperazino group which is substituted in the 4 position by the group $R_{10}$ and is additionally substituted at a cyclic carbon atom by an $R_6O$—CO, ($R_7O$—PO—$OR_8$), ($R_7O$—PO—$R_9$), $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$alkyl group wherein $R_6$ to $R_9$ are as hereinbefore defined and $R_{10}$ denotes a hydrogen atom, a $C_{1-6}$-alkyl, formyl, $R_{1-4}$-alkylcarbonyl or $C_{1-4}$-alkylsulphonyl group, a piperazino or homopiperazino group which is substituted in the 4 position by the group $R_{10}$ and additionally at cyclic carbon atoms by two $R_6O$—CO or $R_6O$—CO—$C_{1-4}$-alkyl groups or by an $R_6O$—CO-group and an $R_6O$—CO—$C_{1-6}$-alkyl group wherein $R_6$ and $R_{10}$ are as hereinbefore defined, a piperazino or homopiperazino group which is substituted in each case in the 4 position by an $R_6O$—CO—$C_{1-4}$-alkyl, bis-($R_6O$—CO)—$C_{2-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_9$ are as hereinbefore defined, a piperazino or homopiperazino group which is substituted in the 4 position by an $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group and is additionally substituted at cyclic carbon atoms by one or two $R_6O$—CO or $R_6O$—CO—$C_{1-4}$-alkyl groups or by an $R_6O$—CO-group and an $R_6O$—CO—$C_{1-4}$-alkyl group wherein $R_6$ to $R_9$ are as hereinbefore defined, a morpholino or homomorpholino group which is substituted in each case by an $R_6O$—CO, ($R_7O$—PO—$OR_8$), ($R_7$—O—PO—$R_9$), $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_9$ are as hereinbefore defined, a morpholino or homomorpholino group which is substituted by two $R_6O$—CO or $R_6O$—CO—$C_{1-4}$-alkyl groups or by an $R_6O$—CO-group and an $R_6O$—CO—$C_{1-4}$-alkyl group wherein $R_6$ is as hereinbefore defined, a pyrrolidinyl piperidinyl or hexahydroazepinyl group substituted in the 1 position by the group $R_{10}$, whilst the abovementioned 5- to 7-membered rings are additionally substituted in each case at a carbon atom by an $R_6O$—CO, ($R_7O$—PO—$R_9$), ($R_7O$—PO—$R_9$), $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_{10}$ are as hereinbefore defined, a pyrrolidinyl, piperadinyl or hexahydroazepinyl group substituted in the 1 position by the group $R_{10}$, while the abovementioned 5- to 7-membered rings are in each case additionally substituted at carbon atoms by two $R_6C$—CO or $R_6O$—CO—$C_{1-4}$-alkyl groups or by an $R_6O$—CO-group and an $R_6O$—CO—$C_{1-4}$-alkyl group wherein $R_6$ and $R_{10}$ are as hereinbefore defined, a pyrrolidinyl, piperidinyl or hexahydroazepinyl group substituted in the 1 position by an $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_9$ are as hereinbefore defined, a pyrrolidinyl, piperidinyl or hexahydroazepinyl group substituted in the 1 position by an $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group, while the abovementioned 5- to 7-membered rings are in each case additionally substituted at carbon atoms by one or two $R_6O$—CO or $R_6O$—CO—$C_{1-4}$-alkyl groups or by an $R_6O$—CO-group and an $R_6O$—CO—$C_{1-4}$-alkyl group wherein $R_6$ to $R_9$ are as hereinbefore defined, a 2-oxo-morpholino group which may be substituted by 1 to 4 $C_{1-2}$-alkyl groups, a 2-oxo-thiomorpholino group which may be substituted by 1 to 4 $C_{1-2}$-alkyl groups, a morpholino or thiomorpholino group which is substituted in the 2 position by a $C_{1-4}$-alkoxy group, a morpholino or thiomorpholino group which is substituted in the 2 and 6 positions by a $C_{1-4}$-alkoxy group.

a $C_{1-4}$-alkyl-$NR_5$-group wherein the $C_{1-4}$-alkyl moiety, which is straight-chained and may additionally be substituted by one or two methyl groups, is in each case terminally substituted by a di-($C_{1-4}$-alkoxy)-methyl or tri-($C_{1-4}$-alkoxy)-methyl group, whilst $R_5$ is as hereinbefore defined, a $C_{1-4}$-alkyl-$NR_5$-group wherein the $C_{1-4}$-alkyl moiety, which is straight-chained and may additionally be substituted by one or two methyl groups, is in each case terminally substituted by a 1,3-dioxolan-2-yl or 1,3-dioxan-2-yl group optionally substituted by one or two methyl groups, while $R_5$ is as hereinbefore defined, an $R_{11}NR_5$-group wherein $R_5$ is as hereinbefore defined and $R_{11}$ denotes a 2-oxo-tetrahydrofuran-3-yl, 2-oxo-tetrahydrofuran-4-yl, 2-oxo-tetrahydropyran-3-yl, 2-oxo-tetrahydropyran-4-yl, 2-oxo-tetrahydropyran-5-yl, 2-oxo-tetrahydrothiophen-3-yl, 2-oxo-tetrahydrothiophen-4-yl, 2-oxo-tetrahydrothipyran-3-yl, 2-oxo-tetrahydrothiopyran-4-yl or 2-oxo-tetrahydrothiopyran-5-yl group optionally substituted by one or two methyl groups, or D together with E denotes an $R_gCO$—O—($R_eCR_f$)—O—CO, ($R_7O$—PO—$OR_8$) or ($R_7O$—PO—$R_9$)-group wherein $R_e$ to $R_g$ and $R_7$ to $R_9$ are as hereinbefore defined, F and G together denote a hydrogen atom, a $C_{1-4}$-alkoxy group optionally substituted from position 2 onwards by a hydroxy or $C_{1-4}$-alkoxy group, a $C_{3-7}$-cycloalkoxy or $C_{3-7}$-cycloalkyl-$C_{1-4}$-alkoxy group, whilst by the aryl moieties mentioned in the definitions of the abovementioned groups is meant a phenyl group which in each case may be monosubstituted by $R_{12}$, mono-, di- or trisubstituted by $R_{13}$ or monosubstituted by $R_{12}$ and additionally mono- or disubstituted by $R_{13}$, whilst the substituents may be identical or different and $R_{12}$ denotes a cyano, carboxy, $C_{1-4}$-alkoxycarbonyl, aminocarbonyl, $C_{1-4}$-alkylaminocarbonyl, di-($C_{1-4}$-alkyl)-aminocarbonyl, $C_{1-4}$-alkylsulphenyl, $C_{1-4}$-alkylsulphinyl, $C_{1-4}$-alkylsulphonyl, hydroxy, $C_{1-4}$-alkylsulphonyloxy, trifluoromethyloxy, nitro, amino, $C_{1-4}$-alkylamino, di-($C_{1-4}$-alkyl)-amino, $C_{1-4}$-alkylcarbonylamino, N-($C_{1-4}$-alkyl)-$C_{1-4}$-alkylcarbonylamino, $C_{1-4}$-alkylsulphonylamino, N-($C_{1-4}$-alkyl)-$C_{1-4}$-alkylsulphonylamino, aminosulphonyl, $C_{1-4}$-alkylaminosulphonyl or di-($C_{1-4}$-alkyl)-aminosulphonyl group or a carbamoyl group, which is substituted by a 5- to 7-membered alkyleneimino group, wherein in the abovementioned 6- to 7-membered alkyleneimino groups in each case a methylene group in the 4 position may be replaced by an oxygen or sulphur atom, by a sulphinyl, sulphonyl, imino or N-($C_{1-4}$-alkyl)-imino-group, and $R_{13}$ denotes a fluorine, chlorine, bromine or iodine atom, a $C_{1-4}$-alkyl, trifluoromethyl or $C_{1-4}$-alkoxy group or two groups $R_{12}$, if they are bound to adjacent carbon atoms, together denote a $C_{3-5}$-alkylene, methylenedioxy or 1,3-butadien-1,4-ylene group, the tautomers, the stereoisomers and the salts thereof.

Subgeneric aspect (6) of the invention is bicyclic heterocycles of general formula I, wherein $R_a$ denotes a hydrogen atom, $R_b$ denotes a phenyl, benzyl or 1-phenylethyl group wherein the phenyl nucleus is substituted in each case by the groups $R_1$ to $R_3$, while $R_1$ and $R_2$, which may be identical or different, each denote a hydrogen, fluorine, chlorine, bromine or iodine atom, a methyl, ethyl, hydroxy, methoxy, ethoxy, amino, cyano, vinyl or ethynyl group, an aryl, aryloxy, arylmethyl or arylmethoxy group, a methyl or methoxy group substituted by 1 to 3 fluorine atoms or $R_1$ together with $R_2$, if they are bound to adjacent carbon atoms, denote a —CH=CH—CH=CH, —CH=CH—NH or —CH=N—NH group and $R_3$ denotes a hydrogen, fluorine, chlorine or bromine atom, $R_c$ and $R_d$ in each case denote a hydrogen atom, X denotes a methine group substituted by a cyano group or a nitrogen atom, A denotes an —NH— group optionally substituted by a methyl or ethyl group, B denotes a carbonyl group, C denotes a 1,1- or 1,2-vinylene group which is substituted in each case by one or two methyl groups or may be substituted by a trifluoromethyl group, an ethylene group or a 1,3-butadien-1,4-ylene group optionally substituted by a methyl or trifluoromethyl group, D denotes an alkylene or —CO-alkylene group wherein the akylene moiety in each case contains 1 to 4 carbon atoms, while the linking of the —CO-alkylene group to the adjacent group C in each case must take place via the carbonyl group, a —CO—O-alkylene or —CO—NR$_4$-alkylene-group wherein the alkylene moiety in each case contains 1 to 4 carbon atoms, while the linking to the adjacent group C in each case must take place via the carbonyl group wherein $R_4$ denotes a hydrogen atom or a methyl or ethyl group, or, if D is bound to a carbon atom of the group E, it may also denote a bond or, if D is bound to a nitrogen atom of the group E, it may also denote a carbonyl or sulphonyl group, E denotes an $R_6$O—CO-alkylene-NR$_5$, ($R_7$O—PO—OR$_8$)-alkylene-NR$_5$ or ($R_7$O—PO—R$_9$)-alkylene-NR$_5$ group wherein in each case the alkylene moiety, which is straight-chained and contains 1 to 4 carbon atoms, may additionally be substituted by one or two $C_{1-2}$-alkyl groups or by an $R_6$O—CO or $R_6$O—CO—$C_{1-2}$ alkyl group, while $R_5$ denotes a hydrogen atom, a $C_{1-4}$-alkyl group which may be substituted by an $R_4$O—CO group, an ethyl or propyl group optionally substituted by one or two methyl or ethyl groups which is terminally substituted in each case by a hydroxy, $C_{1-4}$-alkoxy, di-($C_{1-4}$-alkyl)amino, $C_{1-6}$-alkylcarbonylsulphenyl, $C_{3-6}$-cycloalkylcarbonylsulphenyl, $C_{3-6}$-cycloalkyl-$C_{1-2}$-alkylcarbonylsulphenyl, arylcarbonylsulphenyl or aryl-$C_{1-3}$-alkylcarbonylsulphenyl group, an ethyl or propyl group optionally substituted by one or two methyl or ethyl groups which is terminally substituted in each case by a $C_{1-6}$-alkylcarbonyloxy, $C_{3-6}$-cycloalkylcarbonyloxy, $C_{3-6}$-cycloalkyl-$C_{1-3}$-alkylcarbonyloxy, arylcarbonyloxy or aryl-$C_{1-3}$-alkylcarbonyloxy group, a $C_{1-6}$-cycloalkyl or $C_{3-6}$-cycloalkyl-$C_{1-3}$-alkyl group, $R_6$, $R_7$ and $R_8$, which may be identical or different, in each case denote a hydrogen atom, a $C_{1-8}$-alkyl group which may be substituted by a hydroxy, $C_{1-4}$-alkoxy, or di-($C_{1-4}$-alkyl)-amino group or by a 4- to 7-membered alkyleneimino group, while in the abovementioned 6- to 7-membered alkyleneimino groups in each case a methylene group in the 4 position may be replaced by an oxygen atom or by an N-($C_{1-2}$-alkyl)-imino group, a $C_{4-6}$-cycloalkyl group, a $C_{3-5}$-alkenyl or $C_{3-5}$-alkynyl group, while the unsaturated moiety may not be linked to the oxygen atom, a $C_{3-6}$-cycloalkyl-$C_{1-4}$-alkyl, aryl, aryl-$C_{1-4}$-alkyl or $R_6$CO—O—($R_eCR_f$) group, while $R_e$ and $R_f$, which may be identical or different, in each case denote a hydrogen atom or a $C_{1-4}$-alkyl group and $R_g$ denotes a $C_{1-4}$-alkyl, $C_{3-6}$-cycloalkyl, $C_{1-4}$-alkoxy or $C_{5-6}$-cycloalkoxy group, and $R_9$ denotes a $C_{1-4}$-alkyl group, a 4- to 7-membered alkyleneimino group which is substituted by an $R_6$O—CO, $R_6$O—CO—$C_{1-4}$-alkyl or bis-($R_6$O—CO)—$C_{1-4}$-alkyl group wherein $R_6$ is as hereinbefore defined, a 4- to 7-membered alkyleneimino group which is substituted by two $R_6$O—CO or $R_6$O—CO—$C_{1-4}$-alkyl groups wherein $R_6$ is as hereinbefore defined, a piperazino or homopiperazino group which is substituted in the 4 position by the group $R_{10}$ and additionally at a cyclic carbon atom by an $R_6$O—CO, $R_6$O—CO—$C_{1-4}$-alkyl or bis-($R_6$O—CO)—$C_{1-4}$-alkyl group wherein $R_6$ is as hereinbefore defined and $R_{10}$ denotes a hydrogen atom, a methyl or ethyl group, a piperazino or homopiperazino group which is substituted in the 4 position by the group $R_{10}$ and is additionally substituted at cyclic carbon atoms by two $R_6O$—CO or $R_6O$—CO—$C_{1-4}$-alkyl groups wherein $R_4$ and $R_{10}$ are as hereinbefore defined, a piperazino or homopiperazino group which is substituted in each case in the 4 position by an $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_9$ are as hereinbefore defined, a piperazino or homopiperazino group which is substituted in the 4 position by an $R_6O$—CO—$C_{1-6}$-alkyl or bis-($R_6O$—CO)—$C_{1-4}$-alkyl group and is additionally substituted by cyclic carbon atoms by one or two $R_6O$—CO or $R_6O$—CO—$C_{1-4}$-alkyl groups wherein $R_6$ is as hereinbefore defined, a morpholino or homomorpholino group which is substituted in each case by an $R_6O$—CO, $R_6O$—CO—$C_{1-4}$-alkyl, or bis-($R_6O$—CO)—$C_{1-4}$-alkyl group wherein $R_6$ is as hereinbefore defined, a morpholino or homomorpholino group which is substituted by two $R_6O$—CO or $R_6O$—CO—$C_{1-4}$-alkyl groups wherein $R_4$ is as hereinbefore defined, a pyrrolidinyl, piperidinyl or hexahydroazepinyl group substituted in the 1 position by the group $R_{10}$, while the abovementioned 5- to 7-membered rings in each case are additionally substituted at a carbon atom by an $R_6O$—CO, $R_6O$—CO—$C_{1-4}$-alkyl or bis-($R_6O$—CO)—$C_{1-4}$-alkyl group wherein $R_6$ and $R_{10}$ are as hereinbefore defined, a pyrrolidinyl, piperidinyl or hexahydroazepinyl group substituted in the 1 position by the group $R_{10}$, while the abovementioned 5- to 7-membered rings in each case are additionally substituted at carbon atoms by two $R_6O$—CO or $R_6O$—CO—$C_{1-4}$-alkyl groups wherein $R_6$ and $R_{10}$ are as hereinbefore defined, a pyrrolidinyl, piperidinyl or hexahydroazepinyl group substituted in the 1 position by an $R_6O$—CO—$C_{1-6}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_9$ are as hereinbefore defined, a pyrrolidinyl, piperidinyl or hexahydroazepinyl group substituted in the 1 position by an $R_6O$—CO—$C_{1-4}$-alkyl or bis-($R_6O$—CO)—$C_{1-4}$-alkyl group, while the abovementioned 5- to 7-membered rings in each case are additionally substituted at carbon atoms by one or two $R_6O$—CO or $R_6O$—CO—$C_{1-4}$-alkyl groups wherein $R_6$ is as hereinbefore defined, a 2-oxo-morpholino group which may be substituted by 1 to 4 $C_{1-2}$-alkyl groups, a 2-oxo-thiomorpholino group which may be substituted by 1 to 4 $C_{1-2}$-alkyl groups, a morpholino group which is substituted in the 2 position by a $C_{1-4}$-alkoxy group, a morpholino group which is substituted in the 2 and 6 positions in each case by a $C_{1-4}$-alkoxy group, a $C_{1-4}$-alkyl-$NR_5$ group wherein the $C_{1-4}$-alkyl moiety, which is straight-chained, is terminally substituted by a di-($C_{1-6}$-alkoxy)-methyl group, while $R_6$ is as hereinbefore defined, a $C_{1-4}$-alkyl-$NR_5$ group wherein the $C_{1-6}$-alkyl moiety, which is straight-chained, is terminally substituted by a 1,3-dioxolan-2-yl or 1,3-dioxan-2-yl group, while $R_5$ is as hereinbefore defined, a $R_{11}NR_5$ group wherein $R_5$ is as hereinbefore defined and $R_{11}$ denotes a 2-oxo-tetrahydrofuran-3-yl, 2-oxo-tetrahydrofuran-4-yl, 2-oxo-tetrahydropyran-3-yl, 2-oxo-tetrahydropyran-4-yl, 2-oxo-tetrahydropyran-5-yl, 2-oxo-tetrahydrothiophen-3-yl, 2-oxo-tetrahydrothiophen-4-yl, 2-oxo-tetrahydrothiopyran-3-yl, 2-oxo-tetrahydrothiopyran-4-yl or 2-oxo-tetrahydrothiopyran-5-yl group optionally substituted by one or two methyl groups, or D together with E denotes an $R_gCO$—O—($R_eCR_f$)—O—CO or ($R_7O$—PO—$OR_8$) group wherein $R_e$ to $R_g$ and $R_7$ to $R_9$ are as hereinbefore defined, F and G together denote a hydrogen atom, a $C_{1-4}$-alkoxy group optionally substituted from position 2 by a hydroxy or $C_{1-4}$-alkoxy group, a $C_{4-7}$-cycloalkoxy or $C_{3-7}$-cycloalkyl-$C_{1-4}$-alkoxy group, whilst by the aryl moieties mentioned in the definitions of the abovementioned groups is meant a phenyl group which in each case may be monosubstituted by $R_{11}$, mono- or disubstituted by $R_{13}$ or monosubstituted by $R_{12}$ and additionally mono- or disubstituted by $R_{13}$, whilst the substituents may be identical or different and $R_{12}$ denotes a cyano, $C_{1-2}$-alkoxycarbonyl, aminocarbonyl, $C_{1-2}$-alkylaminocarbonyl, di-($C_{1-2}$-alkyl)-aminocarbonyl, $C_{1-2}$-alkylsulphenyl, $C_{1-2}$-alkylsulphinyl, $C_{1-2}$-alkylsulphonyl, hydroxy, nitro, amino, $C_{1-2}$-alkylamino or di-($C_{1-2}$-alkyl)-amino, and $R_{13}$ denotes a fluorine, chlorine, bromine or iodine atom, a $C_{1-2}$-alkyl, trifluoromethyl or $C_{1-2}$-alkoxy group or two groups $R_{13}$, if they are bound to adjacent carbon atoms, together denote a $C_{3-5}$-alkylene, methylenedioxy or 1,3-butadien-1,4-ylene group, the tautomers, the stereoisomers and the salts thereof.

Subgeneric aspect (7) of the invention is bicyclic heterocycles of general formula I, wherein $R_a$ denotes a hydrogen atom, $R_b$ denotes a phenyl, benzyl or 1-phenylethyl group wherein the phenyl nucleus is substituted in each case by the groups $R_1$ to $R_2$, while $R_1$ and $R_2$, which may be identical or different, each denote a hydrogen, fluorine, chlorine or bromine atom, or a methyl, trifluoromethyl, methoxy, ethynyl or cyano group, $R_3$ denotes a hydrogen atom, $R_c$ and $R_d$ in each case denote a hydrogen atom, X denotes a methine group substituted by a cyano group, or a nitrogen atom, A denotes an —NH— group, B denotes a carbonyl group, C denotes a 1,1- or 1,2-vinylene group, an ethylene group or a 1,3-butadien-1,4-ylene group, D denotes a $C_{1-4}$-alkylene group, a —CO—$NR_4$-alkylene group wherein the alkylene moiety contains 2 to 4 carbon atoms, while the linking to the adjacent group C in each case must take place via the carbonyl group, wherein $R_4$ denotes a hydrogen atom, or, if D is bound to a carbon atom of the group E, it may also denote a bond or, if D is bound to a nitrogen atom of the group E, it may also denote a carbonyl group, E denotes an $R_6O$—CO-alkylene-$NR_5$, ($R_7O$—PO—$OR_8$)-alkylene-$NR_5$ or ($R_7O$—PO—$R_6$)-alkylene-$NR_5$ group wherein in each case the alkylene moiety, which is straight-chained and contains 1 to 4 carbon atoms, may additionally be substituted by one or two $C_{1-2}$-alkyl groups or by an $R_6O$—CO or $R_6O$—CO—$C_{1-2}$-alkyl group, while $R_5$ denotes a hydrogen atom, a $C_{1-4}$-alkyl group which may be substituted by an $R_4O$—CO group, an ethyl group optionally substituted by one or two methyl or ethyl groups which is terminally substituted by a $C_{1-4}$-alkylcarbonylsulphenyl), arylcarbonylsulphenyl or arylmethylcarbonylsulphenyl group,
    an ethyl group optionally substituted by one or two methyl or ethyl groups which is terminally substituted by a hydroxy, $C_{1-4}$-alkoxycarbonyloxy, arylcarbonyloxy or arylmethylcarbonyloxy group,
    a 2,2-dimethoxyethyl or 2,2,-diethoxyethyl group,
    a $C_{3-6}$-cycloalkyl or $C_{3-6}$-cycloalkyl-methyl group,
$R_4$, $R_7$ and $R_8$, which may be identical or different, in each case denote a hydrogen atom,
    a $C_{2-8}$-alkyl group,
    a cyclopentyl, cyclopentylmethyl, cyclohexyl or cyclohexylmethyl group,
    an aryl, arylmethyl or $R_gCO—O—(R_eCR_f)$ group, wherein
    $R_e$ denotes a hydrogen atom or a $C_{1-4}$-alkyl group,
    $R_f$ denotes a hydrogen atom and
    $R_g$ denotes a $C_{1-4}$-alkyl, cyclopentyl, cyclohexyl, $C_{1-4}$-alkoxy, cyclopentyloxy or cyclohexyloxy group,
    and $R_1$ denotes a methyl or ethyl group
a pyrrolidino or piperidino group which is substituted by an $R_6O—CO$ or $R_6O—CO—C_{1-2}$-alkyl group wherein $R_6$ is as hereinbefore defined,
a pyrrolidino or piperidino group which is substituted by two $R_6O—CO$ or $R_6O—CO—C_{1-2}$-alkyl groups wherein $R_6$ is as hereinbefore defined,
a piperazino group which is substituted in the 4 position by the group $R_{10}$ and is additionally substituted at a cyclic carbon atom by an $R_6O—CO$ or $R_6O—CO—C_{1-2}$-alkyl group, while $R_6$ is as hereinbefore defined and
    $R_{10}$ denotes a hydrogen atom, a methyl or ethyl group,
a piperazino group which is substituted in the 4 position by an $R_6O—CO—C_{1-4}$-alkyl, bis-$(R_6O—CO)—C_{1-4}$-alkyl or $(R_7O—PO—OR_8)—C_{1-2}$-alkyl group wherein $R_6$ to $R_8$ are as hereinbefore defined,
a piperazino group which is substituted in the 4 position by a $R_6O—CO—C_{1-2}$-alkyl group and is additionally substituted at a cyclic carbon atom by an $R_6O—CO$ or $R_6O—CO—C_{1-2}$-alkyl group wherein $R_6$ is as hereinbefore defined,
a morpholino group which is substituted by an $R_6O—CO$ or $R_6—CO—C_{1-2}$-alkyl group, while $R_6$ is as hereinbefore defined,
a piperidinyl group substituted in the 1 position by an $R_6O—CO—C_{1-4}$-alkyl, bis-$(R_6O—CO)—C_{1-4}$-alkyl or $(R_7O—PO—OR_8)—C_{1-2}$-alkyl group wherein $R_6$ to $R_8$ are as hereinbefore defined,
a 2-oxo-morpholino group which may be substituted by 1 to 2 $C_{1-2}$-alkyl groups,
a 2-oxo-thiomorpholino group which may be substituted by 1 to 2 $C_{1-2}$-alkyl groups,
a morpholino group which is substituted in the 2 position by a methoxy or ethoxy group,
a morpholino group which is substituted in the 2 and 6 positions in each case by a methoxy or ethoxy group,
a 2,2-dimethoxyethyl-$NR_5$, 2,2-diethoxyethyl-$NR_5$, 1,3-dioxolan-2-yl-methyl-$NR_5$ or 1,3-dioxan-2-yl-methyl-$NR_5$ group wherein $R_5$ is as hereinbefore defined,
a N-methyl-$R_{12}N$ or N-ethyl-$R_{11}N$ group wherein
    $R_{11}$ denotes a 2-oxo-tetrahydrofuran-3-yl, 2-oxo-tetrahydrofuran-4-yl, 2-oxo-tetrahydropyran-3-yl, 2-oxo-tetrahydropyran-4-yl, 2-oxo-tetrahydropyran-5-yl, 2-oxo-tetrahydrothiophen-3-yl, 2-oxo-tetrahydrothiophen-4-yl, 2-oxo-tetrahydrothiopyran-3-yl, 2-oxo-tetrahydrothipyran-4-yl or 2-oxo-tetrahydrothiopyran-5-yl group optionally substituted by one or two methyl groups,
or D together with E denotes an $R_gCO—O—(R_eCR_f)—O—CO—$ or $(R_7O—PO—OR_6)$ group wherein $R_e$ to $R_f$ and $R_7$ and $R_8$ are as hereinbefore defined, F and G together denote a hydrogen atom, a methoxy, ethoxy, $C_{4-6}$-cycloalkoxy or $C_{3-4}$-cycloalkyl-$C_{1-3}$-alkoxy group, while the aryl moieties mentioned in the definition of the abovementioned groups denote a phenyl group which may be mono- or disubstituted by $R_{12}$, while the substituents may be identical or different and
$R_{13}$ denotes a fluorine, chlorine, bromine or iodine atom, a $C_{1-2}$-alkyl, trifluoromethyl or $C_{1-2}$-alkoxy group or
two groups $R_{12}$, if they are bound to adjacent carbon atoms, together denote a $C_{3-4}$-alkylene, methylenedioxy or 1,3-butadien-1,4-ylene group,
the tautomers, the stereoisomers and the salts thereof.
    Subgeneric aspect (8) of the invention is bicyclic heterocycles of general formula I, wherein
$R_a$ denotes a hydrogen atom,
$R_b$ denotes a phenyl, benzyl or 1-phenylethyl group wherein the phenyl nucleus is substituted in each case by the groups $R_1$ to $R_3$, while
    $R_1$ and $R_2$, which may be identical or different, each denote a hydrogen, fluorine, chlorine or bromine atom or a methyl group and
    $R_3$ denotes a hydrogen atom,
$R_c$ and $R_d$ each denote a hydrogen atom,
X denotes a methine group substituted by a cyano group, or a nitrogen atom,
A denotes an —NH— group,
B denotes a carbonyl group,
C denotes a 1,2-vinylene or an ethylene group,
D denotes a $C_{1-4}$-alkylene group,
A —CO—$NH_4$-alkylene group wherein the alkylene moiety contains 2 or 3 carbon atoms, while the linking to the adjacent group C must take place via the carbonyl group wherein
    $R_4$ denotes a hydrogen atom,
or, if D is bound to a nitrogen atom of the group E, it may also denote a carbonyl group,
E denotes an $R_6O—CO$-alkylene-$NR_5$ or $(R_7O—PO—OR_8)$-alkylene-$NR_5$ group wherein in each case the alkylene moiety, which is straight-chained and contains 1 to 2 carbon atoms, may additionally be substituted by a methyl group or by an $R_6O—CO$ or $R_6O—CO$-methyl group, while
    $R_5$ denotes a hydrogen atom,
    a $C_{1-3}$-alkyl group which may be substituted by an $R_6O—CO$ group,
    an ethyl group optionally substituted by one or two methyl groups, which is terminally substituted by a hydroxy, $C_{1-2}$-alkylcarbonylsulphinyl or $C_{1-2}$-alkylcarbonyloxy group,
    a 2,2-dimethoxyethyl or 2,2-diethoxyethyl group,
    $R_6$ denotes a hydrogen atom,
    a $C_{1-8}$-alkyl group,
    a cyclopentyl, cyclopentylmethyl, cyclohexyl or cyclohexylmethyl group,
    a phenyl group optionally substituted by one or two methyl groups, a phenylmethyl group which may be substituted in the phenyl moiety by one or two methyl groups, a 5-indanyl group or an $R_9CO—O-(R_eCR_f)$ group, while
    $R_e$ denotes a hydrogen atom or a methyl group,
    $R_f$ denotes a hydrogen atom and
    $R_g$ denotes a $C_{1-4}$-alkyl or $C_{1-2}$-alkoxy group,
    $R_7$ and $R_8$, which may be identical or different, in each case denote a hydrogen atom, a methyl, ethyl or phenyl group,
a pyrrolidino or piperidino group which is substituted by an $R_6O—CO$ or $R_6O—CO$-methyl group, wherein $R_6$ is as hereinbefore defined, a pyrrolidino or piperidino group which is substituted by two $R_6O$—CO or $R_6O$—CO-methyl groups wherein $R_6$ is as hereinbefore defined, A piperazino group which is substituted in the 4 position by the group $R_{10}$ and additionally at a cyclic carbon atom by an $R_6O$—CO group, while $R_6$ is as hereinbefore defined and $R_{10}$ denotes a hydrogen atom, a methyl or ethyl group, a piperazino group which is substituted in the 4 position by an $R_6O$—CO—$C_{1-4}$-alkyl, bis-($R_6O$—CO)—$C_{1-4}$-alkyl or ($R_7O$—PO—$OR_8$)—$C_{1-2}$-alkyl group wherein $R_6$ to $R_8$ are as hereinbefore defined, a piperazino group which is substituted in the 4 position by an $R_6O$—CO-methyl group and additionally at a cyclic carbon atom by an $R_6O$—CO group wherein $R_6$ is as hereinbefore defined, a morpholino group which is substituted by an $R_6O$—CO— group, wherein $R_6$ is as hereinbefore defined, a 2-oxo-morpholino group which may be substituted by 1 to 2 $C_{1-2}$-alkyl groups, a 2-oxo-morpholino group which may be substituted by 1 to 2 $C_{1-2}$-alkyl groups, a morpholino group which is substituted in the 2 position by a methoxy or ethoxy group, a morpholino group which is substituted in the 2 and 6 positions in each case by a methoxy or ethoxy group, a 2,2-dimethoxyethyl-$NR_5$, 2,2-diethoxyethyl-$NR_5$ or 1,3-dioxolan-2-yl-methyl-$NR_5$— group wherein $R_5$ is as hereinbefore defined, an N-methyl-$R_{11}$-N or N-ethyl-$R_{11}$N group wherein $R_{11}$ denotes a 2-oxo-tetrahydrofuran-3-yl or 2-oxo-tetrahydrofuran-4-yl group, or D together with E denotes an $R_cCO$—O—($R_eCR_f$)—O—CO group wherein $R_e$ to $R_g$ are as hereinbefore defined, F and G together denote a hydrogen atom, a methoxy, ethoxy, $C_{4-6}$-cycloalkoxy or $C_{3-6}$-cycloalkyl-$C_{1-3}$-alkoxy group, the tautomers, the stereoisomers and the salts thereof.

Subgeneric aspect (9) of the invention is bicyclic heterocycles of general formula I, characterised in that $R_b$ denotes one of the optionally substituted 1-phenyl-ethyl groups mentioned in the respective subgeneric aspects 5, 6, 7 or 8, the tautomers, the stereoisomers and the salts thereof.

Subgeneric aspect (10) of the invention is bicyclic heterocycles of general formula I according to at least one of subgeneric aspects 5 to 8, characterised in that F and G together denote one of the cycloalkoxy or cycloalkyl-alkoxy groups mentioned in the respective subgeneric aspects 5, 6, 7 or 8, the tautomers, the stereoisomers and the salts thereof.

Subgeneric aspect (11) of the invention is bicyclic heterocycles of general formula I according to at least one of subgeneric aspects 5 to 8, characterised in that E denotes one of the optionally substituted 2-oxo-morpholino groups mentioned in the respective subgeneric aspects 5, 6, 7 or 8.

Subgeneric aspect (12) of the invention is bicyclic heterocycles of general formula (I)

wherein $R_a$ denotes a hydrogen atom or a $C_{1-4}$-alkyl group, $R_b$ denotes a phenyl, benzyl or 1-phenylethyl group wherein the phenyl nucleus is substituted in each case by the groups $R_1$ to $R_3$, whilst $R_1$ and $R_2$, which may be identical or different, in each case denote a hydrogen, fluorine, chlorine, bromine or iodine atom, a $C_{1-4}$-alkyl, hydroxy, $C_{1-4}$-alkoxy, $C_{3-6}$-cycloalkyl, $C_{4-6}$-cycloalkoxy, $C_{2-5}$-alkenyl or $C_{2-5}$-alkynyl group, an aryl, aryloxy, arylmethyl or arylmethoxy group, a $C_{3-5}$-alkenyloxy or $C_{3-5}$-alkynyloxy group, wherein the unsaturated moiety may not be linked to the oxygen atom, a $C_{1-4}$-alkylsulphenyl, $C_{1-4}$-alkylsulphinyl, $C_{1-4}$-alkylsulphonyl, $C_{1-4}$-alkylsulphonyloxy, trifluoromethylsulphenyl, trifluoromethylsulphinyl or trifluoromethylsulphonyl group, a methyl or methoxy group substituted by 1 to 3 fluorine atoms, an ethyl or ethoxy group substituted by 1 to 5 fluorine atoms, a cyano or nitro group or an amino group optionally substituted by one or two $C_{1-4}$-alkyl groups, wherein the substituents may be identical or different, or $R_1$ together with $R_2$, if they are bound to adjacent carbon atoms, denote a —CH=CH—CH=CH, —CH=CH—NH or —CH=N—NH group and $R_1$ denotes a hydrogen, fluorine, chlorine or bromine atom, a $C_{1-4}$-alkyl, trifluoromethyl or $C_{1-4}$-alkoxy group, $R_c$ and $R_d$, which may be identical or different, in each case denote a hydrogen, fluorine or chlorine atom, a methoxy group, or a methyl group optionally substituted by a methoxy, dimethylamino, diethylamino, pyrrolidino, piperidino or morpholino group, X denotes a methine group substituted by a cyano group or a nitrogen atom, A denotes an oxygen atom or an —NH— group optionally substituted by a $C_{1-4}$-alkyl group, B denotes a carbonyl or sulphonyl group, C denotes a 1,3-allenylene, 1,1 or 1,2-vinylene group which may be substituted in each case by one or two methyl groups or by a trifluoromethyl group, an ethynylene group or a 1,3-butadien-1,4-ylene group optionally substituted by 1 to 4 methyl groups or by a trifluoromethyl group, D together with E denotes a hydrogen atom, a $C_{1-4}$-alkyl group optionally substituted by 1 to 5 fluorine atoms, a $C_{1-4}$-cycloalkyl group, an aryl, heteroaryl, $C_{1-4}$-alkylcarbonyl, arylcarbonyl or $C_{1-4}$-alkoxycarbonyl group, an aminocarbonyl, $C_{1-4}$-alkylaminocarbonyl or di-($C_{1-4}$-alkyl)-aminocarbonyl group or a carbonyl group, which is substituted by a 4- to 7-membered alkyleneimino group, whilst in the abovementioned 6- to 7-membered alkyleneimino groups, a methylene group in the 4 position may be replaced by an oxygen or sulphur atom, by an imino group substituted by the group $R_{10}$, by a sulphinyl or sulphonyl group, wherein $R_{10}$ is a hydrogen atom, a $C_{1-4}$-alkyl, formyl, $C_{1-4}$-alkylcarbonyl or $C_{1-4}$-alkylsulphonyl group, F denotes a $C_{1-4}$-alkylene group, a —O—$C_{1-4}$-alkylene group, wherein the alkylene moiety is linked to the group G, or an oxygen atom, whilst the latter may not be linked to a nitrogen atom of the group G, and G denotes an $R_6O$—CO-alkylene-$NR_5$, ($R_7O$—PO—$OR_8$)-alkylene-$NR_5$ or ($R_7O$—PO—$R_9$)-alkylene-$NR_5$-group wherein in each case the alkylene moiety, which is straight-chained and contains 1 to 6 carbon atoms, may additionally be substituted by one or two $C_{1-2}$-alkyl groups or by an $R_6O$—CO or $R_6O$—CO—$C_{1-2}$-alkyl group, wherein:

$R_5$ denotes a hydrogen atom, a $C_{1-4}$-alkyl group, which may be substituted by an $R_6O$—CO, $(R_7O$—PO—$OR_8)$ or $(R_7O$—PO—$R_9)$ group, an ethyl or propyl group optionally substituted by one or two methyl or ethyl groups, which may be terminally substituted in each case by a $C_{1-6}$-alkylcarbonylsulphenyl, $C_{3-7}$-cycloalkylcarbonylsulphenyl, $C_{3-7}$-cycloalkyl-$C_{1-3}$-alkylcarbonylsulphenyl, arylcarbonylsulphenyl or aryl-$C_{1-3}$-alkylcarbonylsulphenyl group, an ethyl or propyl group optionally substituted by one or two methyl or ethyl groups which is terminally substituted in each case by a $C_{1-4}$-alkylcarbonyloxy, $C_{3-7}$-cycloalkylcarbonyloxy, $C_{3-7}$-cycloalkyl-$C_{1-3}$-alkylcarbonyloxy, arylcarbonyloxy or aryl-$C_{1-3}$-alkylcarbonyloxy group, an ethyl or propyl group optionally substituted by one or two methyl or ethyl groups, each of which may be terminally substituted by a hydroxy, $C_{1-4}$-alkoxy, amino, $C_{1-4}$-alkylamino or di-($C_{1-4}$-alkyl)-amino group or by a 4- to 7-membered alkyleneimino group, whilst in the abovementioned 6- to 7-membered alkyleneimino groups a methylene group in the 4 position may be replaced by an oxygen or sulphur atom, by a sulphinyl, sulphonyl, imino or N-($C_{1-4}$-alkyl)-imino group, a $C_{3-7}$-cycloalkyl or $C_{3-7}$-cycloalkyl-$C_{1-3}$-alkyl group, $R_6$, $R_7$ and $R_8$, which may be identical or different, in each case denote a hydrogen atom, a $C_{1-8}$-alkyl group, which may be substituted by a hydroxy, $C_{1-4}$-alkoxy, amino, $C_{1-4}$-alkylamino or di-($C_{1-4}$-alkyl)-amino group or by a 4- to 7-membered alkyleneimino group, whilst in the abovementioned 6- to 7-membered alkyleneimino groups in each case a methylene group in the 4 position may be replaced by an oxygen or sulphur atom or by a sulphinyl, sulphonyl, imino or N-($C_{1-4}$-alkyl)-imino group, a $C_{4-7}$-cycloalkyl group optionally substituted by 1 or 2 methyl groups, $C_{3-5}$-alkenyl or $C_{3-5}$-alkynyl group, wherein the unsaturated moiety may not be linked to the oxygen atom, a $C_{3-7}$-cycloalkyl-$C_{1-4}$-alkyl, aryl, aryl-$C_{1-4}$-alkyl, or $R_gCO$—O—$(R_eCR_f)$-group, whilst $R_e$ and $R_f$, which may be identical or different, each denote a hydrogen atom or a $C_{1-4}$-alkyl group and $R_g$ denotes a $C_{1-4}$-alkyl, $C_{3-7}$-cycloalkyl, $C_{1-4}$-alkoxy or $C_{5-7}$-cycloalkoxy group, and $R_2$ denotes a $C_{1-4}$-alkyl, aryl or aryl-$C_{1-4}$-alkyl group, a 4- to 7-membered alkyleneimino group which is substituted by an $R_6O$—CO, $(R_7O$—PO—$OR_8)$, $(R_7O$—PO—$R_9)$, $R_6O$—CO—$C_{1-4}$-alkyl, bis-$(R_6O$—CO)-$C_{1-4}$-alkyl, $(R_7O$—PO—$OR_8)$-$C_{1-4}$-alkyl or $(R_7O$—PO—$R_9)$-$C_{1-4}$-alkyl group wherein $R_4$ to $R_9$ are defined as above in this subgeneric aspect (12), a 4- to 7-membered alkyleneimino group which is substituted by two $R_6O$—CO or $R_6O$—CO—$C_{1-4}$-alkyl groups or by an $R_6O$—CO-group and an $R_6O$—CO—$C_{1-4}$-alkyl group wherein $R_4$ is defined as above in this subgeneric aspect (12), a piperazino or homopiperazino group which is substituted in the 4 position by the group $R_{10}$ and is additionally substituted at a cyclic carbon atom by an $R_6O$—CO, $(R_7O$—PO—$OR_8)$, $(R_7O$—PO—$R_9)$, $R_6O$—CO—$C_{1-4}$-alkyl, bis-$(R_6O$—CO)-$C_{1-4}$-alkyl, $(R_7O$—PO—$OR_8)$-$C_{1-4}$-alkyl or $(R_7O$—PO—$R_9)$-$C_{1-4}$-alkyl group wherein $R_6$ to $R_{10}$ are defined as above in this subgeneric aspect (12), a piperazino or homopiperazino group which is substituted in the 4 position by the group $R_{10}$ and is additionally substituted at cyclic carbon atoms by two $R_6O$—CO or $R_6O$—CO—$C_{1-4}$-alkyl groups or by an $R_6O$—CO group and an $R_6O$—CO—$C_{1-4}$-alkyl group wherein $R_6$ and $R_{10}$ are defined as above in this subgeneric aspect (12), a piperazino or homopiperazino group which is substituted in each case in the 4 position by an $R_6O$—CO—$C_{1-4}$-alkyl, bis-$(R_6O$—CO)-$C_{1-4}$-alkyl, $(R_7O$—PO—$OR_8)$-$C_{1-4}$-alkyl or $(R_7O$—PO—$R_9)$-$C_{1-4}$-alkyl group wherein $R_6$ to $R_9$ are defined as above in this subgeneric aspect (12), a piperazino or homopiperazino group which is substituted in the 4 position by an $R_6O$—CO—$C_{1-4}$-alkyl, bis-$(R_6O$—CO)-$C_{1-4}$-alkyl, $(R_7O$—PO—$OR_8)$-$C_{1-4}$-alkyl or $(R_7O$—PO—$R_9)$-$C_{1-4}$-alkyl group and is additionally substituted at cyclic carbon atoms by one or two $R_6O$—CO or $R_6O$—CO—$C_{1-4}$-alkyl groups or by an $R_6O$—CO-group and an $R_6O$—CO—$C_{1-4}$-alkyl group wherein $R_6$ to $R_9$ are defined as above in this subgeneric aspect (12), a morpholino or homomorpholino group which is substituted in each case by an $R_6O$—CO, $(R_7O$—PO—$OR_8)$, $(R_7O$—PO—$R_9)$, $R_6O$—CO—$C_{1-4}$-alkyl, bis-$(R_6O$—CO)-$C_{1-4}$-alkyl, $(R_7O$—PO—$OR_8)$-$C_{1-4}$-alkyl or $(R_7O$—PO—$R_9)$-$C_{1-4}$-alkyl group wherein $R_6$ to $R_9$ are defined as above in this subgeneric aspect (12), a morpholino or homomorpholino group which is substituted by two $R_6O$—CO or $R_6O$—CO—$C_{1-4}$-alkyl groups or by an $R_6O$—CO-group and an $R_6O$—CO—$C_{1-4}$-alkyl group wherein $R_6$ is defined as above in this subgeneric aspect (12), a pyrrolidinyl, piperidinyl or hexahydroazepinyl group substituted in the 1 position by the group $R_{10}$, whilst the abovementioned 5- to 7-membered rings are in each case additionally substituted at a carbon atom by an $R_6O$—CO, $(R_7O$—PO—$OR_8)$, $(R_7O$—PO—$R_9)$, $R_6O$—CO—$C_{1-4}$-alkyl, bis-$(R_6O$—CO)-$C_{1-4}$-alkyl, $(R_7O$—PO—$OR_8)$-$C_{1-4}$-alkyl or $(R_7O$—PO—$R_9)$-$C_{1-4}$-alkyl group wherein $R_6$ to $R_{10}$ are defined as above in this subgeneric aspect (12), a pyrrolidinyl, piperidinyl or hexahydroazepinyl group substituted in the 1 position by the group $R_{10}$, while the abovementioned 5- to 7-membered rings are in each case additionally substituted at carbon atoms by two $R_6O$—CO or $R_6O$—CO—$C_{1-4}$-alkyl groups or by an $R_6O$—CO-group and an $R_6O$—CO—$C_{1-4}$-alkyl group wherein $R_6$ and $R_{10}$ are defined as above in this subgeneric aspect (12), a pyrrolidinyl, piperidinyl or hexahydroazepinyl group substituted in the 1 position by an $R_6O$—CO—$C_{1-4}$-alkyl, bis-$(R_6O$—CO)-$C_{1-4}$-alkyl, $(R_7O$—PO—$OR_8)$-$C_{1-4}$alkyl or $(R_7O$—PO—$R_9)$-$C_{1-4}$-alkyl group wherein $R_6$ to $R_9$ are defined as above in this subgeneric aspect (12), a pyrrolidinyl, piperidinyl or hexahydroazepinyl group substituted in the 1 position by an $R_6O$—CO—$C_{1-4}$-alkyl, bis-$(R_6O$—CO)-$C_{1-4}$-alkyl, $(R_7O$—PO—$OR_8)$-$C_{1-4}$alkyl or $(R_7O$—PO—$R_9)$-$C_{1-4}$alkyl group, while the abovementioned 5- to 7-membered rings are in each case additionally substituted at carbon atoms by one or two $R_6O$—CO or $R_6O$—CO—$C_{1-4}$-alkyl groups or by an $R_6O$—CO-group and an $R_6O$—CO—$C_{1-4}$-alkyl group wherein $R_6$ to $R_9$ are defined as above in this subgeneric aspect (12), a 2-oxo-morpholino group which may be substituted by 1 or 2 methyl groups, a 2-oxo-morpholinyl group which is substituted in the 4 position by a hydrogen atom, by a $C_{1-4}$-alkyl, $R_6O$—CO—$C_{1-4}$-alkyl, $(R_7O$—PO—$OR_8)$-$C_{1-4}$-alkyl or $(R_7O$—PO—$R_9)$-$C_{1-4}$-alkyl group, while $R_6$ to $R_9$ are defined as in claim 1 and the abovementioned 2-oxo-morpholinyl groups are in each case linked to a carbon atom of the group F,
a morpholino or thiomorpholino group which is substituted in the 2 position by a $C_{1-4}$-alkoxy group,
a morpholino or thiomorpholino group which is substituted in the 2 and 6 position by a $C_{1-4}$-alkoxy group,
a $C_{1-4}$-alkyl-$NR_5$-group wherein the $C_{1-4}$-alkyl moiety, which is straight-chained and may additionally be substituted by one or two methyl groups, is in each case terminally substituted by a di-($C_{1-4}$-alkoxy)-methyl or tri-($C_{1-4}$-alkoxy)-methyl group, whilst $R_5$ is defined as above in this subgeneric aspect (12),
a $C_{1-4}$-alkyl-$NR_5$-group wherein the $C_{1-4}$-alkyl moiety, which is straight-chained and may additionally be substituted by one or two methyl groups, is terminally substituted in each case by a 1,3-dioxolan-2-yl or 1,3-dioxan-2-yl-group optionally substituted by one or two methyl groups, while $R_5$ is defined as above in this subgeneric aspect (12),
an $R_hNR_5$-group wherein $R_5$ is as hereinbefore defined and $R_h$ denotes a 2-oxo-tetrahydrofuran-3-yl, 2-oxo-tetrahydrofuran-4-yl, 2-oxo-tetrahydropyran-3-yl, 2-oxo-tetrahydropyran-4-yl or 2-oxo-tetrahydropyran-5-yl group optionally substituted by one or two methyl groups,
whilst by the aryl moieties mentioned in the definitions of the abovementioned groups is meant a phenyl group which in each case may be monosubstituted by $R_{12}$, mono-, di- or trisubstituted by $R_{13}$ or monosubstituted by $R_{12}$ and additionally mono- or disubstituted by $R_{13}$, whilst the substituents may be identical or different and $R_{12}$ denotes a cyano, carboxy, $C_{1-4}$-alkoxycarbonyl, aminocarbonyl, $C_{1-4}$-alkylaminocarbonyl, di-($C_{1-4}$-alkyl)-aminocarbonyl, $C_{1-4}$-alkylsulphenyl, $C_{1-4}$-alkylsulphinyl, $C_{1-4}$-alkylsulphonyl, hydroxy, $C_{1-4}$-alkylsulphonyloxy, trifluoromethyloxy, nitro, amino, $C_{1-4}$-alkylamino, di-($C_{1-4}$-alkyl)-amino, $C_{1-4}$-alkylcarbonylamino, N-($C_{1-4}$-alkyl)-$C_{1-4}$-alkylcarbonylamino, $C_{1-4}$-alkylsulphonylamino, N-($C_{1-4}$-alkyl)-$C_{1-4}$-alkylsulphonylamino, aminosulphonyl, $C_{1-4}$-alkylaminosulphonyl or di-($C_{1-4}$-alkyl)-aminosulphonyl group or a carbonyl group, which is substituted by a 5- to 7-membered alkyleneimino group, wherein in the abovementioned 6- to 7-membered alkyleneimino groups in each case a methylene group in the 4 position may be replaced by an oxygen or sulphur atom, by a sulphinyl, sulphonyl, imino or N-($C_{1-4}$-alkyl)-imino group, and $R_{13}$ denotes a fluorine, chlorine, bromine or iodine atom, a $C_{1-4}$-alkyl, trifluoromethyl or $C_{1-4}$-alkoxy group or
two groups $R_{13}$, if they are bound to adjacent carbon atoms, together denote a $C_{3-5}$-alkylene, methylenedioxy or 1,3-butadien-1,4-ylene group,
and moreover, the heteroaryl groups mentioned in the definitions of the abovementioned groups also include a 5-membered heteroaromatic group which contains an imino group, an oxygen or sulphur atom or an imino group, an oxygen or sulphur atom and one or two nitrogen atoms, or a 6-membered heteroaromatic group which contains one, two or three nitrogen atoms,
whilst the abovementioned 5-membered heteroaromatic groups may be substituted in each case by 1 or 2 methyl or ethyl groups and the abovementioned 6-membered heteroaromatic groups may be substituted in each case by 1 or 2 methyl or ethyl groups or by a fluorine, chlorine, bromine or iodine atom, or by a trifluoromethyl, hydroxy, methoxy or ethoxy group,
the tautomers, the stereoisomers and the salts thereof.
Subgeneric aspect (13) of the invention comprises bicyclic heterocycles of general formula I according to subgeneric aspect 12, wherein $R_a$ denotes a hydrogen atom,
$R_b$ denotes a phenyl, benzyl or 1-phenylethyl group wherein the phenyl nucleus is substituted in each case by the groups $R_1$ to $R_2$, while
$R_1$ and $R_2$, which may be identical or different, each denote a hydrogen, fluorine, chlorine, bromine or iodine atom,
a methyl, ethyl, hydroxy, methoxy, ethoxy, amino, cyano, vinyl or ethynyl group,
an aryl, aryloxy, arylmethyl or arylmethoxy group,
a methyl or methoxy group substituted by 1 to 3 fluorine atoms or
$R_1$ together with $R_2$, if they are bound to adjacent carbon atoms, denote a —CH=CH—CH=CH, —CH=CH—NH or —CH=N—NH group and
$R_3$ denotes a hydrogen, fluorine, chlorine or bromine atom,
$R_c$ and $R_d$ in each case denote a hydrogen atom,
X denotes a methine group substituted by a cyano group or a nitrogen atom,
A denotes an —NH— group optionally substituted by a methyl or ethyl group,
B denotes a carbonyl group,
C denotes a 1,1- or 1,2-vinylene group which is substituted in each case by one or two methyl groups or may be substituted by a trifluoromethyl group,
an ethynylene group or
a 1,3-butadien-1,4-ylene group optionally substituted by a methyl or trifluoromethyl group,
D together with E denotes a hydrogen atom,
a methyl, trifluoromethyl or aryl group,
F denotes an —O—$C_{1-4}$-alkylene group, wherein the alkylene moiety is linked to the group G, or an oxygen atom, while this may not be linked to a nitrogen atom of the group G, and
G denotes an $R_6O$—CO-alkylene-$NR_5$, ($R_7O$—PO—$OR_8$)-alkylene-$NR_5$ or ($R_7O$—PO—$R_9$)-alkylene-$NR_5$-group wherein in each case the alkylene moiety, which is straight-chained and contains 1 to 4 carbon atoms, may additionally be substituted by one or two $C_{1-2}$-alkyl groups or by an $R_6O$—CO or $R_6O$—CO—$C_{1-2}$-alkyl group, while:
$R_5$ denotes a hydrogen atom,
a $C_{1-4}$-alkyl group which may be substituted by an $R_6O$—CO group,
an ethyl or propyl group optionally substituted by one or two methyl or ethyl groups which is terminally substituted in each case by a hydroxy, $C_{1-4}$-alkoxy, di-($C_{1-4}$-alkyl)amino, $C_{1-4}$-alkylcarbonylsulphenyl, $C_{3-6}$-cycloalkylcarbonylsulphenyl, $C_{3-6}$-cycloalkyl-$C_{1-3}$-alkylcarbonylsulphenyl, arylcarbonylsulphenyl or aryl-$C_{1-3}$-alkylcarbonylsulphenyl group,
an ethyl or propyl group optionally substituted by one or two methyl or ethyl groups which is terminally substituted in each case by a $C_{1-6}$-alkylcarbonyloxy, $C_{3-6}$-cycloalkylcarbonyloxy, $C_{3-6}$-cycloalkyl-$C_{1-3}$-alkylcarbonyloxy, arylcarbonyloxy or aryl-$C_{1-3}$-alkylcarbonyloxy group,
a $C_{1-6}$-cycloalkyl or $C_{3-6}$-cycloalkyl-$C_{1-3}$-alkyl group,
$R_6$, $R_7$ and $R_8$, which may be identical or different, in each case denote a hydrogen atom,
a $C_{1-8}$-alkyl group which may be substituted by a hydroxy, $C_{1-4}$-alkoxy, or di-($C_{1-4}$-alkyl)-amino group or by a 4- to 7-membered alkyleneimino group, while in the abovementioned 6- to 7-membered alkyleneimino groups, in each case a methylene group in the 4 position may be replaced by an oxygen atom or by an N-($C_{1-2}$-alkyl)-imino group, a $C_{4-6}$-cycloalkyl group, a $C_{3-5}$-alkenyl or $C_{3-5}$-alkynyl group, while the unsaturated moiety may not be linked to the oxygen atom, a $C_{3-6}$-cycloalkyl-$C_{1-4}$-alkyl, aryl, aryl-$C_{1-4}$-alkyl, or $R_gCO$—O—($R_eCR_f$)-group, wherein $R_e$ and $R_f$, which may be identical or different, in each case denote a hydrogen atom or a $C_{1-4}$-alkyl group and $R_g$ denotes a $C_{1-4}$-alkyl, $C_{3-6}$-cycloalkyl, $C_{1-4}$-alkoxy or $C_{3-6}$-cycloalkoxy group, and $R_2$ denotes a $C_{1-4}$-alkyl group, a 4- to 7-membered alkyleneimino group which is substituted by an $R_6O$—CO, $R_6O$—CO—$C_{1-4}$-alkyl or bis-($R_6O$—CO)-$C_{1-4}$-alkyl group wherein $R_6$ is defined as above in this subgeneric aspect (13), a 4- to 7-membered alkyleneimino group which is substituted by two $R_6O$—CO or $R_6O$—CO—$C_{1-4}$-alkyl groups wherein $R_6$ is defined as above in this subgeneric aspect (13), a piperazino or homopiperazino group which is substituted in the 4 position by the group $R_{10}$ and is additionally substituted at a cyclic carbon atom by an $R_6O$—CO, $R_6O$—CO—$C_{1-4}$-alkyl or bis-($R_6O$—CO)-$C_{1-4}$-alkyl group wherein $R_6$ is define as above in this subgeneric aspect (13) and $R_{10}$ is a hydrogen atom, a methyl, ethyl, acetyl or methylsulfonyl group, a piperazino or homopiperazino group which is substituted in the 4 position by the group $R_{10}$ and is additionally substituted at cyclic carbon atoms by two $R_6O$—CO or $R_6O$—CO—$C_{1-4}$-alkyl groups wherein $R_6$ and $R_{10}$ are defined as above in this subgeneric aspect (13), a piperazino or homopiperazino group which is substituted in each case in the 4 position by an $R_6O$—CO—$C_{1-4}$-alkyl, bis-($R_6O$—CO)-$C_{1-4}$-alkyl, ($R_7O$—PO—$OR_8$)-$C_{1-4}$-alkyl or ($R_7O$—PO—$R_9$)-$C_{1-4}$-alkyl group wherein $R_6$ to $R_9$ are defined as above in this subgeneric aspect (13), a piperazino or homopiperazino group which is substituted in the 4 position by an $R_6O$—CO—$C_{1-4}$-alkyl or bis-($R_6O$—CO)-$C_{1-4}$-alkyl group and additionally at cyclic carbon atoms by one or two $R_6O$—CO or $R_6O$—CO—$C_{1-4}$-alkyl groups wherein $R_6$ is defined as above in this subgeneric aspect (13), a morpholino or homomorpholino group which is substituted in each case by an $R_6O$—CO, $R_6O$—CO—$C_{1-4}$-alkyl or bis-($R_6O$—CO)-$C_{1-4}$-alkyl group wherein $R_6$ is defined as above in this subgeneric aspect (13), a morpholino or homomorpholino group which is substituted by two $R_6O$—CO or $R_6O$—CO—$C_{1-4}$-alkyl groups wherein $R_6$ is defined as above in this subgeneric aspect (13), a pyrrolidinyl, piperidinyl or hexahydroazepinyl group substituted in the 1 position by the group $R_{10}$, while the abovementioned 5- to 7-membered rings are in each case are additionally substituted at a carbon atom by an $R_6O$—CO, $R_6O$—CO—$C_{1-4}$-alkyl or bis-($R_6O$—CO)-$C_{1-4}$-alkyl group wherein $R_6$ and $R_{10}$ are defined as above in this subgeneric aspect (13), a pyrrolidinyl, piperidinyl or hexahydroazepinyl group substituted in the 1 position by the group $R_{10}$, while the abovementioned 5- to 7-membered rings in each case are additionally substituted at carbon atoms by two $R_6O$—CO or $R_6O$—CO—$C_{1-4}$-alkyl groups wherein $R_6$ and $R_{10}$ are defined as above in this subgeneric aspect (13), a pyrrolidinyl, piperidinyl or hexahydroazepinyl group substituted in the 1 position by an $R_6O$—CO—$C_{1-4}$-alkyl, bis-($R_6O$—CO)-$C_{1-4}$-alkyl, ($R_7O$—PO—$OR_8$)-$C_{1-4}$-alkyl or ($R_7O$—PO—$R_9$)-$C_{1-4}$-alkyl group wherein $R_6$ to $R_9$ are defined as above in this subgeneric aspect (13), a pyrrolidinyl, piperidinyl or hexahydroazepinyl group substituted in the 1 position by an $R_6O$—CO—$C_{1-4}$-alkyl or bis-($R_6O$—CO)-$C_{1-4}$-alkyl group, while the abovementioned 5- to 7-membered rings in each case are additionally substituted at carbon atoms by one or two $R_6O$—CO or $R_6O$—CO—$C_{1-4}$-alkyl groups wherein $R_6$ is defined as above in this subgeneric aspect (13), a 2-oxo-morpholino group which may be substituted by 1 or 2 methyl groups, a 2-oxo-morpholinyl group which is substituted in the 4 position by a $C_{1-4}$-alkyl or $R_6O$—CO—$C_{1-4}$-alkyl group, while $R_6$ is defined as in claim 2 and the abovementioned 2-oxo-morpholinyl groups are each are linked to a carbon atom of the group F, a morpholino group which is substituted in the 2 position by a $C_{1-4}$-alkoxy group, a morpholino group which is substituted in the 2 and 6 positions in each case by a $C_{1-4}$-alkoxy group, a $C_{1-4}$-alkyl-$NR_5$ group wherein the $C_{1-4}$-alkyl moiety, which is straight-chained, is terminally substituted by a di-($C_{1-4}$-alkoxy)-methyl group, while $R_6$ is defined as above in this subgeneric aspect (13), a $C_{1-4}$-alkyl-$NR_5$ group wherein the $C_{1-4}$-alkyl moiety, which is straight-chained, is terminally substituted by a 1,3-dioxolan-2-yl or 1,3-dioxan-2-yl group, while $R_5$ is defined as above in this subgeneric aspect (13), an $R_hNR_5$ group wherein $R_5$ is defined as in claim 2 and $R_h$ denotes a substituted 2-oxo-tetrahydrofuran-3-yl, 2-oxo-tetrahydrofuran-4-yl, 2-oxo-tetrahydropyran-3-yl, 2-oxo-tetrahydropyran-4-yl or 2-oxo-tetrahydropyran-5-yl group optionally by one or two methyl groups, while the aryl moieties mentioned in the definition of the abovementioned groups denote a phenyl group which may in each case be monosubstituted by $R_{12}$, mono- or disubstituted by $R_{13}$ or monosubstituted by $R_{12}$ and additionally mono or disubstituted by $R_{13}$, whilst the substituents may be identical or different and $R_{12}$ denotes a cyano, $C_{1-2}$-alkoxycarbonyl, aminocarbonyl, $C_{1-2}$-alkylaminocarbonyl, di-($C_{1-2}$-alkyl)-aminocarbonyl, $C_{1-2}$-alkylsulphenyl, $C_{1-2}$-alkylsulphinyl, $C_{1-2}$-alkylsulphonyl, hydroxy, nitro, amino, $C_{1-2}$-alkylamino or di-($C_{1-2}$-alkyl)-amino group and $R_{13}$ denotes a fluorine, chlorine, bromine or iodine atom, a $C_{1-2}$-alkyl, trifluoromethyl or $C_{1-2}$-alkoxy group or two groups $R_{13}$, if they are bound to adjacent carbon atoms, together denote a $C_{3-5}$-alkylene, methylenedioxy or 1,3-butadien-1,4-ylene group, the tautomers, the stereoisomers and the salts thereof.

Subgeneric aspect (14) of the invention comprises bicyclic heterocycles of general formula I according to subgeneric aspect 12, wherein $R_a$ denotes a hydrogen atom, $R_b$ denotes a phenyl, benzyl or 1-phenylethyl group wherein the phenyl nucleus is substituted in each case by the groups $R_1$ to $R_2$, while $R_1$ and $R_2$, which may be identical or different, each denote a hydrogen, fluorine, chlorine or bromine atom, or a methyl, trifluoromethyl, methoxy, ethynyl or cyano group, $R_3$ denotes a hydrogen atom, $R_c$ and $R_d$ in each case denote a hydrogen atom, X denotes a methine group substituted by a cyano group, or a nitrogen atom, A denotes an —NH— group, B denotes a carbonyl group, C denotes a 1,1- or 1,2-vinylene group, an ethynylene group or a 1,3-butadien-1,4-ylene group, D together with E denotes a hydrogen atom,
a methyl, trifluoromethyl or aryl group, F denotes an —O—$C_{1-4}$-alkylene group, wherein the alkylene moiety is linked to the group G, or an oxygen atom, while this may not be linked to a nitrogen atom of the group G, and G denotes an $R_6O$—CO-alkylene-$NR_5$ group wherein the alkylene moiety, which is straight-chained and contains 1 to 4 carbon atoms, may additionally be substituted by one or two $C_{1-2}$-alkyl groups or by an $R_6O$—CO or $R_6O$—CO—$C_{1-2}$-alkyl group, while: $R_5$ denotes a hydrogen atom, a $C_{1-6}$-alkyl group which may be substituted by an $R_6O$—CO group, an ethyl group optionally substituted by one or two methyl or ethyl groups which is terminally substituted by a $C_{1-4}$-alkylcarbonylsulphenyl, arylcarbonylsulphenyl or arylmethylcarbonylsulphenyl group, an ethyl group optionally substituted by one or two methyl or ethyl groups which is terminally substituted by a hydroxy, $C_{1-4}$-alkylcarbonyloxy, arylcarbonyloxy or arylmethylcarbonyloxy group, a 2,2-dimethoxyethyl or 2,2-diethoxyethyl group, a $C_{3-6}$-cycloalkyl or $C_{3-6}$-cycloalkyl-methyl group, and $R_6$ denotes a hydrogen atom, a pyrrolidino or piperidino group which is substituted by an $R_6O$—CO or $R_6O$—CO—$C_{1-4}$-alkyl group wherein $R_6$ is a hydrogen atom, a pyrrolidino or piperidino group which is substituted by two $R_6O$—CO or $R_6O$—CO—$C_{1-2}$-alkyl groups wherein $R_6$ is a hydrogen atom, a piperazino group which is substituted in the 4 position by the group $R_{10}$ and additionally at a cyclic carbon atom by an $R_6O$—CO, or $R_6O$—CO—$C_{1-2}$-alkyl group, while $R_6$ is a hydrogen atom and $R_{10}$ is a hydrogen atom, a methyl, ethyl, acetyl or methylsulfonyl group, a piperazino group which is substituted in the 4 position by an $R_6O$—CO—$C_{1-4}$-alkyl, bis-($R_6O$—CO)-$C_{1-4}$-alkyl or ($R_7O$—PO—$OR_8$)-$C_{1-2}$-alkyl group wherein $R_4$ to $R_8$ are each hydrogen atoms, a piperazino group which is substituted in the 4 position by an $R_6O$—CO—$C_{1-2}$-alkyl group and additionally at a cyclic carbon atom by an $R_6O$—CO or $R_6O$—CO—$C_{1-2}$-alkyl group wherein $R_6$ is a hydrogen atom, a morpholino group which is substituted by an $R_6O$—CO or $R_6O$—CO—$C_{1-2}$-alkyl group, while $R_4$ is a hydrogen atom, a piperidinyl group substituted in the 1 position by an $R_6O$—CO—$C_{1-4}$-alkyl, bis-($R_6O$—CO)-$C_{1-4}$-alkyl or ($R_7O$—PO—$OR_8$)-$C_{1-2}$-alkyl group wherein $R_6$ to $R_8$ are each hydrogen atoms, a 2-oxo-morpholino group which may be substituted by 1 or 2 methyl groups, a 2-oxo-morpholinyl group which is substituted in the 4 position by a methyl, ethyl or $R_6O$—CO—$C_{1-2}$-alkyl group, while $R_6$ is defined as in claim 3 and the above-mentioned 2-oxo-morpholinyl groups in each case are linked to a carbon atom of the group F, a morpholino group which is substituted in the 2 position by a methoxy or ethoxy group, a morpholino group which is substituted in the 2 and 6 positions in each case by a methoxy or ethoxy group, a 2,2-dimethoxyethyl-$NR_5$, 2,2-diethoxyethyl-$NR_5$, 1,3-dioxolan-2-yl-methyl-$NR_5$ or 1,3-dioxan-2-yl-methyl-$NR_5$ group wherein $R_5$ is defined as above in this subgeneric aspect (14), while the aryl moieties mentioned in the definitions of the abovementioned groups denote a phenyl group which may be mono- or disubstituted by $R_{13}$, while the substituents may be identical or different and $R_{13}$ denotes a fluorine, chlorine, bromine or iodine atom, a $C_{1-2}$-alkyl, trifluoromethyl or $C_{1-2}$-alkoxy group or two groups $R_{13}$, if they are bound to adjacent carbon atoms, together denote a $C_{3-4}$-alkylene, methylenedioxy or 1,3-butadien-1,4-ylene group, the tautomers, the stereoisomers and the salts thereof.

Subgeneric aspect (15) of the invention comprises bicyclic heterocycles of general formula I according to subgeneric aspect 12, wherein denotes a hydrogen atom, $R_b$ denotes a phenyl, benzyl or 1-phenylethyl group wherein the phenyl nucleus is substituted in each case by the groups $R_1$ to $R_2$, wherein $R_1$ and $R_2$, which may be identical or different, each denote a hydrogen, fluorine, chlorine or bromine atom or a methyl group and $R_3$ denotes a hydrogen atom, $R_c$ and $R_d$ each denote a hydrogen atom, X denotes a methine group substituted by a cyano group, or a nitrogen atom, A denotes an —NH— group, B denotes a carbonyl group, C denotes a 1,2-vinylene or an ethynylene group, D together with E denotes a hydrogen atom or a methyl group, F denotes an —O—$C_{1-4}$-alkylene group, while the alkylene moiety is linked to the group G, or an oxygen atom, which may not be linked to a nitrogen atom of the group G, and G denotes an $R_6O$—CO-alkylene-$NR_5$ group wherein the alkylene moiety, which is straight-chained and contains 1 or 2 carbon atoms, may additionally be substituted by a methyl group or by an $R_6O$—CO or $R_6O$—CO-methyl group, while:

$R_5$ denotes a hydrogen atom, a $C_{1-2}$-alkyl group which may be substituted by an $R_6O$—CO group, an ethyl group optionally substituted by one or two methyl groups, which is terminally substituted by a hydroxy, $C_{1-2}$-alkylcarbonylsulphenyl or $C_{1-2}$-alkylcarbonyloxy group, a 2,2-dimethoxyethyl or 2,2-diethoxyethyl group, $R_6$ denotes a hydrogen atom, a $C_{1-8}$-alkyl group, a cyclopentyl, cyclopentylmethyl, cyclohexyl or cyclohexylmethyl group, a phenyl group optionally substituted by one or two methyl groups a phenylmethyl group which may be substituted in the phenyl moiety by one or two methyl groups, a 5-indanyl group or an $R_eCO$—O—($R_gCR_f$)-group, while $R_2$ denotes a hydrogen atom or a methyl group, $R_f$ denotes a hydrogen atom and $R_g$ denotes a $C_{1-4}$-alkyl or $C_{1-2}$-alkoxy group, a pyrrolidino or piperidino group which is substituted by an $R_4O$—CO or $R_4O$—CO-methyl group wherein $R_6$ is defined as above in this subgeneric aspect (15), a pyrrolidino or piperidino group which is substituted by two $R_6O$—CO or $R_6O$—CO-methyl groups wherein $R_6$ is defined as in above in this subgeneric aspect (15), a piperazino group which is substituted in the 4 position by an $R_6O$—CO—$C_{1-4}$-alkyl, bis-($R_6O$—CO)—$C_{1-4}$-alkyl or ($R_7O$—PO—$OR_6$)—$C_{1-2}$-alkyl group wherein $R_6$ is define as above in this subgeneric aspect (15) and $R_7$ $R_8$, which may be identical or different, each denote a hydrogen atom, a methyl, ethyl or phenyl group, a piperidinyl group substituted in the 1 position by an $R_4O$—CO—$C_{1-2}$-alkyl group wherein $R_6$ is defined as above in this subgeneric aspect (15), the tautomers, the stereoisomers and the salts thereof.

Subgeneric aspect (16) of the invention comprises bicyclic heterocycles of general formula I according to at least one of subgeneric aspects 12 to 15, characterised in that $R_n$ denotes one of the optionally substituted 1-phenyl-ethyl groups mentioned in the respective subgeneric aspects 12, 13, 14 or 15, the tautomers, the stereoisomers and the salts thereof.

Subgeneric aspect (17) of the invention is the following compounds of general formula I:
(a) 4-[(3-bromophenyl)amino]-7-(3-{4-[(ethoxycarbonyl) methyl]-piperazin-1-yl}propyloxy)-6-((vinylcarbonyl) amino]-quinazoline,
(b) 4-[(3-bromophenyl)amino]-7-(3-{4-(3-(ethoxycarbonyl) propyl]-piperazin-1-yl}propyloxy)-6-((vinylcarbonyl) amino]-quinazoline,
(c) 4-[(3-bromophenyl)amino)-7-({1-((ethoxycarbonyl) methyl]-piperidin-4-yl)oxy}-6-[(vinylcarbonyl)amino]-quinazoline,
(d) 4-[(3-bromophenyl)amino]-7-(3-{4-[(diethoxyphosphoryl)-methyl]-piperazin-1-yl}propyloxy)-6-[(vinylcarbonyl)amino]-quinazoline,
(e) 4-[(3-bromophenyl)amino]-7-{3-(N-[(ethoxycarbonyl) methyl]-N-methylamino}propyloxy)-6-[(vinylcarbonyl) amino]-quinazoline,
(f) 4-[(3-bromophenyl)amino]-6-[(4-{N-[(ethoxycarbonyl) methyl]-N-methylamino]-1-oxo-2-buten-1-yl)amino)-quinazoline,
(g) 4-[(3-bromophenyl)amino]-6-[{4-(N-[(diethoxyphosphoryl)methyl]-N-methylamino)-1-oxo-2-buten-1-yl)amino))-7-methoxy-quinazoline,
(h) (R)-4-[(1-phenylethyl)amino]-6-[(4-(N-[{ethoxycarbonyl)methyl}-N-methylamino)-1-oxo-2-buten-1-yl)amino)-7-methoxy-quinazoline,
(i) 4-[(3-bromophenyl)amino]-6-({4-[N-(2,2-dimethoxyethyl)-N-methylamino]-1-oxo-2-buten-1-yl}amino)-7-methoxy-quinazoline,
(j) 4-[(3-bromophenyl)amino]-6-({-(2-ethoxy-morpholin-4-yl)-1-oxo-2-buten-1-yl]amino)-7-methoxy-quinazoline,
(k) 4-[(3-bromophenyl)amino]-3-cyano-6-[(4-{N-I (ethoxycarbonyl)methyl]-N-methylamino)-1-oxo-2-buten-1-yl)amino)-quinoline,
(l) 4-[(3-chloro-4-fluorophenyl)amino]-6-[(4-(4-[(ethoxycarbonyl)methyl]-piperazin-1-yl-1-oxo-2-buten-1-yl}amino]-7-cyclopropylmethoxy-quinazoline,
(m) 4-[(3-chloro-4-fluorophenyl)amino)-6-[(4-{N-[2-(ethoxycarbonyl)-ethyl]-N-[(ethoxycarbonyl)methyl] amino}-1-oxo-2-buten-yl}amino)-7-cyclopropylmethoxy-quinazoline,
(n) 4-[(3-chloro-4-fluorophenyl)amino)-6-([4-(2-oxo-morpholin-4-yl)-1-oxo-2-buten-1-yl]amino}-7-cyclopropylmethoxy-quinazoline,
(o) 4-[(3-chloro-4-fluorophenyl)amino]-6-[(4-(4-[(ethoxycarbonyl)methyl]-piperazin-1-yl}-1-oxo-2-buten-1-yl)amino]-7-cyclobutyloxy-quinazoline,
(p) 4-[(3-chloro-4-fluorophenyl)amino]-6-[(4-{4-[(ethoxycarbonyl)methyl]-piperazin-1-yl)-1-oxo-2-buten-1-yl)amino-7-(2-cyclopropylethoxy)-quinazoline,
(q) (S)-4-[(3-chloro-4-fluorophenyl)amino)-6-({4-[2-(methoxy-carbonyl)-pyrrolidin-1-yl]-1-oxo-2-buten-1-yl) amino)-7-cyclopropylmethoxy-quinazoline,
(r) 4-[(3-chloro-4-fluorophenyl)amino]-6-[(4-(N-[(ethoxycarbonyl)methyl]-N-[2-(acetylsulphanyl)ethyl) amino)-1-oxo-2-buten-1-yl)amino]-7-cyclopropylmethoxy-quinazoline und
(s) 4-[(3-chloro-4-fluorophenyl)amino]-6-[(4-{N-[(ethoxycarbonyl)-methyl]-N-[2-(methylcarbonyloxy) ethyl)amino}-1-oxo-2-buten-1-yl)amino]-7-cyclopropylmethoxy-quinazoline and the salts thereof.

The compounds of general formula I may be prepared, for example, by the following processes:

a) reacting a compound of general formula

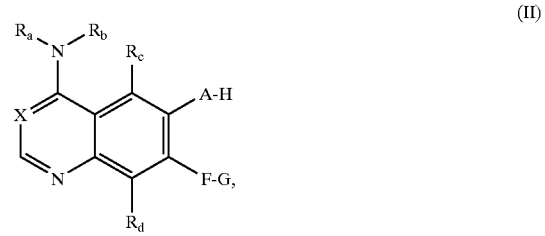

wherein
$R_e$ to $R_d$, A, F, G and X are as hereinbefore defined, with a compound of general formula $$Z_1-B-C-D-E \qquad ,(III)$$

wherein
B to E are as hereinbefore defined and
$Z_1$ denotes a leaving group such as e halogen atom, e.g. a chlorine or bromine atom, or a hydroxy group.

The reaction is optionally carried out in a solvent or mixture of solvents such as methylene chloride, dimethylformamide, benzene, toluene, chlorobenzene, tetrahydrofuran, benzene/tetrahydrofuran or dioxane optionally in the presence of an inorganic or organic base and optionally in the presence of a dehydrating agent expediently at temperatures between −50 and 150° C., preferably at temperatures between −20 and 80° C.

With a compound of general formula III, wherein $Z_1$ denotes a leaving group, the reaction is optionally carried out in a solvent or mixture of solvents such as methylene chloride, dimethylformamide, benzene, toluene, chlorobenzene, tetrahydrofuran, benzene/tetrahydrofuran or dioxane, conveniently in the presence of a tertiary organic base such as triethylamine, pyridine or 2-dimethylaminopyridine, in the presence of N-ethyl-diisopropylamine (Hünig's base), whilst these organic bases may simultaneously serve as solvent, or in the presence of an inorganic base such as sodium carbonate, potassium carbonate or sodium hydroxide solution expediently at temperatures between −50 and 150° C., preferably at temperatures between −20 and 80° C.

With a compound of general formula III, wherein $Z_1$ denotes a hydroxy group, the reaction is preferably carried out in the presence of a dehydrating agent, e.g. in the presence of isobutyl chloroformate, thionyl chloride, trimethylchlorosilane, phosphorus trichloride, phosphorus pentoxide, hexamethyldisilazane, N,N'-dicyclohexylcarbodiimide, N,N'-dicyclohexylcarbodiimide/ N-hydroxysuccinimide or 1-hydroxy-benzotriazole and optionally also in the presence of 4-dimethylamino-pyridine, N,N'-carbonyldiimidazole or triphenylphosphine/carbon tetrachloride, conveniently in a solvent such as methylene chloride, tetrahydrofuran, dioxane, toluene, chlorobenzene, dimethylsulphoxide, ethyleneglycol diethylether or sulpholane and optionally in the presence of a reaction accelerator such as 4-dimethylaminopyridine at temperatures between −50 and 150° C., but preferably at temperatures between −20 and 80° C.

b) In order to prepare compounds of general formula I, wherein the group E is linked to the group D via a nitrogen atom:

reacting a compound of general formula

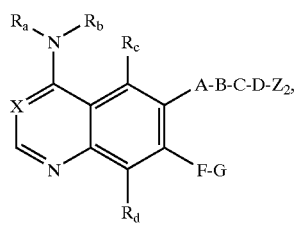
(IV)

wherein $R_e$ to $R_d$, A to D, F, G and X are as hereinbefore defined and $Z_2$ denotes a leaving group such as a halogen atom, a substituted hydroxy or sulphonyloxy group such as a chlorine or bromine atom, a methanesulphonyloxy or p-toluenesulphonyloxy group or a hydroxy group, with a compound of general formula

H—Y ,(V)

wherein

Y denotes one of the groups mentioned for E hereinbefore, which is linked to the group D via a nitrogen atom.

The reaction is conveniently carried out in a solvent such as isopropanol, butanol, tetrahydrofuran, dioxan, toluene, chlorobenzene, dimethylformamide, dimethylsulphoxide, methylene chloride, ethyleneglycol monomethylether, ethyleneglycol diethylether or sulpholane, optionally in the presence of an inorganic or tertiary organic base, e.g. sodium carbonate or potassium hydroxide, a tertiary organic base, e.g. triethylamine, or in the presence of N-ethyl-diisopropylamine (Hünig's base), whilst these organic bases may simultaneously serve as solvent, and optionally in the presence of a reaction accelerator such as an alkali metal halide at temperatures between −20 and 150° C., but preferably at temperatures between −10 and 100° C. The reaction may, however, also be carried out without a solvent or in an excess of the compound of general formula V used.

If $Z_2$ in a compound of general formula IV denotes a hydroxy group, the reaction is preferably carried out in the presence of a dehydrating agent, e.g. in the presence of isobutyl chloroformate, thionylchloride, trimethylchlorosilane, phosphorus trichloride, phosphorus pentoxide, hexamethyldisilazane, N,N,-dicyclohexylcarbodiimide, N,N'-dicyclohexylcarbodiimide/N-hydroxysuccinimide or 1-hydroxy-benzotriazole and optionally also in the presence of 4-dimethylamino-pyridine, N,N'-carbonyldiimidazole or triphenylphosphine/carbon tetrachloride, conveniently in a solvent such as methylene chloride, tetrahydrofuran, dioxane, toluene, chlorobenzene, dimethylsulphoxide, ethyleneglycol diethylether or sulpholane and optionally in the presence of a reaction accelerator such as 4-dimethylaminopyridine at temperatures between −50 and 150° C., but preferably at temperatures between −20 and 80° C.

c) In order to prepare compounds of general formula I wherein D together with E denotes a $R_gCO$—O—$(R_eCR_f)$—O—CO— group:

reacting a compound of general formula:

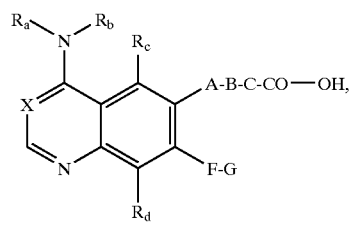
(VI)

wherein $R_a$ to $R_d$ A to C, F, G and X are as hereinbefore defined, with a compound of general formula $R_gCO$—O—$(R_eCR_f)$—$Z_3$ (VII)

wherein $R_e$ to $R_g$ are as hereinbefore defined and $Z_3$ denotes a leaving group such as a halogen atom, e.g. a chlorine, bromine or iodine atom.

The reaction is appropriately carried out in a solvent such as tetrahydrofuran, dioxane, toluene, chlorobenzene, dimethylformamide, dimethylsulphoxide, methylene chloride, acetonitrile, N-methyl-pyrrolidinone, ethylenglycol diethylether or sulpholane, optionally in the presence of an inorganic base, e.g. sodium carbonate or potassium hydroxide, or a tertiary organic base, e.g. triethylamine, N-ethyl-diisopropylamine (Hünig's base), 1,8-diazabicyclo [5,4,0] undec-7-ene or N,N'-dicyclohexyl-morpholinocarboxamidine, whilst these organic bases may simultaneously serve as solvents, and optionally in the presence of a reaction accelerator such as an alkali metal halide at temperatures between −20 and 150° C., but preferably at temperatures between −10 and 100° C. However, the reaction may also be carried out without a solvent or in an excess of the compound of general formula VII used.

If according to the invention a compound of general formula I is obtained which contains a hydroxy, amino, alkylamino or imino group, this may be converted by acylation or sulphonylation into a corresponding acyloxy, acylamino, N-alkyl-acyl-amino, acyl-imino, sulphonyloxy, sulphonylamino, N-alkyl-sulphonylamino or sulphonylimino compound, whilst a sulphonyloxy compound thus obtained may further be converted into a corresponding sulphenyl compound by reacting with an alkali metal salt of a thin compound, or if a compound of general formula I is obtained which contains an amino, alkylamino or imino group, this may be converted by alkylation or reductive alkylation into a corresponding alkyl compound of general formula I or if a compound of general formula I is obtained wherein E denotes a bis-[2,2-di-($C_{1-4}$-alkoxyethyl]amino group, this may be converted by intramolecular cyclisation into a corresponding morpholino compound of general formula I, or if a compound of general formula I is obtained wherein E or G denotes an optionally substituted N-(2-hydroxyethyl)-glycine or N-(2-hydroxyethyl)-glycine ester group, this may be converted by intramolecular cyclisation into a corresponding 2-oxo-morpholino compound, or if a compound of general formula I is obtained which contains a carboxy or hydroxyphosphoryl group, this may be converted by alkylation into a corresponding ester of general formula I.

The subsequent acylation or sulphonylation is optionally carried out in a solvent or mixture of solvents such as methylene chloride, dimethylformamide, benzene, toluene, chlorobenzene, tetrahydrofuran, benzene/tetrahydrofuran or dioxane with a corresponding acyl or sulphonyl derivative optionally in the presence of a tertiary organic base or in the presence of an inorganic base or in the presence of a dehydrating agent, e.g. in the presence of isobutyl chloroformate, thionyl chloride, trimethyl chlorosilane, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide or 1-hydroxy-benzotriazole and optionally additionally in the presence of 4-dimethylaminopyridine, N,N'-carbonyldiimidazole or triphenylphosphine/carbon tetrachloride, expediently at temperatures between 0 and 150° C., preferably at temperatures between 0 and 80° C.

The subsequent alkylation is optionally carried out in a solvent or mixture of solvents such as methylene chloride, dimethylformamide, benzene, toluene, chlorobenzene, tetrahydrofuran, benzene/tetrahydrofuran or dioxan with an alkylating agent such as a corresponding halide or sulphonic acid ester, e.g. with methyl iodide, ethyl bromide, dimethylsulphate or benzyl chloride, optionally in the presence of a tertiary organic base or in the presence of an inorganic base, expediently at temperatures between 0 and 150° C., preferably at temperatures between 0 and 100° C.

The subsequent reductive alkylation is carried out with a corresponding carbonyl compound such as formaldehyde, acetaldehyde, propionaldehyde, acetone or butyraldehyde in the presence of a complex metal hydride such as sodium borohydride, lithium borohydride, sodium triacetoxyborohydride or sodium cyanoborohydride expediently at a pH of –7 and at ambient temperature or in the presence of a hydrogenation catalyst, e.g. with hydrogen in the presence of palladium/charcoal, at a hydrogen pressure of 1 to 5 bar. The methylation may also be carried out in the presence of formic acid as reducing agent at elevated temperatures, e.g. at temperatures between 60 and 120° C.

The subsequent intramolecular cyclisation is optionally carried out in a solvent such as acetonitrile, methylene chloride, tetrahydrofuran, dioxan or toluene in the presence of an axis such as hydrochloric acid or p-toluenesulphonic acid at temperatures between –10 and 120° C.

The subsequent esterification is carried out by reacting a corresponding carboxylic acid, phosphonic acid, phosphinic acid or the salts thereof with a corresponding alkyl halide, optionally in a solvent or mixture of solvents such as methylene chloride, dimethylformamide, dimethylsulphoxide, sulpholane, acetonitrile, N-methylpyrrolidinone, benzene, toluene, chlorobenzene, tetrahydrofuran, benzene/tetrahydrofuran or dioxane, optionally in the presence of an inorganic or tertiary organic base, conveniently at temperatures between 0 and 150° C., preferably at temperatures between 0 and 80° C.

Moreover, compounds of general formula 1 wherein E or G denotes a piperazino or homopiperazino group each substituted in position 4 by an $R_4O\!-\!CO\!-\!C_{1-4}$-alkyl group wherein R, is as hereinbefore defined may also be prepared, for example, by reacting a corresponding compound containing a piperazino or homopiperazino group each unsubstituted in position 4 with a compound of general formula $$R_6O\!-\!CO\!-\!C_{1-4}\text{-alkyl}\!-\!Z_6 \qquad (VIII)$$

wherein
$R_6$ is as hereinbefore defined and
$Z_4$ denotes a leaving group such as a chlorine or bromine atom or an alkyl or arylsulfonyloxy group, or compounds of general formula I wherein E or G denotes a piperazino or homopiperazino group each substituted in position 4 by an $R_6O\!-\!CO\!-\!CH_3CH_3$-group wherein $R_6$ is as hereinbefore defined may also be prepared, for example, by reacting a corresponding compound containing a piperazino or homopiperazino group each unsubstituted in position 4 with a compound of general formula

$$R_6O\!-\!CO\!-\!CH|CH_2, \qquad (IX)$$

wherein
$R_4$ is as hereinbefore defined, or
compounds of general formula I wherein C denotes a 1,2-vinylene group may also be prepared, for example, by reacting a compound of general formula

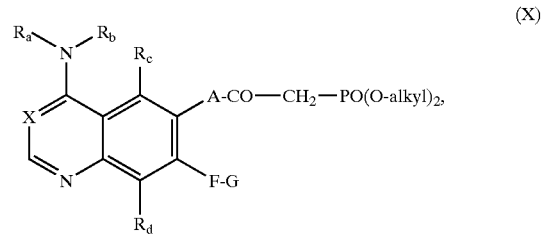

wherein $R_e$ to $R_dA$, F, G and X are as hereinbefore defined and alkyl denotes a lower alkyl group, with a compound of general formula

$$OCH\!-\!D\!-\!E \qquad ,(XI)$$

wherein
D and E are as hereinbefore defined according to known methods.

In the reactions described above, any reactive groups-present such as hydroxy, carboxy, phosphono, O-alkylphosphono, amino, alkylamino or imino groups may be protected during the reaction by conventional protecting groups which are cleaved again after the reaction.

For example, a protecting group for a hydroxy group may be a trimethylsilyl, acetyl, benzoyl, methyl, ethyl, tert.-butyl, trityl, benzyl or tetrahydropyranyl group, protecting groups for a carboxy group may be the trimethylsilyl, methyl, ethyl, tert.-butyl, benzyl or tetrahydropyranyl group, protecting groups for a phosphono group may be an alkyl group such as the methyl, ethyl, isopropyl or n-butyl group, the phenyl or benzyl group and protecting groups for an amino, alkylamino or imino group may be a formyl, acetyl, trifluoroacetyl, ethoxycarbonyl, tert.-butoxycarbonyl, benzyloxycarbonyl, benzyl, methoxybenzyl or 2,4-dimethoxybenzyl group and for the amino group additionally a phthalyl group.

Any protecting group used is optionally subsequently cleaved for example by hydrolysis in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C.

However, a benzyl, methoxybenzyl or benzyloxycarbonyl group is cleaved, for example, hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at temperatures between 20 and 60° C., and at a hydrogen pressure of 1 to 7 bar, but preferably 3 to 5 bar. A 2,4-dimethoxybenzyl group however, is preferably cleaved in trifluoroacetic acid in the presence of anisol.

A tert-butyl or tert.butyloxycarbonyl group is preferably cleaved by treating with an acid such as trifluoroacetic acid or hydrochloric acid or by treating with iodotrimethylsilane optionally using a solvent such as methylene chloride, dioxane, methanol or diethylether.

A trifluoroacetyl group is preferably cleaved by treating with an acid such as hydrochloric acid, optionally in the presence of a solvent such as acetic acid at temperatures between 50 and 120° C. or by treating with sodium hydroxide solution optionally in the presence of a solvent such as tetrahydrofuran at temperatures between 0 and 50° C.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

A single alkyl group may be cleaved from an O,O'-dialkylphosphono group with sodium iodide, for example, in a solvent such as acetone, methylethylketone, acetonitrile or dimethylformamide at temperatures between 90 and 150° C., but preferably at temperatures between 60 and 100° C.

Both alkyl groups may be cleaved from an O,O'-dialkylphosphono group with iodotrimethylsilane, bromotrimethylsilane or chlorotrimethylsilane/sodium iodide, for example, in a solvent such as methyl chloride, chloroform or acetonitrile at temperatures between 0° C. and the boiling temperature of the reaction mixture, but preferably at temperatures between 20 and 60° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-menthyloxycarbonyl.

Furthermore, the compounds of formula I may be converted into the salts thereof, and particularly for pharmaceutical use into the physiologically acceptable salts with inorganic or organic acids. Acids which may be used for this purpose include for example hydrochloric acid, hydrobromic acid, sulphuric acid, phosphoric acid, fumaric acid, succinic acid, lactic acid, citric acid, tartaric acid or maleic acid.

Moreover, if the new compounds of formula I thus obtained contain a carboxy or hydroxyphosphoryl group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, arginine, cyclohexylamine, ethanolamine, diethanolamine and triethanolamine.

The compounds of general formulae II to XI used as starting materials are known from the literature in some eases or may be obtained by methods known from the literature (cf. Examples I to XVIII).

For example, a starting compound of general formula II is obtained by reacting a corresponding fluoronitro compound with a corresponding alkoxide and subsequently reducing the nitro compound thus obtained or a starting compound of general formula IV is obtained by reacting a corresponding fluoronitro compound with a corresponding alkoxide, subsequently reducing the nitro compound thus obtained and then acylating with a corresponding compound.

As already mentioned hereinbefore, the compounds of general formula I according to the invention and the physiologically acceptable salts thereof have valuable pharmacological properties, particularly an inhibiting effect on signal transduction mediated by the Epidermal Growth Factor receptor (EGF-R), whilst this may be achieved for example by inhibiting ligand bonding, receptor dimerisation or tyrosinekinase itself. It is also possible to block the transmission of signals to components located further down.

The biological properties of the new compounds were investigated as follows:

The inhibition of the EGF-R-mediated signal transmission can be demonstrated e.g. with cells which express human EGF-R and whose survival and proliferation depend on stimulation by EGF or TGF-alpha. A cell line of murine origin dependent on interleukin-3 (IL-3) which was genetically modified to express functional human EGF-R was used here. The proliferation of these cells known as F/L-HERc can therefore be stimulated either by murine IL-3 or by EGF (cf. von Rüden, T. et al. in EMBO J. 7, 2749–2756 (1988) and Pierce, J. H. et al. in Science 239. 628–631 (1988)).

The starting material used for the F/L-HERc cells was the cell line FDC-PI, the production of which has been described by Dexter, T. M. et al, in J. Exp. Med. 152, 1036–1047 (1980). alternatively, however, other growth-factor-dependent cells may also be used (cf. for example Pierce, J. H. et al. in Science 239, 628–631 (1988), Shibuya, H. et al. in Cell 70, 57–67 (1992) and alexander, W. S. et al. in EMBO J. 10, 3683–3691 (1991)). For expressing the human EGF-R cDNA (cf. Ullrich, A. et al. in Nature 309, 418–425 (1984)) recombinant retroviruses were used as described by von Rüden, T. et al., EMBO J. 7, 2749–2756 (1988), except that the retroviral vector LXSN (cf. Miller, A. D. et al. in BioTechniques 1, 980–990 (1989)) was used for the expression of the EGF-R cDNA and the line GP+E86 (cf, Markowitz, D, et al. in J. Virol. 62, 1120–1124 (1988)) was used as the packaging cell.

The test was performed as follows:

F/L-HERC cells were cultivated in RPMI/1640 medium (BioWhittaker), supplemented with 10% foetal calf serum (FCS, Boehringer Mannheim). 2 mM glutamine (BioWhittaker), standard antibiotics and 20 ng/ml of human EGF (Promega), at 37° C. and 5% $CO_2$. In order to investigate the inhibitory activity of the compounds according to the invention, $1.5 \times 10^4$ cells per well were cultivated in triplicate in 96-well plates in the above medium (200 ml), the cell proliferation being stimulated with either EGF (20 ng/ml) or murine IL-3. The IL-3 used was obtained from culture supernatants of the cell line X63/0 mIL-3 (cf. Karasuyama, 4. et al. in Eur. J. Immunol. 18, 97–104 (19881). The compounds according to the invention were dissolved in 100% dimethylsulphoxide (DMSO) and added to the cultures in various dilutions, the maximum DMSO concentration being 1%. The cultures were incubated for 48 hours at 37° C.

In order to determine the inhibitory activity of the compounds according to the invention the relative cell number was measured in O.D. units using the Cell Titer 96™ $AQ_{ueous}$ Non-Radioactive Cell Proliferation Assay (Promega). The relative cell number was calculated as a percentage of the control (F/LHERc cells without inhibitor) and the concentration of active substance which inhibits the proliferation of the cells by 50% ($IC_{50}$) was derived therefrom. The following results were obtained:

| Compound (Example no.) | Inhibition of EGF-dependent proliferation $IC_{50}$ [nM] |
|---|---|
| 1 | 2.6 |
| 1(4) | 15 |
| 1(6) | 15 |
| 1(10) | 21 |
| 1(13) | 8.7 |
| 2 | 5.2 |
| 2(4) | 6.7 |
| 5(2) | 9 |
| 5(8) | 1.8 |
| 5(10) | 1.8 |
| 5(12) | 18 |
| 5(18) | 7.4 |
| 5(22) | 58 |
| 5(25) | 74 |
| 5(29) | 1.9 |
| 5(32) | 17 |
| 5(36) | 3 |
| 8(1) | 109 |
| 11 | 74 |

The compounds of general formula I according to the invention thus inhibit the signal transduction by tyrosine kinases, as demonstrated by the example of the human EGF receptor, and are therefore useful for treating pathophysiological processes caused by hyperfunction of tyrosinekinases. These are e.g. benign or malignant tumours, particularly tumours of epithelial and neuroepithelial origin, metastasisation and the abnormal proliferation of vascular endothelial cells (neoangiogenesis).

The compounds according to the invention are also useful for preventing and treating diseases of the airways and lungs which are accompanied by increased or altered production of mucus caused by stimulation by tyrosine kinases, e.g. in inflammatory diseases of the airways such as chronic bronchitis, chronic obstructive bronchitis, asthma, bronchiectasias, allergic or non-allergic rhinitis or sinusitis, cystic fibrosis, α1-antitrypsin deficiency, or coughs, pulmonary emphysema, pulmonary fibrosis and hyperreactive airways.

The compounds are also suitable for treating diseases of the gastrointestinal tract and bile duct and gall bladder which are associated with disrupted activity of the tyrosine kinases, such as may be found e.g. in chronic inflammatory changes such as cholecystitis, Crohn's disease, ulcerative colitis, and ulcers in the gastrointestinal tract or such as may occur in diseases of the gastrointestinal tract which are associated with increased secretions such as Ménétrier's disease, secreting adenomas and protein loss syndrome, and also for treating nasal polyps and polyps of the gastrointestinal tract of varying origins, such as villous or adenomatous polyps of the large bowel, but also polyps in *familial polyposis coli*, intestinal polyps in Gardner's syndrome, polyps throughout the entire gastrointestinal tract in Peutz-Jeghers syndrome, in inflammatory Pseudopolyps, in juvenile polyps, in *colitis cystica profunda* and in *pneumatosis cystoides intestinales*.

In addition, the compounds of general formula I and the physiologically acceptable salts thereof may be used to treat kidney diseases, particularly in cystic changes such as cystic kidneys, for treating renal cysts which may be of idiopathic origin or which occur in syndromes such as tuberous sclerosis, in von Hippel-Lindau syndrome, in nephronophthisis and spongy kidney and other diseases caused by abnormal function of tyrosine kinases, such as e.g. epidermal hyperproliferation (psoriasis), inflammatory processes, diseases of the immune system, hyperproliferation of haematopoietic cells, etc.

By reason of their biological properties the compounds according to the invention may be used on their own or in conjunction with other pharmacologically active compounds, for example in tumour therapy, in monotherapy or in conjunction with other anti-tumour therapeutic agents, for example in combination with topoisomerase inhibitors (e.g. etoposide), mitosis inhibitors (e.g. vinblastin), compounds which interact with nucleic acids (e.g. cis-platin, cyclophosphamide, adriamycin), hormone antagonists (e.g. tamoxifen), inhibitors of metabolic processes (e.g. 5-FU etc.), cytokines (e.g. interferons), antibodies, etc. For treating respiratory tract diseases, these compounds may be used on their own or in conjunction with other therapeutic agents for the airways, such as substances with a secretolytic, broncholytic and/or antiinflammatory activity. For treating diseases in the region of the gastrointestinal tract, these compounds may also be administered on their own or in conjunction with substances having an effect on motility or secretion or with antiinflammatories. These combinations may be administered either simultaneously or sequentially.

These compounds may be administered either on their own or in conjunction with other active substances by intravenous, subcutaneous, intramuscular, intrarectal, intraperitoneal or intranasal route, by inhalation or transdermally or orally, whilst aerosol formulations are particularly suitable for inhalation.

For pharmaceutical use the compounds according to the invention are generally used for warm-blooded vertebrates, particularly humans, in doses of 0.01–100 mg/kg of body weight, preferably 0.1–15 mg/kg. For administration they are formulated with one or more conventional inert carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearylalcohol, carboxymethylcellulose or fatty substances such as hard fat or suitable mixtures thereof in conventional galenic preparations such as plain or coated tablets, capsules, powders, suspensions, solutions, sprays or suppositories.

The following Examples are intended to illustrate the present invention without restricting it:
Preparation of the starting compounds:

Example I 6-amino-4-[(3-bromophenyl)amino]-7-(3-{4-[(ethoxycarbonyl)methyl]-piperazin-1-yl}propyloxy)-quinazoline 180 mg of iron powder are added to 465 mg of 4-[(3-bormophenyl)amino]-7-(3-{4-[(ethoxycarbonyl)methyl]-piperazin-1-yl}propyloxy)-6-nitro-quinazoline in 20 ml of ethanol. The reaction mixture is heated to boiling and combined with 0.6 ml of glacial acetic acid, then a further 2 ml of water are pipetted in. The reaction solution turns dark and is heated for about another half hour until the reaction is complete. The solvent is distilled off using the rotary evaporator, the residue is taken up in methylene chloride and made alkaline with 3 ml of 4N sodium hydroxide solution. The organic phase is separated off and the aqueous phase extracted with methylene chloride. The combined extracts are dried over magnesium sulphate and concentrated by evaporation. The crude product is stirred with a little diethyl ether, suction filtered and washed again. The light grey crystals obtained are dried in the desiccator. Yield: 350 mg (79% of theory), Melting point: 183–189° C. Mass spectrum (ESI*): m/z=543, 545 [M+H]*

The following compounds are obtained analogously to Example I:

(1) 6-amino-4-[(3-bromophenyl)amino]-7-(3-{4-[(isopropyloxycarbonyl)methyl]-piperazin-1-yl}propyloxy)-quinazoline (the reaction is carried out in dioxane instead of ethanol) Melting point: 188–193° C. Mass spectrum (ESI*): m/z=557, 559 [M+H]*

(2) 6-amino-4-[(3-bromophenyl)amino]-7-(3-{4-[(cyclohexyloxycarbonyl)methyl]-piperazin-1-yl}propyloxy)-quinazoline (the reaction is carried out in dioxane instead of ethanol) Melting point: 166–169° C. Mass spectrum (ESI*): m/z=597, 599 [M+H]*

(3) 6-amino-4-[(3-bromophenyl)amino]-7-(3-{4-[2-(ethoxycarbonyl)ethyl]-piperazin-1-yl}propyloxy)-quinazoline Melting point: 120–123° C. Mass spectrum (ESI*): m/z=557, 559 [M+H]*

(4) 6-amino-4-[(3-bromophenyl)amino]-7-(3-{4-[3-(ethoxycarbonyl)propyl]-piperazin-1-yl}propyloxy)-quinazoline Melting point: 119–122° C. Mass spectrum (ESI*): m/z=571, 573 [M+H]*

(5) 6-amino-4-[(3-bromophenyl)amino]-7-(2-{4-[(ethoxycarbonyl)methyl]-piperazin-1-yl}ethoxy)-quinazoline Melting point: 147–161° C. Mass spectrum (ESI*): m/z=529, 531 [M+H]*

(6) 6-amino-4-[(3-bromophenyl)amino]-7-{(1-[(ethoxycarbonyl)methyl]-piperidin-4-yl}oxy)-quinazoline Melting point: 202° C. Mass spectrum (ESI*): m/z=500, 502 [M+H]*

(7) 6-amino-4-[(3-bromophenyl)amino]-7-({1-[(ethoxycarbonyl)methyl]-piperidin-4-yl}methoxy)-quinazoline Melting point: 155° C. Mass spectrum (ESI*): m/z=514, 516 [M+H]*

(8) 6-amino-4-[(3-bromophenyl)amino]-7-(2-{1-[(ethoxycarbonyl)methyl]-piperidin-4-yl}ethoxy)-quinazoline Melting point: 143° C. Mass spectrum (ESI*): m/z=528, 530 [M+H]*

(9) 6-amino-4-[(3-bromophenyl)amino]-7-(3-{1-[(ethoxycarbonyl)methyl]-piperidin-4-yl}propyloxy)-quinazoline Melting point: 181° C. Mass spectrum (ESI*): m/z=542, 544 [M+H]*

(10) 6-amino-4-[(3-bromophenyl)amino]-7-(3-{4-[(diethoxyphosphoryl)methyl]-piperazin-1-yl}propyloxy)-quinazoline Melting point: 201–205° C. Mass spectrum (ESI*): m/z=607, 609 [M+H]*

(11) 6-amino-4-[(3-bromophenyl)amino]-7-(3-{4-[(butyloxycarbonyl)methyl]-piperazin-1-yl}propyloxy)-quinazoline Melting point: 158–160° C. Mass spectrum (ESI*): m/z=571, 573 [M+H]*

(12) 6-amino-4-[(3-bromophenyl)amino]-7-(3-{N-[(ethoxycarbonyl)methyl]-N-methylamino}propyloxy)-quinazoline $R_f$ value: 0.49 (silica gel, methylene chloride/methanol/concentrated aqueous ammonia solution=90:10:0.1) Mass spectrum (ESI*): m/z=488, 490 [M+H]*

(13) 6-amino-4-[(3-bromophenyl)amino]-7-(2-{N-[(ethoxycarbonyl)methyl]-N-methylamino}ethoxy)-quinazoline $R_f$ value: 0.50 (silica gel, methylene chloride/methanol/concentrated aqueous ammonia solution=90:10:0.1)

(14) 6-amino-4-[(3-chloro-4-fluorophenyl)amino]-7-cyclopropylmethoxy-quinazoline Melting point: 209° C. $R_f$ value: 0.68 (silica gel, ethyl acetate)

(15) 6-amino-4-[(3-bromophenyl)amino]-7-(4-{N-[(ethoxycarbonyl)methyl]-N-methylamino}butyloxy)-quinazoline $R_f$ value: 0.44 (silica gel, methylene chloride/methanol/concentrated aqueous ammonia solution=90:10:0.1)

(16) 6-amino-4-[(3-chloro-4-fluorophenyl)amino]-7-cyclohexylmethoxy-quinazoline Melting point: 234° C. Mass spectrum (ESI*): m/z=401, 403 [M+H]*

(17) 6-amino-4-[(3-chloro-4-fluorophenyl)amino]-7-cyclohexyloxy-quinazoline Melting point: 176° C. Mass spectrum (ESI*): m/z=387, 389 [M+H]*

(18) 6-amino-4-[(3-chloro-4-fluorophenyl)amino]-7-cyclobutyloxy-quinazoline Melting point: 238–239° C. Mass spectrum (ESI*): m/z=359, 361 [M+H]*

(19) 6-amino-4-[(3-chloro-4-fluorophenyl)amino]-7-cyclobutylmethoxy-quinazoline Melting point: 214–215° C. Mass spectrum (ESI*): m/z=373, 375 [M+H]*

(20) 6-amino-4-[(3-chloro-4-fluorophenyl)amino]-7-cyclopentylmethoxy-quinazoline Melting point: 218–219° C. Mass spectrum (ESI*): m/z=387, 389 [M+H]*

(21) 6-amino-4-[(3-chloro-4-fluorophenyl)amino]-7-(2-cyclopropylethoxy)-quinazoline Melting point: 188–190° C. Mass spectrum (ESI*): m/z=373, 375 [M+H]*

(22) 6-amino-4-[(3-chloro-4-fluorophenyl)amino]-7-cyclopentyloxy-quinazoline Melting point: 204° C. Mass spectrum (ESI*): m/z=373, 375 [M+H]*

(23) 6-amino-4-[(3-chlorophenyl)amino]-7-methoxy-quinazoline Melting point: 208–209° C. Mass spectrum (ESI*): m/z=301, 303 [M+H]*

(24) (R)-6-amino-4-[(1-phenylethyl)amino]-7-methoxy-quinazoline $R_f$ value: 0.42 (silica gel, methylene chloride/methanol/concentrated aqueous ammonia solution=9:1:0.1) Mass spectrum (ESI*): m/z=295 [M+H]*

(25) 6-Amino-4-[(R)-(1-phenyl-ethyl)amino]-7-{2-[2-(methoxycarbonyl)-piperidin-1-yl]-ethoxy}-quinazoline $R_f$ value: 0.50 (silica gel, methylene chloride/methanol/concentrated aqueous ammonia=90:10:1) Mass spectrum (ESI*): m/z=448 [M–H]*

(26) 6-Amino-4-[(R)-(1-phenyl-ethyl)amino]-7-{2-[(R)-2-(methoxycarbonyl)-pyrrolidin-1-yl]-ethoxy}-quinazoline R$_f$ value: 0.20 (silica gel, methylene chloride/methanol= 95:5) Mass spectrum (ESI*): m/z=434 [M–H]*
(27) 6-Amino-4-[(R)-(1-phenyl-ethyl)amino]-7-[(S)-2-(methoxycarbonyl)-pyrrolidin-1-yl]-ethoxy}-quinazoline R$_f$ value: 0.20 (silica gel, methylene chloride/methanol= 95:5) Mass spectrum (ESI*): m/z=434 [M–H]*
(28) 6-Amino-4-[(R)-(1-phenyl-ethyl)amino]-7-{3-[(R)-2-(methoxycarbonyl)-pyrrolidin-1-yl]-propyloxy}-quinazoline R$_f$ value: 0.40 (silica gel, methylene chloride/methanol=9:1) Mass spectrum (ESI*): m/z=448 [M–H]*
(29) 6-Amino-4-[(R)-(1-phenyl-ethyl)amino]-7-{4-[2-(methoxycarbonyl)-piperidin-1-yl]-butyloxy}-quinazoline R$_f$ value: 0.20 (silica gel, methylene chloride/methanol=95:5) Mass spectrum (ESI*): m/z=476 [M–H]*
(30) 6-Amino-4-[(R)-(1-phenyl-ethyl)amino]-7-cyclobutyloxy-quinazoline R$_f$ value: 0.28 (silica gel, ethyl acetate) Mass spectrum (ESI*): m/z=335 [M+H]*
(31) 6-Amino-4-[(R)-(1-phenyl-ethyl)amino]-7-cyclopentyloxy-quinazoline
R$_f$ value: 0.20 (silica gel, ethyl acetate) Mass spectrum (ESI*): m/z=349 [M+H]*
(32) 6-Amino-4-[(R)-(1-phenyl-ethyl)amino]-7-cyclopropylmethoxy-quinazoline Melting point: 183° C. Mass spectrum (ESI*): m/z=335 [M+H]*
(33) 6-Amino-4-benzylamino-7-cyclopropylmethoxy-quinazoline Melting point: 190° C. Mass spectrum (ESI*): m/z=321 [M+H]*
(34) 6-Amino-4-[(R)-(1-phenyl-ethyl)amino]-7-(2-(N-[(methoxycarbonyl)methyl)-N-methylamino)-ethoxy]-quinazoline R$_f$ value: 0.16 (silica gel, methylene chloride/methanol=95:5) Mass spectrum (EI): m/z=409 [M]*

Example II

4-[(3-bromophenyl)amino]-7-(3-{4-[(ethoxycarbonyl)methyl]-piperazin-1-yl}propyloxy)-6-nitro-quinazoline 292 mg of ethyl bromoacetate are added to 780 mg of 4-[(3-bromophenyl)amino]-7-[3-(piperazin-1-yl)propyloxy]-6-nitroquinazoline and 0.55 ml of triethylamine in 7 ml of acetonitrile. The reaction mixture is stirred for one hour at ambient temperature, then for about 1.5 hours at 65° C. and then for a further 2 days at ambient temperature. As the reaction is incomplete, 2 drops of ethyl bromoacetate are added twice more. The reaction solution is concentrated by evaporation and the residue is partitioned between copious amounts of ethyl acetate and dilute potassium carbonate solution. The organic phase is washed with water and saturated sodium chloride solution, dried over magnesium sulphate and concentrated by evaporation. The yellowish, resin-like crude product is recrystallised from 7 ml of ethanol. The yellow crystals are washed with some cold ethanol and dried in the desiccator. Yield: 640 mg (70% of theory), Melting point: 75° C. Mass spectrum (ESI*): m/z=573, 575 [M+H]*

The following compounds are obtained analogously to Example II:
(1) 4-[(3-bromophenyl)amino]-7-(3-{4-[(isopropyloxycarbonyl)methyl]-piperazin-1-yl)propyloxy)-6-nitro-quinazoline Melting point: 71–74° C. Mass spectrum (ESI*): m/z=587, 589 [M+H]*
(2) 4-[(3-bromophenyl)amino]-7-(3-{4-[(cyclohexyloxycarbonyl)methyl]-piperazin-1-yl}propyloxy)-6-nitro-quinazoline Melting point: 80–100° C. Mass spectrum (ESI*): m/z=627, 629 [M+H]*
(3) 4-[(3-bromophenyl)amino]-7-(3-{4-[2-ethoxycarbonyl)ethyl]-piperazin-1-yl}propyloxy)-6-nitro-quinazoline (reaction is carried out with ethyl acrylate in ethanol) Melting point: 153–156° C. Mass spectrum (ESI*): m/z=587, 589 [M+H]*
(4) 4-[(3-bromophenyl)amino]-7-(3-{4-[3-(ethoxycarbonyl)propyl]-piperazin-1-yl}propyloxy)-6-nitro-quinazoline Melting point: 50–58° C. Mass spectrum (ESI*): m/z=601, 603 [M+H]*
(5) 4-[(3-bromophenyl)amino]-7-(2-{4-[(ethoxycarbonyl)methyl]-piperazin-1-yl}ethoxy)-6-nitro-quinazoline Melting point: 103–120° C. Mass spectrum (ESI*): m/z=559, 561 [M+H]*
(6) 4-[(3-bromophenyl)amino]-7-({(1-[(ethoxycarbonyl)methyl]-piperidin-4-yl]oxy)-6-nitro-quinazoline Melting point: 151° C. Mass spectrum (ESI*): m/z=530, 532 [M+H]*
(7) 4-[(3-bromophenyl)amino]-7-({1-[(ethoxycarbonyl)methyl]-piperidin-4-yl}methoxy)-6-nitro-quinazoline Melting point: 189° C. Mass spectrum (ESI*): m/z=544, 546 [M+H]*
(8) 4-[(3-bromophenyl)amino]-7-(2-{1-[(ethoxycarbonyl)methyl]-piperidin-4-yl}ethoxy)-6-nitro-quinazoline Melting point: 185–187° C. Mass spectrum (ESI*): m/z=558, 560 [M+H]*
(9) 4-[(3-bromophenyl)amino]-7-(3-(1-[(ethoxycarbonyl)methyl]-piperidin-4-yl}propyloxy)-6-nitro-quinazoline Melting point: 101° C. Mass spectrum (ESI*): m/z=572, 574 [M+H]*
(10) 4-[(3-bromophenyl)amino]-7-(3-{4-[(butyloxycarbonyl)methyl]-piperazin-1-yl}propyloxy)-6-nitro-quinazoline Melting point: 70–75° C. Mass spectrum (ESI*): m/z=601, 603 [M+H]*

Example III

4-[(3-bromophenyl)amino]-6-nitro-7-[3-(piperazin-1-yl)propyloxy]-quinazoline 15 ml of trifluoroacetic acid are added dropwise to a suspension of 7.05 g of 4-[(3-bromophenyl)amino]-6-nitro-7-{3-[4-(tert-butyloxycarbonyl)-piperazin-1-yl]propyloxy}-quinazoline in 80 ml of methylene chloride at ambient temperature with stirring. While gas is given off, a dark solution is rapidly formed which is stirred for approximately a further 1.5 hours at ambient temperature. The reaction solution is concentrated by evaporation using the rotary evaporator. The resin-like residue is taken up in methylene chloride, combined with ice water and carefully made alkaline with 4N sodium hydroxide solution. Partially precipitated product is dissolved by the addition of more methylene chloride and methanol. The aqueous phase is separated off and extracted with methylene chloride/methanol (9:1). The combined extracts are washed with water, dried over magnesium sulphate and concentrated by evaporation. The crude product is heated to boiling with 25 ml of tert. butylmethylether, cooled with stirring and suction filtered. The yellow crystals thus obtained are washed with diethylether and dried. Yield: 5.16 g (88% of theory). Melting point: 179–182° C. Mass spectrum (ESI*): m/z=487, 489 [M+H]*

The following compounds are obtained analogously to Example III:
(1) 4-[(3-bromophenyl)amino]-6-nitro-7-[2-(piperazin-1-yl)ethoxy]-quinazoline Melting point: 133–136° C. Mass spectrum (ESI*): m/z=473, 475 [M+H]*
(2) 4-[(3-bromophenyl)amino]-6-nitro-7-[(piperidin-4-yl)oxy]-quinazoline Melting point: 131° C. Mass spectrum (ESI*): m/z=444, 446 [M+H]*
(3) 4-[(3-bromophenyl)amino]-6-nitro-7-[(piperidin-4-yl)methoxy]-quinazoline Melting point: 145° C. Mass spectrum (ESI*): m/z=458, 460 [M+H]*
(4) 4-[(3-bromophenyl)amino]-6-nitro-7-[2-(piperidin-4-yl)ethoxy]-quinazoline Melting point: 228° C. Mass spectrum (ESI*): m/z=472, 474 [M+H]*

(5) 4-[(3-bromophenyl)amino]-6-nitro-7-[3-(piperidin-4-yl)propyloxy]-quinazoline Melting point: 194° C. Mass spectrum (ESI*): m/z=486, 488 [M+H]*

(6) 4-[(3-Chloro-4-fluoro-phenyl)amino]-6-{[4-(piperazin-1-yl)-1-oxo-2-buten-1-yl]amino}-7-cyclopropylmethoxy-quinazoline $R_f$ value: 0.60 (reversed phase TLC-plate (E. Merck), acetonitrile/water/trifluoroacetic acid=50:50:1) Mass spectrum (ESI*): m/z=511, 513 [M+H]*

Example IV

4-[(3-bromophenyl)amino]-6-nitro-7-{3-[4-(tert-butyloxycarbonyl}-piperazin-1-yl]propyloxy)-quinazoline 1.08 g sodium hydride are added to a solution of 6.35 g of 3-[4-(tert-butyloxycarbonyl)-piperazin-1-yl]-propan-1-ol in 100 ml of tetrahydrofuran under a nitrogen atmosphere. The suspension is stirred for about 10 minutes at ambient temperature, then 4.72 g of 4-[(3- bromophenyl)amino]-7-fluoro-6-nitro-quinazoline in 20 ml of tetrahydrofuran are added thereto. The reaction mixture turns dark reddish-brown, while giving off gas, and is gently refluxed for about 25 minutes. Since only a partial reaction has taken place, a further 0.52 g of sodium hydride are added. The reaction mixture is heated for a further 40 minutes until the reaction has ended. The cooled reaction solution is poured onto about 250 ml of ice-water and neutralised with a little citric acid. The partially precipitated product is extracted with ethyl acetate. The combined extracts are washed with a little water, followed by saturated sodium chloride solution, dried over magnesium sulphate and concentrated by evaporation. 11.30 g of crude product is obtained as a dark resin which is heated to boiling with 25 ml of methanol with stirring, whereupon the product crystallises out. The suspension is cooled with ice-water and suction filtered. The brownish-yellow crystals obtained are washed again with 10 ml of cold methanol and dried in the desiccator. Yield: 7.08 g (92% of theory), Melting point: 152–156° C. Mass spectrum (ESI*): m/z=587, 589 [M+H]*

The following compounds are obtained analogously to Example IV:

(1) 4-[(3-bromophenyl)amino]-6-nitro-7-(2-[4-(tert-butyloxycarbonyl)-piperazin-1-yl]ethoxy)-quinazoline Melting point: 219–222° C. Mass spectrum (ESI*): m/z=573, 575 [M+H]*

(2) 4-[(3-bromophenyl)amino]-6-nitro-7-{[1-(tert-butyloxycarbonyl)-piperidin-4-yl]oxy}-quinazoline Melting point: 190° C. Mass spectrum (ESI*): m/z=542, 544 [M–H]*

(3) 4-[(3-bromophenyl)amino]-6-nitro-7-{[1-(tert-butyloxycarbonyl)-piperidin-4-yl]methoxy}-quinazoline Melting point: 240° C. Mass spectrum (ESI*): m/z=558, 560 [M+H]*

(4) 4-[(3-bromophenyl)amino]-6-nitro-7-{2-[1-(tert-butyloxycarbonyl)-piperidin-4-yl]ethoxy}-quinazoline Melting point: 208° C. Mass spectrum (ESI*): m/z=572, 574 [M+H]*

(5) 4-[(3-bromophenyl)amino]-6-nitro-7-{3-[1-(tert-butyloxycarbonyl)-piperidin-4-yl]propyloxy}-quinazoline Melting point: 203° C. Mass spectrum (ESI*): m/z=584, 586 [M–H]*

(6) 4-[(3-bromophenyl)amino]-7-[3-(tert-butyldimethylsilyloxy)-propyloxy]-6-nitro-quinazoline $R_f$ value: 0.84 (silica gel, petroleum ether/ethyl acetate=1:1) Mass spectrum (ESI*): m/z=533, 535 [M+H]*

(7) 4-[(3-bromophenyl)amino]-7-[2-(tert-butyldimethylsilyloxy)-ethoxy]-6-nitro-quinazoline Melting point: 206–208° C. Mass spectrum (ESI*): m/z=519, 521 [M+H]*

(8) 4-[(3-chloro-4-fluorophenyl)amino]-7-cyclopropylmethoxy-6-nitro-quinazoline (carried out in dimethylformamide with potassium tert-butoxide as base) Melting point: 211–213° C. Mass spectrum (ESI*): m/z=389, 391 [M+H]*

(9) 4-[(3-bromophenyl)amino]-7-[4-(tert-butyldimethylsilyloxy)-butoxy]-6-nitro-quinazoline $R_f$ value: 0.73 (silica gel, petroleum ether/ethyl acetate=1:1) Mass spectrum (ESI*): m/z=545, 547 [M–H]*

(10) 4-[(3-chloro-4-fluorophenyl)amino]-7-cyclohexylmethoxy-6-nitro-quinazoline (carried out in dimethylformamide with potassium-tert. butoxide as base) Melting point: 258° C. Mass spectrum (ESI*): m/z=431, 433 [M+H]*

(11) 4-[(3-chloro-4-fluorophenyl)amino]-7-cyclohexyloxy-6-nitro-quinazoline (carried out in dimethylformamide with potassium-tert-butoxide as base) Melting point: 196° C. Mass spectrum (ESI*): m/z=417, 419 [M+H]*

(12) 4-[(3-chloro-4-fluorophenyl)amino]-7-cyclobutyloxy-6-nitro-quinazoline (carried out in dimethylformamide with potassium tert-butoxide as base) Melting point: 230–231° C. Mass spectrum (ESI*): m/z=389, 391 [M+H]*

(13) 4-[(3-chloro-4-fluorophenyl)amino]-7-cyclobutylmethoxy-6-nitro-quinazoline (carried out in dimethylformamide with potassium tert-butoxide as base) Melting point: 223–225° C. Mass spectrum (ESI*): m/z=403, 405 [M+H]*

(14) 4-[(3-chloro-4-fluorophenyl)amino]-7-cyclopentylmethoxy-6-nitro-quinazoline (carried out in dimethylformamide with potassium-tert. butoxide as base) Melting point: 220–224° C. Mass spectrum (ESI*): m/z=417, 419 [M+H]*

(15) 4-[(3-chloro-4-fluorophenyl)amino]-7-cyclopropylethoxy)-6-nitro-quinazoline (carried out in dimethylformamide with potassium tert-butoxide as base) Melting point: 200–202° C. Mass spectrum (ESI*): m/z=403, 405 [M+H]*

(16) 4-[(3-chloro-4-fluorophenyl)amino]-7-cyclopentyloxy-6-nitro-quinazoline (carried out in dimethylformamide with potassium tert-butoxide as base) Melting point: 224° C. Mass spectrum (ESI*): m/z=403, 405 [M+H]*

(17) 4-[(3-chlorophenyl)amino]-7-methoxy-6-nitro-quinazoline (carried out with sodium methoxide in tetrahydrofuran) Melting point: 199–201° C. Mass spectrum (ESI*): m/z=331, 333 [M+H]*

(18) (R)-4-[(1-phenylethyl)amino]-7-methoxy-6-nitro-quinazoline (carried out with sodium methoxide in tetrahydrofuran) $R_f$ value: 0.17 (silica gel, cyclohexane/ethyl acetate=1:1) Mass spectrum (ESI*): m/z=325 [M+H]*

(19) 4-[(R)-(1-Phenyl-ethyl)amino]-7-[2-(tetrahydro-pyran-2-yloxy)-ethoxy]-6-nitro-quinazoline $R_f$ value: 0.11 (silica gel, cyclohexane/ethyl acetate=1:1) Mass spectrum (EI): m/z=438 [M]*

(20) 4-[(R)-(1-Phenyl-ethyl)amino]-7-[3-(tetrahydro-pyran-2-yloxy)-propyloxy]-6-nitro-quinazoline $R_f$ value: 0.19 (silica gel, cyclohexane/ethyl acetate=1:1) Mass spectrum (EI): m/z=452 [M]*

(21) 4-[(R)-(1-Phenyl-ethyl)amino]-7-[4-(tetrahydro-pyran-2-yloxy)-butyloxy]-6-nitro-quinazoline $R_f$ value: 0.18 (silica gel, cyclohexane/ethyl acetate=1:1) Mass spectrum (ESI*): m/z=465 [M–H]*

(22) 4-[(R)-(1-Phenyl-ethyl)amino]-7-cyclobutyloxy-6-nitro-quinazoline (reaction is carried out with potassium tert.butylate in N,N-dimethyl-formamide) $R_f$ value: 0.54 (silica gel, ethyl acetate) Mass spectrum (ESI*): m/z=363 [M–H]*

(23) 4-[(R)-(1-Phenyl-ethyl)amino]-7-cyclopentyloxy-6-nitro-quinazoline (reaction is carried out with potassium tert.butylate in N,N-dimethyl-formamide) $R_f$ value: 0.24 (silica gel, petroleum ether/ethyl acetate=1:1) Mass spectrum (ESI*): m/z=379 [M+H]*

(24) 4-[(R)-(1-Phenyl-ethyl)amino]-7-cyclopropylmethoxy-6-nitro-quinazoline (reaction is carried out with potassium tert.butylate in N,N-dimethyl-formamide) Melting point: 155° C. Mass spectrum (ESI*): m/z=365 [M+H]*

(25) 4-Benzylamino-7-cyclopropylmethoxy-6-nitro-quinazoline (reaction is carried out with potassium tert.butylate in N,N-dimethyl-formamide) Melting point: 168° C. Mass spectrum (ESI*): m/z=351 [M+H]*

Example V

4-[(3-bromophenyl)amino]-6-[(4-bromo-1-oxo-2-buten-1-yl)amino]-quinazoline 1.74 ml of oxalylchloride and one drop of dimethylformamide are added to a solution of 1.65 g of 4-bromo-2-butenoic acid in 15 ml of methylene chloride at ambient temperature. The reaction mixture is stirred for about one hour at ambient temperature until the development of gas has ceased. The acid chloride formed is largely freed from the solvent in vacuo using the rotary evaporator. The oily brown crude product is taken up in 25 ml of tetrahydrofuran and added dropwise, while cooling with a ice bath, to a solution of 3.15 g of 4-[(3-bromophenyl)amino]-6-amino-quinazoline and 2.30 ml of Hünig base in 25 ml of tetrahydrofuran. The reaction mixture is stirred for 30 minutes while cooling with ice and then stirred for another 1.5 hours at ambient temperature. For working up, 25 ml of water and 50 ml of ethyl acetate are added. The organic phase is separated off, washed with saturated sodium chloride solution, dried over magnesium sulphate and concentrated by evaporation. The residue is boiled in 30 ml of ethyl acetate to purify it further and filtered while hot. The yellow crystalline product is washed with hot ethyl acetate and dried. Yield: 3.00 g (65% of theory), $R_f$ value: 0.33 (silica gel, methylene chloride/methanol/concentrated aqueous ammonia solution=9:1:0.1) Mass spectrum (ESI*): m/z=463 [M+H]*

The following compound is obtained analogously to Example V:

(1) 4-[(3-bromophenyl)amino]-6-[(4-bromo-1-oxo-2-buten-1-yl)amino]-7-methoxy-quinazoline Rf value: 0.38 (reversed phase ready-made TLC plates (E. Merck), acetonitrile/water, trifluoroacetic acid=50:50:1)

Example VI

3-{N-[(ethoxycarbonyl)methyl]-N-methylamino}propylamine-hydrochloride 20 ml of trifluoroacetic acid are added dropwise to a solution of 6.10 g of N-[3-(tert. butyloxycarbonylamino)-propyl]-sarcosine ethyl ester in 40 ml of methylene chloride whilst cooling with an ice bath. The reaction mixture is then stirred for about another three hours at 0° C. until the evaluation of gas has ended. For working up, the solvent is largely distilled off in vacuo in the rotary evaporator. The residue is taken up in ethereal hydrochloric acid solution and again evaporated to dryness. Yield: 4.72 g (86% of theory), $R_f$ value: 0.80 (silica gel, acetonitrile/water/trifluoroacetic acid=50:50:1) Mass spectrum (EI): m/z=174 [M]*

The following compound is obtained analogously to Example VI:

(1) 2-{N-[(ethoxycarbonyl)methyl]-N-methylamino}ethylamine-dihydrochloride $R_f$ value: 0.74 (Reversed phase ready-made TLC plate (E. Merck), acetonitrile/water/trifluoroacetic acid=50:50:1) Mass spectrum (ESI*): m/z=161 [M+H]*

Example VII

N-[3-(tert-butyloxycarbonylamino)-propyl]-sarcosine ethyl ester A solution of 17.90 g 3-(tert-butyloxycarbonylamino)propyl bromide in 50 ml of acetonitrile is added dropwise to a mixture of 11.55 g of sarcosine ethylester hydrochloride and 28.8 ml of Hünig base in 200 ml of acetonitrile within 30 minutes while cooling with an ice bath. The reaction mixture is allowed to come up to ambient temperature overnight in the ice bath. Then the solvent is distilled off using the rotary evaporator, the residue is taken up in tert-butyl-methylether and washed with ice water. The organic phase is dried over magnesium sulphate and concentrated by evaporation. The crude product is chromatographed on a silica gel column with methylene chloride/methanol/concentrated aqueous ammonia solution (100:2:0.1). Yield: 20.62 g (30% of theory), $R_f$ value: 0.50 (silica gel, methylene chloride/methanol/concentrated aqueous ammonia solution=20:1:0.1) Mass spectrum (ESI*): m/z=275 [M+H]*

The following compound is obtained analogously to Example VII:

(1) N-[2-(tert.butyloxycarbonylamino)-ethyl]-sarcosine ethyl-ester $R_f$ value: 0.45 (silica gel, methylene chloride/methanol/concentrated aqueous ammonia solution= 90:10:0.5) Mass spectrum (ESI*): m/z=261 [M+H]*

Example VIII

4-[(3-bromophenyl)amino]-7-(3-[4-[(diethoxyphosphoryl)methyl]-piperazin-1-yl)propyloxy)-6-nitro-quinazoline 0.08 ml of a 37% formaldehyde solution is added to a suspension of 487 mg of 4-[(3-bromophenyl)amino]-6-nitro-7-[3-(piperazin-1-yl)propyloxy]-quinazoline in 3 ml of dioxane. The suspension is briefly heated in an oil bath until a clear solution is obtained. Then 0.16 ml of diethylphosphite are pipetted in with stirring at ambient temperature. The reaction mixture is then stirred for a further half hour at ambient temperature, then heated to 90–100° C. in an oil bath. After another three hours the reaction is complete. The reaction solution is concentrated by evaporation, the residue is stirred with ice-water, filtered off and dried in the desiccator. The crude product is purified by chromatography over a silica gel column with methylene chloride/ethanol (9:1). Yield: 540 mg (85% of theory), Melting point: 140–143° C. Mass spectrum (ESI*): m/z= 637, 639 [M+H]*

Example IX 6-amino-4-[(3-bromophenyl)amino]-7-{3-[4-(carboxymethyl)piperazin-1-yl]propyloxy}-quinazoline 2.0 ml of 1.0 N sodium hydroxide solution are added to a solution of 440 mg of 6-amino-4-[(3-bromophenyl)amino]-7-(3-{4-[(butyloxycarbonyl)methyl]-piperazin-1-yl}propyloxy)-quinazoline in 25 ml of tetrahydrofuran and 5 ml of methanol. The dark solution formed is stirred overnight at ambient temperature. The reaction mixture is neutralised with 2.0 ml of 1.0 N hydrochloric acid and freed from solvent in the rotary evaporator. The brown, resin-like residue is taken up in methylene chloride/methanol (9:1) and suction filtered. The filtrate is concentrated by evaporation, moistened with toluene and dried in the desiccator. The brown crude product is reacted without any further purification. Yield: 460 mg (116% of theory) $R_f$ value: 0.50 (Reversed phase ready-made TLC plate (E. merck), acetonitrile/water/trifluoroacetic acid=90:10:1) Mass spectrum (ESI*): m/z=513, 515 [M–H]*

The following compound is obtained analogously to Example IX:

(1) 4-[(3-chloro-4-fluorophenyl)amino]-6-{[(2-carboxyvinyl)carbonyl]amino}-7-cyclopropylmethoxyquinazoline R$_f$ value: 0.55 (Reversed phase ready-made TLC plate (E. Merck), acetonitrile/water/trifluoroacetic acid=50:50:1) Mass spectrum (ESI*): m/z=457, 459 [M+H]*

Example X

4-[(3-Bromophenyl)amino]-7-(3-{N-[(ethoxycarbonyl)methyl]-N-methylamino}propyloxy)-6-nitro-quinazoline A mixture of 1.40 g 4-[(3-bromophenyl)amino]-7-[3-(methylsulphonyloxy)-propyloxy]-6-nitro-quinazoline and 5.60 g sarcosine ethylester is stirred for 2.5 hours at 110° C. The reaction mixture is stirred with 100 ml of ice-water. The yellow supernatant emulsion is decanted and the orange-yellow mucilaginous precipitate is dissolved in methylene chloride, dried over sodium sulphate and concentrated by evaporation. The brownish-orange crude product is purified by chromatography over a silica gel column with methylene chloride/methanol (96:4). Yield: 763 mg (52% of theory) R$_f$ value: 0.65 (silica gel, methylene chloride/methanol=9:1) Mass spectrum (ESI*): m/z=518, 520 [M+H]*

The following compounds are obtained analogously to Example X:

(1) 4-[(3-bromophenyl)amino]-7-(2-{N-[(ethoxycarbonyl)methyl]-N-methylamino}ethoxy)-6-nitro-quinazoline R$_f$ value: 0.71 (silica gel, methylene chloride/methanol=9:1) Mass spectrum (ESI*): m/z=504, 506 [M+H]*

(2) 4-[(3-bromophenyl)amino]-7-(4-{N-[(ethoxycarbonyl)methyl]-N-methylamino}butyloxy)-6-nitro-quinazoline R$_f$ value: 0.55 (silica gel, methylene chloride/methanol=9:1) Mass spectrum (EI): m/z=531, 533 [M]*

(3) 4-[(R)-(1-Phenyl-ethyl)amino]-7-(2-[2-(methoxycarbonyl)-piperidin-1-yl]-ethoxy)-6-nitroquinazoline (reaction is carried out in acetonitrile in the presence of diisopropylethylamine and sodium iodide) R$_f$ value: 0.21 (silica gel, methylene chloride/methanol=95:5) Mass spectrum (ESI*): m/z=478 [M–H]⁻

(4) 4-[(R)-(1-Phenyl-ethyl)amino]-7-(2-[(R)-2-(methoxycarbonyl)-pyrrolidin-1-yl]-ethoxy)-6-nitroquinazoline (reaction is carried out in acetonitrile in the presence of diisopropylethylamine and sodium iodide) R$_f$ value: 0.25 (silica gel, methylene chloride/methanol=95:5) Mass spectrum (ESI*): m/z=464 [M–H]⁻

(5) 4-[(R)-(1-Phenyl-ethyl)amino]-7-(2-[(S)-2-(methoxycarbonyl)-pyrrolidin-1-yl]-ethoxy)-6-nitroquinazoline (reaction is carried out in acetonitrile in the presence of diisopropylethylamine and sodium iodide) R$_f$ value: 0.30 (silica gel, methylene chloride/methanol=95:5) Mass spectrum (ESI*): m/z=464 [M–H]⁻

(6) 4-[(R)-(1-Phenyl-ethyl)amino]-7-(3-[(R)-2-(methoxycarbonyl)-pyrrolidin-1-yl]-propyloxy)-6-nitroquinazoline (reaction is carried out in acetonitrile in the presence of diisopropylethylamine, potassium carbonate, and sodium iodide) R$_f$ value: 0.23 (silica gel, methylene chloride/methanol=95:5) Mass spectrum (ESI*): m/z=478 [M–H]⁻

(7) 4-[(R)-(1-Phenyl-ethyl)amino]-7-(4-[2-(methoxycarbonyl)piperidin-1-yl]-butyloxy)-6-nitroquinazoline (reaction is carried out in acetonitrile in the presence of potassium carbonate and sodium iodide) R$_f$ value: 0.25 (silica gel, methylene chloride/methanol=95:5) Mass spectrum (ESI*): m/z=506 [M–H]⁻

(8) 4-[(R)-(1-Phenyl-ethyl)amino]-7-(2-{N-[(methoxycarbonyl)-methyl]-N-methylamino}-ethoxy)-6-nitro-quinazoline (reaction is carried out in acetonitrile in the presence of diisopropylethylamine and sodium iodide) R$_f$ value: 0.35 (silica gel, methylene chloride/methanol=95:5) Mass spectrum (ESI*): m/z=438 [M–H]⁻

Example XI

4-[(3-Bromophenyl)amino]-7-[3-(methylsulphonyloxy)-propyloxy]-6-nitro-quinazoline 1.10 ml of the triethylamine are added to 1.28 g of 4-[(3-bromophenyl)amino]-7-(3-hydroxy-propyloxy)-6-nitro-quinazoline in 55 ml of methylene chloride. Then, whilst cooling with an ice bath, a solution of 0.47 ml of methanesulphonic acid chloride in 5 ml of methylene chloride is added dropwise. The reaction mixture is stirred for about one hour at ambient temperature. Since some starting material can still be detected, another 20 drops of triethylamine and 10 drops of methanesulphonic acid chloride are added, whilst cooling with an ice bath. The mixture is stirred for a further 30 minutes at ambient temperature, whereupon a clear, reddish-orange solution is formed. For work-up, this is diluted with methylene chloride and added to 100 ml of water. The organic phase is washed with 3% sodium hydrogen carbonate solution and water, dried over sodium sulphate and concentrated by evaporation. A brownish-yellow resin remains, which is further reacted as the crude product. Yield: 1.4 g (92% of theory) R$_f$ value: 0.70 (silica gel, methylene chloride/methanol=9:1)

The following compounds are obtained analogously to Example XI:

(1) 4-[(3-bromophenyl)amino]-7-[2-(methylsulphonyloxy)-ethoxy]-6-nitro-quinazoline R$_f$ value: 0.73 (silica gel, methylene chloride/methanol=9:1) Mass spectrum (ESI*): m/z=483, 485 [M+H]⁻

(2) 4-[(3-bromophenyl)amino]-7-[4-(methylsulphonyloxy)-butyloxy]-6-nitro-quinazoline R$_f$ value: 0.73 (silica gel, methylene chloride/methanol=9:1) Mass spectrum (ESI*): m/z=509, 511 [M–H]⁻

(3) 4-[(3-bromophenyl)amino]-6-[(4-(N-[(tert-butyloxycarbonyl)methyl]-N-[2-(methylsulphonyloxy)ethyl]amino)-1-oxo-2-buten-1-yl)amino]-7-methoxyquinazoline R$_f$ value: 0.65 (silica gel, methylene chloride/methanol=9:1)

(4) 4-[(3-chloro-4-fluorophenyl)amino]-6-[(4-(N-[(ethoxycarbonyl)methyl]-N-[2-(methylsulphonyloxy)ethyl]amino)-1-oxo-2-buten-1-yl)amino]-7-cyclopropylmethoxy-quinazoline R$_f$ value: 0.68 (silica gel, ethyl acetate)

(5) 4-[(R)-(1-Phenyl-ethyl)amino]-7-[2-(methylsulfonyloxy)-ethoxy]-6-nitro-quinazoline R$_f$ value: 0.45 (silica gel, methylene chloride/methanol=95:5) Mass spectrum (ESI*): m/z=431 [M–H]⁻

(6) 4-[(R)-(1-Phenyl-ethyl)amino]-7-[3-(methylsulfonyloxy)propyloxy]-6-nitro-quinazoline R$_f$ value: 0.40 (silica gel, methylene chloride/methanol=95:5) Mass spectrum (ESI*): m/z=445 [M–H]⁻

(7) 4-[(R)-(1-Phenyl-ethyl)amino]-7-[4-(methylsulfonyloxy)-butyloxy]-6-nitro-quinazoline R$_f$ value: 0.45 (silica gel, methylene chloride/methanol=95:5)

Example XII

4-[(3-Bromophenyl)amino]-7-(3-hydroxy-propyloxy)-6-nitro-quinazoline 5.60 g tetrabutylammonium fluoride-trihydrate are added to 2.50 g of 4-[(3-bromophenyl)amino]-7-[3-(tert.

butyldimethylsilyloxy)-propyloxy]-6-nitro-quinazoline in 25 ml of tetrahydrofuran. The reaction mixture is stirred for about 2 hours at ambient temperature. After the cleavage is complete, the reaction mixture is combined with 150 ml of a 2% ammonium chloride solution and cooled in the ice bath. A yellow precipitate is formed which is suction filtered and washed with water. The precipitate, while still damp, is dissolved in methylene chloride/methanol (6:4), dried over sodium sulphate and concentrated by evaporation. The yellow residue is stirred with a little petroleum ether and suction filtered, washed with petroleum ether and dried in vacuo. Yield: 1.29 g (66% of theory) $R_f$ value: 0.63 (silica gel, methylene chloride/methanol=9:1) Mass spectrum (ESI*): m/z=417, 419 [M–H]⁻

The following compounds are obtained analogously to Example XII:
(1) 4-[(3-bromophenyl)amino]-7-(2-hydroxy-ethoxy)-6-nitro-quinazoline $R_f$ value: 0.66 (silica gel, methylene chloride/methanol=9:1) Mass spectrum (ESI*): m/z=405, 407 [M+H]*
(2) 4-[(3-bromophenyl)amino]-7-(4-hydroxy-butyloxy)-6-nitro-quinazoline $R_f$ value: 0.62 (silica gel, methylene chloride/methanol=9:1) Mass spectrum (ESI*): m/z=431, 433 [M–H]*

Example XIII

4-[(3-chlorophenyl)amino]-7-fluoro-6-nitro-quinazoline

A solution of 2.76 ml of 3-chloroaniline in 7 ml of dioxan is added dropwise to 5.0 g of 4-chloro-7-fluoro-6-nitro-quinazoline in 40 ml of methylene chloride at 15° C. within 15 minutes. The reaction mixture is stirred for a further 15 minutes at this temperature before being poured onto 100 ml of n-hexane for working up. The mixture is stirred for about one hour while cooling with an ice bath, then the precipitate formed is filtered off. The hydrochloride thus obtained is suspended in 30 ml of methanol, made alkaline with triethylamine while cooling with an ice bath and combined with 100 ml of water. The precipitate formed is suction filtered and washed with water. The crude product is purified by chromatography on a silica gel column with methylene chloride/methanol (20:1) as eluant. Yield: 3.50 g (50% of theory), Melting point: 223–225° C. Mass spectrum (ESI*): m/z=319, 321 [M+H]*

The following compounds are obtained analogously to Example XIII:
(1) (R)-4-[(1-phenylethyl)amino]-7-fluoro-6-nitro-quinazoline Melting point: 204–206° C. Mass spectrum (ESI*): m/z=313 [M+H]*
(2) 4-Benzylamino-7-fluoro-6-nitro-quinazoline Melting point: 223–225° C. Mass spectrum (ESI*): m/z=299 [M+H]*

Example XIV

4-[(3-chloro-4-fluorophenyl)amino]-6-[(3-ethoxycarbonyl-1-oxo-2-propen-1-yl)-amino]-7-cyclopropylmethoxy-quinazoline A solution of 3.00 g of ethyl 3-chlorocarbonyl-acrylate in 50 ml of tetrahydrofuran is added dropwise to 5.00 g of 6-amino-4-[(3-chloro-4-fluorophenyl)amino]-7-cyclopropylmethoxy-quinazoline and 3.5 ml of diisopropylethylamine in 150 ml of tetrahydrofuran while cooling with an ice bath. The reaction mixture is stirred for a further hour while cooling with an ice bath and then stirred overnight at ambient temperature. Next, the solvent is largely distilled off in the rotary evaporator and the residue is partitioned between water and ethyl acetate. The organic phase is washed with saturated sodium chloride solution, dried over magnesium sulphate and concentrated by evaporation. The brown, oily crude product is stirred with diethylether, the precipitate formed is suction filtered and washed with a little diethylether. Yield: 3.20 g (47% of theory), $R_f$ value: 0.80 (silica gel, ethyl acetate) Mass spectrum (ESI*): m/z=485, 487 [M+]*

Example XV

4-[(R)-(1-Phenyl-ethyl)amino]-7-(2-hydroxy-ethoxy)-6-nitro-quinazoline

To a stirred solution of 7.70 g 4-[(R)-(1-phenyl-ethyl)amino]-7-[2-(tetrahydro-pyran-2-yloxy)-ethoxy]-6-nitro-quinazoline in 120 ml of methanol are added 2 ml of concentrated hydrochloric acid. The reaction mixture is stirred for 1.5 hours at 50° C. After cooling, the mixture is neutralized with solid sodium bicarbonate and concentrated in vacuo. The solid residue is dissolved in ethyl acetate, washed with concentrated aqueous sodium bicarbonate solution, dried over magnesium sulfate, and concentrated. The residue is triturated with 30 ml of diethyl ether, filtered off with suction, and dried. Yield: 4,34 g (88% of theory), Melting point: 187–192° C. Mass spectrum (ESI*): m/z=355 [M+H]*

The following compounds are obtained analogously to Example XV:
(1) 4-[(R)-(1-Phenyl-ethyl)amino]-7-(3-hydroxy-propyloxy)-6-nitro-quinazoline Melting point: 178–183° C. Mass spectrum (ESI*): m/z=369 [M+H]*
(2) 4-[(R)-(1-Phenyl-ethyl)amino]-7-(4-hydroxy-butyloxy)-6-nitro-quinazoline Melting point: 143–146° C. Mass spectrum (ESI*): m/z=383 [M+H]*

Example XVI

4-[(3-Chloro-4-fluoro-phenyl)amino]-6-({4-[4-(tert.butyloxy-carbonyl)-piperazin-1-yl]-1-oxo-2-buten-1-yl}amino)-7-cyclo-propylmethoxy-quinazoline 4.7 ml of oxalyl dichloride are added to a solution of 4.51 g 4-bromo-but-2-enoic acid in 100 ml of methylene chloride at room temperature. After addition of one drop of N,N-dimethyl-formamide, the reaction mixture is stirred for approximately 45 minutes until the gas evolution has ceased. The solvent is distilled off in vacuo to give the crude acid chloride. In the meantime, a mixture of 7.00 g 6-amino-4-[(3-chloro-4-fluoro-phenyl)amino]-7-cyclopropylmethoxy-quinazoline and 10.2 ml diisopropylethylamine in 250 ml tetrahydrofuran is cooled to 0° C. in an ice/water bath. The crude 4-bromo-but-2-enoic acid chloride is dissolved in 20 ml of methylene chloride and added dropwise to this mixture within 5 minutes. After stirring for 45 minutes at 0° C. and one hour at room temperature, 18.17 g of piperazine-1-carboxylic acid tert.butyl ester suspended in 5 ml of N,N-dimethyl-formamide are added. After stirring for 48 hours at room temperature, the solvent is distilled off in vacuo and the residue is partitioned between 100 ml of water and 200 ml of ethyl acetate. The aqueous layer is extracted with ethyl acetate, the combined organic layers are washed with concentrated aqueous sodium chloride solution, dried over magnesium sulfate, and concentrated in vacuo. The crude product is purified by column chromatography on silica gel with ethyl acetate/methanol (15:1 to 9:1). Yield: 5.2 g (44% of theory), $R_f$ value: 0.42 (silica gel, methylene chloride/methanol=9:1) Mass spectrum (ESI*): m/z=609, 611 [M–H]*

The following compounds is obtained analogously to Example XVI:

(1) 4-[(3-Chloro-4-fluoro-phenyl)amino]-6-({4-[2-(ethoxycarbonyl)-4-(tert.butyloxycarbonyl)-piperazin-1-yl]-1-oxo-2-buten-1-yl}amino)-7-cyclopropylmethoxy-quinazoline (The starting material 1-(tert.butyloxycarbonyl)-3-(ethoxycarbonyl)-piperazine was obtained by treatment of piperazine-2-carboxylic acid ethyl ester with tert.butyl carbonic anhydride in ethanol.) $R_f$ value: 0.26 (silica gel, ethyl acetate/cyclohexane=7:3) Mass spectrum (ESI*): m/z=683, 685 [M+H]*

Example XVII

Ethyl [4-(1,1-Dimethyl-2-oxo-ethyl)-piperazin-1-yl]-acetate

A solution of 100 g 2-bromo-2-methyl-propionaldehyde in 20 ml of ethanol is added dropwise to a mixture of 25.0 g N-[(ethoxycarbonyl)methyl]-piperazine in 80 ml of ethanol at room temperature. The resulting mixture is stirred for 72 hours, concentrated in vacuo, and submitted directly to column chromatography on silica gel with methylene chloride/methanol (95:5 to 80:20) to give the title compound as a yellow oil. Yield: 10.0 g (62% of theory), $R_f$ value: 0.60 (silica gel, methylene chloride/methanol=9:1) Mass spectrum (ESI*): m/z=241 [M−H]*

Example XVIII

4-[(3-Chloro-4-fluoro-phenyl)amino]-6-{[2-(diethoxyphosphoryl)-1-oxo-ethyl]amino}-7-cyclopropylmethoxy-quinazoline 137 mg (diethoxyphosphoryl)-acetic acid and 225 mg benzotriazol-1-yl-N,N,N',N'-tetramethyluronium tetrafluoroborate are added subsequently to a solution of 200 mg 6-amino-4-[(3-chloro-4-fluoro-phenyl)amino]-7-cyclopropylmethoxy-quinazoline and 0.11 ml triethylamine in 1 ml of anhydrous N,N-dimethyl-formamide. The reaction mixture is stirred for one hour at room temperature, quenched with 10 ml of water, and extracted with ethyl acetate/methanol (10:1). The combined extracts are washed with water and brine, dried over magnesium sulfate, and concentrated in vacuo. The crude product is recrystallized from diethyl ether. Yield: 190 mg (64% of theory), Melting point: 185–187° C. Mass spectrum (ESI*): m/z=537, 539 [M+H]*

Preparation of the end products:

Example 1

4-[(3-Bromophenyl)amino]-7-(3-{4-[(ethoxycarbonyl)methyl]-piperazin-1-yl)propyloxy)-6-[(vinylcarbonyl)amino]-quinazoline 440 mg of 6-amino-4-[(3-bromophenyl)amino]-7-(3-{4-[(ethoxycarbonyl)methyl]-piperazin-1-yl}propyloxy)-quinazoline are suspended in 20 ml of methylene chloride at ambient temperature and combined with 0.24 ml of triethylamine under a nitrogen atmosphere. The reaction mixture is cooled to −10° C. with an ice/sodium chloride bath, then a solution of 84 mg of acrylic acid chloride in 5 ml of methylene chloride is added dropwise within about 10 minutes. After another 10 minutes the reaction is complete. The reaction solution is washed with a litte dilute potassium carbonate solution and water, dried and concentrated by evaporation. 526 mg of crude product are obtained as a brown resin which is purified by chromatography on a silica gel column with methylene chloride/ethanol (95:5). Yield: 300 mg (62% of theory). Melting point: 110–113° C. Mass spectrum (ESI*): m/z=597, 599 [M+H]*

The following compounds are obtained analogously to Example 1:

(1) 4-[(3-bromophenyl)amino]-7-(3-{5-[(isopropyloxycarbonyl)methyl]-piperazin-1-yl}propyloxy)-6-[(vinylcarbonyl)amino]-quinazoline Melting point: 95–100° C. Mass spectrum (ESI*): m/z=611, 613 [M+H]*

(2) 4-[(3-bromophenyl)amino]-7-(3-{4-[(cyclohexyloxycarbonyl)-methyl]-piperazin-1-yl}propyloxy)-6-[(vinylcarbonyl)amino]-quinazoline Melting point: 96–104° C. Mass spectrum (ESI*): m/z=651, 653 [M+H]*

(3) 4-[(3-bromophenyl)amino]-7-(3-{4-[2-(ethoxycarbonyl)-ethyl]-piperazin-1-yl}propyloxy)-6-[(vinylcarbonyl)amino]-quinazoline Melting point: 97–102° C. Mass spectrum (ESI*): m/z=611, 613 [M+H]*

(4) 4-[(3-bromophenyl)amino]-7-(3-{4-[3-(ethoxycarbonyl)propyl]-piperazin-1-yl}propyloxy)-6-[(vinylcarbonyl)amino]-quinazoline Melting point: 107–111° C. Mass spectrum (ESI*): m/z=625, 627 [M+H]*

(5) 4-[(3-bromophenyl)amino]-7-(2-(4-[(ethoxycarbonyl)methyl]-piperazin-1-yl)ethoxy)-6-[(vinylcarbonyl)amino]-quinazoline Melting point: 75–79° C. Mass spectrum (ESI*): m/z=583, 585 [M+H]*

(6) 4-[(3-bromophenyl)amino]-7-((1-[(ethoxycarbonyl)methyl]-piperidin-4-yl)oxy)-6-[(vinylcarbonyl)amino]-quinazoline Melting point: 95° C. Mass spectrum (ESI*): m/z=554, 556 [M+H]*

(7) 4-[(3-bromophenyl)amino]-7-((1-[(ethoxycarbonyl)methyl]-piperidin-4-yl)methoxy)-6-[(vinylcarbonyl)amino]-quinazoline Melting point: 141° C. Mass spectrum (ESI*): m/z=568, 570 [M+H]*

(8) (4-[(3-bromophenyl)amino]-7-(2-{1-[(ethoxycarbonyl)methyl]-piperidin-4-yl}ethoxy)-6-[(vinylcarbonyl)amino]-quinazoline Melting point: 156° C. Mass spectrum (ESI*): m/z=582, 584 [M+H]*

(9) 4-[(3-bromophenyl)amino]-7-(3-{1-[(ethoxycarbonyl)methyl]-piperidin-4-yl}propyloxy)-6-[(vinylcarbonyl)amino]-quinazoline Melting point: 124° C. Mass spectrum (ESI(): m/z=596, 598 [M+H]*

(10) 4-[(3-bromophenyl)amino]-7-(3-{4-[(diethoxyphosphoryl)-methyl]-piperazin-1-yl}propyloxy)-6-[(vinylcarbonyl)amino]-quinazoline Melting point: 80–85° C. Mass spectrum (ESI*): m/z=661, 663 [M+H]*

(11) 4-[(3-bromophenyl)amino]-7-(3-{4-[(diethoxyphosphoryl)-methyl]-piperazin-1-yl}propyloxy)-6-[(1-oxo-2-butyn-1-yl)amino]-quinazoline (the reaction is carried out with 2-butyn-carboxylic acid and isobutyl chloroformate in tetrahydrofuran) Melting point: 137–139° C. Mass spectrum (ESI*): m/z=673, 675 [M+H]*

(12) 4-[(3-bromophenyl)amino]-7-(3-{4-[(butyloxycarbonyl)-piperazin-1-yl}propyloxy]-6-[(vinylcarbonyl)amino]-quinazoline $R_f$ value: 0.53 (silica gel, methylene chloride/methanol/concentrated aqueous ammonia solution=90:10:1) Mass spectrum (ESI*): m/z=625, 627 [M+H]*

(13) 4-[(3-bromophenyl)amino]-7-(3-{N-[(ethoxycarbonyl)methyl]-N-methylamino)propyloxy)-6-[(vinylcarbonyl)amino]-quinazoline $R_f$ value: 0.68 (silica gel, methylene chloride/methanol=9:1) Mass spectrum (ESI*): m/z=542, 544 [M+H]*

(14) 4-[(3-bromophenyl)amino]-7-(2-{N-[(ethoxycarbonyl)methyl]-N-methylamino}ethoxy)-6-[(vinylcarbonyl)amino]-quinazoline $R_f$ value: 0.71 (silica gel, methylene chloride/methanol=9:1) Mass spectrum (ESI*): m/z=528, 530 [M+H]*

(15) 4-[(3-bromophenyl)amino]-7-(4-{N-[(ethoxycarbonyl) methyl]-N-methylamino}butyloxy)-6-[(vinylcarbonyl) amino]-quinazoline $R_f$ value: 0.67 (silica gel, methylene chloride/methanol=9:1) Mass spectrum (EI): m/z=555, 557 [M]*

(16) 4-[(R)-(1-Phenyl-ethyl)amino]-7-{2-[2-(methoxycarbonyl)-piperidin-1-yl]-ethoxy}-6-[(vinylcarbonyl)amino]-quinazoline $R_f$ value: 0.70 (silica gel, methylene chloride/methanol/concentrated aqueous ammonia=90:10:1) Mass spectrum (ESI*): m/z=502 [M−H]*

(17) 4-[(R)-(1-Phenyl-ethyl)amino]-7-{2-[(R)-2-(methoxycarbonyl)-pyrrolidin-1-yl]-ethoxy}-6-[(vinylcarbonyl)amino]-quinazoline $R_f$ value: 0.30 (silica gel, methylene chloride/methanol=95:5) Mass spectrum (ESI*): m/z=488 [M−H]*

(18) 4-[(R)-(1-Phenyl-ethyl)amino]-7-(2-[(S)-2-(methoxycarbonyl)-pyrrolidin-1-yl]-ethoxy}-6-[(vinylcarbonyl)amino]-quinazoline $R_f$ value: 0.32 (silica gel, methylene chloride/methanol=95:5) Mass spectrum (ESI*): m/z=488 [M−H]*

(19) 4-[(R)-(1-Phenyl-ethyl)amino]-7-{3-[(R)-2-(methoxycarbonyl)-pyrrolidin-1-yl]-propyloxy}-6-[(vinylcarbonyl)amino]-quinazoline $R_f$ value: 0.30 (silica gel, methylene chloride/methanol=95:5) Mass spectrum (ESI*): m/z=502 [M−H]*

(20) 4-[(R)-(1-Phenyl-ethyl)amino]-7-{4-[2-(methoxycarbonyl)-piperidin-1-yl]-butyloxy}-6-[(vinylcarbonyl)amino]-quinazoline $R_f$ value: 0.27 (silica gel, methylene chloride/methanol=95:5) Mass spectrum (ESI*): m/z=532 [M+H]*

(21) 4-[(R)-(1-Phenyl-ethyl)amino]-7-(2-(N-[(methoxycarbonyl)-methyl]-N-methylamino}-ethoxy-6-[(vinylcarbonyl)amino]-quinazoline $R_f$ value: 0.30 (silica gel, methylene chloride/methanol=95:5) Mass spectrum (ESI*): m/z=464 [M+H]*

Example 2

4-[(3-Bromophenyl)amino]-6-[(4-{N-[(ethoxycarbonyl) methyl]-N-methylamino}-1-oxo-2-buten-1-yl)-amino]-quinazoline 13.94 ml of Hünig base are pipetted into a suspension of 9.37 g of sarcosine ethylester hydrochloride in 25 ml of tetrahydrofuran while cooling with an ice bath. Then a solution of 2.00 g of 4-[(3-bromophenyl)amino]-6-[(4-bromo-1-oxo-2-buten-1-yl)amino]-quinazoline in 10 ml of dimethylformamide is added dropwise within 15 minutes. The reaction mixture is allowed to come up to ambient temperature overnight in an ice bath. For working up, 25 ml of saturated sodium hydrogen carbonate solution and 50 ml of ethyl acetate are added. The organic phase is separated off and the aqueous phase is extracted with ethyl acetate. The combined organic phases are washed with saturated sodium chloride solution, dried over magnesium sulphate and concentrated by evaporation. The dark-brown oily residue is stirred with 50 ml of water, the precipitate formed is suction filtered and washed with water. The crude product is purified by chromatography on a silica gel column with methylene chloride/methanol (50:1 to 20:1). Yield: 1.00 g (46% of theory), Melting point: 182–183° C. Mass spectrum (ESI*): m/z=496, 498 [M−H]*

The following compounds are obtained analogously to Example 2:

(1) 4-[(3-bromophenyl)amino-6-[(4-{N-[(ethoxycarbonyl) methyl]-N-methylamino}-1-oxo-2-buten-1-yl)amino]-7-methoxy-quinazoline Melting point: 121–125° C. Mass spectrum (EI): m/z=527, 529 [M]*

(2) 4-[(3-bromophenyl)amino]-6-[(4-{N,N-bis [(ethoxycarbonyl)methyl]-amino)-1-oxo-2-buten-1-yl}amino]-quinazoline Melting point: 150–154° C. Mass spectrum (EI): m/z=541, 543 [M]*

(3) 4-[(3-bromophenyl)amino]-6-({4-[2-(methoxycarbonyl)-pyrolidin-1-yl]-1-oxo-2-buten-1-yl) amino)-7-methoxy-quinazoline $R_f$ value: 0.43 (silica gel, methylene chloride/methanol=9:1) Mass spectrum (ESI*): m/z=539, 541 [M+H]*

(4) 4-[(3-bromophenyl)amino]-6-[(4-{N-[(diethoxyphosphoryl)methyl]-N-methylamino}-1-oxo-2-buten-1-yl)amino]-7-methoxy-quinazoline $R_f$ value: 0.38 (silica gel, methylene chloride/methanol=9:1) Mass spectrum (ESI*): m/z=590, 592 [M−H]*

(5) 4-[(3-bromophenyl)amino]-6-[(4-{4-[(ethoxycarbonyl) methyl]-piperazin-1-yl}-1-oxo-2-buten-1-yl)amino] quinazoline $R_f$ value: 0.37 (silica gel, methylene chloride/ methanol=9:1) Mass spectrum (ESI*): m/=553, 555 [M+H]*

(6) 4-[(3-bromophenyl)amino]-6-[(4-{N-[1,2-bis (methoxycarbonyl)-ethyl]-N-methylamino}-1-oxo-2-buten-1-yl)amino]-7-methoxy-quinazoline (reaction took place in acetonitrile under reflux) $R_f$ value: 0.50 (silica gel, ethyl acetate/methanol=15:1) Mass spectrum (EI): m/z=585, 587 [M]*

Example 3

4-[(3-Bromophenyl)amino]-6-{[4-(3-{N-[(ethoxycarbonyl)methyl]-N-methylamino)propylamino)-1, 4-dioxo-2-buten-1-yl]amino}-quinazoline 106 mg of benzotriazol-1-yl-N-tetramethyl-uronium-tetrafluoroborate and 68 mg of 1-hydroxybenzotriazole are added to a solution of 200 mg of 4-[(3-bromophenyl) amino]-6-{[(2-carboxyvinyl)carbonyl]amino}-quinazoline in 2.5 ml of dimethyl-formamide. The solution is stirred for 20 minutes at ambient temperature, then 0.5 ml of Hünig's base and 148 mg of 3-{N-[(ethoxycarbonyl)methyl]-N-methylamino}propylamine, dissolved in 0.5 ml of dimethylformamide, are added. The reaction mixture is stirred for a further two hours at ambient temperature before being poured onto 50 ml of water for working king up. The aqueous phase is extracted with ethyl acetate, the combined organic phases are washed with saturated sodium chloride solution, dried over magnesium sulphate and concentrated by evaporation. The crude product is purified by chromatography on a silica gel column with methylene chloride/ ethanol (20:1 to 9:1). Yield: 106 mg (39% of theory), Melting point: 278–279° C. Mass spectrum (ESI*): m/z= 569, 571 [M+H]*

The following compounds are obtained analogously to Example 3:

(1) 4-[(3-chloro-4-fluorophenyl)amino]-6-{[4-(3-{N-[(ethoxycarbonyl)methyl}-N-propylamino)-1,4-dioxo-2-buten-1-yl]amino}-7-cyclopropylmethoxy-quinazoline Melting point: 155–158° C. Mass spectrum (EI): m/z= 612, 614 [M]*

(2) 4-[(3-chloro-4-fluorophenyl)amino]-6-{{4-(2-{N-[(ethoxycarbonyl)methyl]-N-methylamino}ethylamino)-1,4-dioxo-2-butene-1-yl]amino}-7-cyclopropylmethoxy-quinazoline $R_f$ value: 0.56 (silica gel, ethyl acetate/ methanol=9:1) Mass spectrum (ESI*): m/z=599, 601 [M+H]*

(3) 4-[(3-Chloro-4-fluoro-phenyl)amino]-6-[(4-{4-[(ethoxycarbonyl)methyl]-piperazin-1-yl}-1,4-dioxo-2-buten-1-yl)amino]-7-cyclopropylmethoxy-quinazoline Melting point: 199° C. Mass spectrum (ESI): m/z=609, 611 (M−H)*

(4) (S)-4-[(3-Chloro-4-fluoro-phenyl)amino]-6-((4-[2-(methoxycarbonyl)-pyrrolidin-1-yl]-1,4-dioxo-2-buten-1-yl)amino]-7-cyclopropylmethoxy-quinazoline $R_f$ value: 0.57 (silica gel, ethyl acetate/methanol=95:5) Mass spectrum (ESI*): m/z=566, 568 [M–H]*

Example 4

4-[(3-Bromophenyl)amino]-6-({4-[(tert-butylcarbonyloxy)methoxy]-1,4-dioxo-2-buten-1-yl}amino) quinazoline 207 mg of potassium carbonate and 0.144 ml of chloromethyl pivalate are added to 200 mg of 4-[(3-bromophenyl)amino]-6{[(2-carboxy-vinyl)carbonyl]amino}-quinazoline in 2 ml of dimethylsulphoxide. Then a further 30 mg of sodium iodide are added and the reaction mixture is stirred for 48 hours at ambient temperature. For working up, the reaction mixture is diluted with 20 ml of water and extracted with ethyl acetate. The combined extracts are washed with saturated sodium chloride solution, dried over magnesium sulphate and concentrated by evaporation. The crude product mixture is purified by chromatography on a silica gel column with methylene chloride/methanol (20:1). Yield: 10 mg (4% of theoryl), $R_f$ value: 0.42 (silica gel, methylene chloride/methanol=9:1) Mass spectrum (EI): m/z=526 [M]*

The following compounds are obtained analogously to Example 4:
(1) 4-[(3-bromophenyl)amino]-6-({4-[1-(ethyloxycarbonyloxy)-ethoxy]-1,4-dioxo-2-buten-1-yl}amino) quinazoline (the reaction is carried out in dimethylformamide) $R_f$ value: 0.43 (silica gel, methylene chloride/methanol=9:1) Mass spectrum (ESI*): m/z=529, 531 [M+H]*
(2) 4-[(3-Chloro-4-fluoro-phenyl)amino]-6-{[4-(4-([(tert.butylcarbonyl)methoxycarbonyl]methyl)-piperazin-1-yl)-1-oxo-2-buten-1-yl]amino}-7-cyclopropylmethoxy-quinazoline (by reaction of the compound of Example 9(1) with chloromethyl pivalate in N,N-dimethyl-formamide in the presence of triethylamine) $R_f$ value: 0.50 (silica gel, methylene chloride/methanol=9:1) Mass spectrum (ESI*): m/z=681, 683 [M–H]*

Example 5

4-[(3-methylphenyl)amino]-6-[(4-{N-[(ethoxycarbonyl)methyl]-N-methylamino}-1-oxo-2-buten-1-yl)amino]-7-methoxy-quinazoline 0.86 ml of oxalylchloride and one drop of dimethylformamide are added to a solution of 842 mg of 4-bromo-2-butenoic acid in 15 ml of methylene chloride at ambient temperature. The reaction mixture is stirred for about a further hour at ambient temperature until the evaluation of gas has ended. The acid chloride formed is largely freed from solvent in the rotary evaporator in vacuo. Then the crude product is taken up in 10 ml of methylene chloride and, while cooling with an ice bath, added dropwise within five minutes to a mixture of 1.0 g of 6-amino-4-[(3-methylphenyl)amino]-7-methoxy-quinazoline and 2.0 ml of Hünig's base in 50 ml of tetrahydrofuran. The reaction mixture is stirred for two hours whilst cooling with an ice bath and for a further two hours at ambient temperature. 6.7 ml of Hünig base, 5.48 g of sarcosine ethylester hydrochloride and 3 ml of dimethylformamide are then added and the resulting mixture is stirred overnight at ambient temperature. For working up, the reaction mixture is concentrated by evaporation in the rotary evaporator in vacuo and the residue from the flask is partitioned between 75 ml of ethyl acetate and 75 ml of water. The organic phase is washed with water and saturated sodium chloride solution, dried over magnesium sulphate and concentrated by evaporation. The crude product is purified by chromatography on a silica gel column with methylene chloride/methanol (20:1). Yield: 326 mg (20% of theory) Melting point: 122–124° C. Mass spectrum (ESI*): m/z=464 [M+H]*

The following compounds are obtained analogously to Example 5:
(1) 4-[(3-chlorophenyl)amino]-6-[(4-{N-[(ethoxycarbonyl)methyl]-N-methylamino}-1-oxo-2-buten-1-yl)amino]-7-methoxy-quinazoline Melting point: 118–120° C. Mass spectrum (ESI*): m/z=484 [M+H]*
(2) (R)-4-[(1-phenylethyl)amino]-6-[(4-(N-[(ethoxycarbonyl)methyl]-N-methylamino}-1-oxo-2-buten-1-yl)amino]-7-methoxy-quinazoline $R_f$ value: 0.49 (silica gel, methylene chloride/methanol=9:10 Mass spectrum (ESI*): m/z=478 [M+H]*
(3) 4-[(3-bromophenyl)amino]-6-[(4-(N-[(methoxycarbonyl)methyl]-N-methylamino}-1-oxo-2-buten-1-yl)amino]-7-methoxy-quinazoline Melting point: 197–199° C. Mass spectrum (EI): m/z=513, 515 [M]*
(4) 4-[(3-bromophenyl)amino]-6-[(4-[(butyloxycarbonyl)methyl]-N-methylamino}-1-oxo-2-buten-1-yl)amino]-7-methoxy-quinazoline Melting point: 120–123° C. Mass spectrum (EI): m/z=555, 557 [M]*
(5) 4-[(3-bromophenyl)amino]-6-[(4-{N-[(cyclohexyloxycarbonyl)methyl]-N-methylamino)-1-oxo-2-buten-1-yl)amino]-7-methoxy-quinazoline (The sarcosine cyclohexylester used was obtained by treating sarcosine in cyclohexanol with gaseous hydrochloric acid) Melting point: 124–125° C. Mass spectrum (ESI*): m/z=582, 584 [M+H]*
(6) 4-[(3-bromophenyl)amino]-6-[(4-{4-[(ethoxycarbonyl)methyl]-piperazin-1-yl}-1-oxo-2-buten-1-yl)amino]-7-methoxy-quinazoline Melting point: 147–150° C. Mass spectrum (ESI*): m/z=583, 585 [M+H]*
(7) 4-[(3-bromophenyl)amino]-6-[(4-(4-[(isopropyloxycarbonyl)-methyl]-piperazin-1-yl)-1-oxo-2-buten-1-yl)amino]-7-methoxy-quinazoline (The isopropyl piperazin-1-yl-acetate used was obtained from N-benzylpiperazine by reacting with isopropyl bromoacetate and subsequently cleaving the benzyl group by hydrogenolysis.) Melting point: 125–127° C. Mass spectrum (ESI*): m/z=597, 599 [M+H]*
(8) 4-[(3-bromophenyl)amino]-6-({4-[N-(2,2-dimethoxyethyl)-N-methylamino]-1-oxo-2-buten-1-yl}amino)-7-methoxy-quinazoline Melting point: 135–137° C. Mass spectrum (ESI*): m/z=530, 532 [M+H]*
(9) 4-[(3-bromophenyl)amino]-6-((4-[N-(1,3-dioxolan-2-yl-methyl)-N-methylamino]-1-oxo-2-buten-1-yl}amino)-7-methoxy-quinazoline Melting point: 120–123° C. Mass spectrum (ESI*): m/z=528, 530 [M+H]*
(10) 4-[(3-bromophenyl)amino]-6-([4-(2-ethoxy-morpholin-4-yl)-1-oxo-2-buten-1-yl]amino)-7-methoxy-quinazoline Melting point: 118–120° C. Mass spectrum (ESI*): m/z=542, 544 [M+H]*
(11) 4-[(3-bromophenyl)amino]-6-{[4-(2-oxo-morpholin-4-yl)-1-oxo-2-buten-1-yl]amino}-7-methoxy-quinazoline $R_f$ value: 0.43 (silica gel, methylene chloride/methanol= 9:1) Mass spectrum (EI): m/z=511, 513 [M]*
(12) 4-[(3-bromophenyl)amino]-3-cyano-6-[(4-{N-[(ethoxycarbonyl)methyl]-N-methylamino}-1-oxo-2-buten-1-yl)amino]-quinoline Melting point: 156° C. Mass spectrum (ESI*): m/z=522, 524 [M+H]*
(13) 4-[(3-bromophenyl)amino]-6-({4-[N,N-bis(2,2-diethoxyethyl)amino]-1-oxo-2-buten-1-yl)amino}-7- methoxy-quinazoline R$_f$ value: 0.43 (aluminum oxide, cyclohexane/ethyl acetate=1:1) Mass spectrum (ESI$^+$): m/z=660, 662 [M+H]$^+$

(14) 4-[(3-bromophenyl)amino)-6-[(4-{4-[bis(methoxycarbonyl)methyl]-piperazin-1-yl}-1-oxo-2-buten-1-yl)amino]-quinazoline (The N-bis(methoxycarbonyl)methyl-piperazine used is obtained by reacting N-tert-butyloxycarbonyl-piperazine with dimethyl bromomalonate and subsequently cleaving the BOC protecting group.) R$_f$ value: 0.45 (silica gel, ethyl acetate/methanol=9:1) Mass spectrum (ESI$^+$): m/z=597, 599 [M+H]$^+$

(15) 4-[(3-bromophenyl)amino]-6-[4-(4-[1,2-bis(methoxycarbonyl)ethyl]-piperazin-1-yl)-1-oxo-2-buten-1yl)amino]-quinazoline (The N-[1,2-bis(methoxycarbonyl)ethyl]-piperazine used is obtained by reacting N-benzylpiperazine with dimethyl maleinate and subsequently cleaving the benzyl protecting group by hydrogenolysis.) R$_f$ value: 0.51 (silica gel, ethyl acetate/methanol=9:1)

(16) 4-[(3-bromophenyl)amino]-6-[(4-{N-[(tert.butyloxycarbonyl)methyl]-N-(2-hydroxyethyl)amino}-1-oxo-2-buten-1-yl)amino]-7-methoxy-quinazoline R$_f$ value: 0.45 (silica gel, methylene chloride/methanol=9:1) Mass spectrum (ESI$^-$): m/z=584, 586 [M–H]$^-$

(17) 4-[(3-chlorine-4-fluorophenyl)amino]-6-[(4-{N-[(ethoxy-carbonyl)methyl]-N-methylamino}-1-oxo-2-buten-1-yl)amino]-7-cyclopropylmethoxy-quinazoline Melting point 113–118° C. Mass spectrum (EI): m/z=541, 543 [M]$^+$

(18) 4-[(3-chlorone-4-fluorophenyl)amino]-6-[(4-{4-(ethoxycarbonyl)methyl]-piperazin-1-yl}-1-oxo-2-buten-1-yl)amino]-7-cyclopropylmethoxy-quinazoline Melting point: 115–117° C. Mass spectrum (EI): m/z=596, 598 [M]$^+$

(19) 4-[(3-bromophenyl)amino]-6-[(4-{4-[1,3-bis(methoxycarbonyl)prop-2-yl]-piperazin-1-yl}-1-oxo-2-buten-1-yl)amino]-quinazoline R$_f$ value: 0.62 (silica gel, ethyl acetate/methanol=9:1) Mass spectrum (ESI$^+$): m/z=625, 627 [M+H]$^+$

(20) 4-[(3-chloro-4-fluorophenyl)amino]-6-[(4-(N-[1,1-bis-(methoxycarbonyl)-methyl]-N-methylamino)-1-oxo-2-buten-1-yl)-amino]-7-cyclopropylmethoxy-quinazoline Melting point: 120–125° C. Mass spectrum (EI): m/z=585, 587 [M]$^+$

(21) 4-[(3-bromophenyl)amino]-6-[(4-(4-[(diethoxyphosphoryl)-methyl]-piperazin-1-yl)-1-oxo-2-buten-1-yl)amino]-quinazoline (The N-(diethoxyphosphoryl)methyl]-piperazine used is obtained by reacting N-benzylpiperazine with formaldehyde and diethyl phosphorate and subsequently cleaving the benzyl protecting group by hydrogenolysis.) R$_f$ value: 0.18 (silica gel, ethyl acetate/methanol=9:1) Mass spectrum (ESI$^+$): m/z=617, 619 [M+H]$^+$

(22) 4-[(3-chloro-4-fluorophenyl)amino]-6-[(4-{N-[2-ethoxycarbonyl)-ethyl]-N-[(ethoxycarbonyl)methyl]amino}-1-oxo-2-buten-1-yl)amino]-7-cyclopropylmethoxy-quinazoline R$_f$ value: 0.62 (aluminum oxide, cyclohexane/ethyl acetate=1:1) Mass spectrum (EI): m/z=627, 629 [M]$^+$

(23) 4-[{3-chloro-4-fluorophenyl)amino]-6-[(4-(4-[(tert-butyl-oxycarbonyl)methyl]-piperazin-1-yl}-1-oxo-2-buten-1-yl)amino]-7-cyclopropylmethoxy-quinazoline R$_f$ value: 0.42 (silica gel, ethyl acetate/methanol=9:1) Mass spectrum (ESI$^+$): m/z=625, 627 [M+H]$^+$

(24) 4-[{3-chloro-4-fluorophenyl)amino]-6-[(4-(N,N-bis[2-(ethoxycarbonyl)-ethyl]-amino}-1-oxo-2-buten-1-yl)amino]-7-cyclopropylmethoxy-quinazoline R$_f$ value: 0.37 (aluminum oxide, cyclohexane/ethyl acetate=1:1) Mass spectrum (ESI$^+$): m/z=642, 644 [M+H]$^+$

(25) 4-[(3-chloro-4-fluorophenyl)amino]-6-{[4-(2-oxo-morpholin-4-yl)-1-oxo-2-buten-1-yl]amino}-7-cyclopropylmethoxy-quinazoline Melting point: 230–232° C. Mass spectrum (EI): m/z=525, 527 [M]$^+$

(26) 4-[(3-chloro-4-fluorophenyl)amino]-6-[(4-{N-[(ethoxy-carbonyl)methyl]-N-(2-hydroxyethyl)amino}-1-oxo-2-buten-1-yl)amino]-7-cyclopropylmethoxy-quinazoline R$_f$ value: 0.25 (silica gel, methylene chloride/methanol=9:1) Mass spectrum (EI): m/z=571, 573 [M]$^+$

(27) 4[(3-chloro-4-fluorophenyl)amino]-6-[(4-(4-[(ethoxycarbonyl)methyl]-piperazin-1yl)-1-oxo-2-buten-1-yl)amino]-7-cyclohexylmethoxy-quinazoline Melting point: 110–114° C. Mass spectrum (EI): m/z=638, 640 [M]$^+$

(28) 4-[(3-chloro-4-fluorophenyl)amino]-6-[(4-{4-[ethoxycarbonyl)methyl]-piperazin-1-yl}-1-oxo-2-buten-1-yl)amino]-7-cyclohexyloxy-quinazoline Melting point: 117° C. Mass spectrum (EI): m/z=624, 626 [M]$^+$

(29) 4-[(3-chloro-4-fluorophenyl)amino]-6-[(4-{4-[(ethoxycarbonyl)methyl]-piperazin-1-yl)-1-oxo-2-buten-1-yl}amino]-7-cyclobutyloxy-quinazoline Melting point: 194–195° C. Mass spectrum (EI): m/z=596, 598 [M]$^+$

(30) 4-[(3-chloro-4-fluorophenyl)amino]-6-[(4-{4-[(ethoxycarbonyl)methyl]-piperazin-1-yl}-1-oxo-2-buten-1-yl)amino]-7-cyclobutylmethoxy-quinazoline R$_f$ value: 0.53 (silica gel, methylene chloride/methanol=9:1) Mass spectrum (EI): m/z=610, 612 [M]$^+$

(31) 4-[(3-chloro-4-fluorophenyl)amino]-6-[(4-(4-[(ethoxycarbonyl)methyl]-piperazin-1-yl)-1-oxo-2-buten-1-yl)amino]-7-cyclopentyloxy-quinazoline R$^r$ value: 0.53 (silica gel, methylene chloride/methanol=9:1) Mass spectrum (EI): m/z=624, 626 [M]$^+$

(32) 4-[(3-chloro-4-fluorophenyl)amino]-6-[(4-{4-[(ethoxycarbonyl)methyl]-piperazin-1-yl}-1-oxo-2-buten-1-yl)amino]-7-(2-cyclopropylmethoxy)-quinazoline R$_f$ value: 0.53 (silica gel, methylene chloride/methanol=9:1) Mass spectrum (EI): m/z=610, 612 [M]$^+$

(33) 4-[(3-chloro-4-fluorophenyl)amino]-6-[(4-{4-[(ethoxycarbonyl)methyl]-piperazin-1-yl}-1-oxo-2-buten-1-yl)amino]-7-cyclopentyloxy-quinazoline R$_f$ value: 0.35 (silica gel, ethyl acetate/methanol=9:1) Mass spectrum (EI): m/z=610, 612 [M]$^+$

(34) 4-[(3-chloro-4fluorophenyl)amino]-6-[(4-(N-[(ethoxycarbonyl)methyl]-N-(2-hydroxy-2-methyl-propyl)amino)-1-oxo-2-buten-1-yl)amino]-7-cyclopropylmethoxy-quinazoline R$_f$ value: 0.42 (silica gel, methylene chloride/methanol=9:1) Mass spectrum (ESI$^+$): m/z=600, 602 [M+H]$^+$

(35) 4-[(3-chloro-4-fluorophenyl)amino]-6-{(4-[2-methoxycarbonyl)-piperidin-1-yl]-1-oxo-2-buten-1-yl}amino)-7-cyclopropylmethoxy-quinazoline R$_f$ value: 0.42 (silica gel, ethyl acetate) Mass spectrum (ESI$^+$): m/z=568, 570 [M+H]$^+$

(36) (S)-4-[(3-chloro-4-fluorophenyl)amino]-6-({4-[2-methoxycarbonyl)-pyrrolidin-1-yl]-1-oxo-2-buten-1-yl}amino)-7-cyclopropylmethoxy-quinazoline Melting point: 135–138° C. Mass spectrum (EI): m/z=553, 555 [M]$^+$

(37) 4-[(3-chloro-4-fluorophenyl)amino]-6-[(4-{N,N-bis[(methoxycarbonyl)methyl]amino}-1-oxo-2-buten-1-yl)amino]-7-cyclopropylmethoxy-quinazoline Melting point: 122° C. Mass spectrum (ESI$^+$): m/z=586, 588 [M+H]$^+$

(38) 4-[(3-chloro-4-fluorophenyl)amino]-6-{[4-(5,5-dimethyl-2-oxo-morpholin-4-yl)-1-oxo-2-buten-1-yl]-amino}-7-cyclo-propylmethoxy-quinazoline $R_f$ value: 0.39 (silica gel, ethyl acetate) Mass spectrum (ESI$^+$): m/z=554, 556 [M+H]$^+$

(39) 4-[(3-chloro-4-fluorophenyl)amino]-6-{[4-(5-methyl-2-oxo-morpholin-4-yl)-1-oxo-2-buten-1yl]amino}-7-cyclopropylmethoxy-quinazoline $R_f$ value: 0.15 (silica gel, ethyl acetate/cyclohexane=4:1) Mass spectrum (ESI$^+$): m/z=540,542 [M+H]$^+$

(40) (R)-4-[(3-chloro-4-fluorophenyl)amino]-6-({4-[2-methoxycarbonyl)-pyrrolidin-1-yl]-1-oxo-2-buten-1-yl}amino)-7-cyclopropylmethoxy-quinazoline Melting point: 133° C. Mass spectrum (ESI$^+$): m/z=554, 556 [M+H]$^+$

(41) cis-4-[(3-chloro-4-fluorophenyl)amino]-6-({4-[2,5-bis-(ethoxycarbonyl)-pyrrolidin-1-yl]-1-oxo-2-buten-1-yl}amino)-7-cyclopropylmethoxy-quinazoline Melting point: 117–120° C. Mass spectrum (ESI$^+$): m/z=640, 642 [M+H]$^+$

(42) cis-4-[(3-Chloro-4-fluoro-phenyl)amino]-6-({4-[2,6-bis-(methoxycarbonyl)-piperidin-1-yl]-1-oxo-2-buten-1-yl}amino)-7-cyclopropylmethoxy-quinazoline $R_f$ value: 0.20 (silica gel, cyclohexane/ethyl acetate=2.3) Mass spectrum (EI): m/z=625, 627 [M]$^+$

(43) trans-4-[(3-Chloro-4-fluoro-phenyl)amino]-6-({4-[2,6-bis-(methoxycarbonyl)-piperidin-1-yl]-1-oxo-2-buten-1-yl}amino)-7-cyclopropylmethoxy-quinazoline $R_f$ value: 0.28 (silica gel, cyclohexane/ethyl acetate=2.3) Mass spectrum (EI): m/z=625, 627 [M]$^+$

(44) cis-4-[(3-Chloro-4-fluoro-phenyl)amino]-6-({4-[2,5-bis-(methoxycarbonyl)-pyrrolidin-1-yl]-1-oxo-2-buten-1-yl}amino)-7-cyclopropylmethoxy-quinazoline Melting point: 125° C. Mass spectrum (ESI$^+$): m/z=610, 612 [M–H]$^-$

(45) trans-4-[(3-Chloro-4-fluoro-phenyl)amino]-6-({4-[2,5-bis-(methoxycarbonyl)-pyrrolidin-1-yl]-1-oxo-2-buten-1-yl}amino)-7-cyclopropylmethoxy-quinazoline Melting point: 165° C. Mass spectrum (EI): m/z=611, 613 [M]$^+$

(46) 4-[(3-Chloro-4-fluoro-phenyl)amino]-6-[(4-[4-[(ethoxycarbonyl)methyl]-piperazin-1-yl)-4-methyl-1-oxo-2-buten-1-yl)-amino]-7-cyclopropylmethoxy-quinazoline $R_f$ value: 0.45 (silica gel, ethyl acetate/methanol=9:1) Mass spectrum (ESI$^-$): m/z=609, 611 [M–H]$^-$

(47) 4-[(3-Chloro-4-fluoro-phenyl)amino]-6-[(4-[4-[1,2-bis-(methoxycarbonyl)-ethyl]-piperazin-1-yl]-1-oxo-2-buten-1-yl)-amino]-7-cyclobutyloxy-quinazoline (The starting material 2-piperazin-1-yl)-succinic acid dimethyl ester is prepared by reaction of N-benzyl-piperazine with maleic acid dimethyl ester followed by hydrogenolytic cleavage of the benzyl protecting group.) $R_f$ value: 0.39 (silica gel, ethyl acetate/methanol=9:1) Mass spectrum (EI): m/z=654, 656 [M]$^+$

(48) 4-[(3-Chloro-4-fluoro-phenyl)amino]-6-[{4-{N-[1-(methoxycarbonyl)-ethyl]-N-methylamino}-1-oxo-2-buten-1-yl)amino]-7-cyclopropylmethoxy-quinazoline $R_f$ value: 0.41 (silica gel, ethyl acetate) Mass spectrum (ESI$^-$): m/z=540, 542 [M–H]$^-$

(49) (S)-4-[(3-Chloro-4-fluoro-phenyl)amino]-6-({4-[2-(benzyl-oxycarbonyl)-pyrrolidin-1-yl]-1-oxo-2-buten-1-yl}amino)-7-cyclopropylmethoxy-quinazoline $R_f$ value: 0.20 (silica gel, cyclohexene/ethyl acetate=2:3) Mass spectrum [ESI$^+$]: m/z=628, 630 [M–H]$^+$

(50) 4-[(R)-(1-Phenyl-ethyl)amino]-6-[(4-[4-(ethoxycarbonyl)-methyl]-piperazin-1-yl]-1-oxo-2-buten-1-yl)amino]-7-cyclobutyloxy-quinazoline $R_f$ value: 0.25 (silica gel, ethyl acetate/methanol=9:1) Mass spectrum (EI): m/z=572 [M]$^+$

(51) 4-[(R)-{1-Phenyl-ethyl)amino]-6-[(4-{4-[(ethoxycarbonyl)-methyl]-piperazin-1-yl}-1-oxo-2-buten-1-yl)amino]-7-cyclopentyloxy-quinazoline $R_f$ value: 0.27 (silica gel, ethyl acetate/methanol=9:1) Mass spectrum (ESI$^-$): m/z=585 [M–H]$^-$

(52) 4-[(R)-(1-Phenyl-ethyl)amino]-6-[(4-{4-[(ethoxycarbonyl)-methyl]-piperazin-1-yl)-1-oxo-2-buten-1-yl)amino]-7-cyclopropylmethoxy-quinazoline $R_f$ value: 0.20 (silica gel, ethyl acetate/methanol=9:1) Mass spectrum (ESI$^-$): m/z=571 [M–H]$^-$

(53) 4-[(3-Chloro-4-fluoro-phenyl)amino]-6-[(4-(2-[(ethoxycarbonyl)methyl]-piperidin1-yl}-1-oxo-2-buten-1-yl)amino]-7-cyclopropylmethoxy-quinazoline $R_f$ value: 0.28 (silica gel, ethyl acetate) Mass spectrum (ESI$^-$): m/z=594, 596 [M–H]$^+$

(54) 4-[{3-Chloro-4-fluoro-phenyl)amino]-6-[(4-(N-[(ethoxycarbonyl)methyl]-N-[1-(ethoxycarbonyl)-ethyl]amino}-1-oxo-2-buten-1-yl)amino]-7-cyclopropylmethoxy-quinazoline $R_f$ value: 0.56 (silica gel, ethyl acetate) Mass spectrum (EI): m/z=627, 629 [M]$^+$

(55) (S)-4-Benzylamino-6-({4-[2-methoxycarbonyl)-pyrrolidin-1-yl]-1-oxo-2-buten-1-yl}amino)-7-cyclopropylmethoxy-quinazoline $R_f$ value: 0.48 (silica gel, ethyl acetate/methanol=9:1) Mass spectrum (ESI$^-$): m/z=514 [M–H]$^+$

(56) 4-Benzylamino-6-[(4-{4-[(ethoxycarbonyl)methyl]-piperazin-1-yl}-1-oxo-2-buten-1-yl)amino]-7-cyclopropylmethoxy-quinazoline $R_f$ value: 0.20 (silica gel, ethyl acetate/methanol=9:1) Mass spectrum (ESI$^-$): m/z=557 [M–H]$^-$

(57) (R)-4-[(3-Chloro-4-fluoro-phenyl)amino]-6-[(4-{N-[1-ethoxycarbonyl)-ethyl]-N-(2-hydroxyethyl)amino}-1-oxo-2-buten-1-yl)amino]-7-cyclopropylmethoxy-quinazoline $R_f$ value: 0.24 (silica gel, ethyl acetate) Mass spectrum (ESI$^-$): m/z=584, 586 [M–H]$^-$

(58) 4-[(3-Chloro-4-fluoro-phenyl)amino]-6-[(4-(4-[(ethoxycarbonyl)methyl]-homopiperazin-1-yl}-1-oxo-2-buten-1-yl)amino]-7-cyclopropylmethoxy-quinazoline (The starting material N-[(ethoxycarbonyl)methyl]-homopiperazin was prepared by reaction of N-benzyl-homopiperazin with ethyl bromo-acetate and subsequent hydrogenolytic removal of the benzyl group.) $R_f$ value: 0.18 (silica gel, ethyl acetate/methanol=9:1) Mass spectrum (ESI$^-$): m/z=609, 611 [M–H]$^-$

(59) 4-[(3-chloro-4-fluorophenyl)amino]-6-[(4-[N-(2-oxo-tetrahydrofuran-3-yl)-N-methyl-amino]-1-oxo-2-buten-1-yl)amino]-7-cyclopropylmethoxy-quinazoline (The starting material 3-methylamino-2-oxo-tetrahydrofuran is prepared by reaction of 3-bromo-2-oxo-tetrahydrofuran with N-methyl-benzylamin followed by hydrogenolytic cleavage of the benzyl group) melting point: 109° C. Mass spectrum (ESI$^-$): m/z=538, 540 (M–H)$^-$

(60) 4-[(3-chloro-4-fluorophenyl)amino]-6-[(4-(N-(2-oxo-tetrahydrofuran-4-yl)-N-methyl-amino]-1-oxo-2buten-1-yl)amino]-7-cyclopropylmethoxy-quinazoline (The starting material 4-methylamino-2-oxo-tetrahydrofuran is prepared by reaction of (5H)-furan-2-on with N-methyl-benzylamin followed by hydrogenolytic cleavage of the benzyl group) $R_f$-value: 0.56 (silica gel, ethylacetate/methanol=9:1) Mass spectrum (ESI-): m/z=538, 540 (M–H)$^-$ Example 6

4-[(3-Bromophenyl)amino]-7-{3-[4-(carboxymethyl)-piperazin-1-yl]propyloxy}-6-[(vinylcarbonyl)amino]-quinazoline 0.43 ml of triethylamine and 0.15 ml of chlorotrimethyl-silane are added to a suspension of 440 mg of 6-amino-4-

[(3-bromophenyl)amino]-7-{3-[4-(carboxymethyl)-piperazin-1-yl]propyloxy}-quinazoline in 15 ml of methylene chloride at ambient temperature. The reaction mixture is refluxed gently for about 30 minutes and then stirred overnight at ambient temperature. The cloudy solution is cooled with a mixture of ice and sodium chloride and combined with a solution of 82 mg of acrylic acid chloride in 5 ml of methylene chloride. The reaction mixture is stirred for about one hour at ambient temperature, then at intervals of an hour two drops of acrylic acid chloride are added twice until the reaction is almost complete. The reaction mixture is stirred with 20 ml of ice water and a little methanol. The aqueous phase is extracted several times with methylene chloride/methanol (9:1). The combined extracts are washed with a little water, dried over magnesium sulphate and concentrated by evaporation. The crude product obtained is stirred with acetone, suction filtered, washed again with diethylether and dried at 60° C. in vacuo. Yield: 105 mg (24% of theory) Melting point: 140° C. (decomposition) Mass spectrum (ESI$^-$): m/z=567, 569 [M–H]$^-$ Example 7

4-[(3-bromophenyl)amino]-6-{[4-(2,6-diethoxy-morpholin-4-yl)-1-oxo-2-buten-1-yl]amino}-7-methoxy-quinazoline 1 ml of ice-cooled concentrated hydrochloric acid is added to 340 mg of 4-[(3-bromophenyl)amino]-6-((4-[N,N-bis(2,2-diethyoxyethyl)amino]-1-oxo-2-buten-1-yl)amino)-7-methoxy-quinazoline while cooling with an ice bath. The mixture is left to stand for 3 hours before 1.5 ml of concentrated ammonia solution is added dropwise while cooling with an ice bath for working up. The precipitate formed is suction filtered and washed with water. The crude product is purified by chromatography on a silica gel column with methylene chloride/methanol (20:1) Yield: 50 mg (17% of theory) Melting point: 133–138° C. Mass spectrum (EI): m/z=585, 587 [M]$^+$ Example 8

4-[(3-Bromophenyl)amino]-6-[(4-{N-[(tert-butyloxycarbonyl)methyl]-N-[2-(acetylsulphanyl)ethyl]amino)-1-oxo-2-buten-1-yl)-amino]-7-methoxy-quinazoline 34 mg of potassium thioacetate are added to 150 mg of 4-[(3-bromophenyl)amino]-6-[(4-(N-[(tert-butyloxycarbonyl)methyl]-N-[2-(methylsulphonyloxy)ethyl]amino}-1-oxo-2-buten-1-yl)amino]-7-methoxy-quinazoline in 1 ml of dimethylformamide at ambient temperature. The reaction mixture is stirred overnight at ambient temperature and then combined with water for working up. The aqueous phase is separated off and extracted with ethyl acetate, the combined organic phases are dried over magnesium sulphate and freed from solvent in the rotary evaporator. Yield: 20 mg (14% of theory), R$_f$ value: 0.62 (silica gel, ethyl acetate/methanol=15:1) Mass spectrum (EI): m/z=643, 645 [M]$^+$ The following compound is obtained analogously to Example 8:
(1) 4-[(3-chloro-4-fluorophenyl)amino]-6-[(4-(N-[(ethoxycarbonyl)methyl]-N-[2-(acetylsulphanyl)ethyl]amino)-1-oxo-2-buten-1-yl)amino]-7-cyclopropylmethoxy-quinazoline R$_f$ value: 0.64 (silica gel, ethyl acetate) Mass spectrum (EI): m/z=629, 631 [M]$^+$ Example 9

4-[(3-bromophenyl)amino]-6-([4-(N-(carboxymethyl)-N-(2-hydroxyethyl)amino]-1-oxo-2-buten-1-yl)amino)-7-methoxyquinazoline 1 ml of trifluoroacetic acid is added dropwise within two minutes to a solution of 330 mg of 4-[(3-bromophenyl) amino]-6-[(4-{N-[(tert-butyloxycarbonyl)methyl]-N-(2-hydroxyethyl)amino}-1-oxo-2-buten-1-yl)amino]-7-methoxy-quinazoline in 4 ml of methylene chloride while cooling with an ice bath. The reaction mixture is stirred for half an hour while cooling with an ice bath and then for a further 24 hours at ambient temperature. For working up, the mixture is evaporated to dryness in the rotary evaporator. The crude product is stirred with ethyl acetate, the solid precipitate is filtered off, washed with ethyl acetate and dried in vacuo at 50° C. Yield: 169 mg (57% of theory), R$_f$ value: 0.50 (Reversed phase ready-made TLC plate (E. Merck), acetonitrile/water/trifluoroactic acid=50:50:1) Mass spectrum (ESI$^-$): m/z=528, 530 [M–H]$^-$ The following compounds are obtained analogously to Example 9:
(1) 4-[(3-chloro-4-fluorophenyl)amino]-6-({4-(carboxymethyl)-piperazin-1-yl]-1-oxo-2-buten-1-yl}amino)-7-cyclopropylmethoxy-quinazoline R$_f$ value: 0.43 (Reversed phase ready-made TLC plate (E. Merck), acetonitrile/water/trifluoroacetic acid=1:1:1) Mass spectrum (ESI$^-$): m/z=567, 569 [M–H]$^-$
(2) 4-[(3-bromophenyl)amino]-6-[(4-{4-[(phosphono)methyl]-piperazin-1-yl}-1-oxo-2-buten-1-yl)amino]-quinazoline (The substance is obtained by treating the compound obtained in Example 5(21) with trimethylbromosilane in dimethylformamide) R$_f$ value: 0.58 (Reversed phase ready-made TLC plate (E. Merck), acetonitrile/water/trifluoroacetic acid=1:1:1) Mass spectrum (ESI$^-$): m/z=559, 561 [M–H]$^-$ Example 10

4-[(3-chloro-4-fluorophenyl)amino]-6-{[4-(2,2-dimethyl-6-oxo-morpholin-4-yl)-1-oxo-2-buten-1-yl]amino}-7-cyclopropylmethoxy-quinazoline 15 mg of p-toluenesulphonic acid monohydrate are added to 150 mg of 4-[(3-chloro-4-fluorophenyl)amino]-6-[(4-{N-[(ethoxycarbonyl)methyl]-N-(2-hydroxy-2-methyl-propyl)amino}-1-oxo-2-buten-1-yl)amino]-7-cyclopropylmethoxy-quinazoline in 2.5 ml of acetonitrile. The solution formed is stirred first for three hours at ambient temperature, then refluxed for a further two hours until the reaction is complete. For working up, the reaction mixture is combined with 30 ml of ethyl acetate. The organic phase is separated off, washed with saturated sodium hydrogen carbonate solution and saturated sodium chloride solution, dried over magnesium sulphate and concentrated by evaporation. The oily yellow residue is stirred with diethylether, whereupon a light yellow solid crystallises out, which is filtered off and dried. Yield: 85 mg (61% of theory), Melting point: 140–142° C. Mass spectrum (ESI$^+$): m/z=554, 556 [M+H]$^+$ The following compound is obtained analogously to Example 10:
(1) (R)-4-[(3-Chloro-4-fluoro-phenyl)amino]-6-{[4-(3-methyl-2-oxo-morpholin-4-yl)-1-oxo-2-buten-1-yl]amino}-7-cyclopropylmethoxy-quinazoline Melting point: 192° C. Mass spectrum (ESI$^-$): m/z=518, 540 [M–]$^-$ Example 11

4-[(3-chloro-4-fluorophenyl)amino]-6-[(4-(N-[(ethoxycarbonyl)-methyl]-N-[2-(methylcarbonyloxy)ethyl]amino]-1-oxo-2-buten-1-yl)amino]-7-cyclopropylmethoxy-quinazoline 47 μl of acetic anhydride and catalytic amounts of 4-dimethyl-aminopyridine are added to 250 mg of 4-[(3-chloro-4-fluorophenyl)amino]-6-[(4-{N-[(ethoxycarbonyl)

methyl]-N-(2-hydroxyethyl)amino}-1-oxo-2-buten-1-yl) amino]-7-cyclopropylmethoxy-quinazoline in 2 ml of methylene chloride. The reaction mixture is stirred overnight at ambient temperatures and then evaporated to dryness. The crude product is purified by chromatography on a silica gel column with methylene chloride, followed by methylene chloride/methanol (9:1) as eluant. Yield: 150 mg (56% of theory), Melting point: 90–92° C. Mass spectrum (ESI$^+$): m/z=614, 616 [M+H]$^+$ Example 12

4-[(3-Chloro-4-fluoro-phenyl)amino]-6-[(4-{4-[(benzyloxycarbonyl)methyl]-piperazin-1-yl)-1-oxo-2-buten-1-yl}amino]-7-cyclopropylmethoxy-quinazoline 500 mg of 4-[(3-chloro-4-fluoro-phenyl)amino]-6-{[4-(piperazin-1-yl)-1-oxo-2-buten-1-yl]amino}-7-cyclopropylmethoxy-quinazoline are dissolved in 5 ml of acetonitrile, and 0.35 ml of triethylamine followed by 0.17 ml of benzyl bromo-acetate are added dropwise at room temperature. The reaction mixture is stirred for approximately 45 minutes at room temperature and then concentrated in vacuo. The solid residue is triturated with water and filtered off. The crude product is purified by column chromatography on silica gel with methylene chloride/methanol (20:1) followed by recrystallization from ethyl acetate. Yield: 380 mg (59% of theory), Melting point: 174° C. Mass spectrum (ESI$^-$): m/z=657, 659 [M–H]$^-$ The following compounds are obtained analogously to Example 12:

(1) 4-[(3-Chloro-4-fluoro-phenyl)amino]-6-[(4-{4-[(phenyloxycarbonyl)methyl]-piperazin-1-yl}-1-oxo-2-buten-1-yl)amino]-7-cyclopropylmethoxy-quinazoline R$_f$ value: 0.50 (silica gel, methylene chloride/methanol=9:1) Mass spectrum (ESI$^+$): m/z=645, 647 [M+H]$^+$ (2) 4-[(3-Chloro-4-fluoro-phenyl)amino]-6-[(4-{4-[(indan-5-yl-oxycarbonyl)methyl]-piperazin-1-yl}-1-oxo-2-buten-1-yl)amino]-7-cyclopropylmethoxy-quinazoline (reaction is carried out in N,N-dimethyl-formamide) R$_f$ value: 0.52 (silica gel, methylene chloride/methanol=9:1) Mass spectrum (ESI$^+$): m/z=685, 687 [M+H]$^+$ (3) 4-[(3-Chloro-4-fluoro-phenyl)amino]-6-[(4-{4-[(cyclohexyl-methoxycarbonyl)methyl]-piperazin-1-yl}-1-oxo-2-buten-1-yl)-amino]-7-cyclopropylmethoxy-quinazoline (reaction is carried out in tetrahydrofuran) R$_f$ value: 0.52 (silica gel, methylene chloride/methanol=9:1) Mass spectrum (ESI$^+$): m/z=655, 667 [M+H]$^+$ (4) 4-[(3-Chloro-4-fluoro-phenyl)amino]-6-[(4-{4-[(octyloxycarbonyl)methyl]-piperazin-1-yl}-1-oxo-2-buten-1-yl)amino]-7-cyclopropylmethoxy-quinazoline (reaction is carried out in tetrahydrofuran) R$_f$ value: 0.50 (silica gel, methylene chloride/methanol=9:1) Mass spectrum (ESI$^+$): m/z=681, 683 [M+H]$^+$ (5) 4-[(3-Chloro-4-fluoro-phenyl)amino]-6-[(4-{4-[(hexyloxycarbonyl)methyl]-piperazin-1-yl}-1-oxo-2-buten-1-yl)amino]-7-cyclopropylmethoxy-quinazoline R$_f$ value: 0.52 (silica gel, methylene chloride/methanol=9:1) Mass spectrum (ESI$^+$): m/z=653, 655 [M+H]$^+$ (6) 4-[(3-Chloro-4-fluoro-phenyl)amino]-6-[(4-(2-(ethoxycarbonyl-4-[(ethoxycarbonyl)methyl]-piperazin-1-yl)-1-oxo-2-buten-1-yl)amino]-7-cyclopropylmethoxy-quinazoline (reaction is carried out in tetrahydrofuran) R$_f$ value: 0.60 (silica gel, ethyl acetate/methanol=9:1) Mass spectrum (EI): m/z=668, 670 [M]$^+$ (7) 4-[(3-Chloro-4-fluoro-phenyl)amino]-6-[(4-(4-[3-ethoxycarbonyl)-propyl]-piperazin-1-yl)-1-oxo-2-buten-1-yl)amino]-7-cyclopropylmethoxy-quinazoline (reaction is carried out with ethyl 4-bromobutyrate in tetrahydrofuran) R$_f$ value: 0.42 (silica gel, methylene chloride/methanol/concentrated aqueous ammonia= 9:10:1) Mass spectrum (ESI$^-$): m/z=623, 625 [M–H]$^-$ Example 13

4-[(3-Chloro-4-fluoro-phenyl)amino]-6-{(4-[2-ethoxycarbonyl)-piperazin-1-yl]-1-oxo-2-buten-1yl)amino)-7-cyclopropyl-methoxy-quinazoline 5 ml of trifluoro-acetic acid are added dropwise to a mixture of 4.00 g 4-[(3-chloro-4-fluoro-phenyl)amino]-6-((4-[2-ethoxycarbonyl)-4-(tert-butyloxycarbonyl)-piperazin-1-yl]-1-oxo-2-buten-1-yl}amino)-7-cyclopropylmethoxy-quinazoline in 15 ml of methylene chloride cooled to 0° C. in an ice water/bath. The resulting mixture is stirred for one hour at 0° C. and then allowed to warm to room temperature over night. The solvent is distilled off in vacuo and the residue is partitioned between 150 ml of methylene chloride/methanol (9:1) and 100 ml of 1N aqueous sodium hydroxide. The aqueous layer is extracted with methylene chloride/methanol (9:1), the combined organic extracts are dried over magnesium sulfate, and concentrated in vacuo to give the title compound. Yield: 3.08 g (90% of theory), R$_f$ value: 0.40 (reversed phase TLC-plate (E. Merck), acetonitrile/water/trifluoro-acetic acid=50:50:1) Mass spectrum (ESI$^+$): m/z=583, 585 [M+H]$^+$ Example 14

4-[(3-Chloro-4-fluoro-phenyl)amino]-6-((4-[2-ethoxycarbonyl)-4-methyl-piperazin-1-yl]-1-oxo-2-buten-1-yl)amino)-7-cyclopropylmethoxy-quinazoline A mixture of 500 mg 4-[(3-chloro-4-fluoro-phenyl) amino]-6-({4-[2-ethoxycarbonyl)-piperazin-1-yl]-1oxo-2-buten-1-yl}amino)-7-cyclopropylmethoxy-quinazoline, 50 μl glacial acetic acid, and 80 μl of an aqueous formaldehyde solution (37 weight %) in 5 ml methanol is treated with 270 mg sodium triacetoxyborohydride at room temperature. After 6 hours, insoluble salts are removed by filtration and the filtrate is concentrated in vacuo. The residue is made alkaline with 0.1N aqueous sodium hydroxide solution and extracted with ethyl acetate. The combined extracts are dried over magnesium sulfate and concentrated in vacuo. The crude product is purified by column chromatography on silica gel with ethyl acetate/methanol (90:10 to 85:15). Yield: 350 mg (68% of theory), R$_f$: 0.27 (silica gel, ethyl acetate/methanol=9:1) Mass spectrum (ESI$^+$): m/z=597, 597 [M+H]$^+$ Example 15

4-[(3-Chloro-4-fluoro-phenyl)amino]-6-({4-[2-(ethoxycarbonyl)-4-(methylsulfonyl)-piperazin-1-yl]-1-oxo-2-buten-1-yl)amino)-7-cyclopropylmethoxyquinazoline A stirred mixture of 500 mg 4-[(3-chloro-4-fluoro-phenyl)-amino]-6-({4-[2-(ethoxycarbonyl)-piperazin-1-yl]-1-oxo-2-buten-1-yl}amino)-7-cyclopropylmethoxy-quinazoline and 0.20 ml triethylamine in 5 ml of methylene chloride is cooled in an ice/water bath, and 80 μl of methanesulfonyl chloride are added dropwise. The reaction mixture is stirred for one hour at 0° C. and another two hours at room temperature. Aqueous work-up followed by column chromatography on silica gel with methylene chloride/methanol (97:2) gives the title compound as a slightly yellow solid. Yield: 395 mg (70% of theory), Melting point: 170–173° C. Mass spectrum (ESI$^+$): m/z=661, 663 [M+H]$^+$ Example 16

4-[(3-Chloro-4-fluoro-phenyl)amino]-6-[(4-{4-[2-(ethoxycarbonyl)-ethyl]-piperazin-1-yl}-1-oxo-2-buten-1-yl)amino]-7-cyclopropylmethoxy-quinazoline A mixture of 200 mg of 4-[(3-chloro-4-fluoro-phenyl) amino]-6-{[4-(piperazin-1-yl)-1-oxo-2-buten-1-yl]amino}-

7-cyclopropylmethoxy-quinazoline and 0.11 ml of ethyl acrylate in 2 ml of ethanol is heated under reflux for one hour. The solvent is evaporated in vacuo and the crude product is purified by column chromatography on silica gel with methylene chloride/methanol (95:5 to 90:10) followed by recrystallization from diethyl ether. Yield: 164 mg (69% of theory), Melting point: 183–185° C. Mass spectrum (ESI$^-$): m/z=609, 611 [M–H]$^-$ Example 17

4-[(3-Chloro-4-fluoro-phenyl)amino]-6-[(4,4-dimethyl-4-{4-[(ethoxycarbonyl)methyl]-piperazin-1-yl)-1-oxo-2-buten-1-yl)amino]-7-cyclopropylmethoxy-quinazoline A mixture of 150 mg 4-[(3-chloro-4-fluoro-phenyl)amino]-6-{[2-diethoxyphosphoryl)-1-oxo-ethyl]amino}-7-cyclopropyl-methoxy-quinazoline and 12 mg dry lithium chloride in 2 ml of anhydrous tetrahydrofuran is stirred for 15 minutes at room temperature under an argon atmosphere. The mixture is cooled to 0° C. and 43 μl of 1,8-diazabicyclo[5.4.0]undec-7-ene are added. After 30 minutes at 0° C., 84 mg of [4-(1,1-dimethyl-2-oxo-ethyl)-piperazin-1-yl]-acetic acid ethyl ester are added and the resulting mixture is allowed to warm to room temperature over night. The reaction mixture is diluted with ethyl acetate/methanol (15:1) and washed with water. The organic layer is directly submitted to column chromatography on silica gel with ethyl acetate/methanol (95:5 to 90:10). Yield: 36 mg (21% of theory), Melting point: 165–167° C. Mass spectrum (ESI$^+$): m/z=625, 627 [M+H]$^+$ Example 18

4-[(3-Chloro-4-fluoro-phenyl)amino]-6-({4-[2-(ethoxycarbonyl)-4-(methylcarbonyl)-piperazin-1-yl]-1-oxo-2-buten-1-yl}amino)-7-cyclopropylmethoxy-quinazoline 0.12 ml of acetic acid anhydride are added dropwise to a mixture of 500 mg of 4-[(3-chloro-4-fluoro-phenyl)amino]-6-({4-[2-(ethoxycarbonyl)-piperazin-1-yl]-1-oxo-2-buten-1-yl}amino)-7-cyclopropylmethoxy-quinazoline and 0.18 ml of triethylamine in 5 ml of methylene chloride at 0° C. The reaction mixture is stirred for one hour at 0° C. followed by one hour at room temperature, washed with water, concentrated sodium chloride solution, dried over magnesium sulfate, and concentrated in vacuo. The crude product is purified by column chromatography on silica gel with ethyl acetate/methanol (98:2 to 95:5). Yield: 291 mg (54% of theory), Melting point: 152–156° C. Mass spectrum (ESI$^+$): m/z=625, 627 [M+H]$^+$ The following compounds may also be obtained analogously to the preceding Examples and other methods known from the literature:

(1) 4-[(3-bromophenyl)amino]-7-(3-(4-[(butoxycarbonyl)methyl]-piperazin-1-yl}propyloxy)-6-[(vinylcarbonyl)amino]-quinazoline (2) 4-[(3-bromophenyl)amino]-7-(3-[4-(diethoxyphosphoryl)-methyl]-piperazin-1-yl)propyloxy)-6-[(vinylcarbonyl)amino]-quinazoline (3) 4-[(3-bromophenyl)amino]-7-(2-(N-[(ethoxycarbonyl)methyl]-N-methylamino)ethoxy}-6-[(vinylcarbonyl)amino]-quinazoline (4) 4-[(3-bromophenyl)amino]-7-(3-{N-[(ethoxycarbonyl)methyl]-N-methylamino}propyloxy)-[(vinylcarbonylamino]-quinazoline (5) 4-[(3-bromophenyl)amino]-7-(4-{N-[(ethoxycarbonyl)methyl]-N-methylamino}butyloxy)-6-[(vinylcarbonyl)amino]-quinazoline (6) 4-[(3-bromophenyl)amino]-7-{3-[4-(carboxymethyl)-piperazine-1-yl)propyloxy)-6-[(vinylcarbonyl)amino]-quinazoline (7) 4-[(3-bromophenyl)amino]-7-(3-(4-diethoxyphosphoryl)methyl)-piperazin-1-yl)propyloxy-6-[(1-oxo-2-butyn-1-yl)amino]-quinazoline (8) [(3-bromophenyl)amino]-6-[(4-{N-[( methoxycarbonyl)methyl]-N-methylamino}-1-oxo-2-buten-1-yl)amino]-7-methoxy-quinazoline (9) 4-[(3-bromophenyl)amino]-6-[(4-[N-[(propyloxycarbonyl)-methyl]-N-methylamino-1-oxo-2-buten-1-yl)amino]-7-methoxy-quinazoline

(10) 4-[(3-bromophenyl)amino]-6-[(4-(N-[(isobutyloxycarbonyl)-methyl]-N-methylamino)-1-oxo-2-buten-1-yl)amino]-7-methoxy-quinazoline

(11) 4-[(3-bromophenyl)amino]-6-[(4-(N-[(cyclohexyloxycarbonyl)methyl]-N-methylamino}-1-oxo-2-buten-1-yl)amino]-7-methoxy-quinazoline

(12) 4-[(3-bromophenyl)amino]-6-[(4-(N-[(hexyloxycarbonyl)methyl]-N-methylamino)-1-oxo-2-buten-1-yl)amino]-7-methoxy-quinazoline

(13) 4-[(3-bromophenyl)amino]-6-[(4-(N-[(cyclopropylmethoxycarbonyl)methyl]-N-methylamino)-1-oxo-2-buten-1-yl)amino]-7-methoxy-quinazoline

(14) 4-[(3-bromophenyl)amino]-6-[(4-(N-[(cyclohexylmethoxycarbonyl)methyl]-N-methylamino]-1-oxo-2-buten-1-yl)amino]-7-methoxy-quinazoline

(15) 4-[(3-bromophenyl)amino]-6-[(4-[(benzyloxycarbonyl)methyl]-N-methylamino)-1-oxo-2-buten-1-yl)amino]-7-methoxy-quinazoline

(16) 4-[(3-bromophenyl)amino]-6-[(4-N-[(ethoxycarbonyl)-methyl]-N-ethylamino-1-oxo-2-buten-1-yl)amino]-7-methoxy-quinazoline

(17) 4-[(3-bromophenyl)amino]-6-[(4-(N-[(ethoxycarbonyl)-methyl]-N-butylamino)-1-oxo-2-buten-1-yl)amino]-7-methoxy-quinazoline

(18) 4-[(3-bromophenyl)amino]-6-[(4-{N-[(ethoxycarbonyl)methyl]-N-cyclopropylamino]-1-oxo-2-buten-1-yl)amino]-7-methoxy-quinazoline

(19) 4-[(3-bromophenyl)amino]-6-[(4-(N-[(ethoxycarbonyl)methyl]-N-(cyclopropylmethyl)amino}-1-oxo-2-buten-1-yl)amino]-7-methoxy-quinazoline

(20) 4-[(3-bromophenyl)amino]-6-[(4-(N-[2-ethoxycarbonyl)-ethyl]-N-methylamino)-1-oxo-2-buten-1-yl)amino]-7-methoxy-quinazoline

(21) 4-[(3-bromophenyl)amino]-6-[(4-[N-[3-ethoxycarbonyl)-propyl]-N-methylamino)-1-oxo-2-buten-1-yl)amino]-7-methoxy-quinazoline

(22) 4-((3-bromophenyl)amino]-6-[(4-(N-[1-(ethoxycarbonyl)-ethyl]-N-methylamino)-1-oxo-2-buten-1-yl)amino]-7-methoxy-quinazoline

(23) 4-[(3-bromophenyl)amino]-6-({4-[2-ethoxycarbonyl)-pyrrolidin-1-yl]-1-oxo-2-buten-1-yl}amino)-7-methoxy-quinazoline

(24) 4-[(3-bromophenyl)amino]-6-({4-[4-(ethoxycarbonyl)-piperidin-1-yl]-1-oxo-2-buten-1-yl}amino)-7-methoxy-quinazoline

(25) 4-[(3-bromophenyl)amino]-6[(4-{4-[(ethoxycarbonyl)methyl)-piperidin-1-yl]-1-oxo-2-buten-1-yl}amino]-7-methoxy-quinazoline

(26) 4-[(3-bromophenyl)amino]-6-[(4-{4-[(ethoxycarbonyl)methyl]-piperazin-1-yl}-1-oxo-2-buten-1-yl)amino]-7-methoxy-quinazoline

(27) 4-[(3-bromophenyl)amino]-6-[(6-{N-[(ethoxycarbonyl)methyl]-N-methylamino}-1-oxo-2-hexen-1-yl)amino]-7-methoxy-quinazoline

(28) 4-[(3-bromophenyl)amino]-6-[(3-{1-[(ethoxycarbonyl)methyl]-piperidin-4-yl}-1-oxo-2-propen-1-yl)amino]-7-methoxy-quinazoline
(29) 4-[(3-bromophenyl)amino]-6-([4-[3-(ethoxycarbonyl)-4-methyl-piperazin-1-yl]-1-oxo-2-buten-1-yl)amino)-7-methoxy-quinazoline
(30) 4-[(3-bromophenyl)amino]-6-[(4-{N-[(diethoxyphosphoryl)-methyl]-N-methylamino}-1-oxo-2-buten-1-yl)amino]-7-methoxy-quinazoline
(31) 4-[(3-bromophenyl)amino]-6-[(4-{N-[(ethoxycarbonyl)methyl]-N-methylamino}-1-oxo-2-butyn-1-yl)amino]-7-methoxy-quinazoline
(32) 4-[(3-bromophenyl)amino]-6-[(4-{N-[2-(ethoxycarbonyl)-ethyl]-N-methylamino}-1-oxo-2-butyn-1-yl)amino]-7-methoxy-quinazoline
(33) 4-[(3-bromophenyl)amino]-6-[(4-{N-[3-(ethoxycarbonyl)-propyl]-N-methylamino}-1-oxo-2-butyn-1-yl)amino]-7-methoxy-quinazoline
(34) 4-[(3-bromophenyl)amino]-6-{(4-(2-{N-[(ethoxycarbonyl)-methyl]-N-methylamino}ethylamino)-1,4-dioxo-2-buten-1-yl]-amino}-7-methoxy-quinazoline
(35) 4-[(3-bromophenyl)amino]-6-{[4-(2-{N-[2-(ethoxycarbonyl)-ethyl]-N-methylamino)ethylamino}-1,4-dioxo-2-buten-1-yl]amino}-7-methoxy-quinazoline
(36) 4-[(3-bromophenyl)amino]-6-{[4-(3-{N-[(ethoxycarbonyl)-methyl)-N-methylamino}propylamino)-1,4-dioxo-2-buten-1-yl]-amino}-7-methoxy-quinazoline
(37) 4-[(3-bromophenyl)amino]-6-{[4-(3-{N-[(methoxycarbonyl)-methyl]-N-methylamino}propylamino)-1,4-dioxo-2-buten-1-yl]-amino}-7-methoxy-quinazoline
(38) 4-[(3-bromophenyl)amino]-6-{[4-(3-{N-[(butyloxycarbonyl)-methyl]-N-methylamino}propylamino)-1,4-dioxo-2-buten-1-yl]-amino}-7-methoxy-quinazoline
(39) 4-[(3-bromophenyl)amino]-6-{[4-(3-{N-[(cyclohexyloxycarbonyl)methyl]-N-methylamino}propylamino)-1,4-dioxo-2-buten-1-yl]amino}-7-methoxy-quinazoline
(40) 4-[(3-bromophenyl)amino]-6-[(4-{3-[2-(ethoxycarbonyl)-pyrrolidin-1-yl]propylamino}-1,4-dioxo-2-buten-1-yl)amino]-7-methoxy-quinazoline
(41) 4-[(3-bromophenyl)amino]-6-[(4-{3-[2-(methoxycarbonyl)-piperidin-1-yl]propylamino}-1,4-dioxo-2-buten-1-yl)amino]-7-methoxy-quinazoline
(42) 4-[(3-bromophenyl)amino]-6-[(4-{3-[4-(ethoxycarbonyl)-piperidin-1-yl]propylamino}-1,4-dioxo-2-buten-1-yl)amino]-7-methoxy-quinazoline
(43) 4-[(3-bromophenyl)amino]-6-[(4-{3-[3-(ethoxycarbonyl)-piperidin-1-yl]propylamino}-1,4-dioxo-2-buten-1-yl)amino]-7-methoxy-quinazoline
(44) 4-[(3-bromophenyl)amino]-6-{[4-(3-{4-[(ethoxycarbonyl)-methyl]-piperazin-1-yl}propylamino)-1,4-dioxo-2-buten-1-yl]-amino}-7-methoxy-quinazoline
(45) 4-[(3-bromophenyl)amino]-6-{[4-(3-{4-[(ethoxycarbonyl)-methyl]-piperazin-1-yl}propylamino)-1,4-dioxo-2-buten-1-yl]-amino}-quinazoline
(46) 4-[(3-bromophenyl)amino]-6-[(4-{3-[2-(ethoxycarbonyl)-pyrrolidin-1-yl]propylamino}-1,4-dioxo-2-buten-1-yl)amino]-quinazoline
(47) 4-[(3-bromophenyl)amino]-6-{[4-(N-{1-[(ethoxycarbonyl)methyl]-2-(ethoxycarbonyl)-ethyl}-N-methylamino)-1-oxo-2-buten-1-yl]amino}-7-methoxy-quinazoline
(48) 4-[(3-bromophenyl)amino]-6-[(4-{N-[1,2-bis(ethoxycarbonyl)-ethyl]-N-methylamino}-1-oxo-2-buten-1-yl)amino]-7-methoxy-quinazoline
(49) 4-[(3-bromophenyl)amino]-6-{[4-(N-{[(ethoxy)(methyl)-phosphoryl]methyl}-N-methylamino)-1-oxo-2-buten-1-yl]amino}-7-methoxy-quinazoline
(50) 4-[(3-bromophenyl)amino]-7-(3-{N-[(isobutyloxycarbonyl)methyl]-N-methylamino}propyloxy)-6-[(vinylcarbonyl)amino]-quinazoline
(51) 4-[(3-bromophenyl)amino]-7-(3-{N-[(cyclopentyloxycarbonyl)methyl]-N-methylamino}propyloxy)-6-[(vinylcarbonyl)amino]-quinazoline
(52) 4-[(3-bromophenyl)amino]-7-{3-[2-(ethoxycarbonyl)-pyrrolidin-1-yl]propyloxy}-6-[(vinylcarbonyl)amino]-quinazoline
(53) 4-[(3-bromophenyl)amino]-7-{3-[2-(ethoxycarbonyl)-piperidin-1-yl]propyloxy}-6-[(vinylcarbonyl)amino]-quinazoline
(54) 4-[(3-bromophenyl)amino]-7-(3-{N-[1-(ethoxycarbonyl)-ethyl]-N-methylamino}propyloxy)-6-[(vinylcarbonyl)amino]-quinazoline
(55) 4-[(3-bromophenyl)amino]-7-(3-{4-[(ethoxycarbonyl)methyl]-piperazin-1-yl}propyloxy)-6-[(1-oxo-2-buten-1-yl)amino]-quinazoline
(56) 4-[(3-bromophenyl)amino]-7-(3-{4-[(ethoxycarbonyl)methyl]-piperazin-1-yl}propyloxy)-6-[(1-oxo-2,4-hexadien-1-yl)amino]-quinazoline
(57) 4-[(3-bromophenyl)amino]-7-(3-{4-[(ethoxycarbonyl)methyl]-piperazin-1-yl}propyloxy)-6-[(3-phenyl-1-oxo-2-propen-1-yl)-amino]-quinazoline
(58) 4-[(3-bromophenyl)amino]-7-(3-{4-[(ethoxycarbonyl)methyl]-piperazin-1-yl}propyloxy)-6-[(1-oxo-2-butyn-1-yl)amino]-quinazoline
(59) 4-[(3-bromophenyl)amino]-7-(3-{4-[(ethoxycarbonyl)methyl]-piperazin-1-yl}propyloxy)-6-[(1-oxo-4,4,4-trifluor-2-buten-1-yl)amino]-quinazoline
(60) 4-[(3-bromophenyl)amino]-7-(3-{N-[(ethoxycarbonyl)methyl]-N-methylamino}propyloxy)-6-[(1-oxo-4,4,4-trifluor-2-buten-1-yl)amino]-quinazoline
(61) 4-[(3-bromophenyl)amino]-7-(3-{N-[(ethoxycarbonyl)methyl]-N-methylamino}propyloxy)-[(1-oxo-2-buten-1-yl)amino]-quinazoline
(62) 4-[(3-bromophenyl)amino]-7-(3-{N-[(ethoxycarbonyl)methyl]-N-methylamino}propyloxy)-[(1-oxo-2-butyn-1-yl)amino]-quinazoline
(63) 4-[(3-bromophenyl)amino]-7-(3-{N-[(ethoxycarbonyl)methyl]-N-methylamino}propyloxy)-[(1-oxo-2,4-hexadien-1-yl)amino]-quinazoline
(64) 4-[(3-bromophenyl)amino]-6-{[2-({N-[(ethoxycarbonyl)methyl]-N-methylamino}methyl)-1-oxo-2-propen-1-yl]amino]amino}-7-methoxy-quinazoline
(65) 4-[(3-bromophenyl)amino]-6-{[2-({N-[(ethoxycarbonyl)methyl]-N-methylamino}methyl)-1-oxo-2-propen-1-yl]amino}-quinazoline
(66) 4-[(3-chlorophenyl)amino]-6-[(4-{N-[(ethoxycarbonyl)methyl]-N-methylamino}-1-oxo-2-buten-1-yl)amino]-7-methoxy-quinazoline
(67) 4-[(3-chloro-4-fluorophenyl)amino]-6-[(4-{N-[(ethoxycarbonyl)methyl]-N-methylamino}-1-oxo-2-buten-1-yl)amino]-7-methoxy-quinazoline
(68) 4-[(3-methylphenyl)amino]-6-[(4-{N-[(ethoxycarbonyl)methyl]-N-methylamino}-1-oxo-2-buten-1-yl)amino]-7-methoxy-quinazoline
(69) 4-[(3-trifluoromethylphenyl)amino]-6-[(4-{N-[(ethoxycarbonyl)methyl]-N-methylamino}-1-oxo-2-buten-1-yl)amino]-7-methoxy-quinazoline
(70) 4-[(3-ethynylphenyl)amino]-6-[(4-{N-[(ethoxycarbonyl)-methyl]-N-methylamino}-1-oxo-2-buten-1-yl)amino]-7-methoxy-quinazoline

(71) 4-[(3-cyanophenyl)amino]-6-[(4-{N-[(ethoxycarbonyl)methyl]-N-methylamino}-1-oxo-2-buten-1-yl)amino]-7-methoxy-quinazoline

(72) 4-[(3-methoxyphenyl)amino]-6-[(4-{N-[(ethoxycarbonyl)-methyl]-N-methylamino}-1-oxo-2-buten-1-yl)amino]-7-methoxy-quinazoline

(73) 4-[(3,4-difluorophenyl)amino]-6-[(4-{N-[(ethoxycarbonyl)-methyl]-N-methylamino}-1-oxo-2-buten-1-yl)amino]-7-methoxy-quinazoline

(74) 4-[(3-bromo-4-fluorophenyl)amino]-6-[(4-{N-[(ethoxycarbonyl)methyl]-N-methylamino}-1-oxo-2-buten-1-yl)amino]-7-methoxy-quinazoline

(75) 4-[(3-chlorophenyl)amino]-7-(3-{4-[(ethoxycarbonyl)methyl]-piperazin-1-yl}propyloxy)-6-[(vinylcarbonyl)amino]-quinazoline

(76) 4-[(3-chloro-4-fluorophenyl)amino]-7-(3-{4-[(ethoxycarbonyl)methyl]-piperazin-1-yl}propyloxy)-6-[(vinylcarbonyl)-amino]-quinazoline

(77) 4-[(3-bromo-4-fluorophenyl)amino]-7-(3-{4-[(ethoxycarbonyl)methyl]-piperazin-1-yl}propyloxy)-6-[(vinylcarbonyl)amino]-quinazoline

(78) 4-[(3,4-difluorophenyl)amino]-7-(3-{4-[(ethoxycarbonyl)-methyl]-piperazin-1-yl}propyloxy)-6-[(vinylcarbonyl)amino]-quinazoline

(79) 4-[(3-cyanophenyl)amino]-7-(3-{4-[(ethoxycarbonyl)methyl]-piperazin-1-yl}propyloxy)-6-[(vinylcarbonyl)amino]-quinazoline

(80) 4-[(3-methoxyphenyl)amino]-7-(3-{4-[(ethoxycarbonyl)methyl]-piperazin-1-yl}propyloxy)-6-[(vinylcarbony)amino]-quinazoline

(81) 4-[(3-methylphenyl)amino]-7-(3-{4-[(ethoxycarbonyl)methyl]-piperazin-1-yl}propyloxy)-6-[(vinylcarbonyl)amino]-quinazoline

(82) 4-[(3-trifluoromethylphenyl)amino]-7-(3-{4-[(ethoxycarbonyl)methyl]-piperazin-1-yl}propyloxy)-6-[(vinylcarbonyl)-amino]-quinazoline

(83) 4-[(3-ethynylphenyl)amino]-7-(3-{4-[(ethoxycarbonyl)methyl]-piperazin-1-yl}propyloxy)-6-[(vinylcarbonyl)amino]-quinazoline

(84) 4-[(3-bromophenyl)amino]-3-cyano-7-(3-{4-[(ethoxycarbonyl)methyl]-piperazin-1-yl}propyloxy)-6-[(vinylcarbonyl)-amino]-quinoline

(85) 4-[(3-bromophenyl)amino]-3-cyano-7-(2-{4-[(ethoxycarbonyl)methyl]-piperazin-1-yl}ethoxy)-6-[(vinylcarbonyl)amino]-quinoline

(86) 4-[(3-bromophenyl)amino]-3-cyano-7-(3-{1-[(ethoxycarbonyl)methyl]-piperidin-4-yl}propyloxy)-6-[(vinylcarbonyl)amino]-quinoline

(87) 4-[(3-bromophenyl)amino]-3-cyano-7-(2-{1-[(ethoxycarbonyl)methyl]-piperidin-4-yl}ethoxy)-6-[(vinylcarbonyl)amino]-quinoline

(88) 4-[(3-bromophenyl)amino]-3-cyano-7-({1-[(ethoxycarbonyl)-methyl]-piperidin-4-yl}methoxy)-6-[(vinylcarbonyl)amino]-quinoline

(89) 4-[(3-bromophenyl)amino]-3-cyano-7-(3-{N-[(ethoxycarbonyl)methyl]-N-methylamino}propyloxy)-6-[(vinylcarbonyl)amino]-quinoline

(90) 4-[(3-bromophenyl)amino]-3-cyano-7-(4-{N-[(ethoxycarbonyl)methyl]-N-methylamino}butyloxy)-6-[(vinylcarbonyl)amino]-quinoline

(91) 4-[(3-bromophenyl)amino]-3-cyano-6-[(4-{N-[(ethoxycarbonyl)methyl]-N-methylamino}-1-oxo-2-buten-1-yl)amino]-quinoline

(92) 4-[(3-bromophenyl)amino]-3-cyano-6-[(4-{N-[(ethoxycarbonyl)methyl]-N-methylamino}-1-oxo-2-buten-1-yl)amino]-7-methoxy-quinoline

(93) 4-[(3-bromophenyl)amino]-3-cyano-6-[(4-{N-[(ethoxycarbonyl)methyl]-N-ethylamino}-1-oxo-2-buten-1-yl)amino]-7-methoxy-quinoline

(94) 4-[(3-bromophenyl)amino]-3-cyano-6-[(4-{N,N-bis[(ethoxycarbonyl)methyl]amino}-1-oxo-2-buten-1-yl)amino]-7-methoxy-quinoline

(95) 4-[(3-bromophenyl)amino]-3-cyano-6-({4-[2-(ethoxycarbonyl)-pyrrolidin-1-yl]-1-oxo-2-buten-1-yl}amino)-7-methoxy-quinoline

(96) 4-[(3-bromophenyl)amino]-3-cyano-6-[(4-{4-[(ethoxycarbonyl)methyl]-piperidin-1-yl}-1-oxo-2-buten-1-yl)amino]-7-methoxy-quinoline

(97) 4-[(3-bromophenyl)amino]-3-cyano-6-[(4-{N-[(diethoxy-phosphoryl)methyl]-N-methylamino}-1-oxo-2-buten-1-yl)amino]-7-methoxy-quinoline

(98) 4-[(3-bromophenyl)amino]-3-cyano-6-[(4-{N-[(ethoxycarbonyl)methyl]-N-methylamino}-1-oxo-2-butyn-1-yl)amino]-7-methoxy-quinoline

(99) 4-[(3-bromophenyl)amino]-3-cyano-6-{(2-({N-[(ethoxycarbonyl)methyl]-N-methylamino}methyl)-1-oxo-2-propen-1-yl]amino}-7-methoxy-quinoline (100) 4-[(3-bromophenyl)amino]-3-cyano-6-([4-(3-{N-[{ethoxycarbonyl}methyl]-N-methylamino}propylamino}-1,4-dioxo-2-buten-1-yl]amino)-7-methoxy-quinoline (101) 4-[(3-bromophenyl)amino]-3-cyano-6-{[4-(3-{N,N-bis[(ethoxycarbonyl)methyl]-amino}propylamino)-1,4-dioxo-2-buten-1-yl]amino}-7-methoxy-quinoline (102) 4-[(3-bromophenyl)amino]-3-cyano-6-[(4-{3-[2-(ethoxycarbonyl)-pyrrolidin-1-yl]propylamino}-1,4-dioxo-2-buten-1-yl)-amino]-7-methoxy-quinoline (103) 4-[(3-bromophenyl)amino]-3-cyano-6-{[4-(3-[4-[(ethoxycarbonyl)methyl]-piperazin-1-yl}propylamino)-1,4-dioxo-2-buten-1-yl]amino)-7-methoxy-quinoline (104) 4-[(3-bromophenyl)amino]-6-{[4-(2-oxo-morpholin-4-yl)-1-oxo-2-buten-1-yl]amino}-7-methoxy-quinazoline (105) 4-[(3-bromophenyl)amino]-7-[3-(2-oxo-morpholin-4-yl)propyloxy]-6-[(vinylcarbonyl)amino]-quinazoline (106) 4-[(3-bromophenyl)amino]-7-[3-(2-oxo-morpholin-4-yl)propyloxy]-6-[(1-oxo-2-butyn-1-yl)amino]-quinazoline (107) 4-[(3-bromophenyl)amino]-7-[(4-methyl-2-oxo-morpholin-6-yl)methyloxy]-6-[(1-oxo-2-butyn-1-yl)amino]-quinazoline (108) 4-[(3-chloro-4-fluorophenyl)amino]-6-[(4-{N-[(ethoxycarbonyl)methyl]-N-methylamino}-1-oxo-2-buten-1-yl)amino]-7-cyclopropylmethoxy-quinazoline (109) 4-[(3-chloro-4-fluorophenyl)amino]-6-[(4-{N,N-bis[(methoxycarbonyl)methyl]amino}-1-oxo-2-buten-1-yl)amino]-7-cyclopropylmethoxy-quinazoline (110) 4-[(3-chloro-4-fluorophenyl)amino]-6-[(4-{N-[(diethoxyphosphoryl)methyl]-N-methylamino}-1-oxo-2-buten-1-yl)amino]-7-cyclopropylmethoxy-quinazoline (111) 4-[(3-chloro-4-fluorophenyl)amino]-6-({4-[2-(methoxycarbonyl)-pyrrolidin-1-yl]-1-oxo-2-buten-1-yl}amino)-7-cyclopropylmethoxy-quinazoline (112) 4-[(3-chloro-4-fluorophenyl)amino]-6-({4-[2-(methoxycarbonyl)-piperidin-1-yl]-1-oxo-2-buten-1-yl}amino)-7-cyclopropylmethoxy-quinazoline (113) 4-[(3-chloro-4-fluorophenyl)amino]-6-[(4-{4-[(ethoxycarbonyl)methyl]-piperazin-1-yl}-1-oxo-2-buten-1-yl)amino]-7-cyclopropylmethoxy-quinazoline (114) 4-[(3-chloro-4-fluorophenyl)amino]-6-[(4-{4-[(diethoxyphosphoryl)methyl]-piperazin-1-yl}-1-oxo-2-buten-1-yl)amino]-7-cyclopropylmethoxy-quinazoline (115) 4-[(3-chloro-4-fluorophenyl)amino]-6-({4-[3-(methoxycarbonyl)-morpholin-4-yl]-1-oxo-2-buten-1-yl}amino)-7-cyclopropylmethoxy-quinazoline (116) 4-[(3-chloro-4-fluorophenyl)amino]-6-{[4-(2-methoxycarbonyl-4-methyl-piperazin-1-yl)-1-oxo-2-buten-1-yl]amino}-7-cyclopropylmethoxy-quinazoline (117) 4-[(3-chloro-4-fluorophenyl)amino]-6-{[4-(2-oxo-morpholin-4-yl)-1-oxo-2-buten-1-yl]amino}-7-cyclopropylmethoxy-quinazoline
(118) 4-[(3-chloro-4-fluorophenyl)amino]-6-{[4-(3-methyl-2-oxo-morpholin-4-yl)-1-oxo-2-buten-1-yl]amino}-7-cyclopropylmethoxy-quinazoline
(119) 4-[(3-chloro-4-fluorophenyl)amino]-6-{[4-(6-methyl-2-oxo-morpholin-4-yl)-1-oxo-2-buten-1-yl]amino}-7-cyclopropylmethoxy-quinazoline
(120) 4-[(3-chloro-4-fluorophenyl)amino]-6-{[4-(6,6-dimethyl-2-oxo-morpholin-4-yl)-1-oxo-2-buten-1-yl]amino}-7-cyclopropylmethoxy-quinazoline
(121) 4-[(3-chloro-4-fluorophenyl)amino]-6-{[4-(2-ethoxy-morpholin-4-yl)-1-oxo-2-buten-1-yl]amino}-7-cyclopropylmethoxy-quinazoline
(122) 4-[(3-chloro-4-fluorophenyl)amino]-6-{[4-(2,6-diethoxymorpholin-4-yl)-1-oxo-2-buten-1-yl]amino}-7-cyclopropylmethoxy-quinazoline
(123) 4-[(3-chloro-4-fluorophenyl)amino]-6-[{4-[N-(2,2-dimethoxyethyl)-N-methylamino]-1-oxo-2-buten-1-yl)amino}-7-cyclopropylmethoxy-quinazoline
(124) 4-[(3-chloro-4-fluorophenyl)amino]-6-[(4-[N-(1,3-dioxolan-2-ylmethyl)-N-methylamino]-1-oxo-2-buten-1-yl)amino]-7-cyclopropylmethoxy-quinazoline
(125) 4-[(3-chloro-4-fluorophenyl)amino]-6-[(4-[N-(2-oxo-tetra-hydrofuran-3-yl)-N-methylamino]-1-oxo-2-buten-1-yl)amino]-7-cyclopropylmethoxy-quinazoline
(126) 4-[(3-chloro-4-fluorophenyl)amino]-6-[(4-[N-(2-oxo-tetra-hydrofuran-4-yl)-N-methylamino]-1-oxo-2-buten-1-yl)amino]-7-cyclopropylmethoxy-quinazoline
(127) 4-[(3-chloro-4-fluorophenyl)amino]-6-[(4-{N-[(ethoxycarbonyl)methyl]-N-[2-(acetyl-sulphanyl)ethyl]amino}-1-oxo-2-buten-1-yl)amino]-7-cyclopropylmethoxy-quinazoline
(128) 4-[(3-chloro-4-fluorophenyl)amino]-6-[(4-{N-[(ethoxycarbonyl)methyl]-N-[2-(isobutylcarbonylsulphanyl)ethyl]amino}-1-oxo-2-buten-1-yl)amino]-7-cyclopropylmethoxy-quinazoline
(129) 4-[(3-chloro-4-fluorophenyl)amino]-6-[(4-{N-[(ethoxycarbonyl)methyl]-N-methylamino}-1-oxo-2-butyn-1-yl)amino]-7-cyclopropylmethoxy-quinazoline
(130) 4-[(3-chloro-4-fluorophenyl)amino]-6-[(4-{N,N-bis[(methoxycarbonyl)methyl]amino}-1-oxo-2-butyn-1-yl)amino]-7-cyclopropylmethoxy-quinazoline
(131) 4-[(3-chloro-4-fluorophenyl)amino]-6-({4-[2-(methoxycarbonyl)-pyrrolidin-1-yl]-1-oxo-2-butyn-1-yl}amino)-7-cyclopropylmethoxy-quinazoline
(132) 4-[(3-chloro-4-fluorophenyl)amino]-6-[(4-{4-[(ethoxycarbonyl)methyl]-piperazin-1-yl}-1-oxo-2-butyn-1-yl)amino]-7-cyclopropylmethoxy-quinazoline
(133) 4-[(3-chloro-4-fluorophenyl)amino]-6-[(4-{4-[bis(methoxycarbonyl)methyl]-piperazin-1-yl}-1-oxo-2-buten-1-yl)amino]-7-cyclopropylmethoxy-quinazoline
(134) 4-[(3-chloro-4-fluorophenyl)amino]-6-[(4-{4-[1,2-bis-(methoxycarbonyl]ethyl]-piperazin-1-yl}-1-oxo-2-buten-1-yl)-amino]-7-cyclopropylmethoxy-quinazoline
(135) 4-[(3-chloro-4-fluorophenyl)amino]-6-{[4-(4-(1-[(methoxycarbonyl)methyl]-2-(methoxycarbonyl)-ethyl}-piperazin-1-yl)-1-oxo-2-buten-1-yl]amino)-7-cyclopropylmethoxy-quinazoline
(136) 4-[(3-chloro-4-fluorophenyl)amino]-6-{[4-(3-{N,N-bis-[(methoxycarbonyl)methyl]amino}propylamino)-1,4-dioxo-2-buten-1-yl]amino}-7-cyclopropylmethoxy-quinazoline
(137) 4-[(3-chloro-4-fluorophenyl)amino]-6-{[4-(3-{N-[(methoxy-carbonyl)methyl]-N-methylamino}propylamino)-1,4-dioxo-2-buten-1-yl]amino}-7-cyclopropylmethoxy-quinazoline

Example 19

Coated tablets containing 75 mg of active substance

| 1 tablet core contains: | |
| --- | --- |
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

Weight of core: 230 mg die: 9 mm, convex

The tablet cores thus produced are coated with a film consisting essentially of hydroxypropylmethylcellulose. The finished film-coated tablets are polished with beeswax.

Weight of coated tablet: 245 mg.

Example 20

Tablets containing 100 mg of active substance

| Composition: | |
| --- | --- |
| 1 tablet contains: | |
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

Example 21

Tablets containing 150 mg of active substance

| Composition: | |
|---|---|
| 1 tablet contains: | |
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg die: 10 mm, flat

Example 22

Hard gelatine capsules containing 150 mg of active substance

| 1 capsule contains: | | |
|---|---|---|
| active substance | | 150.0 mg |
| corn starch (dried) | approx. | 180.0 mg |
| lactose (powdered) | approx. | 87.0 mg |
| magnesium stearate | | 3.0 mg |
| | approx. | 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

Example 23

Suppositories containing 150 mg of active substance

| 1 suppository contains: | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

Example 24

Suspension containing 50 mg of active substance

| 100 ml of suspension contain: | |
|---|---|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water ad | 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

Example 25

Ampoules containing 10 mg active substance

| Composition: | |
|---|---|
| active substance | 10.0 mg |
| 0.01 N hydrochloric acid q.s. | |
| double-distilled water ad | 2.0 ml |

Preparation:

The active substance is dissolved in the necessary amount of 0.01 N HCl, made isotonic with common salt, filtered sterile and transferred into 2 ml ampoules.

Example 26

Ampoules containing 50 mg of active substance

| Composition: | |
|---|---|
| active substance | 50.0 mg |
| 0.01 N hydrochloric acid q.s. | |
| double-distilled water ad | 10.0 ml |

Preparation:

The active substance is dissolved in the necessary amount of 0.01 N HCl, made isotonic with common salt, filtered sterile and transferred into 10 ml ampoules.

Example 27

Capsules for powder inhalation containing 5 mg of active substance

| 1 capsule contains: | |
|---|---|
| active substance | 5.0 mg |
| lactose for inhalation | 15.0 mg |
| | 20.0 mg |

Preparation:

The active substance is mixed with lactose for inhalation. The mixture is packed into capsules in a capsule-making machine (weight of the empty capsule approx. 50 mg).

weight of capsule: 70.0 mg
size of capsule=3

Example 28

Solution for inhalation for hand-held nebulisers containing 2.5 mg active substance

| 1 spray contains: | |
|---|---|
| active substance | 2.500 mg |
| benzalkonium chloride | 0.001 mg |
| 1 N hydrochloric acid q.s. | |
| ethanol/water (50/50) ad | 15.000 mg |

Preparation:

The active substance and benzalkonium chloride are dissolved in ethanol/water (50/50). The pH of the solution is adjusted with 1N hydrochloric acid. The resulting solution is filtered and transferred into suitable containers for use in hand-held nebulisers (cartridges).

Contents of the container: 4.5 g

What is claimed is:

1. A compound of the formula

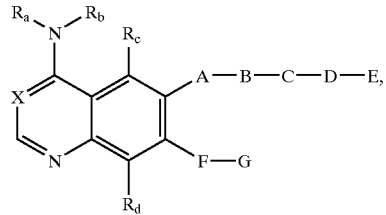

(I)

wherein $R_a$ denotes a hydrogen atom or a $C_{1-4}$-alkyl group, $R_b$ denotes a phenyl, benzyl or 1-phenylethyl group wherein the phenyl nucleus is substituted in each case by the groups $R_1$ to $R_3$, whilst $R_1$ and $R_2$, which may be identical or different, in each case denote a hydrogen, fluorine, chlorine, bromine or iodine atom, a $C_{1-4}$-alkyl, hydroxy, $C_{1-4}$-alkoxy, $C_{3-6}$-cycloalkyl, $C_{4-6}$-cycloalkoxy, $C_{2-5}$-alkenyl or $C_{2-5}$-alkynyl group, an aryl, aryloxy, arylmethyl or arylmethoxy group, a $C_{3-5}$-alkenyloxy or $C_{3-5}$-alkynyloxy group, wherein the unsaturated moiety may not be linked to the oxygen atom, a $C_{1-4}$-alkylsulphenyl, $C_{1-4}$-alkylsulphinyl, $C_{1-4}$-alkylsulphonyl, $C_{1-4}$-alkylsulphonyloxy, trifluoromethylsulphenyl, trifluoromethylsulphinyl or trifluoromethylsulphonyl group, a methyl or methoxy group substituted by 1 to 3 fluorine atoms, an ethyl or ethoxy group substituted by 1 to 5 fluorine atoms, a cyano or nitro group or an amino group optionally substituted by one or two $C_{1-4}$-alkyl groups, wherein the substituents may be identical or different, or $R_1$ together with $R_2$, if they are bound to adjacent carbon atoms, denote a —CH=CH—CH=CH, —CH=CH—NH or —CH=N—NH group and $R_3$ denotes a hydrogen, fluorine, chlorine or bromine atom, a $C_{1-4}$-alkyl, trifluoromethyl or $C_{1-4}$-alkoxy group, $R_c$ and $R_d$, which may be identical or different, in each case denote a hydrogen, fluorine or chlorine atom, a methoxy group, or a methyl group optionally substituted by a methoxy, dimethylamino, diethylamino, pyrrolidino, piperidino or morpholino group, X denotes a nitrogen atom, A denotes an oxygen atom or an —NH— group optionally substituted by a $C_{1-4}$-alkyl group, B denotes a carbonyl or sulphonyl group, C denotes a 1,3-allenylene, 1,1 or 1,2-vinylene group which may be substituted in each case by one or two methyl groups or by a trifluoromethyl group, an ethynylene group or a 1,3-butadien-1,4-ylene group optionally substituted by 1 to 4 methyl groups or by a trifluoromethyl group, D denotes an alkylene, —CO-alkylene or —SO$_2$-alkylene group wherein the alkylene moiety in each case contains 1 to 8 carbon atoms and additionally 1 to 4 hydrogen atoms in the alkylene moiety may be replaced by fluorine atoms, whilst the linking of the —CO-alkylene and —SO$_2$-alkylene group to the adjacent group C in each case must take place via the carbonyl or sulphonyl group, a —CO—O-alkylene, —CO—NR$_4$-alkylene or —SO$_2$—NR$_4$-alkylene group wherein the alkylene moiety in each case contains 1 to 8 carbon atoms, whilst the linking to the adjacent group C in each case must take place via the carbonyl or sulphonyl group wherein $R_4$ denotes a hydrogen atom or a $C_{1-4}$-alkyl group, or, if D is bound to a carbon atom of the group E, it may also denote a bond or, if D is bound to a nitrogen atom of the group E, it may also denote a carbonyl or sulphonyl group, E denotes an —(R$_7$O—PO—OR$_8$)-alkylene-NR$_5$ or (R$_7$O—PO—R$_9$)-alkylene-NR$_5$-group wherein in each case the alkylene moiety, which is straight-chained and contains 1 to 6 carbon atoms, may additionally be substituted by one or two $C_{1-2}$-alkyl groups or by an R$_6$O—CO or R$_6$O—CO—C$_{1-2}$-alkyl group, wherein $R_5$ denotes a hydrogen atom, a $C_{1-4}$-alkyl group, which may be substituted by an R$_6$O—CO, (R$_7$O—PO—OR$_8$) or (R$_7$O—PO—R$_9$) group, an ethyl or propyl group optionally substituted by one or two methyl or ethyl groups, which may be terminally substituted in each case by a $C_{1-6}$-alkylcarbonylsulphenyl, $C_{3-7}$-cycloalkylcarbonylsulphenyl, $C_{3-7}$-cycloalkyl-$C_{1-3}$- alkylcarbonylsulphenyl, arylcarbonylsulphenyl or aryl-$C_{1-3}$-alkylcarbonylsulphenyl group, an ethyl or propyl group optionally substituted by one or two methyl or ethyl groups which may be terminally substituted in each case by a $C_{1-6}$-alkylcarbonyloxy, $C_{3-7}$-cycloalkylcarbonyloxy, $C_{3-7}$-cycloalkyl-$C_{1-3}$-alkylcarbonyloxy, arylcarbonyloxy or aryl-$C_{1-3}$-alkylcarbonyloxy group, an ethyl or propyl group optionally substituted by one or two methyl or ethyl groups, each of which may be terminally substituted by a hydroxy, $C_{1-4}$-alkoxy, amino, $C_{1-4}$-alkylamino or di-($C_{1-4}$-alkyl)-amino group or by a 4- to 7-membered alkyleneimino group, whilst in the abovementioned 6- to 7-membered alkyleneimino groups a methylene group in the 4 position may be replaced by an oxygen or sulphur atom, by a sulphinyl, sulphonyl, imino or N—($C_{1-4}$-alkyl)-imino group, a $C_{3-7}$-cycloalkyl or $C_{3-7}$-cycloalkyl-$C_{1-3}$-alkyl group, $R_6$, $R_7$ and $R_8$, which may be identical or different, in each case denote a hydrogen atom, a $C_{1-8}$-alkyl group, which may be substituted by a hydroxy, $C_{1-4}$-alkoxy, amino, $C_{1-4}$-alkylamino or di-($C_{1-4}$-alkyl)-amino group or by a 4- to 7-membered alkyleneimino group, whilst in the abovementioned 6- to 7-membered alkyleneimino groups in each case a methylene group in the 4 position may be replaced by an oxygen or sulphur atom or by a sulphinyl, sulphonyl, imino or N—($C_{1-4}$-alkyl)-imino group, a $C_{4-7}$-cycloalkyl group optionally substituted by 1 or 2 methyl groups, a $C_{3-5}$-alkenyl or $C_{3-5}$-alkynyl group, wherein the unsaturated part may not be linked to the oxygen atom, a $C_{3-7}$-cycloalkyl-$C_{1-4}$-alkyl, aryl, aryl-$C_{1-4}$-alkyl or $R_g$CO—O—($R_eCR_f$)-group, whilst
  $R_e$ and $R_f$, which may be identical or different, in each case denote a hydrogen atom or a $C_{1-4}$-alkyl group and
  $R_g$ denotes a $C_{1-4}$-alkyl, $C_{3-7}$-cycloalkyl, $C_{1-4}$-alkoxy or $C_{5-7}$-cycloalkoxy group, and $R_9$ denotes a $C_{1-4}$-alkyl, aryl or aryl-$C_{1-4}$-alkyl group, a 4- to 7-membered alkyleneimino group which may be substituted by an $R_6O$—CO, ($R_7O$—PO—$OR_8$), ($R_7O$—PO—$R_9$), $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_9$ are as hereinbefore defined, a 4- to 7-membered alkyleneimino group which is substituted by two $R_6OCO$ or $R_6OCO$—$C_{1-4}$-alkyl groups or by an $R_6OCO$-group and an $R_6OCO$—$C_{1-4}$-alkyl group wherein $R_6$ is as hereinbefore defined, a piperazino or homopiperazino group which is substituted in the 4 position by the group $R_{10}$ and is additionally substituted at a cyclic carbon atom by an $R_6O$—CO, ($R_7O$—PO—$OR_8$), ($R_7O$—PO—$R_9$), $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_9$ are as hereinbefore defined and
  $R_{10}$ denotes a hydrogen atom, a $C_{1-4}$-alkyl, formyl, $C_{1-4}$-alkylcarbonyl or $C_{1-4}$-alkylsulphonyl group, a piperazino or homopiperazino group which is substituted in the 4 position by the group $R_{10}$ and additionally at cyclic carbon atoms by two $R_6O$—CO or $R_6O$—CO—$C_{1-4}$-alkyl groups or by an $R_6O$—CO-group and an $R_6O$—CO—$C_{1-4}$-alkyl group wherein $R_6$ and $R_{10}$ are as hereinbefore defined, a piperazino or homopiperazino group which is substituted in each case in the 4 position by an $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_9$ are as hereinbefore defined, a piperazino or homopiperazino group which is substituted in the 4 position by an $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group and is additionally substituted at cyclic carbon atoms by one or two $R_6O$—CO or $R_6O$—CO—$C_{1-4}$-alkyl groups or by an $R_6O$—CO-group and an $R_6O$—CO—$C_{1-4}$-alkyl group wherein $R_6$ to $R_9$ are as hereinbefore defined, a morpholino or homomorpholino group which is substituted in each case by an $R_6O$—CO, ($R_7O$—PO—$OR_8$), ($R_7O$—PO—$R_9$), $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_9$ are as hereinbefore defined, a morpholino or homomorpholino group which is substituted by two $R_6O$—CO or $R_6O$—CO—$C_{1-4}$-alkyl groups or by an $R_6O$—CO-group and an $R_6O$—CO—$C_{1-4}$-alkyl group wherein $R_6$ is as hereinbefore defined, a pyrrolidinyl, piperidinyl or hexahydroazepinyl group substituted in the 1 position by the group $R_{10}$, whilst the abovementioned 5- to 7-membered rings are additionally substituted in each case at a carbon atom by an $R_6O$—CO, ($R_7O$—PO—$OR_8$), ($R_7O$—PO—$R_9$), $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_{10}$ are as hereinbefore defined, a pyrrolidinyl, piperidinyl or hexahydroazepinyl group substituted in the 1 position by the group $R_{10}$, while the abovementioned 5- to 7-membered rings are in each case additionally substituted at carbon atoms by two $R_6O$—CO or $R_6O$—CO—$C_{1-4}$-alkyl groups or by an $R_6O$—CO-group and an $R_6O$—CO—$C_{1-4}$-alkyl group wherein $R_6$ and $R_{10}$ are as hereinbefore defined, a pyrrolidinyl, piperidinyl or hexahydroazepinyl group substituted in the 1 position by an $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_9$ are as hereinbefore defined, a pyrrolidinyl, piperidinyl or hexahydroazepinyl group substituted in the 1 position by an $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group, while the abovementioned 5- to 7-membered rings are in each case additionally substituted at carbon atoms by one or two $R_6O$—CO or $R_6O$—CO—$C_{1-4}$-alkyl groups or by an $R_6O$—CO-group and an $R_6O$—CO—$C_{1-4}$-alkyl group wherein $R_6$ to $R_9$ are as hereinbefore defined, a morpholino or thiomorpholino group which is substituted in the 2 position by a $C_{1-4}$-alkoxy group, a morpholino or thiomorpholino group which is substituted in the 2 and 6 positions by a $C_{1-4}$-alkoxy group, a $C_{1-4}$-alkyl-$NR_5$-group wherein the $C_{1-4}$-alkyl moiety, which is straight-chained and may additionally be substituted by one or two methyl groups, is in each case terminally substituted by a di-($C_{1-4}$-alkoxy)-methyl or tri-$C_{1-4}$-alkoxy)-methyl group, whilst $R_5$ is as hereinbefore defined, a $C_{1-4}$-alkyl-NR$_5$-group wherein the $C_{1-4}$-alkyl moiety, which is straight-chained and may additionally be substituted by one or two methyl groups, is in each case terminally substituted by a 1,3-dioxolan-2-yl or 1,3-dioxan-2-yl group optionally substituted by one or two methyl groups, while R$_5$ is as hereinbefore defined, an R$_{11}$NR$_5$-group wherein R$_5$ is as hereinbefore defined and R$_{11}$ denotes a 2-oxo-tetrahydrofuran-3-yl, 2-oxo-tetrahydrofuran-4-yl, 2-oxo-tetrahydropyran-3-yl, 2-oxo-tetrahydropyran-4-yl, 2-oxo-tetrahydropyran-5-yl, 2-oxo-tetrahydrothiophen-3-yl, 2-oxo-tetrahydrothiophen-4-yl, 2-oxo-tetrahydrothiopyran-3-yl, 2-oxo-tetrahydrothiopyran-4-yl or 2-oxo-tetrahydrothiopyran-5-yl group optionally substituted by one or two methyl groups, or D together with E denotes an R$_g$CO—O—(R$_e$CR$_f$)—O—CO, (R$_7$O—PO—OR$_8$) or (R$_7$O—PO—R$_9$)-group wherein R$_e$ to R$_g$ and R$_7$ to R$_9$ are as hereinbefore defined, F and G together denote a hydrogen atom, a $C_{1-6}$-alkoxy group optionally substituted from position 2 onwards by a hydroxy or $C_{1-4}$-alkoxy group, a $C_{3-7}$-cycloalkoxy or $C_{3-7}$-cycloalkyl-$C_{1-4}$-alkoxy group, whilst by the aryl moieties mentioned in the definitions of the abovementioned groups is meant a phenyl group which in each case may be monosubsituted by R$_{12}$, mono-, di or trisubstituted by R$_{13}$ or monosubstituted by R$_{12}$ and additionally mono- or disubstituted by R$_{13}$, whilst the substituents may be identical or different and R$_{12}$ denotes a cyano, carboxy, $C_{1-4}$-alkoxycarbonyl, aminocarbonyl, $C_{1-4}$-alkylaminocarbonyl, di-($C_{1-4}$-alkyl)-aminocarbonyl, $C_{1-4}$-alkylsulphenyl, $C_{1-4}$-alkylsulphinyl, $C_{1-4}$-alkylsulphonyl, hydroxy, $C_{1-4}$-alkylsulphonyloxy, trifluoromethyloxy, nitro, amino, $C_{1-4}$-alkylamino, di-($C_{1-4}$-alkyl)-amino, $C_{1-4}$-alkylcarbonylamino, N—($C_{1-4}$-alkyl)—$C_{1-4}$-alkylcarbonylamino, $C_{1-4}$-alkylsulphonylamino, N—($C_{1-4}$-alkyl)—$C_{1-4}$-alkylsulphonylamino, aminosulphonyl, $C_{1-4}$-alkylaminosulphonyl or di—($C_{1-4}$-alkyl)-aminosulphonyl group or a carbonyl group, which is substituted by a 5- to 7-membered alkyleneimino group, wherein in the abovementioned 6- to 7-membered alkyleneimino groups in each case a methylene group in the 4 position may be replaced by an oxygen or sulphur atom, by a sulphinyl, sulphonyl, imino or N—($C_{1-4}$-alkyl)-imino-group, and R$_{13}$ denotes a fluorine, chlorine, bromine or iodine atom, a $C_{1-4}$-alkyl, trifluoromethyl or $C_{1-4}$-alkoxy group or two groups R$_{13}$, if they are bound to adjacent carbon atoms, together denote a $C_{3-5}$-alkylene, methylenedioxy or 1,3-butadien-1,4-ylene group, or a tautomer or salt thereof.

2. A compound of the formula I according to claim 1, wherein

R$_a$ denotes a hydrogen atom,

R$_b$ denotes a phenyl, benzyl or 1-phenylethyl group wherein the phenyl nucleus is substituted in each case by the groups R$_1$ to R$_3$, while R$_1$ and R$_2$, which may be identical or different, each denote a hydrogen, fluorine, chlorine, bromine or iodine atom, a methyl, ethyl, hydroxy, methoxy, ethoxy, amino, cyano, vinyl or ethynyl group, an aryl, aryloxy, arylmethyl or arylmethoxy group, a methyl or methoxy group substituted by 1 to 3 fluorine atoms or R$_1$ together with R$_2$, if they are bound to adjacent carbon atoms, denote a —CH═CH—CH═CH, —CH═CH—NH or —CH═N—NH group and R$_3$ denotes a hydrogen, fluorine, chlorine or bromine atom, R$_c$ and R$_d$ in each case denote a hydrogen atom, X denotes a nitrogen atom, A denotes an —NH— group optionally substituted by a methyl or ethyl group, B denotes a carbonyl group, C denotes a 1,1- or 1,2-vinylene group which is substituted in each case by one or two methyl groups or may be substituted by a trifluoromethyl group, an ethynylene group or a 1,3-butadien-1,4-ylene group optionally substituted by a methyl or trifluoromethyl group, D denotes an alkylene or —CO-alkylene group wherein the alkylene moiety in each case contains 1 to 4 carbon atoms, while the linking of the —CO-alkylene group to the adjacent group C in each case must take place via the carbonyl group, a —CO—O-alkylene or —CO—NR$_4$-alkylene-group wherein the alkylene moiety in each case contains 1 to 4 carbon atoms, while the linking to the adjacent group C in each case must take place via the carbonyl group wherein R$_4$ denotes a hydrogen atom or a methyl or ethyl group, or, if D is bound to a carbon atom of the group E, it may also denote a bond or, if D is bound to a nitrogen atom of the group E, it may also denote a carbonyl or sulphonyl group, E denotes an —(R$_7$O—PO—OR$_8$)-alkylene-NR$_5$ or (R$_7$O—PO—R$_9$)-alkylene-NR$_5$ group wherein in each case the alkylene moiety, which is straight-chained and contains 1 to 4 carbon atoms, may additionally be substituted by one or two $C_{1-2}$-alkyl groups or by an R$_6$O—CO or R$_6$O—CO—$C_{1-2}$-alkyl group, while R$_5$ denotes a hydrogen atom, a $C_{1-4}$-alkyl group which may be substituted by an R$_6$O—CO group, an ethyl or propyl group optionally substituted by one or two methyl or ethyl groups which is terminally substituted in each case by a hydroxy, $C_{1-4}$-alkoxy, di-($C_{1-4}$-alkyl)amino, $C_{1-6}$-alkylcarbonylsulphenyl, $C_{3-6}$-cycloalkylcarbonylsulphenyl, $C_{3-6}$-cycloalkyl-$C_{1-3}$-alkylcarbonylsulphenyl, arylcarbonylsulphenyl or aryl-$C_{1-3}$-alkylcarbonylsulphenyl group, an ethyl or propyl group optionally substituted by one or two methyl or ethyl groups which is terminally substituted in each case by a $C_{1-6}$-alkylcarbonyloxy, $C_{3-6}$-cycloalkylcarbonyloxy, $C_{3-6}$-cycloalkyl-$C_{1-3}$-alkylcarbonyloxy, arylcarbonyloxy or aryl-$C_{1-3}$-alkylcarbonyloxy group, a $C_{3-6}$-cycloalkyl or $C_{3-6}$-cycloalkyl-$C_{1-3}$-alkyl group, R$_6$, R$_7$ and R$_8$, which may be identical or different, in each case denote a hydrogen atom, a $C_{1-8}$-alkyl group which may be substituted by a hydroxy, $C_{1-4}$-alkoxy, or di-($C_{1-4}$-alkyl)-amino group or by a 4- to 7-membered alkyleneimino group, while in the abovementioned 6- to 7-membered alkyleneimino groups in each case a methylene group in the 4 position may be replaced by an oxygen atom or by an N—($C_{1-2}$-alkyl)-imino group, a $C_{4-6}$-cycloalkyl group, a $C_{3-5}$-alkenyl or $C_{3-5}$-alkynyl group, while the unsaturated moiety may not be linked to the oxygen atom, a $C_{3-6}$-cycloalkyl-$C_{1-4}$-alkyl, aryl, aryl-$C_{1-4}$-alkyl or $R_gCO$—O—($R_eCR_f$) group, while $R_e$ and $R_f$, which may be identical or different, in each case denote a hydrogen atom or a $C_{1-4}$-alkyl group and $R_g$ denotes a $C_{1-4}$-alkyl, $C_{3-6}$-cycloalkyl, $C_{1-4}$-alkoxy or $C_{5-6}$-cycloalkoxy group, and $R_9$ denotes a $C_{1-4}$-alkyl group, a 4- to 7-membered alkyleneimino group which is substituted by an $R_6O$—CO, $R_6O$—CO—$C_{1-4}$-alkyl or bis-($R_6O$—CO)—$C_{1-4}$-alkyl group wherein $R_6$ is as hereinbefore defined, a 4- to 7-membered alkyleneimino group which is substituted by two $R_6O$—CO or $R_6O$—CO—$C_{1-4}$-alkyl groups wherein $R_6$ is as hereinbefore defined, a piperazino or homopiperazino group which is substituted in the 4 position by the group $R_{10}$ and additionally at a cyclic carbon atom by an $R_6O$—CO, $R_6O$—CO—$C_{1-4}$-alkyl or bis-($R_6O$—CO)—$C_{1-4}$-alkyl group wherein $R_6$ is as hereinbefore defined and $R_{10}$ denotes a hydrogen atom, a methyl or ethyl group, a piperazino or homopiperazino group which is substituted in the 4 position by the group $R_{10}$ and is additionally substituted at cyclic carbon atoms by two $R_6O$—CO or $R_6O$—CO—$C_{1-4}$-alkyl groups wherein $R_6$ and $R_{10}$ are as hereinbefore defined, a piperazino or homopiperazino group which is substituted in each case in the 4 position by an $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_9$ are as hereinbefore defined, a piperazino or homopiperazino group which is substituted in the 4 position by an $R_6O$—CO—$C_{1-4}$-alkyl or bis-($R_6O$—CO)—$C_{1-4}$-alkyl group and is additionally substituted at cyclic carbon atoms by one or two $R_6O$—CO or $R_6O$—CO—$C_{1-4}$-alkyl groups wherein $R_6$ is as hereinbefore defined, a morpholino or homomorpholino group which is substituted in each case by an $R_6O$—CO, $R_6O$—CO—$C_{1-4}$-alkyl, or bis-($R_6O$—CO)—$C_{1-4}$-alkyl group wherein $R_6$ is as hereinbefore defined, a morpholino or homomorpholino group which is substituted by two $R_6O$—CO or $R_6O$—CO—$C_{1-4}$-alkyl groups wherein $R_6$ is as hereinbefore defined, a pyrrolidinyl, piperidinyl or hexahydroazepinyl group substituted in the 1 position by the group $R_{10}$, while the abovementioned 5- to 7-membered rings in each case are additionally substituted at a carbon atom by an $R_6O$—CO, $R_6O$—CO—$C_{1-4}$-alkyl or bis-($R_6O$—CO)—$C_{1-4}$-alkyl group wherein $R_6$ and $R_{10}$ are as hereinbefore defined, a pyrrolidinyl, piperidinyl or hexahydroazepinyl group substituted in the 1 position by the group $R_{10}$, while the abovementioned 5- to 7-membered rings in each case are additionally substituted at carbon atoms by two $R_6O$—CO or $R_6O$—CO—$C_{1-4}$-alkyl groups wherein $R_6$ and $R_{10}$ are as hereinbefore defined, a pyrrolidinyl, piperidinyl or hexahydroazepinyl group substituted in the 1 position by an $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_9$ are as hereinbefore defined, a pyrrolidinyl, piperidinyl or hexahydroazepinyl group substituted in the 1 position by an $R_6O$—CO—$C_{1-4}$-alkyl or bis-($R_6O$—CO)—$C_{1-4}$-alkyl group, while the abovementioned 5- to 7-membered rings in each case are additionally substituted at carbon atoms by one or two $R_6O$—CO or $R_6O$—CO—$C_{1-4}$-alkyl groups wherein $R_6$ is as hereinbefore defined, a morpholino group which is substituted in the 2 position by a $C_{1-4}$-alkoxy group, a morpholino group which is substituted in the 2 and 6 positions in each case by a $C_{1-4}$-alkoxy group, a $C_{1-4}$-alkyl-$NR_5$ group wherein the $C_{1-4}$-alkyl moiety, which is straight-chained, is terminally substituted by a di-($C_{1-4}$-alkoxy)-methyl group, while $R_5$ is as hereinbefore defined, a $C_{1-4}$-alkyl-$NR_5$ group wherein the $C_{1-4}$-alkyl moiety, which is straight-chained, is terminally substituted by a 1,3-dioxolan-2-yl or 1,3-dioxan-2-yl group, while $R_5$ is as hereinbefore defined, a $R_{11}NR_5$ group wherein $R_5$ is as hereinbefore defined and $R_{11}$ denotes a 2-oxo-tetrahydrofuran-3-yl, 2-oxo-tetrahydrofuran-4-yl, 2-oxo-tetrahydropyran-3-yl, 2-oxo-tetrahydropyran-4-yl, 2-oxo-tetrahydropyran-5-yl, 2-oxo-tetrahydrothiophen-3-yl, 2-oxo-tetrahydrothiophen-4-yl, 2-oxo-tetrahydrothiopyran-3-yl, 2-oxo-tetrahydrothiopyran-4-yl or 2-oxo-tetrahydrothiopyran-5-yl group optionally substituted by one or two methyl groups, or D together with E denotes an $R_gCO$—O—($R_eCR_f$)—O—CO or ($R_7O$—PO—$OR_8$) group wherein $R_e$ to $R_g$ and $R_7$ to $R_9$ are as hereinbefore defined, F and G together denote a hydrogen atom, a $C_{1-6}$-alkoxy group optionally substituted from position 2 by a hydroxy or $C_{1-4}$-alkoxy group, a $C_{4-7}$-cycloalkoxy or $C_{3-7}$-cycloalkyl-$C_{1-4}$-alkoxy group, whilst by the aryl moieties mentioned in the definitions of the abovementioned groups is meant a phenyl group which in each case may be monosubstituted by $R_{12}$, mono- or disubstituted by $R_{13}$ or monosubstituted by $R_{12}$ and additionally mono- or disubstituted by $R_{13}$, whilst the substituents may be identical or different and $R_{12}$ denotes a cyano, $C_{1-2}$-alkoxycarbonyl, aminocarbonyl, $C_{1-2}$-alkylaminocarbonyl, di-($C_{1-2}$-alkyl)-aminocarbonyl, $C_{1-2}$-alkylsulphenyl, $C_{1-2}$-alkylsulphinyl, $C_{1-2}$-alkylsulphonyl, hydroxy, nitro, amino, $C_{1-2}$-alkylamino or di-($C_{1-2}$-alkyl)-amino, and $R_{13}$ denotes a fluorine, chlorine, bromine or iodine atom, a $C_{1-2}$-alkyl, trifluoromethyl or $C_{1-2}$-alkoxy group or two groups $R_{13}$, if they are bound to adjacent carbon atoms, together denote a $C_{3-5}$-alkylene, methylenedioxy or 1,3-butadien-1,4-ylene group, or a tautomer or salt thereof.

3. A compound of the formula I according to claim 1, wherein $R_a$ denotes a hydrogen atom, $R_b$ denotes a phenyl, benzyl or 1-phenylethyl group wherein the phenyl nucleus is substituted in each case by the groups $R_1$ to $R_3$, while $R_1$ and $R_2$, which may be identical or different, each denote a hydrogen, fluorine, chlorine or bromine atom, or a methyl, trifluoromethyl, methoxy, ethynyl or cyano group, $R_3$ denotes a hydrogen atom, $R_c$ and $R_d$ in each case denote a hydrogen atom, X denotes a nitrogen atom, A denotes an —NH— group, B denotes a carbonyl group, C denotes a 1,1- or 1,2-vinylene group, an ethynylene group or a 1,3-butadien-1,4-ylene group, D denotes a $C_{1-4}$-alkylene group, a —CO—$NR_4$-alkylene group wherein the alkylene moiety contains 2 to 4 carbon atoms, while the linking to the adjacent group C in each case must take place via the carbonyl group, wherein $R_4$ denotes a hydrogen atom, or, if D is bound to a carbon atom of the group E, it may also denote a bond or, if D is bound to a nitrogen atom of the group E, it may also denote a carbonyl group, E denotes an —($R_7O$—PO—$OR_8$)-alkylene-$NR_5$ or ($R_7O$—PO—$R_9$)-alkylene-$NR_5$ group wherein in each case the alkylene moiety, which is straight-chained and contains 1 to 4 carbon atoms, may additionally be substituted by one or two $C_{1-2}$-alkyl groups or by an $R_6O$—CO or $R_6O$—CO—$C_{1-2}$-alkyl group, while $R_5$ denotes a hydrogen atom, a $C_{1-4}$-alkyl group which may be substituted by an $R_6O$—CO group, an ethyl group optionally substituted by one or two methyl or ethyl groups which is terminally substituted by a $C_{1-4}$-alkylcarbonylsulphenyl, arylcarbonylsulphenyl or arylmethylcarbonylsulphenyl group, an ethyl group optionally substituted by one or two methyl or ethyl groups which is terminally substituted by a hydroxy, $C_{1-4}$-alkylcarbonyloxy, arylcarbonyloxy or arylmethylcarbonyloxy group, a 2,2-dimethoxyethyl or 2,2-diethoxyethyl group, a $C_{3-6}$-cycloalkyl or $C_{3-6}$-cycloalkyl-methyl group, $R_6$, $R_7$ and $R_8$, which may be identical or different, in each case denote a hydrogen atom, a $C_{1-8}$-alkyl group, a cyclopentyl, cyclopentylmethyl, cyclohexyl or cyclohexylmethyl group, an aryl, arylmethyl or $R_gCO$—O—($R_eCR_f$) group, wherein $R_e$ denotes a hydrogen atom or a $C_{1-4}$-alkyl group, $R_f$ denotes a hydrogen atom and $R_g$ denotes a $C_{1-4}$-alkyl, cyclopentyl, cyclohexyl, $C_{1-4}$-alkoxy, cyclopentyloxy or cyclohexyloxy group, and $R_9$ denotes a methyl or ethyl group, a pyrrolidino or piperidino group which is substituted by an $R_6O$—CO or $R_6O$—CO—$C_{1-2}$-alkyl group wherein $R_6$ is as hereinbefore defined, a pyrrolidino or piperidino group which is substituted by two $R_6O$—CO or $R_6O$—CO—$C_{1-2}$-alkyl groups wherein $R_6$ is as hereinbefore defined, a piperazino group which is substituted in the 4 position by the group $R_{10}$ and is additionally substituted at a cyclic carbon atom by an $R_6O$—CO or $R_6O$—CO—$C_{1-2}$-alkyl group, while $R_6$ is as hereinbefore defined and $R_{10}$ denotes a hydrogen atom, a methyl or ethyl group, a piperazino group which is substituted in the 4 position by an $R_6O$—CO—$C_{1-4}$-alkyl, bis-($R_6O$—CO)—$C_{1-4}$-alkyl or ($R_7O$—PO—$OR_8$)—$C_{1-2}$-alkyl group wherein $R_6$ to $R_8$ are as hereinbefore defined, a piperazino group which is substituted in the 4 position by an $R_6O$—CO—$C_{1-2}$-alkyl group and is additionally substituted at a cyclic carbon atom by an $R_6O$—CO or $R_6O$—CO—$C_{1-2}$-alkyl group wherein $R_6$ is as hereinbefore defined, a morpholino group which is substituted by an $R_6O$—CO or $R_6O$—CO—$C_{1-2}$-alkyl group, while $R_6$ is as hereinbefore defined, a piperidinyl group substituted in the 1 position by an $R_6O$—CO—$C_{1-4}$-alkyl, bis-($R_6O$—CO)—$C_{1-4}$-alkyl or ($R_7O$—PO—$OR_8$)—$C_{1-2}$-alkyl group wherein $R_6$ to $R_8$ are as hereinbefore defined, a morpholino group which is substituted in the 2 position by a methoxy or ethoxy group, a morpholino group which is substituted in the 2 and 6 positions in each case by a methoxy or ethoxy group, a 2,2-dimethoxyethyl-$NR_5$, 2,2-diethoxyethyl-$NR_5$, 1,3-dioxolan-2-yl-methyl-$NR_5$ or 1,3-dioxan-2-yl-methyl-$NR_5$ group wherein $R_5$ is as hereinbefore defined, a N-methyl-$R_{11}$N or N-ethyl-$R_{11}$N group wherein $R_{11}$ denotes a 2-oxo-tetrahydrofuran-3-yl, 2-oxo-tetrahydrofuran-4-yl, 2-oxo-tetrahydropyran-3-yl, 2-oxo-tetrahydropyran-4-yl, 2-oxo-tetrahydropyran-5-yl, 2-oxo-tetrahydrothiophen-3-yl, 2-oxo-tetrahydrothiophen-4-yl, 2-oxo-tetrahydrothiopyran-3-yl, 2-oxo-tetrahydrothiopyran-4-yl or 2-oxo-tetrahydrothiopyran-5-yl group optionally substituted by one or two methyl groups, or D together with E denotes an $R_gCO$—O—($R_eCR_f$)—O—CO or ($R_7O$—PO—$OR_8$) group wherein $R_e$ to $R_g$ and $R_7$ and $R_8$ are as hereinbefore defined, F and G together denote a hydrogen atom, a methoxy, ethoxy, $C_{4-6}$-cycloalkoxy or $C_{3-6}$-cycloalkyl-$C_{1-3}$-alkoxy group, while the aryl moieties mentioned in the definition of the abovementioned groups denote a phenyl group which may be mono- or disubstituted by $R_{13}$, while the substituents may be identical or different and $R_{13}$ denotes a fluorine, chlorine, bromine or iodine atom, a $C_{1-2}$-alkyl, trifluoromethyl or $C_{1-2}$-alkoxy group or two groups $R_{13}$, if they are bound to adjacent carbon atoms, together denote a $C_{3-4}$-alkylene, methylenedioxy or 1,3-butadien-1,4-ylene group, or a tautomer or salt thereof.

4. A compound of the formula I according to claim 1, wherein $R_a$ denotes a hydrogen atom, $R_b$ denotes a phenyl, benzyl or 1-phenylethyl group wherein the phenyl nucleus is substituted in each case by the groups $R_1$ to $R_3$, wherein $R_1$ and $R_2$, which may be identical or different, each denote a hydrogen, fluorine, chlorine or bromine atom or a methyl group and $R_3$ denotes a hydrogen atom, $R_c$ and $R_d$ each denote a hydrogen atom, X denotes a nitrogen atom, A denotes an —NH— group, B denotes a carbonyl group, C denotes a 1,2-vinylene or an ethynylene group, D denotes a $C_{1-4}$-alkylene group, a —CO—$NR_4$-alkylene group wherein the alkylene moiety contains 2 or 3 carbon atoms, while the linking to the adjacent group C must take place via the carbonyl group wherein $R_4$ denotes a hydrogen atom, or, if D is bound to a nitrogen atom of the group E, it may also denote a carbonyl group, E denotes an —(R$_7$O—PO—OR$_8$)-alkylene-NR$_5$ group wherein in each case the alkylene moiety, which is straight-chained and contains 1 to 2 carbon atoms, may additionally be substituted by a methyl group or by an R$_6$O—CO or R$_6$O—CO-methyl group, while R$_5$ denotes a hydrogen atom,
a C$_{1-2}$-alkyl group which may be substituted by an R$_6$O—CO group,
an ethyl group optionally substituted by one or two methyl groups, which is terminally substituted by a hydroxy, C$_{1-2}$-alkylcarbonylsulphenyl or C$_{1-2}$-alkylcarbonyloxy group,
a 2,2-dimethoxyethyl or 2,2-diethoxyethyl group, R$_6$ denotes a hydrogen atom,
a C$_{1-8}$-alkyl group,
a cyclopentyl, cyclopentylmethyl, cyclohexyl or cyclohexylmethyl group,
a phenyl group optionally substituted by one or two methyl groups, a phenylmethyl group which may be substituted in the phenyl moiety by one or two methyl groups, a 5-indanyl group or an R$_g$CO—O—(R$_e$CR$_f$) group, while
R$_e$ denotes a hydrogen atom or a methyl group,
R$_f$ denotes a hydrogen atom and
R$_g$ denotes a C$_{1-4}$-alkyl or C$_{1-2}$-alkoxy group, R$_7$ and R$_8$, which may be identical or different, in each case denote a hydrogen atom, a methyl, ethyl or phenyl group,
a pyrrolidino or piperidino group which is substituted by an R$_6$O—CO or R$_6$O—CO-methyl group, wherein R$_6$ is as hereinbefore defined,
a pyrrolidino or piperidino group which is substituted by two R$_6$O—CO or R$_6$O—CO-methyl groups wherein R$_6$ is as hereinbefore defined,
a piperazino group which is substituted in the 4 position by the group R$_{10}$ and additionally at a cyclic carbon atom by an R$_6$O—CO group, while R$_6$ is as hereinbefore defined and
R$_{10}$ denotes a hydrogen atom, a methyl or ethyl group,
a piperazino group which is substituted in the 4 position by an R$_6$O—CO—C$_{1-4}$-alkyl, bis-(R$_6$O—CO)—C$_{1-4}$-alkyl or (R$_7$O—PO—OR$_8$)—C$_{1-2}$-alkyl group wherein R$_6$ to R$_8$ are as hereinbefore defined,
a piperazino group which is substituted in the 4 position by an R$_6$O—CO-methyl group and additionally at a cyclic carbon atom by an R$_6$O—CO group wherein R$_6$ is as hereinbefore defined,
a morpholino group which is substituted by an R$_6$O—CO— group, wherein R$_6$ is as hereinbefore defined,
a morpholino group which is substituted in the 2 position by a methoxy or ethoxy group,
a morpholino group which is substituted in the 2 and 6 positions in each case by a methoxy or ethoxy group,
a 2,2-dimethoxyethyl-NR$_5$, 2,2-diethoxyethyl-NR$_5$ or 1,3-dioxolan-2-yl-methyl-NR$_5$— group wherein R$_5$ is as hereinbefore defined,
an N-methyl-R$_{11}$N or N-ethyl-R$_{11}$N group wherein
R$_{11}$ denotes a 2-oxo-tetrahydrofuran-3-yl or 2-oxo-tetrahydrofuran-4-yl group,
or D together with E denotes an R$_g$CO—O—(R$_e$CR$_f$)—O—CO group wherein R$_e$ to R$_g$ are as hreinbefore defined, F and G together denote a hydrogen atom,
a methoxy, ethoxy, C$_{4-6}$-cycloalkoxy or C$_{3-6}$-cycloalkyl-C$_{1-3}$-alkoxy group,
or a tautomer or salt thereof.

5. A compound of the formula I according to claim 4, wherein R$_b$ denotes a 1-phenylethyl group wherein the phenyl nucleus is substituted in each case by the groups R$_1$ to R$_3$, wherein
R$_1$ and R$_2$, which may be identical or different, each denote a hydrogen, fluorine, chlorine or bromine atom or a methyl group and
R$_3$ denotes a hydrogen atom,
or a tautomer or salt thereof.

6. A compound of the formula I according to claim 4, wherein F and G together denote a C$_{4-6}$-cycloalkoxy or C$_{3-6}$-cycloalkyl-C$_{1-3}$-alkoxy group,
or a tautomer or salt thereof.

7. A compound of the formula

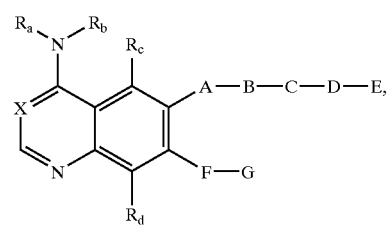

(I)

wherein
R$_a$ denotes a hydrogen atom or a C$_{1-4}$-alkyl group,
R$_b$ denotes a phenyl, benzyl or 1-phenylethyl group wherein the phenyl nucleus is substituted in each case by the groups R$_1$ to R$_3$, whilst
R$_1$ and R$_2$, which may be identical or different, in each case denote a hydrogen, fluorine, chlorine, bromine or iodine atom,
a C$_{1-4}$-alkyl, hydroxy, C$_{1-4}$-alkoxy, C$_{3-6}$-cycloalkyl, C$_{4-6}$-cycloalkoxy, C$_{2-5}$-alkenyl or C$_{2-5}$-alkynyl group,
an aryl, aryloxy, arylmethyl or arylmethoxy group,
a C$_{3-5}$-alkenyloxy or C$_{3-5}$-alkynyloxy group, wherein the unsaturated moiety may not be linked to the oxygen atom,
a C$_{1-4}$-alkylsulphenyl, C$_{1-4}$-alkylsulphinyl, C$_{1-4}$-alkylsulphonyl, C$_{1-4}$-alkylsulphonyloxy, trifluoromethylsulphenyl, trifluoromethylsulphinyl or trifluoromethylsulphonyl group,
a methyl or methoxy group substituted by 1 to 3 fluorine atoms,
an ethyl or ethoxy group substituted by 1 to 5 fluorine atoms,
a cyano or nitro group or an amino group optionally substituted by one or two C$_{1-4}$-alkyl groups, wherein the substituents may be identical or different, or
R$_1$ together with R$_2$, if they are bound to adjacent carbon atoms, denote a —CH=CH—CH=CH, —CH=CH—NH or —CH=N—NH group and
R$_3$ denotes a hydrogen, fluorine, chlorine or bromine atom,
a C$_{1-4}$-alkyl, trifluoromethyl or C$_{1-4}$-alkoxy group,
R$_c$ and R$_d$, which may be identical or different, in each case denote a hydrogen, fluorine or chlorine atom a methoxy group, or a methyl group optionally substituted by a methoxy, dimethylamino, diethylamino, pyrrolidino, piperidino or morpholino group,
X denotes a nitrogen atom, A denotes an oxygen atom or an —NH— group optionally substituted by a $C_{1-4}$-alkyl group, B denotes a carbonyl or sulphonyl group, C denotes a 1,3-allenylene, 1,1 or 1,2-vinylene group which may be substituted in each case by one or two methyl groups or by a trifluoromethyl group, an ethynylene group or a 1,3-butadien-1,4-ylene group optionally substituted by 1 to 4 methyl groups or by a trifluoromethyl group, D together with E denotes a hydrogen atom, a $C_{1-4}$-alkyl group optionally substituted by 1 to 5 fluorine atoms, a $C_{3-6}$-cycloalkyl group, an aryl, heteroaryl, $C_{1-4}$-alkylcarbonyl, arylcarbonyl or $C_{1-4}$-alkoxycarbonyl group, an aminocarbonyl, $C_{1-4}$-alkylaminocarbonyl or di-($C_{1-4}$-alkyl)-aminocarbonyl group or a carbonyl group, which is substituted by a 4- to 7-membered alkyleneimino group, whilst in the abovementioned 6- to 7-membered alkyleneimino groups, a methylene group in the 4 position may be replaced by an oxygen or sulphur atom, by an imino group substituted by the group $R_{10}$, by a sulphinyl or sulphonyl group, wherein $R_{10}$ denotes a hydrogen atom, a $C_{1-4}$-alkyl, formyl, $C_{1-4}$-alkylcarbonyl or $C_{1-4}$-alkylsulphonyl group, F denotes a $C_{1-6}$-alkylene group, a —O—$C_{1-6}$-alkylene group, wherein the alkylene moiety is linked to the group G, or an oxygen atom, whilst the latter may not be linked to a nitrogen atom of the group G, and G denotes an $R_6O$—CO-alkylene-$NR_5$, ($R_7O$—PO—$OR_8$)-alkylene-$NR_5$ or ($R_7O$—PO—$R_9$)-alkylene-$NR_5$-group wherein in each case the alkylene moiety, which is straight-chained and contains 1 to 6 carbon atoms, may additionally be substituted by one or two $C_{1-2}$-alkyl groups or by an $R_6O$—CO or $R_6O$—CO—$C_{1-2}$-alkyl group, wherein, $R_5$ denotes a hydrogen atom, a $C_{1-4}$-alkyl group, which may be substituted by an $R_6O$—CO, ($R_7O$—PO—$OR_8$) or ($R_7O$—PO—$R_9$) group, an ethyl or propyl group optionally substituted by one or two methyl or ethyl groups, which may be terminally substituted in each case by a $C_{1-6}$-alkylcarbonylsulphenyl, $C_{3-7}$-cycloalkylcarbonylsulphenyl, $C_{3-7}$-cycloalkyl-$C_{1-3}$-alkylcarbonylsulphenyl, arylcarbonylsulphenyl or aryl-$C_{1-3}$-alkylcarbonylsulphenyl group, an ethyl or propyl group optionally substituted by one or two methyl or ethyl groups which may be terminally substituted in each case by a $C_{1-6}$-alkylcarbonyloxy, $C_{3-7}$-cycloalkylcarbonyloxy, $C_{3-7}$-cycloalkyl-$C_{1-3}$-alkylcarbonyloxy, arylcarbonyloxy or aryl-$C_{1-3}$-alkylcarbonyloxy group, an ethyl or propyl group optionally substituted by one or two methyl or ethyl groups, each of which may be terminally substituted by a hydroxy, $C_{1-4}$-alkoxy, amino, $C_{1-4}$-alkylamino or di-($C_{1-4}$-alkyl)-amino group or by a 4- to 7-membered alkyleneimino group, whilst in the abovementioned 6- to 7-membered alkyleneimino groups a methylene group in the 4 position may be replaced by an oxygen or sulphur atom, by a sulphinyl, sulphonyl, imino or N—($C_{1-4}$-alkyl)-imino group, a $C_{3-7}$-cycloalkyl or $C_{3-7}$-cycloalkyl-$C_{1-3}$-alkyl group, $R_6$, $R_7$ and $R_8$, which may be identical or different, in each case denote a hydrogen atom, a $C_{1-8}$-alkyl group, which may be substituted by a hydroxy, $C_{1-4}$-alkoxy, amino, $C_{1-4}$-alkylamino or di-($C_{1-4}$-alkyl)-amino group or by a 4- to 7-membered alkyleneimino group, whilst in the abovementioned 6- to 7-membered alkyleneimino groups in each case a methylene group in the 4 position may be replaced by an oxygen or sulphur atom or by a sulphinyl, sulphonyl, imino or N—($C_{1-4}$-alkyl)-imino group, a $C_{4-7}$-cycloalkyl group optionally substituted by 1 or 2 methyl groups, a $C_{3-5}$-alkenyl or $C_{3-5}$-alkynyl group, wherein the unsaturated part may not be linked to the oxygen atom, a $C_{3-7}$-cycloalkyl-$C_{1-4}$-alkyl, aryl, aryl-$C_{1-4}$-alkyl or $R_gCO$—O—($R_eCR_f$)-group, whilst $R_e$ and $R_f$, which may be identical or different, in each case denote a hydrogen atom or a $C_{1-4}$-alkyl group and $R_g$ denotes a $C_{1-4}$-alkyl, $C_{3-7}$-cycloalkyl, $C_{1-4}$-alkoxy or $C_{5-7}$-cycloalkoxy group, and $R_9$ denotes a $C_{1-4}$-alkyl, aryl or aryl-$C_{1-4}$-alkyl group, a 4- to 7-membered alkyleneimino group which is substituted by an $R_6O$—CO, ($R_7O$—PO—$OR_8$), ($R_7O$—PO—$R_9$), $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_9$ are defined as set forth previously in this claim, a 4- to 7-membered alkyleneimino group which is substituted by two $R_6O$—CO or $R_6O$—CO—$C_{1-4}$-alkyl groups or by an $R_6O$—CO-group and an $R_6O$—CO—$C_{1-4}$-alkyl group wherein $R_6$ is defined as set forth previously in this claim, a piperazino or homopiperazino group which is substituted in the 4 position by the group $R_{10}$ and is additionally substituted at a cyclic carbon atom by an $R_6O$—CO, ($R_7O$—PO—$OR_8$), ($R_7O$—PO—$R_9$), $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_{10}$ are defined as set forth previously in this claim, a piperazino or homopiperazino group which is substituted in the 4 position by the group $R_{10}$ and is additionally substituted at cyclic carbon atoms by two $R_6O$—CO or $R_6O$—CO—$C_{1-4}$-alkyl groups or by an $R_6O$—CO group and an $R_6O$—CO—$C_{1-4}$-alkyl group wherein $R_6$ and $R_{10}$ are defined as set forth previously in this claim, a piperazino or homopiperazino group which is substituted in each case in the 4 position by an $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_9$ are defined as set forth previously in this claim, a piperazino or homopiperazino group which is substituted in the 4 position by an $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group and is additionally substituted at cyclic carbon atoms by one or two $R_6O$—CO or $R_6O$—CO—$C_{1-4}$-alkyl groups or by an $R_6O$—CO-group and an $R_6O$—CO—$C_{1-4}$-alkyl group wherein $R_6$ to $R_9$ are defined as set forth previously in this claim, a morpholino or homomorpholino group which is substituted in each case by an $R_6O$—CO, ($R_7O$—PO—$OR_8$), ($R_7O$—PO—$R_9$), $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_9$ are defined as set forth previously in this claim, a morpholino or homomorpholino group which is substituted by two $R_6O$—CO or $R_6O$—CO—$C_{1-4}$-alkyl groups or by an $R_6O$—CO-group and an $R_6O$—CO—$C_{1-4}$-alkyl group wherein $R_6$ is defined as set forth previously in this claim, a pyrrolidinyl, piperidinyl or hexahydroazepinyl group substituted in the 1 position by the group $R_{10}$, whilst the abovementioned 5- to 7-membered rings are in each case additionally substituted at a carbon atom by an $R_6O$—CO, ($R_7O$—PO—$OR_8$), ($R_7O$—PO—$R_9$), $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_{10}$ are define as set forth previously in this claim, a pyrrolidinyl, piperidinyl or hexahydroazepinyl group substituted in the 1 position by the group $R_{10}$, while the abovementioned 5- to 7-membered rings are in each case additionally substituted at carbon atoms by two $R_6O$—CO or $R_6O$—CO—$C_{1-4}$-alkyl groups or by an $R_6O$—CO-group and an $R_6O$—CO—$C_{1-4}$-alkyl group wherein $R_6$ and $R_{10}$ are defined as set forth previously in this claim, a pyrrolidinyl, piperidinyl or hexahydroazepinyl group substituted in the 1 position by an $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_9$ are defined as set forth previously in this claim, a pyrrolidinyl, piperidinyl or hexahydroazepinyl group substituted in the 1 position by an $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group, while the abovementioned 5- to 7-membered rings are in each case additionally substituted at carbon atoms by one or two $R_6O$—CO or $R_6O$—CO—$C_{1-4}$-alkyl groups or by an $R_6O$—CO-group and an $R_6O$—CO—$C_{1-4}$-alkyl group wherein $R_6$ to $R_9$ are defined as set forth previously in this claim, a 2-oxo-morpholino group which may be substituted by 1 or 2 methyl groups, a 2-oxo-morpholinyl group which is substituted in the 4 position by a hydrogen atom, by a $C_{1-4}$-alkyl, $R_6O$—CO—$C_{1-4}$-alkyl, ($R_7O$—PO—$OR_8$)—$C_{1-4}$-alkyl or ($R_7O$—PO—$R_9$)—$C_{1-4}$-alkyl group, while $R_6$ to $R_9$ are defined as in claim 1 and the abovementioned 2-oxo-morpholinyl groups are in each case linked to a carbon atom of the group F, a morpholino or thiomorpholino group which is substituted in the 2 position by a $C_{1-4}$-alkoxy group, a morpholino or thiomorpholino group which is substituted in the 2 and 6 position by a $C_{1-4}$-alkoxy group, a $C_{1-4}$-alkyl-$NR_5$-group wherein the $C_{1-4}$-alkyl moiety, which is straight-chained and may additionally be substituted by one or two methyl groups, is in each case terminally substituted by a di-($C_{1-4}$-alkoxy)-methyl or tri-($C_{1-4}$-alkoxy)-methyl group, whilst $R_5$ is defined as set forth previously in this claim, a $C_{1-4}$-alkyl-$NR_5$-group wherein the $C_{1-4}$-alkyl moiety, which is straight-chained and may additionally be substituted by one or two methyl groups, is terminally substituted in each case by a 1,3-dioxolan-2-yl or 1,3-dioxan-2-yl-group optionally substituted by one or two methyl groups, while $R_5$ is defined as set forth previously in this claim, an $R_hNR_5$-group wherein $R_5$ is as hereinbefore defined and $R_h$ denotes a 2-oxo-tetrahydrofuran-3-yl, 2-oxo-tetrahydrofuran-4-yl, 2-oxo-tetrahydropyran-3-yl, 2-oxo-tetrahydropyran-4-yl or 2-oxo-tetrahydropyran-5-yl group optionally substituted by one or two methyl groups, whilst by the aryl moieties mentioned in the definitions of the abovementioned groups is meant a phenyl group which in each case may be monosubstituted by $R_{12}$, mono-, di- or trisubstituted by $R_{13}$ or monosubstituted by $R_{12}$ and additionally mono- or disubstituted by $R_{13}$, whilst the substituents may be identical or different and $R_{12}$ denotes a cyano, carboxy, $C_{1-4}$-alkoxycarbonyl, aminocarbonyl, $C_{1-4}$-alkylaminocarbonyl, di-($C_{1-4}$-alkyl)-aminocarbonyl, $C_{1-4}$-alkylsulphenyl, $C_{1-4}$-alkylsulphinyl, $C_{1-4}$-alkylsulphonyl, hydroxy, $C_{1-4}$-alkylsulphonyloxy, trifluoromethyloxy, nitro, amino, $C_{1-4}$-alkylamino, di-($C_{1-4}$-alkyl)-amino, $C_{1-4}$-alkylcarbonylamino, N—($C_{1-4}$-alkyl)—$C_{1-4}$-alkylcarbonylamino, $C_{1-4}$-alkylsulphonylamino, N—($C_{1-4}$-alkyl)-$C_{1-4}$-alkylsulphonylamino, aminosulphonyl, $C_{1-4}$-alkylaminosulphonyl or di-($C_{1-4}$-alkyl)-aminosulphonyl group or a carbonyl group, which is substituted by a 5- to 7-membered alkyleneimino group, wherein in the abovementioned 6- to 7-membered alkyleneimino groups in each case a methylene group in the 4 position may be replaced by an oxygen or sulphur atom, by a sulphinyl, sulphonyl, imino or N—($C_{1-4}$-alkyl)-imino group, and $R_{13}$ denotes a fluorine, chlorine, bromine or iodine atom, a $C_{1-4}$-alkyl, trifluoromethyl or $C_{1-4}$-alkoxy group or two groups $R_{13}$, if they are bound to adjacent carbon atoms, together denote a $C_{3-5}$-alkylene, methylenedioxy or 1,3-butadien-1,4-ylene group, and moreover, the heteroaryl groups mentioned in the definitions of the abovementioned groups also include a 5-membered heteroaromatic group which contains an imino group, an oxygen or sulphur atom or an imino group, an oxygen or sulphur atom and one or two nitrogen atoms, or a 6-membered heteroaromatic group which contains one, two or three nitrogen atoms, whilst the abovementioned 5-membered heteroaromatic groups may be substituted in each case by 1 or 2 methyl or ethyl groups and the abovementioned 6-membered heteroaromatic groups may be substituted in each case by 1 or 2 methyl or ethyl groups or by a fluorine, chlorine, bromine or iodine atom, or by a trifluoromethyl, hydroxy, methoxy or ethoxy group, or a tautomer or salt thereof.

8. A compound of the formula I according to claim 7, wherein $R_a$ denotes a hydrogen atom, $R_b$ denotes a phenyl, benzyl or 1-phenylethyl group wherein the phenyl nucleus is substituted in each case by the groups $R_1$ to $R_3$, while $R_1$ and $R_2$, which may be identical or different, each denote a hydrogen, fluorine, chlorine, bromine or iodine atom, a methyl, ethyl, hydroxy, methoxy, ethoxy, amino, cyano, vinyl or ethynyl group, an aryl, aryloxy, arylmethyl or arylmethoxy group,
a methyl or methoxy group substituted by 1 to 3 fluorine atoms or
$R_1$ together with $R_2$, if they are bound to adjacent carbon atoms, denote a —CH=CH—CH=CH, —CH=CH—NH or —CH=N—NH group and
$R_3$ denotes a hydrogen, fluorine, chlorine or bromine atom,
$R_c$ and $R_d$ in each case denote a hydrogen atom,
X denotes a nitrogen atom,
A denotes an —NH— group optionally substituted by a methyl or ethyl group,
B denotes a carbonyl group,
C denotes a 1,1- or 1,2-vinylene group which is substituted in each case by one or two methyl groups or may be substituted by a trifluoromethyl group,
an ethynylene group or
a 1,3-butadien-1,4-ylene group optionally substituted by a methyl or trifluoromethyl group,
D together with E denotes a hydrogen atom,
a methyl, trifluoromethyl or aryl group,
F denotes an —O—$C_{1-4}$-alkylene group, wherein the alkylene moiety is liked to the group G, or an oxygen atom, while this may not be linked to a nitrogen atom of the group G, and
G denotes an $R_6O$—CO-alkylene-$NR_5$, ($R_7O$—PO—$OR_8$)-alkylene-$NR_5$ or ($R_7O$—PO—$R_9$)-alkylene-$NR_5$ group wherein in each case the alkylene moiety, which is straight-chained and contains 1 to 4 carbon atoms, may additionally be substituted by one or two $C_{1-2}$-alkyl groups or by an $R_6O$—CO or $R_6O$—CO—$C_{1-2}$-alkyl group, while $R_5$ to $R_9$ are defined as in claim 7,
a 4- to 7-membered alkyleneimino group which is substituted by an $R_6O$—CO, $R_6O$—CO—$C_{1-4}$-alkyl or bis-($R_6O$—CO)—$C_{1-4}$-alkyl group wherein $R_6$ is defined as in claim 7,
a 4- to 7-membered alkyleneimino group which is substituted by two $R_6O$—CO or $R_6O$—CO—$C_{1-4}$-alkyl groups wherein $R_6$ is defined as in claim 7,
a piperazino or homopiperazino group which is substituted in the 4 position by the group $R_{10}$ and is additionally substituted at a cyclic carbon atom by an $R_6O$—CO, $R_6O$—CO—$C_{1-4}$-alkyl or bis-($R_6O$—CO)—$C_{1-4}$-alkyl group wherein $R_6$ and $R_{10}$ are defined as in claim 7,
a piperazino or homopiperazino group which is substituted in the 4 position by the group $R_{10}$ and is additionally substituted at cyclic carbon atoms by two $R_6O$—CO or $R_6O$—CO—$C_{1-4}$-alkyl groups wherein $R_6$ and $R_{10}$ are defined as in claim 7,
a piperazino or homopiperazino group which is substituted in each case in the 4 position by an $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_9$ are defined as in claim 7,
a piperazino or homopiperazino group which is substituted in the 4 position by an $R_6O$—CO—$C_{1-4}$-alkyl or bis-($R_6O$—CO)—$C_{1-4}$-alkyl group and additionally at cyclic carbon atoms by one or two $R_6O$—CO or $R_6O$—CO—$C_{1-4}$-alkyl groups wherein $R_6$ is defined as in claim 7,
a morpholino or homomorpholino group which is substituted in each case by an $R_6O$—CO, $R_6O$—CO—$C_{1-4}$-alkyl or bis-($R_6O$—CO)—$C_{1-4}$-alkyl group wherein $R_6$ is defined as in claim 7,
a morpholino or homomorpholino group which is substituted by two $R_6O$—CO or $R_6O$—CO—$C_{1-4}$-alkyl groups wherein $R_6$ is defined as in claim 7,
a pyrrolidinyl, piperidinyl or hexahydroazepinyl group substituted in the 1 position by the group $R_{10}$, while the abovementioned 5- to 7-membered rings in each case are additionally substituted at a carbon atom by an $R_6O$—CO, $R_6O$—CO—$C_{1-4}$-alkyl or bis-($R_6O$—CO)—$C_{1-4}$-alkyl group wherein $R_6$ and $R_{10}$ are defined as in claim 7,
a pyrrolidinyl, piperidinyl or hexahydroazepinyl group substituted in the 1 position by the group $R_{10}$, while the abovementioned 5- to 7-membered rings in each case are additionally substituted at carbon atoms by two $R_6O$—CO or $R_6O$—CO—$C_{1-4}$-alkyl groups wherein $R_6$ and $R_{10}$ are defined as in claim 7,
a pyrrolidinyl, piperidinyl or hexahydroazepinyl group substituted in the 1 position by an $R_6O$—CO—$C_{1-4}$-alkyl, bis-($R_6O$—CO)—$C_{1-4}$-alkyl, ($R_7O$—PO—$OR_8$)—$C_{1-4}$-alkyl or ($R_7O$—PO—$R_9$)—$C_{1-4}$-alkyl group wherein $R_6$ to $R_9$ are defined as in claim 7,
a pyrrolidinyl, piperidinyl or hexahydroazepinyl group substituted in the 1 position by an $R_6O$—CO—$C_{1-4}$-alkyl or bis-($R_6O$—CO)—$C_{1-4}$-alkyl group, while the abovementioned 5- to 7-membered rings in each case are additionally substituted at carbon atoms by one or two $R_6O$—CO or $R_6O$—CO—$C_{1-4}$-alkyl groups wherein $R_6$ is defined as in claim 7,
a 2-oxo-morpholino group which may be substituted by 1 or 2 methyl groups,
a 2-oxo-morpholinyl group which is substituted in the 4 position by a $C_{1-4}$-alkyl or $R_6O$—CO—$C_{1-4}$-alkyl group, while $R_6$ is defined as in claim 2 and the abovementioned 2-oxo-morpholinyl groups are each are linked to a carbon atom of the group F,
a morpholino group which is substituted in the 2 position by a $C_{1-4}$-alkoxy group,
a morpholino group which is substituted in the 2 and 6 positions in each case by a $C_{1-4}$-alkoxy group,
a $C_{1-4}$-alkyl-$NR_5$ group wherein the $C_{1-4}$-alkyl moiety, which is straight-chained, is terminally substituted by a di-($C_{1-4}$-alkoxy)-methyl group, while $R_5$ is defined as in claim 7,
a $C_{1-4}$-alkyl-$NR_5$ group wherein the $C_{1-4}$-alkyl moiety, which is straight-chained, is terminally substituted by a 1,3-dioxolan-2-yl or 1,3-dioxan-2-yl group, while $R_5$ is defined as in claim 7,
a $R_h NR_5$ group wherein $R_5$ is defined as in claim 2 and $R_h$ denotes a substituted 2-oxo-tetrahydrofuran-3-yl, 2-oxo-tetrahydrofuran-4-yl, 2-oxo-tetrahydropyran-3-yl, 2-oxo-tetrahydropyran-4-yl or 2-oxo-tetrahydropyran-5-yl group optionally by one or two methyl groups,
while the aryl moieties mentioned in the definition of the abovementioned groups denote a phenyl group which may in each case be monosubstituted by $R_{12}$, mono- or disubstituted by $R_{13}$ or monosubstituted by $R_{12}$ and additionally mono or disubstituted by $R_{13}$, while the substituents may be identical or different and
$R_{12}$ denotes a cyano, $C_{1-2}$-alkoxycarbonyl, aminocarbonyl, $C_{1-2}$-alkylaminocarbonyl, di-($C_{1-2}$-alkyl)-aminocarbonyl, $C_{1-2}$-alkylsulphenyl, $C_{1-2}$-alkylsulphinyl, $C_{1-2}$-alkylsulphonyl, hydroxy, nitro, amino, $C_{1-2}$-alkylamino or di-($C_{1-2}$-alkyl)-amino group and $R_{13}$ denotes a fluorine, chlorine, bromine or iodine atom, a $C_{1-2}$-alkyl, trifluoromethyl or $C_{1-2}$-alkoxy group or two groups $R_{13}$, if they are bound to adjacent carbon atoms, together denote a $C_{3-5}$-alkylene, methylenedioxy or 1,3-butadien-1,4-ylene group, or a tautomer or salt thereof.

9. A compound of the formula I according to claim 7, wherein $R_a$ denotes a hydrogen atom, $R_b$ denotes a phenyl, benzyl or 1-phenylethyl group wherein the phenyl nucleus is substituted in each case by the groups $R_1$ to $R_3$, while $R_1$ and $R_2$, which may be identical or different, each denote a hydrogen, fluorine, chlorine or bromine atom, or a methyl, trifluoromethyl, methoxy, ethynyl or cyano group, $R_3$ denotes a hydrogen atom, $R_c$ and $R_d$ in each case denote a hydrogen atom, X denotes a nitrogen atom, A denotes an —NH— group, B denotes a carbonyl group, C denotes a 1,1- or 1,2-vinylene group, an ethynylene group or a 1,3-butadien-1,4-ylene group, D together with E denotes a hydrogen atom, a methyl, trifluoromethyl or aryl group, F denotes an —O—$C_{1-4}$-alkylene group, wherein the alkylene moiety is linked to the group G, or an oxygen atom, while this may not be linked to a nitrogen atom of the group G, and G denotes an $R_6O$—CO-alkylene-$NR_5$ group wherein the alkylene moiety, which is straight-chained and contains 1 to 4 carbon atoms, may additionally be substituted by one or two $C_{1-2}$-alkyl groups or by an $R_6O$—CO or $R_6O$—CO—$C_{1-2}$-alkyl group, while $R_5$ and $R_6$ are defined as in claim 7, a pyrrolidino or piperidino group which is substituted by an $R_6O$—CO or $R_6O$—CO—$C_{1-2}$-alkyl group wherein $R_6$ is defined as in claim 7, a pyrrolidino or piperidino group which is substituted by two $R_6O$—CO or $R_6O$—CO—$C_{1-2}$-alkyl groups wherein $R_6$ is defined as in claim 7, a piperazino group which is substituted in the 4 position by the group $R_{10}$ and additionally at a cyclic carbon atom by an $R_6O$—CO, or $R_6O$—CO—$C_{1-2}$-alkyl group, while $R_6$ and $R_{10}$ are defined as in claim 7, a piperazino group which is substituted in the 4 position by an $R_6O$—CO—$C_{1-4}$-alkyl, bis-($R_6O$—CO)—$C_{1-4}$-alkyl or ($R_7O$—PO—$OR_8$)—$C_{1-2}$-alkyl group wherein $R_6$ to $R_8$ are defined as in claim 7, a piperazino group which is substituted in the 4 position by an $R_6O$—CO—$C_{1-2}$-alkyl group and additionally at a cyclic carbon atom by an $R_6O$—CO or $R_6O$—CO—$C_{1-2}$-alkyl group wherein $R_6$ is defined as in claim 7, a morpholino group which is substituted by an $R_6O$—CO or $R_6O$—CO—$C_{1-2}$-alkyl group, while $R_6$ is defined as in claim 7, a piperidinyl group substituted in the 1 position by an $R_6O$—CO—$C_{1-4}$-alkyl, bis-($R_6O$—CO)—$C_{1-4}$-alkyl or ($R_7O$—PO—$OR_8$)—$C_{1-2}$-alkyl group wherein $R_6$ to $R_8$ are defined as in claim 7, a 2-oxo-morpholino group which may be substituted by 1 or 2 methyl groups, a 2-oxo-morpholinyl group which is substituted in the 4 position by a methyl, ethyl or $R_6O$—CO—$C_{1-2}$-alkyl group, while $R_6$ is defined as in claim 3 and the abovementioned 2-oxo-morpholinyl groups in each case are linked to a carbon atom of the group F, a morpholino group which is substituted in the 2 position by a methoxy or ethoxy group, a morpholino group which is substituted in the 2 and 6 positions in each case by a methoxy or ethoxy group, a 2,2-dimethoxyethyl-$NR_5$, 2,2-diethoxyethyl-$NR_5$, 1,3-dioxolan-2-yl-methyl-$NR_5$ or 1,3-dioxan-2-yl-methyl-$NR_5$ group wherein $R_5$ is defined as in claim 7, while the aryl moieties mentioned in the definition of the abovementioned groups denote a phenyl group which may be mono- or disubstituted by $R_{13}$, while the substituents may be identical or different and $R_{13}$ denotes a fluorine, chlorine, bromine or iodine atom, a $C_{1-2}$-alkyl, trifluoromethyl or $C_{1-2}$-alkoxy group or two groups $R_{13}$, if they are bound to adjacent carbon atoms, together denote a $C_{3-4}$-alkylene, methylenedioxy or 1,3-butadien-1,4-ylene group, or a tautomer or salt thereof.

10. A compound of the formula I according to claim 7, wherein $R_a$ denotes a hydrogen atom, $R_b$ denotes a phenyl, benzyl or 1-phenylethyl group wherein the phenyl nucleus is substituted in each case by the groups $R_1$ to $R_3$, wherein $R_1$ and $R_2$, which may be identical or different, each denote a hydrogen, fluorine, chlorine or bromine atom or a methyl group and $R_3$ denotes a hydrogen atom, $R_c$ and $R_d$ each denote a hydrogen atom, X denotes a nitrogen atom, A denotes an —NH— group, B denotes a carbonyl group, C denotes a 1,2-vinylene or an ethynylene group, D together with E denotes a hydrogen atom or a methyl group, F denotes an —O—$C_{1-4}$-alkylene group, while the alkylene moiety is linked to the group G, or an oxygen atom, which may not be linked to a nitrogen atom of the group G, and G denotes an $R_6O$—CO-alkylene-$NR_5$ group wherein the alkylene moiety, which is straight-chained and contains 1 or 2 carbon atoms, may additionally be substituted by a methyl group or by an $R_6O$—CO or $R_6O$—CO-methyl group, while $R_5$ and $R_6$ are defined as in claim 7, a pyrrolidino or piperidino group which is substituted by an $R_6O$—CO or $R_6O$—CO-methyl group wherein $R_6$ is defined as in claim 7, a pyrrolidino or piperidino group which is substituted by two $R_6O$—CO or $R_6O$—CO-methyl groups wherein $R_6$ is defined as in claim 7, a piperazino group which is substituted in the 4 position by an $R_6O$—CO—$C_{1-4}$-alkyl, bis-($R_6O$—CO)—$C_{1-4}$-alkyl or ($R_7O$—PO—$OR_8$)—$C_{1-2}$-alkyl group wherein $R_6$ to $R_8$ are defined as in claim 7, a piperidinyl group substituted in the 1 position by an $R_6O$—CO—$C_{1-2}$-alkyl group wherein $R_6$ is defined as in claim 7, or a tautomer or salt thereof.

11. A compound of the formula I according to claim 10, wherein $R_b$ denotes a 1-phenylethyl group wherein the phenyl nucleus is substituted in each case by the groups $R_1$ to $R_3$, wherein $R_1$ and $R_2$, which may be identical or different, each denote a hydrogen, fluorine, chlorine, or bromine atom or a methyl group and $R_3$ denotes a hydrogen atom, or a tautomer or salt thereof.

12. A compound selected from the group consisting of:
(a) 4-[(3-bromophenyl)amino]-7-(3-{4-[(ethoxycarbonyl) methyl]-piperazin-1-yl}propyloxy)-6-[(vinylcarbonyl) amino]-quinazoline,
(b) 4-[(3-bromophenyl)amino]-7-(3-{4-[3-(ethoxycarbonyl)propyl]-piperazin-1-yl}propyloxy)-6-[(vinylcarbonyl)amino]-quinazoline,
(c) 4-[(3-bromophenyl)amino]-7-({1-[(ethoxycarbonyl) methyl]-piperidin-4-yl}oxy)-6-[(vinylcarbonyl) amino]-quinazoline,
(d) 4-[(3-bromophenyl)amino]-7-(3-{4-[(diethoxyphosphoryl)methyl]-piperazin-1-yl}propyloxy)-6-[(vinylcarbonyl)amino]-quinazoline,
(e) 4-[(3-bromophenyl)amino]-7-(3-{N-[(ethoxycarbonyl)methyl]-N-methylamino}propyloxy)-6-[(vinylcarbonyl)amino]-quinazoline,
(f) 4-[(3-bromophenyl)amino]-6-[(4-{N-[(diethoxyphosphoryl)methyl]-N-methylamino}-1-oxo-2-buten-1-yl)amino]-7-methoxy-quinazoline,
(g) 4-[(3-bromophenyl)amino]-6-({4-[N-(2,2-dimethoxyethyl)-N-methylamino]-1-oxo-2-buten-1-yl}amino)-7-methoxy-quinazoline,
(h) 4-[(3-bromophenyl)amino]-6-{[4-(2-ethoxy-morpholin-4-yl)-1-oxo-2-buten-1-yl]amino}-7-methoxy-quinazoline,
(i) 4-[(3-chloro-4-fluorophenyl)amino]-6-[(4-{4-[(ethoxycarbonyl)methyl]-piperazin-1-yl}-1-oxo-2-buten-1-yl)amino]-7-cyclopropylmethoxy-quinazoline,
(j) 4-[(3-chloro-4-fluorophenyl)amino]-6-[(4-{4-[(ethoxycarbonyl)methyl]-piperazin-1-yl}-1-oxo-2-buten-1-yl)amino]-7-cyclobutyloxy-quinazoline,
(k) 4-[(3-chloro-4-fluorophenyl)amino]-6-[(4-{4-[(ethoxycarbonyl)methyl]-piperazin-1-yl}-1-oxo-2-buten-1-yl)amino]-7-(2-cyclopropylethoxy)-quinazoline,
(l) (S)-4-[(3-chloro-4-fluorophenyl)amino]-6-({4-[2-(methoxycarbonyl)-pyrrolidin-1-yl]-1-oxo-2-buten-1-yl}amino)-7-cyclopropylmethoxy-quinazoline,
(m) 4-[(3-chloro-4-fluorophenyl)amino]-6-[(4-{N-[(ethoxycarbonyl)methyl]-N-[2-(acetylsulphanyl) ethyl]amino}-1-oxo-2-buten-1-yl)amino]-7-cyclopropylmethoxy-quinazoline, and
(n) 4-[(3-chloro-4-fluorophenyl)amino]-6-[(4-{N-[(ethoxycarbonyl)-methyl]-N-[2-(methylcarbonyloxy) ethyl]amino}-1-oxo-2-buten-1-yl)amino]-7-cyclopropylmethoxy-quinazoline, or a salt thereof.

13. A physiologically acceptable salt of a compound according to claim 1.

14. A pharmaceutical composition comprising a compound according to claim 1, 2, 3, 4, 5, 6, 7, 8, 9, 10, 11 or 12 or a physiologically acceptable salt thereof and a pharmaceutically acceptable carrier or diluent.

15. A method for treating a benign or malignant tumour, which method comprises administering a therapeutically effective amount of a compound according to claim 1, 2, 3, 4, 5, 6, 7, 8, 9, 10, 11 or 12 or a physiologically acceptable salt thereof.

* * * * *